US011466077B2

(12) United States Patent
Seredenina et al.

(10) Patent No.: US 11,466,077 B2
(45) Date of Patent: Oct. 11, 2022

(54) MISFOLDED TDP-43 BINDING MOLECULES

(71) Applicant: AC Immune SA, Lausanne (CH)

(72) Inventors: Tamara Seredenina, Lausanne (CH);
Oskar Adolfsson, Lausanne (CH)

(73) Assignee: AC Immune SA, Lausanne (CH)

( * ) Notice: Subject to any disclaimer, the term of this patent is extended or adjusted under 35 U.S.C. 154(b) by 25 days.

(21) Appl. No.: 16/959,385

(22) PCT Filed: Jan. 4, 2019

(86) PCT No.: PCT/EP2019/050185
§ 371 (c)(1),
(2) Date: Jun. 30, 2020

(87) PCT Pub. No.: WO2019/134981
PCT Pub. Date: Jul. 11, 2019

(65) Prior Publication Data
US 2022/0025023 A1 Jan. 27, 2022

(30) Foreign Application Priority Data
Jan. 5, 2018 (EP) ..................................... 18150517

(51) Int. Cl.
| | | |
|---|---|---|
| *C07K 16/18* | (2006.01) | |
| *A61K 47/68* | (2017.01) | |
| *A61K 45/06* | (2006.01) | |
| *G01N 33/68* | (2006.01) | |

(52) U.S. Cl.
CPC .............. *C07K 16/18* (2013.01); *A61K 45/06* (2013.01); *A61K 47/6803* (2017.08); *A61K 47/6843* (2017.08); *G01N 33/6896* (2013.01); *C07K 2317/34* (2013.01); *C07K 2317/92* (2013.01); *G01N 2800/28* (2013.01)

(58) Field of Classification Search
None
See application file for complete search history.

(56) References Cited

U.S. PATENT DOCUMENTS

| | | | | |
|---|---|---|---|---|
| 2014/0255304 A1* | 9/2014 | Roger | ..................... | A61P 43/00 424/1.49 |
| 2015/0196663 A1* | 7/2015 | Shusta | .................. | A61K 9/0085 424/178.1 |
| 2015/0266947 A1* | 9/2015 | Sierks | ................. | G01N 33/6896 424/135.1 |
| 2017/0298124 A1 | 10/2017 | Chen | | |
| 2017/0355756 A1* | 12/2017 | Julien | ..................... | A61P 21/02 |

FOREIGN PATENT DOCUMENTS

| | | | |
|---|---|---|---|
| WO | WO 2008068048 | * | 6/2008 |
| WO | WO 2013061163 | | 5/2013 |
| WO | WO 2015117088 | | 8/2015 |

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Reitz "Toward precision medicine in Alzheimer's disease" Ann transl med 4(6):107 (Year: 2016).*
Stanford "Alzheimer's prevention, treatment and research—A Q and A with Dr Frank Longo" accessed from Stanfordhealthcare.org on May 3, 2016 (Year: 2016).*
European Search Report dated Oct. 24, 2018, Appl. No. EP 18150517. 3, 8 pp.
Kwong et al. (2014) "Novel monoclonal antibodies to normal and pathologically altered human TDP-43 proteins" ACTA Neuropathologica Communications 2:1 33.
Shodai et al. (2012) "Conserved Acidic Amino Acid Residues in a Second RNA Recognition Motif Regulate Assembly and Function of TDP-43", PLOS ONE, 7:12 e52776.
Zhang et al. (2008) "Epitope mapping of 2E2-D3, a monoclonal antibody directed against human TDP-43" Neuroscience Letters 434:2 170-174.
Written Opinion dated Feb. 4, 2022, Appl. No. SG11202006348V, 12 pp.
Zhang et al. (2008) "TDP-43-immunoreactive neuronal and glial inclusions in the neostriatum in amyotrophic lateral sclerosis with and without dementia" Acta Neuropathol, 115:115-122.

* cited by examiner

*Primary Examiner* — Adam Weidner
(74) *Attorney, Agent, or Firm* — Brian E. Davy; Bozicevic, Field & Francis LLP

(57) ABSTRACT

The present invention is in the field of transactive response DNA binding protein with a molecular weight of 43 kDa (TARDB or also TDP-43). The invention relates to TDP-43 specific binding molecules, in particular to anti-TDP-43 antibodies or an antigen-binding fragment or a derivative thereof and uses thereof. The present invention provides means and methods to diagnose, prevent, alleviate and/or treat a disorder and/or abnormality associated with misfolded TDP-43 including but not limited to frontotemporal dementia (FTD), amyotrophic lateral sclerosis (ALS), Alzheimer's disease (AD, sporadic and familial), and/or Parkinson's disease (PD). The present invention provides modified conformation-specific antigenic peptides and peptide fragments derived from the TDP-43 protein and the antibodies obtainable by said peptides or fragments for use in the diagnosis, prevention, alleviation and/or treatment of TDP-43-related disorders and/or abnormalities.

31 Claims, 10 Drawing Sheets
Specification includes a Sequence Listing.

MISFOLDED TDP-43 BINDING MOLECULES

FIELD OF THE INVENTION

The present invention is in the field of transactive response DNA binding protein with a molecular weight of 43 kDa (TARDB or also TDP-43). The invention relates to TDP-43 specific binding molecules, in particular to anti-TDP-43 antibodies or an antigen-binding fragment or a derivative thereof and uses thereof. The present invention provides means and methods to diagnose, prevent, alleviate and/or treat a disorder and/or abnormality associated with misfolded TDP-43 including but not limited to frontotemporal dementia (FTD), amyotrophic lateral sclerosis (ALS), Alzheimer's disease (AD, sporadic and familial), and/or Parkinson's disease (PD). The present invention provides modified conformation-specific antigenic peptides and peptide fragments derived from the TDP-43 protein and the antibodies obtainable by said peptides or fragments for use in the diagnosis, prevention, alleviation and/or treatment of TDP-43-related disorders and/or abnormalities.

INCORPORATION BY REFERENCE OF SEQUENCE LISTING PROVIDED AS A TEXT FILE

A sequence Listing is provided herewith a text file, BOULT-032_Seqlist_ST25.txt, created on Jan. 19, 2021 and having a size of 140 KB. The contents of the text file are incorporated by reference herein in their entirety.

BACKGROUND

Age-associated brain disorders characterized by pathological aggregation of proteins in the central nervous system (CNS) (proteinopathies) and peripheral organs represent one of the leading causes of disability and mortality in the world. The best characterized protein that forms extracellular aggregates is amyloid beta in Alzheimer's disease and related disorders. Other disease-associated, aggregation-prone proteins leading to neurodegeneration include but are not limited to tau, alpha-synuclein (aSyn), huntingtin, fused in sarcoma (FUS), dipeptide repeat proteins (DPRs) produced by unconventional translation of the C9orf72 repeat expansion, superoxide dismutase 1 (SOD1), and TDP-43. Diseases involving TDP-43 aggregates am generally listed as TDP-43 proteinopathies including, but not limited to, ALS and FTD.

I. TDP-43 Introduction

Transactive response (TAR) DNA binding protein 43 kDa (TDP-43) is a 414-amino acid protein encoded by the TARDBP gene on chromosome 1p36.2 (ALS10). TARDBP is comprised of six exons (exon 1 is non-coding; exons 2-6 are protein-coding). TDP-43 belongs to the family of heterogeneous ribonucleoprotein (hnRNP) RNA binding proteins (Wang et al., Trends in Molecular Medicine Vol. 14 No. 11, 2008, 479-485; Lagier-Tourenne et al., Human Molecular Genetics, 2010, Vol. 19, Review Issue 1 R46-R64). TDP-43 contains five functional domains (FIG. 1 in Warraich et al., The International Journal of Biochemistry & Cell Biology 42 (2010) 1606-1609): two RNA recognition motifs (RRM1 and RRM2), which have two highly conserved hexameric ribonucleoprotein 2 (RNP2) and octameric ribonucleoprotein 1 (RNP1) regions, a nuclear export signal (NES) and a nuclear localization signal (NLS) enabling it to shuttle between the nucleus and the cytoplasm transporting bound mRNA, and a glycine rich domain at the C-terminal, which mediates protein-protein interactions. TDP-43 is involved in multiple aspects of RNA processing, including transcription, splicing, transport, and stabilization (Buratti and Baralle, FEBS Journal 277 (2010) 2268-2281). It is a highly conserved, ubiquitously expressed protein with a tightly autoregulated expression level that shuttles continuously between the nucleus and cytoplasm, but is predominantly localized to the nucleus. In 2006, TDP-43 was identified as the protein that accumulates in the vast majority of cases of frontotemporal lobar degeneration (FTLD) with tau-negative, ubiquitin-positive inclusions (then referred to as FTLD-TDP), and in most cases of amyotrophic lateral sclerosis (ALS) (Arai et al., Biochemical and Biophysical Research Communications 351 (2006) 602-611; Neumann et al., Science 314, (2006), 130-133).

Thirty-eight negative-dominant mutations in TDP-43 have been identified in sporadic and familial ALS patients as well as in patients with inherited FTD mainly located in the glycine rich domain (FIG. 1; Lagier-Tourenne and Cleveland, Cell 136, 2009, 1001-1004). TDP-43 is inherently aggregation-prone, as shown by sedimentation assays, and this propensity is further increased by some of the ALS-associated TARDBP mutations (Ticozzi et al., CNS Neurol. Disord. Drug Targets. 2010, 9(3), 285-296) connecting TDP-43 aggregation with clinical disease manifestation.

II. TDP-43 in Neurodegeneration

TDP-43 aggregates have been identified in a growing list of neurodegenerative conditions (Lagier-Tourenne et al., Human Molecular Genetics, 2010, Vol. 19, Review Issue 1 R46-R64), including but not limited to: Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

Aggregated TDP-43 from patient brains shows a number of abnormal modifications, including hyperphosphorylation, ubiquitination, acetylation and C-terminal fragments through proteolytic cleavage (Arai et al., Biochemical and Biophysical Research Communications 351 (2006) 602-611; Neumann et al., Science 314, (2006), 130-133; Neumann et al., Acta Neuropathol. (2009) 117: 137-149; Hasegawa et al., (2008) Annals of Neurology Vol 64 No 1, 60-70; Cohen et al., Nat Commun. 6: 5845, 2015). Another characteristic feature of TDP-43 pathology is redistribution and accumulation of TDP-43 from nucleus to cytoplasm. The hallmark lesions of FTLD-TDP are neuronal and glial cytoplasmic inclusions (NCI and GCI, respectively) and dystrophic neurites (DN) that are immunoreactive for TDP- 43, as well as ubiquitin and p62, but negative for other neurodegenerative disease-related proteins. Differences in inclusion morphology and tissue distribution thereof are associated with specific mutations and/or clinical representations. Four types of TDP-43 pathology are described so far by histological classification (Mackenzie and Neumann, J. Neurochem. (2016) 138 (Suppl. 1), 54-70). FTLD-TDP type A cases are characterized by abundant short DN (dystrophic neuritis) and compact oval or crescentic NCI (neuronal cytoplasmic inclusions), predominantly in layer II of the neocortex (FIG. 2f in Mackenzie et al., 2016 J. Neurochem. 138 (Suppl. 1), 54-70). Cases with this pathology usually present clinically with either behavioral-variant frontotemporal dementia (bvFTD) or nonfluent/agrammatic variants of Primary Progressive Aphasia (nfvPPA) and are associated with progranulin (GRN) mutations. Type B cases show moderate numbers of compact or granular NCI in both superficial and deep cortical layers with relatively few DN and NII (neuronal intranuclear inclusions; FIG. 2g in Mackenzie et al., 2016 J. Neurochem. 138 (Suppl. 1), 54-70). Most cases with co-appearance of FTD and ALS symptoms are found to have FTLD-TDP type B pathology. Type C cases have an abundance of long tortuous neurites, predominantly in the superficial cortical laminae, with few or no NCI (FIG. 2j in Mackenzie et al., 2016 J. Neurochem. 138 (Suppl. 1), 54-70). This pathology is particularly found in cases presenting with semantic variant of primary progressive aphasia (svPPA). FTLD-TDP type D displays with abundant lentiform neuronal intranuclear inclusions (NII) and short DN in the neocortex with only rare NCI (FIG. 2k in Mackenzie et al., 2016 J. Neurochem. 138 (Suppl. 1), 54-70). This pattern of pathology is only found in cases with VCP in association with inclusion body myositis.

III. TDP-43 in FTD

Frontotemporal dementia (FTD) is a clinical term that covers a wide spectrum of disorders based on the degeneration of frontal and temporal lobes—a pathological feature termed frontotemporal lobar degeneration (FTLD). FTD is the second most abundant cause of early degenerative dementias in the age group below 65 years (Le Ber, Revue Neurologique 169 (2013) 811-819). FTD is presented by several syndromes including bvFTD which is characterized by changes in personality and behavior; semantic dementia (SD) and progressive nonfluent aphasia (PNFA) characterized by changes in the language function; corticobasal syndrome (CBS), progressive supranuclear palsy syndrome and motor neuron disease (FTD-MND) characterized by movement dysfunction. Diagnosis of these syndromes is complicated and final conclusion can only be achieved through postmortem tissue analysis based on immunohistochemistry to detect aggregated protein and description of the affected brain regions. In terms of pathological, proteinaceous inclusions, about 45% of cases show pathological accumulation of misfolded Tau, 45% of cases have pathological TDP-43 and a smaller subgroup has aggregates of FUS and other proteins.

IV. TDP-43 in ALS

Amyotrophic lateral sclerosis (ALS) is a neurodegenerative disorder characterized by the premature loss of upper and lower motor neurons. The progression of ALS is marked by fatal paralysis and respiratory failure with a disease course from diagnosis to death of 1 to 5 years. In most cases of sporadic ALS, the neuropathology is characterized by abnormal cytoplasmic accumulations of TDP-43 in neurons and glia of the primary motor cortex, brainstem motor nuclei, spinal cord and the associated white matter tracts. ALS with dementia involves accumulation of TDP-43 in extramotor neocortex and hippocampus. The role of phosphorylation of TDP-43 in ALS patients has been explored with the help of antibodies that specifically bind to phosphorylated TDP-43 in nuclear and cytoplasmic inclusions with amino acids S379, S403, S404, S409, S410 as the major sites of phosphorylation of TDP-43 (Hasegawa et al., Ann Neurol 2008; 64: 60-70; Neumann et al., Acta Neuropathol (2009) 117: 137-149).

V. TDP-43 in AD and Other Diseases

TDP-43 pathology occurs in up to 57% of brains of patients with Alzheimer's disease (Josephs K A et al., Acta Neuropathol. 2014; 127(6): 811-824; Josephs K A et al., Acta Neuropathol. 2014; 127(3): 441-450; McAleese et al., Brain Pathol. 2017 July; 27(4): 472-479). TDP-43 aggregation is associated with patient's age and correlates with cognitive decline, memory loss and medial temporal atrophy in AD. TDP-43 positive patients are 10-fold more likely to be cognitively impaired at death compared to TDP-43 negative subjects. It appears that in AD TDP-43 represents a secondary or independent pathology that shares overlapping brain distribution with amyloid beta and tau pathologies in the medial temporal lobe. Pathologic TDP-43 follows a stereotypical pattern of progressive deposition that has been described by the so-called TDP-43 in AD (TAD) staging scheme: TDP-43 first deposits in the amygdala (stage I) followed by hippocampus, limbic, temporal, and finally the frontostriatum (stage V) (Josephs K A et al., Acta Neuropathol. 2014; 127(6): 811-824; Josephs K A et al., Acta Neuropathol. 2014; 127(3): 441-450).

VI. TDP-43 Spreading

Recent evidence supports the notion of protein propagation in neuronal tissue for amyloid-beta, tau, alpha-synuclein and TDP-43 by a prion-like mechanism (Hasegawa et al., 2017), although the starting points and the topographical spreading patterns are fundamentally different for the four proteins (Brettschneider J et al., Nature Rev. Neuroscience, 2015, 109). Although ALS onset and first symptoms vary significantly between patients, the common feature of disease progression is spreading of pathology from an initial focal area to most neurons. The continuous worsening of symptoms might be explained by this progressive spreading of TDP-43 pathology. TDP-43 pathology in an ALS patient's brain appears to be spreading in a four-stage process and it is believed that propagation occurs transynaptically via corticofugal axonal projections using anterograde axonal transport (Brettschneider et al., Ann Neurol. 2013 July; 74(1): 20-38).

Some recent reports address TDP-43 spreading at molecular level in various in vitro models. Insoluble TDP-43 preparations from patient brain are able to induce intracellular aggregate formation in vitro (Nonaka et al., Cell Reports 4 (2013), 124-134; Feiler et al., 2015; Porta et al., Nat. Comm., 2018). Also, it has been shown recently that patient-derived, pathological TDP-43 can lead to widespread deposition of endogenous TDP-43 following inoculation into transgenic and wildtype mice (Porta et al., Nat. Comm., 2018). Further it has been shown that intracellular TDP-43 aggregates are released in association with exosome prior to spreading to the next cell (Nonaka et al., Cell Reports 4 (2013, 124-134)). Similarly, adenovirus-transduced TDP-43 expression lead to cytoplasmic aggregates which were phosphorylated, ubiquitinated and most importantly acted as seeds initiating cell to cell spreading (Ishii et al., PLoS ONE 12(6): e0179375, 2017).

VII. Prevention and Treatment of TDP-43 Proteinopathies

TDP-43 aggregation and spreading of pathology are major hallmarks of ALS and FTD—fatal diseases for which currently no cure is available. Mutations in TDP-43 are associated with familial cases of ALS and FTD providing causative link between TDP-43 misfolding and disease progression. Therefore there is a need for a prevention and treatment therapy which aims at preventing and/or slowing down the development and propagation of TDP-43 aggregates, in diseases with clinical symptoms associated with TDP-43 proteinopahies.

Without wishing to be bound by any hypothesis, the present invention was developed based on the assumption that modified conformation-specific antigenic peptides and peptide fragments derived from TDP-43 protein or the whole TDP-43 protein and the antibodies obtainable or obtained by said peptides or fragments or the whole TDP-43 protein block TDP-43 cell-to-cell spreading, and/or disaggregate TDP-43 aggregates and/or inhibit the aggregation of TDP-43 protein or fragments thereof. The binding molecules of the invention, in particular polypeptides, more particularly antibodies or antigen-binding fragments thereof, specifically bind to misfolded TDP-43, particularly to cytoplasmic and extracellular misfolded TDP-43. In one embodiment, the binding molecules of the invention, in particular polypeptides, more particularly antibodies or antigen-binding fragments thereof, specifically bind to cytoplasmic misfolded TDP-43.

In one embodiment, the binding molecules of the invention, in particular polypeptides, more particularly antibodies or antigen-binding fragments thereof, specifically bind to extracellular misfolded TDP-43.

VIII. Diagnostics of TDP-43 Proteinopathies

The diagnosis of FTD based on clinical manifestations is insufficient since the clinical representation can overlap with other diseases in particular in the earlier stages. Therefore, the development of sensitive and specific biomarkers allowing the differentiation between types of pathology within the FTD spectrum is an urgent task. Such tools will allow better detecting and understanding the specific type of pathology causing neurodegeneration. Eventually this will lead to the development of diagnostic biomarkers enabling more efficient and precise patient selection for longitudinal monitoring in clinical studies, supporting the development of novel therapeutics for TDP-43 proteinopathies.

A number of approaches aim at development of biochemical biomarkers to distinguish different types of FTD pathology. Development of antibodies against different conformations of TDP-43 may permit generating more sensitive and specific diagnostic tools. In parallel to biochemical biomarkers the development of imaging biomarkers may enable early and specific detection of the pathology in TDP-43 proteinopathies. The ability to image TDP-43 deposition in the brain may be a substantial achievement for diagnosis and drug development for TDP-43 proteinopathies. Using cell permeable antibody fragments will enable such detection.

The earliest event in neurodegenerative diseases based on misfolding of different proteins is the acquisition of an alternative conformation that renders the protein toxic. Furthermore, this misfolded conformation can self-propagate by recruiting the endogenous, normal protein into the misfolded conformation as mechanistic basis for the observed spread through affected tissue. Therefore, targeting the misfolded over the normal conformation of a protein target offers a very precise therapeutic and diagnostic approach.

To develop antibodies against different conformational states of a given protein supramolecular antigenic constructs were designed in which the conformation of the presented antigen was controlled to raise conformational-specific antibodies against a given target in a specific conformational state (WO2012/055933 and WO2012/020124). Conformational-specific antibodies offer many advantages since they can discriminate between the disease-associated and the benign, endogenous conformation of these proteins. This approach offers many advantages in the therapeutic application since such antibodies are less likely to be adsorbed by the normal conformation of proteins while targeting the misfolded, disease associated isoform thereof. Similar to this in diagnostic application such antibodies only recognize the structural state of a protein and therefore detect the entity that most likely correlates with disease which is paramount for the development of the most sensitive and specific diagnostics.

IX. Prior Art

Patent application WO 2008/151055 discloses methods and materials for using the levels of TDP-43 polypeptides and/or TDP-43 polypeptide cleavage products (e.g. 25 kD and 35 kD TDP-43 polypeptide cleavage products) in a biological fluid to determine whether or not a mammal has a neurodegenerative disease.

Patent application WO 2013/061163 discloses TDP-43 specific binding molecules including polypeptides such as human antibodies as well as fragments, derivatives and variants thereof.

SUMMARY OF THE INVENTION

The invention relates to binding molecules, in particular antibodies or antigen-binding fragments thereof, which specifically recognize misfolded TDP-43. In a preferred embodiment of the invention, the binding molecules, in particular antibodies or antigen-binding fragments thereof, do not bind physiologically functional TDP-43. Within the invention, misfolded TDP-43 includes misfolded monomeric and/or misfolded oligomeric and/or misfolded aggregated and/or post-translationally modified and/or misfolded truncated TDP-43. Thus, the invention provides binding molecules, in particular antibodies or antigen-binding fragments thereof, which specifically recognize misfolded TDP-43, wherein the misfolded TDP-43 is oligomeric and/or aggregated and/or post translationally modified TDP-43, wherein the binding molecules, in particular antibodies or antigen-binding fragments thereof, do not bind physiologically functional TDP-43.

The misfolded TDP-43 specific binding molecules of the invention, in particular antibodies or antigen-binding fragments thereof, block TDP-43 cell-to-cell spreading, and/or disaggregate TDP-43 aggregates and/or inhibit the aggregation of TDP-43 protein or fragments thereof.

In particular, the misfolded TDP-43 specific binding molecules of the invention, in particular antibodies or antigen-binding fragments thereof, block TDP-43 cell-to-cell spreading.

In one embodiment, the misfolded TDP-43 specific binding molecules of the invention, in particular antibodies or antigen-binding fragments thereof disaggregate TDP-43 aggregates.

In one embodiment, the misfolded TDP-43 specific binding molecules of the invention, in particular antibodies or antigen-binding fragments thereof inhibit the aggregation of TDP-43 protein or fragments thereof.

In the present invention, the binding molecules, in particular antibodies or antigen-binding fragments thereof, specifically recognize misfolded TDP-43. Binding molecules of the invention include polypeptides and/or antibodies and/or antigen-binding fragments thereof specific to/for the TDP-43 protein. "Specifically recognize misfolded TDP-43" means that the binding molecules of the invention specifically, generally, and collectively, bind to misfolded TDP-43, in particular an epitope within TDP-43, in particular an epitope exposed/accessible in one or more pathological conformation(s) of TDP-43 protein, with greater affinity than for other epitopes, in particular epitopes found in physiologically functional TDP-43. The binding molecules of the invention, in particular polypeptides, more particularly antibodies or antigen-binding fragments thereof, that specifically bind to misfolded TDP-43, specifically bind to misfolded monomeric and/or misfolded oligomeric and/or misfolded aggregated and/or misfolded post translationally modified TDP-43. The binding molecules of the invention, in particular polypeptides, more particularly antibodies or antigen-binding fragments thereof, specifically bind to misfolded TDP-43, particularly to cytoplasmic misfolded TDP-43, particularly to extracellular misfolded TDP-43, particularly to cytoplasmic and extracellular misfolded TDP-43. According to one embodiment of the invention, the binding molecules, in particular antibodies or antigen-binding fragments thereof, specifically bind to misfolded TDP-43, including misfolded monomeric, oligomeric, aggregated and post-translationally modified TDP-43, all of which can comprise full-length and/or truncated TDP-43. In one embodiment, the binding molecules, in particular antibodies or antigen-binding fragments thereof, specifically bind to misfolded monomeric TDP-43. In one embodiment, the binding molecules, in particular antibodies or antigen-binding fragments thereof, specifically bind to misfolded oligomeric TDP-43. In one embodiment, the binding molecules, in particular antibodies or antigen-binding fragments thereof, specifically bind to misfolded aggregated TDP-43. In one embodiment, the binding molecules, in particular antibodies or antigen-binding fragments thereof, specifically bind to misfolded post-translationally modified TDP-43. In a preferred embodiment, full-length human TDP-43 comprises, preferably has, the sequence of SEQ ID NO:1. In another preferred embodiment of the invention, the binding molecules, in particular antibodies or antigen-binding fragments thereof, specifically bind to an epitope within full-length and/or truncated TDP-43, wherein the epitope consists of residues 215-222 (SEQ ID NO:5) of the full-length human TDP-43 having the sequence of SEQ ID NO:1. Accordingly, the binding molecules, in particular antibodies or antigen-binding fragments thereof, preferably specifically bind to a peptide comprising, preferably consisting of, residues 215-222 (SEQ ID NO:5) of the full-length human TDP-43 having the sequence of SEQ ID NO:1.

Within the present invention, the binding molecules, in particular antibodies or antigen-binding fragments thereof, specifically bind to misfolded extracellular TDP-43. In some embodiments, the binding molecules, in particular antibodies or antigen-binding fragments thereof of the invention also specifically bind to misfolded cytoplasmic TDP-43.

In some embodiments of the invention, the antibody is a monoclonal antibody. In some embodiments, the antibody is a murine, murinized, human, humanized, or chimeric antibody.

In some embodiments of the invention, the antibody, or antigen-binding fragment or derivative thereof having an immunological binding characteristic of an antibody described herein, is an antibody having the variable regions VL and/or VH of the amino acid sequences set forth in SEQ ID NO: 10 and SEQ ID NO: 20, SEQ ID NO: 30 and SEQ ID NO: 40, SEQ ID NO: 50 and SEQ ID NO: 60, SEQ ID NO: 70 and SEQ ID NO: 80, SEQ ID NO: 90 and SEQ ID NO: 100, SEQ ID NO: 110 and SEQ ID NO: 120, SEQ ID NO: 130 and SEQ ID NO: 140, SEQ ID NO: 150 and SEQ ID NO: 160, SEQ ID NO: 170 and SEQ ID NO: 180, SEQ ID NO: 190 and SEQ ID NO: 200, SEQ ID NO: 210 and SEQ ID NO: 220, SEQ ID NO: 230 and SEQ ID NO: 232, SEQ ID NO: 234 and SEQ ID NO: 236, SEQ ID NO: 238 and SEQ ID NO: 240, SEQ ID NO: 242 and SEQ ID NO: 244, SEQ ID NO: 246 and SEQ ID NO: 248, SEQ ID NO: 250 and SEQ ID NO: 252, SEQ ID NO: 254 and SEQ ID NO: 256 or SEQ ID NO: 258 and SEQ ID NO: 260, respectively. In the above sequences, SEQ ID NOs: 10, 20, 30, 40, 50, 60, 70, 80, 90, 100, 110, 120, 130, 140, 150 and 160 comprise a tail sequence as part of the VH/VL sequence. The part of these sequences corresponding to the tail sequence is provided in the sequence listing, in particular the tail sequence comprised in SEQ ID NO:10 is provided in SEQ ID NO:18, the tail sequence comprised in SEQ ID NO:20 is provided in SEQ ID NO:28 and so forth. The skilled person is aware that a tail sequence C-terminal of FR4 in the VH/VL sequences is sometimes considered as part of the VH or VL sequence, respectively, whereas it is sometimes not considered to be a part thereof. In the present invention, both versions are provided for some of the antibodies, whereby the VH/VL sequence without tail is preferred. The following Table 1 provides an overview of the provided VH and VL sequences of the antibodies of the invention:

TABLE 1

| Antibody name | Hybridoma clone | VL with tail | VL without tail | VH with tail | VH without tail |
|---|---|---|---|---|---|
| ACI-7062-401A2-Ab2 | 401A2C6 | 10 | 230 | 20 | 232 |
| ACI-7062-412A7-Ab1 | 412A7B7 | 30 | 234 | 40 | 236 |
| ACI-7062-406E3-Ab1 | 406E3D5 | 50 | 238 | 60 | 240 |
| ACI-7062-404D6-Ab2 | 404D6E11 | 70 | 242 | 80 | 244 |
| ACI-7062-410H3-Ab1 | 410H3B9 | 90 | 246 | 100 | 248 |

TABLE 1-continued

| Antibody name | Hybridoma clone | VL with tail | VL without tail | VH with tail | VH without tail |
|---|---|---|---|---|---|
| ACI-7062-414A5-Ab1 | 414A5D2 | 110 | 250 | 120 | 252 |
| ACI-7062-412E12-Ab1 | 412E12A2 | 130 | 254 | 140 | 256 |
| ACI-7062-416A11-Ab1 | 416A11B3 | 150 | 258 | 160 | 260 |
| ACI-7062-406E3-Ab2 | 406E3G10 | | 170 | | 180 |
| ACI-7062-415C4-Ab1 | 415C4C6 | | 190 | | 200 |
| ACI-7062-415H10-Ab2 | 415H10B7 | | 210 | | 220 |

In some embodiments, the antibody comprises:
a) a Light Chain Variable Region (VL) comprising the sequence of SEQ ID NO: 10 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 10;
b) a Light Chain Variable Region (VL) comprising the sequence of SEQ ID NO: 30 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 30;
c) a Light Chain Variable Region (VL) comprising the sequence of SEQ ID NO: 50 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 50;
d) a Light Chain Variable Region (VL) comprising the sequence of SEQ ID NO: 70 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 70;
e) a Light Chain Variable Region (VL) comprising the sequence of SEQ ID NO: 90 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 90;
f) a Light Chain Variable Region (VL) comprising the sequence of SEQ ID NO: 110 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 110;
g) a Light Chain Variable Region (VL) comprising the sequence of SEQ ID NO: 130 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 130;
h) a Light Chain Variable Region (VL) comprising the sequence of SEQ ID NO: 150 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 150;
i) a Light Chain Variable Region (VL) comprising the sequence of SEQ ID NO: 170 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 170;
j) a Light Chain Variable Region (VL) comprising the sequence of SEQ ID NO: 190 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 190;
k) a Light Chain Variable Region (VL) comprising the sequence of SEQ ID NO: 210 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 210;
l) a Light Chain Variable Region (VL) comprising the sequence of SEQ ID NO: 230 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 230;
m) a Light Chain Variable Region (VL) comprising the sequence of SEQ ID NO: 234 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 234;
n) a Light Chain Variable Region (VL) comprising the sequence of SEQ ID NO: 238 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 238;
o) a Light Chain Variable Region (VL) comprising the sequence of SEQ ID NO: 242 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 242;
p) a Light Chain Variable Region (VL) comprising the sequence of SEQ ID NO: 246 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 246;
q) a Light Chain Variable Region (VL) comprising the sequence of SEQ ID NO: 250 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 250;
r) a Light Chain Variable Region (VL) comprising the sequence of SEQ ID NO: 254 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 254; or s) a Light Chain Variable Region (VL) comprising the sequence of SEQ ID NO: 258 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 258.

In some embodiments, the antibody comprises:

a) a Heavy Chain Variable Region (VH) comprising the sequence of SEQ ID NO: 20 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 20;

b) a Heavy Chain Variable Region (VH) comprising the sequence of SEQ ID NO: 40 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 40;

c) a Heavy Chain Variable Region (VH) comprising the sequence of SEQ ID NO: 60 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 60;

d) a Heavy Chain Variable Region (VH) comprising the sequence of SEQ ID NO: 80 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 80;

e) a Heavy Chain Variable Region (VH) comprising the sequence of SEQ ID NO: 100 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 100;

f) a Heavy Chain Variable Region (VH) comprising the sequence of SEQ ID NO: 120 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 120;

g) a Heavy Chain Variable Region (VH) comprising the sequence of SEQ ID NO: 140 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 140;

h) a Heavy Chain Variable Region (VH) comprising the sequence of SEQ ID NO:160 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 160;

i) a Heavy Chain Variable Region (VH) comprising the sequence of SEQ ID NO:180 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 180;

j) a Heavy Chain Variable Region (VH) comprising the sequence of SEQ ID NO:200 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 200;

k) a Heavy Chain Variable Region (VH) comprising the sequence of SEQ ID NO:220 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 220;

l) a Heavy Chain Variable Region (VH) comprising the sequence of SEQ ID NO:232 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 232;

m) a Heavy Chain Variable Region (VH) comprising the sequence of SEQ ID NO:236 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 236;

n) a Heavy Chain Variable Region (VH) comprising the sequence of SEQ ID NO:240 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 240;

o) a Heavy Chain Variable Region (VH) comprising the sequence of SEQ ID NO:244 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 244;

p) a Heavy Chain Variable Region (VH) comprising the sequence of SEQ ID NO:248 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 248;

q) a Heavy Chain Variable Region (VH) comprising the sequence of SEQ ID NO:252 or a heavy chain variable region (VH) having at least 70%, 75%, 80%, 85%, 90%, 91%, 92%, 93%, 94%, 95%, 96%, 97%, 98%, 99%, or 1000/a sequence identity to the amino acid sequence of SEQ ID NO: 252;

r) a Heavy Chain Variable Region (VH) comprising the sequence of SEQ ID NO:256 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 256; or s) a Heavy Chain Variable Region (VH) comprising the sequence of SEQ ID NO:260 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 260.

In some embodiments, the antibody comprises:

a) a Light Chain Variable Region (VL) comprising the sequence of SEQ ID NO: 10 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 10 and a Heavy Chain Variable Region (VH) comprising the sequence of SEQ ID NO: 20 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 20;

b) a Light Chain Variable Region (VL) comprising the sequence of SEQ ID NO: 30 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 30 and a Heavy Chain Variable Region (VH) comprising the sequence of SEQ ID NO: 40 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 40;

c) a Light Chain Variable Region (VL) comprising the sequence of SEQ ID NO: 50 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 50 and a Heavy Chain Variable Region (VH) comprising the sequence of SEQ ID NO: 60 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 60;

d) a Light Chain Variable Region (VL) comprising the sequence of SEQ ID NO: 70 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 70 and a Heavy Chain Variable Region (VH) comprising the sequence of SEQ ID NO: 80 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 80;

e) a Light Chain Variable Region (VL) comprising the sequence of SEQ ID NO: 90 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 90 and a Heavy Chain Variable Region (VH) comprising the sequence of SEQ ID NO: 100 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 100;

f) a Light Chain Variable Region (VL) comprising the sequence of SEQ ID NO: 110 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 110 and a Heavy Chain Variable Region (VH) comprising the sequence of SEQ ID NO: 120 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 120;

g) a Light Chain Variable Region (VL) comprising the sequence of SEQ ID NO: 130 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 130 and a Heavy Chain Variable Region (VH) comprising the sequence of SEQ ID NO: 140 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 140;

h) a Light Chain Variable Region (VL) comprising the sequence of SEQ ID NO: 150 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 150 and a Heavy Chain Variable Region (VH) comprising the sequence of SEQ ID NO: 160 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 160;

i) a Light Chain Variable Region (VL) comprising the sequence of SEQ ID NO: 170 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 170 and a Heavy Chain Variable Region (VH) comprising the sequence of SEQ ID NO: 180 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 180;

j) a Light Chain Variable Region (VL) comprising the sequence of SEQ ID NO: 190 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 190 and a Heavy Chain Variable Region (VH) comprising the sequence of SEQ ID NO: 200 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 200;

k) a Light Chain Variable Region (VL) comprising the sequence of SEQ ID NO: 210 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 210 and a Heavy Chain Variable Region (VH) comprising the sequence of SEQ ID NO: 220 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 220;

l) a Light Chain Variable Region (VL) comprising the sequence of SEQ ID NO: 230 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 230 and a Heavy Chain Variable Region (VH) comprising the sequence of SEQ ID NO: 232 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 232;

m) a Light Chain Variable Region (VL) comprising the sequence of SEQ ID NO: 234 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 234 and a Heavy Chain Variable Region (VH) comprising the sequence of SEQ ID NO: 236 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 236;

n) a Light Chain Variable Region (VL) comprising the sequence of SEQ ID NO: 238 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 238 and a Heavy Chain Variable Region (VH) comprising the sequence of SEQ ID NO: 240 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 240;

o) a Light Chain Variable Region (VL) comprising the sequence of SEQ ID NO: 242 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 242 and a Heavy Chain Variable Region (VH) comprising the sequence of SEQ ID NO: 244 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 244;

p) a Light Chain Variable Region (VL) comprising the sequence of SEQ ID NO: 246 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 246 and a Heavy Chain Variable Region (VH) comprising the sequence of SEQ ID NO: 248 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 248;

q) a Light Chain Variable Region (VL) comprising the sequence of SEQ ID NO: 250 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 250 and a Heavy Chain Variable Region (VH) comprising the sequence of SEQ ID NO: 252 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 252;

r) a Light Chain Variable Region (VL) comprising the sequence of SEQ ID NO: 254 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 254 and a Heavy Chain Variable Region (VH) comprising the sequence of SEQ ID NO: 256 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 256; or s) a Light Chain Variable Region (VL) comprising the sequence of SEQ ID NO: 258 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 258 and a Heavy Chain Variable Region (VH) comprising the sequence of SEQ ID NO: 260 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 260.

In some embodiments, the antibody comprises:

a) VL-CDR1 comprising the amino acid sequence of SEQ ID NO: 12; VL-CDR2 comprising the amino acid sequence of SEQ ID NO: 14; and VL-CDR3 comprising the amino acid sequence of SEQ ID NO: 16 or a VL-CDR1 comprising an amino acid sequence having at least 80%, 90% or 95% sequence identity to SEQ ID NO: 12; a VL-CDR2 comprising an amino acid sequence having at least 80%, 90% or 95% sequence identity to SEQ ID NO: 14; and a VL-CDR3 comprising an amino acid sequence having at least 80%, 90% or 95% sequence identity to SEQ ID NO: 16; or b) VL-CDR1 comprising the amino acid sequence of SEQ ID NO: 32; VL-CDR2 comprising the amino acid sequence of SEQ ID NO: 34; and VL-CDR3 comprising the amino acid sequence of SEQ ID NO: 36 or a VL-CDR1 comprising an amino acid sequence having at least 80%, 90% or 95% sequence identity to SEQ ID NO: 32; a VL-CDR2 comprising an amino acid sequence having at least 80%, 90% or 95% sequence identity to SEQ ID NO: 34; and a VL-CDR3 comprising an amino acid sequence having at least 80%, 90% or 95% sequence identity to SEQ ID NO: 36; or c) VL-CDR1 comprising the amino acid sequence of SEQ ID NO: 52; VL-CDR2 comprising the amino acid sequence of SEQ ID NO: 54; and VL-CDR3 comprising the amino acid sequence of SEQ ID NO: 56 or a VL-CDR1 comprising an amino acid sequence having at least 80%, 90% or 95% sequence identity to SEQ ID NO: 52; a VL-CDR2 comprising an amino acid sequence having at least 80%, 90% or 95% sequence identity to SEQ ID NO: 54; and a VL-CDR3 comprising an amino acid sequence having at least 80%, 90% or 95% sequence identity to SEQ ID NO: 56; or d) VL-CDR1 comprising the amino acid sequence of SEQ ID NO: 72; VL-CDR2 comprising the amino acid sequence of SEQ ID NO: 74; and VL-CDR3 comprising the amino acid sequence of SEQ ID NO: 76 or a VL-CDR1 comprising an amino acid sequence having at least 80%, 90% or 95% sequence identity to SEQ ID NO: 72; a VL-CDR2 comprising an amino acid sequence having at least 80%, 90% or 95% sequence identity to SEQ ID NO: 74; and a VL-CDR3 comprising an amino acid sequence having at least 80%, 90% or 95% sequence identity to SEQ ID NO: 76; or e) VL-CDR1 comprising the amino acid sequence of SEQ ID NO: 92; VL-CDR2 comprising the amino acid sequence of SEQ ID NO: 94; and VL-CDR3 comprising the amino acid sequence of SEQ ID NO: 96 or a VL-CDR1 comprising an amino acid sequence having at least 80%, 90% or 95% sequence identity to SEQ ID NO: 92; a VL-CDR2 comprising an amino acid sequence having at least 80%, 90% or 95% sequence identity to SEQ ID NO: 94; and a VL-CDR3 comprising an amino acid sequence having at least 80%, 90% or 95% sequence identity to SEQ ID NO: 96; or f) VL-CDR1 comprising the amino acid sequence of SEQ ID NO: 112; VL-CDR2 comprising the amino acid sequence of SEQ ID NO: 114; and VL-CDR3 comprising the amino acid sequence of SEQ ID NO: 116 or a VL-CDR1 comprising an amino acid sequence having at least 80%, 90% or 95% sequence identity to SEQ ID NO: 112; a VL-CDR2 comprising an amino acid sequence having at least 80%, 90% or 95% sequence identity to SEQ ID NO: 114; and a VL-CDR3 comprising an amino acid sequence having at least 80%, 90% or 95% sequence identity to SEQ ID NO: 116; or g) VL-CDR1 comprising the amino acid sequence of SEQ ID NO: 132; VL-CDR2 comprising the amino acid sequence of SEQ ID NO: 134; and VL-CDR3 comprising the amino acid sequence of SEQ ID NO: 136 or a VL-CDR1 comprising an amino acid sequence having at least 80%, 90% or 95% sequence identity to SEQ ID NO: 132; a VL-CDR2 comprising an amino acid sequence having at least 80%, 90% or 95% sequence identity to SEQ ID NO: 134; and a VL-CDR3 comprising an amino acid sequence having at least 80%, 90% or 95% sequence identity to SEQ ID NO: 136;

h) VL-CDR1 comprising the amino acid sequence of SEQ ID NO: 152; VL-CDR2 comprising the amino acid sequence of SEQ ID NO: 154; and VL-CDR3 comprising the amino acid sequence of SEQ ID NO: 156 or a VL-CDR1 comprising an amino acid sequence having at least 80%, 90% or 95% sequence identity to SEQ ID NO: 152; a VL-CDR2 comprising an amino acid sequence having at least 80%, 90% or 95% sequence identity to SEQ ID NO: 154; and a VL-CDR3 comprising an amino acid sequence having at least 80%, 90% or 95% sequence identity to SEQ ID NO: 156;

i) VL-CDR1 comprising the amino acid sequence of SEQ ID NO: 172; VL-CDR2 comprising the amino acid sequence of SEQ ID NO: 174; and VL-CDR3 comprising the amino acid sequence of SEQ ID NO: 176 or a VL-CDR1 comprising an amino acid sequence having at least 80%, 90% or 95% sequence identity to SEQ ID NO: 172; a VL-CDR2 comprising an amino acid sequence having at least 80%, 90% or 95% sequence identity to SEQ ID NO: 174; and a VL-CDR3 comprising an amino acid sequence having at least 80%, 90% or 95% sequence identity to SEQ ID NO: 176;

j) VL-CDR1 comprising the amino acid sequence of SEQ ID NO: 192; VL-CDR2 comprising the amino acid sequence of SEQ ID NO: 194; and VL-CDR3 comprising the amino acid sequence of SEQ ID NO: 196 or a VL-CDR1 comprising an amino acid sequence having at least 80%, 90% or 95% sequence identity to SEQ ID NO: 192; a VL-CDR2 comprising an amino acid sequence having at least 80%, 90% or 95% sequence identity to SEQ ID NO: 194; and a VL-CDR3 comprising an amino acid sequence having at least 80%, 90% or 95% sequence identity to SEQ ID NO: 196; or k) VL-CDR1 comprising the amino acid sequence of SEQ ID NO: 212; VL-CDR2 comprising the amino acid sequence of SEQ ID NO: 214; and VL-CDR3 comprising the amino acid sequence of SEQ ID NO: 216 or a VL-CDR1 comprising an amino acid sequence having at least 80%, 90% or 95% sequence identity to SEQ ID NO: 212; a VL-CDR2 comprising an amino acid sequence having at least 80%, 90% or 95% sequence identity to SEQ ID NO: 214; and a VL-CDR3 comprising an amino acid sequence having at least 80%, 90% or 95% sequence identity to SEQ ID NO: 216.

In some embodiments, the antibody comprises:

a) VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26 or a VH-CDR1 comprising an amino acid sequence having at least 80%, 90% or 95% sequence identity to SEQ ID NO: 22; a VH-CDR2 comprising an amino acid sequence having at least 80%, 90% or 95% sequence identity to SEQ ID NO: 24; and a VH-CDR3 comprising an amino acid sequence having at least 80%, 90% or 95% sequence identity to SEQ ID NO: 26; or b) VH-CDR1 comprising the amino acid sequence of SEQ ID NO: 42; VH-CDR2 comprising the amino acid sequence of SEQ ID NO: 44; and VH-CDR3 comprising the amino acid sequence of SEQ ID NO: 46 or a VH-CDR1 comprising an amino acid sequence having at least 80%, 90% or 95% sequence identity to SEQ ID NO: 42; a VH-CDR2 comprising an amino acid sequence having at least 80%, 90% or 95% sequence identity to SEQ ID NO: 44; and a VH-CDR3 comprising an amino acid sequence having at least 80%, 90% or 95% sequence identity to SEQ ID NO: 46; or c) VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66 or a VH-CDR1 comprising an amino acid sequence having at least 80%, 90% or 95% sequence identity to SEQ ID NO: 62; a VH-CDR2 comprising an amino acid sequence having at least 80%, 90% or 95% sequence identity to SEQ ID NO: 64; and a VH-CDR3 comprising an amino acid sequence having at least 80%, 90% or 95% sequence identity to SEQ ID NO: 66; or d) VH-CDR1 comprising the amino acid sequence of SEQ ID NO: 82; VH-CDR2 comprising the amino acid sequence of SEQ ID NO: 84; and VH-CDR3 comprising the amino acid sequence of SEQ ID NO: 86 or a VH-CDR1 comprising an amino acid sequence having at least 80%, 90% or 95% sequence identity to SEQ ID NO: 82; a VH-CDR2 comprising an amino acid sequence having at least 80%, 90% or 95% sequence identity to SEQ ID NO: 84; and a VH-CDR3 comprising an amino acid sequence having at least 80%, 90% or 95% sequence identity to SEQ ID NO: 86; or e) VH-CDR1 comprising the amino acid sequence of SEQ ID NO: 102; VH-CDR2 comprising the amino acid sequence of SEQ ID NO: 104; and VH-CDR3 comprising the amino acid sequence of SEQ ID NO: 106 or a VH-CDR1 comprising an amino acid sequence having at least 80%, 90% or 95% sequence identity to SEQ ID NO: 102; a VH-CDR2 comprising an amino acid sequence having at least 80%, 90% or 95% sequence identity to SEQ ID NO: 104; and a VH-CDR3 comprising an amino acid sequence having at least 80%, 90% or 95% sequence identity to SEQ ID NO: 106; or f) VH-CDR1 comprising the amino acid sequence of SEQ ID NO: 122; VH-CDR2 comprising the amino acid sequence of SEQ ID NO: 124; and VH-CDR3 comprising the amino acid sequence of SEQ ID NO: 126 or a VH-CDR1 comprising an amino acid sequence having at least 80%, 90% or 95% sequence identity to SEQ ID NO: 122; a VH-CDR2 comprising an amino acid sequence having at least 80%, 90% or 95% sequence identity to SEQ ID NO: 124; and a VH-CDR3 comprising an amino acid sequence having at least 80%, 90% or 95% sequence identity to SEQ ID NO: 126; or
g) VH-CDR1 comprising the amino acid sequence of SEQ ID NO: 142; VH-CDR2 comprising the amino acid sequence of SEQ ID NO: 144; and VH-CDR3 comprising the amino acid sequence of SEQ ID NO: 146 or a VH-CDR1 comprising an amino acid sequence having at least 80%, 90% or 95% sequence identity to SEQ ID NO: 142; a VH-CDR2 comprising an amino acid sequence having at least 80%, 90% or 95% sequence identity to SEQ ID NO: 144; and a VH-CDR3 comprising an amino acid sequence having at least 80%, 90% or 95% sequence identity to SEQ ID NO: 146;
h) VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166 or a VH-CDR1 comprising an amino acid sequence having at least 80%, 90% or 95% sequence identity to SEQ ID NO: 162; a VH-CDR2 comprising an amino acid sequence having at least 80%, 90% or 95% sequence identity to SEQ ID NO: 164; and a VH-CDR3 comprising an amino acid sequence having at least 80%, 90% or 95% sequence identity to SEQ ID NO: 166;
i) VH-CDR1 comprising the amino acid sequence of SEQ ID NO: 182; VH-CDR2 comprising the amino acid sequence of SEQ ID NO: 184; and VH-CDR3 comprising the amino acid sequence of SEQ ID NO: 186 or a VH-CDR1 comprising an amino acid sequence having at least 80%, 90% or 95% sequence identity to SEQ ID NO: 182; a VH-CDR2 comprising an amino acid sequence having at least 80%, 90% or 95% sequence identity to SEQ ID NO: 184; and a VH-CDR3 comprising an amino acid sequence having at least 80%, 90% or 95% sequence identity to SEQ ID NO: 186;
j) VH-CDR1 comprising the amino acid sequence of SEQ ID NO: 202; VH-CDR2 comprising the amino acid sequence of SEQ ID NO: 204; and VH-CDR3 comprising the amino acid sequence of SEQ ID NO: 206 or a VH-CDR1 comprising an amino acid sequence having at least 80%, 90% or 95% sequence identity to SEQ ID NO: 202; a VH-CDR2 comprising an amino acid sequence having at least 80%, 90% or 95% sequence identity to SEQ ID NO: 204; and a VH-CDR3 comprising an amino acid sequence having at least 80%, 90% or 95% sequence identity to SEQ ID NO: 206; or
k) VH-CDR1 comprising the amino acid sequence of SEQ ID NO: 222; VH-CDR2 comprising the amino acid sequence of SEQ ID NO: 224; and VH-CDR3 comprising the amino acid sequence of SEQ ID NO: 226 or a VH-CDR1 comprising an amino acid sequence having at least 80%, 90% or 95% sequence identity to SEQ ID NO: 222; a VH-CDR2 comprising an amino acid sequence having at least 80%, 90% or 95% sequence identity to SEQ ID NO: 224; and a VH-CDR3 comprising an amino acid sequence having at least 80%, 90% or 95% sequence identity to SEQ ID NO: 226.

In some embodiments, the antibody comprises:
a) VL-CDR1 comprising the amino acid sequence of SEQ ID NO: 12; VL-CDR2 comprising the amino acid sequence of SEQ ID NO: 14; VL-CDR3 comprising the amino acid sequence of SEQ ID NO: 16; VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26; or
b) VL-CDR1 comprising the amino acid sequence of SEQ ID NO: 32; VL-CDR2 comprising the amino acid sequence of SEQ ID NO: 34; VL-CDR3 comprising the amino acid sequence of SEQ ID NO: 36; VH-CDR1 comprising the amino acid sequence of SEQ ID NO: 42; VH-CDR2 comprising the amino acid sequence of SEQ ID NO: 44; and VH-CDR3 comprising the amino acid sequence of SEQ ID NO: 46; or
c) VL-CDR1 comprising the amino acid sequence of SEQ ID NO: 52; VL-CDR2 comprising the amino acid sequence of SEQ ID NO: 54; VL-CDR3 comprising the amino acid sequence of SEQ ID NO: 56; VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66; or
d) VL-CDR1 comprising the amino acid sequence of SEQ ID NO: 72; VL-CDR2 comprising the amino acid sequence of SEQ ID NO: 74; VL-CDR3 comprising the amino acid sequence of SEQ ID NO: 76; VH-CDR1 comprising the amino acid sequence of SEQ ID NO: 82; VH-CDR2 comprising the amino acid sequence of SEQ ID NO: 84; and VH-CDR3 comprising the amino acid sequence of SEQ ID NO: 86; or
e) VL-CDR1 comprising the amino acid sequence of SEQ ID NO: 92; VL-CDR2 comprising the amino acid sequence of SEQ ID NO: 94; VL-CDR3 comprising the amino acid sequence of SEQ ID NO: 96; VH-CDR1 comprising the amino acid sequence of SEQ ID NO: 102; VH-CDR2 comprising the amino acid sequence of SEQ ID NO: 104; and VH-CDR3 comprising the amino acid sequence of SEQ ID NO: 106; or
f) VL-CDR1 comprising the amino acid sequence of SEQ ID NO: 112; VL-CDR2 comprising the amino acid sequence of SEQ ID NO: 114; VL-CDR3 comprising the amino acid sequence of SEQ ID NO: 116; VH-CDR1 comprising the amino acid sequence of SEQ ID NO: 122; VH-CDR2 comprising the amino acid sequence of SEQ ID NO: 124; and VH-CDR3 comprising the amino acid sequence of SEQ ID NO: 126; or
g) VL-CDR1 comprising the amino acid sequence of SEQ ID NO: 132; VL-CDR2 comprising the amino acid sequence of SEQ ID NO: 134; VL-CDR3 comprising the amino acid sequence of SEQ ID NO: 136; VH-CDR1 comprising the amino acid sequence of SEQ ID NO: 142; VH-CDR2 comprising the amino acid sequence of SEQ ID NO: 144; and VH-CDR3 comprising the amino acid sequence of SEQ ID NO: 146;
h) VL-CDR1 comprising the amino acid sequence of SEQ ID NO: 152; VL-CDR2 comprising the amino acid sequence of SEQ ID NO: 154; VL-CDR3 comprising the amino acid sequence of SEQ ID NO: 156; VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166;
i) VL-CDR1 comprising the amino acid sequence of SEQ ID NO: 172; VL-CDR2 comprising the amino acid sequence of SEQ ID NO: 174; VL-CDR3 comprising the amino acid sequence of SEQ ID NO: 176; VH-CDR1 comprising the amino acid sequence of SEQ ID NO: 182; VH-CDR2 comprising the amino acid sequence of SEQ ID NO: 184; and VH-CDR3 comprising the amino acid sequence of SEQ ID NO: 186;

j) VL-CDR1 comprising the amino acid sequence of SEQ ID NO: 192; VL-CDR2 comprising the amino acid sequence of SEQ ID NO: 194; VL-CDR3 comprising the amino acid sequence of SEQ ID NO: 196; VH-CDR1 comprising the amino acid sequence of SEQ ID NO: 202; VH-CDR2 comprising the amino acid sequence of SEQ ID NO: 204; and VH-CDR3 comprising the amino acid sequence of SEQ ID NO: 206; or k) VL-CDR1 comprising the amino acid sequence of SEQ ID NO: 212; VL-CDR2 comprising the amino acid sequence of SEQ ID NO: 214; VL-CDR3 comprising the amino acid sequence of SEQ ID NO: 216; VH-CDR1 comprising the amino acid sequence of SEQ ID NO: 222; VH-CDR2 comprising the amino acid sequence of SEQ ID NO: 224; and VH-CDR3 comprising the amino acid sequence of SEQ ID NO: 226.

In some embodiments, the antibody comprises:

a) a VL-CDR1 comprising an amino acid sequence having at least 80%, 90% or 95% sequence identity to SEQ ID NO: 12; a VL-CDR2 comprising an amino acid sequence having at least 80%, 90% or 95% sequence identity to SEQ ID NO: 14; a VL-CDR3 comprising an amino acid sequence having at least 80%, 90% or 95% sequence identity to SEQ ID NO: 16; a VH-CDR1 comprising an amino acid sequence having at least 80%, 90% or 95% sequence identity to SEQ ID NO: 22; a VH-CDR2 comprising an amino acid sequence having at least 80%, 90% or 95% sequence identity to SEQ ID NO: 24; and a VH-CDR3 comprising an amino acid sequence having at least 80%, 90% or 95% sequence identity to SEQ ID NO: 26; or b) a VL-CDR1 comprising an amino acid sequence having at least 80%, 90% or 95% sequence identity to SEQ ID NO: 32; a VL-CDR2 comprising an amino acid sequence having at least 80%, 90% or 95% sequence identity to SEQ ID NO: 34; a VL-CDR3 comprising an amino acid sequence having at least 80%, 90% or 95% sequence identity to SEQ ID NO: 36; a VH-CDR1 comprising an amino acid sequence having at least 80%, 90% or 95% sequence identity to SEQ ID NO: 42; a VH-CDR2 comprising an amino acid sequence having at least 80%, 90% or 95% sequence identity to SEQ ID NO: 44; and a VH-CDR3 comprising an amino acid sequence having at least 80%, 90% or 95% sequence identity to SEQ ID NO: 46; or c) a VL-CDR1 comprising an amino acid sequence having at least 80%, 90% or 95% sequence identity to SEQ ID NO: 52; a VL-CDR2 comprising an amino acid sequence having at least 80%, 90% or 95% sequence identity to SEQ ID NO: 54; a VL-CDR3 comprising an amino acid sequence having at least 80%, 90% or 95% sequence identity to SEQ ID NO: 56; a VH-CDR1 comprising an amino acid sequence having at least 80%, 90% or 95% sequence identity to SEQ ID NO: 62; a VH-CDR2 comprising an amino acid sequence having at least 80%, 90% or 95% sequence identity to SEQ ID NO: 64; and a VH-CDR3 comprising an amino acid sequence having at least 80%, 90% or 95% sequence identity to SEQ ID NO: 66; or d) a VL-CDR1 comprising an amino acid sequence having at least 80%, 90% or 95% sequence identity to SEQ ID NO: 72; a VL-CDR2 comprising an amino acid sequence having at least 80%, 90% or 95% sequence identity to SEQ ID NO: 74; a VL-CDR3 comprising an amino acid sequence having at least 80%, 90% or 95% sequence identity to SEQ ID NO: 76; a VH-CDR1 comprising an amino acid sequence having at least 80%, 90% or 95% sequence identity to SEQ ID NO: 82; a VH-CDR2 comprising an amino acid sequence having at least 80%, 90% or 95% sequence identity to SEQ ID NO: 84; and a VH-CDR3 comprising an amino acid sequence having at least 80%, 90% or 95% sequence identity to SEQ ID NO: 86; or e) a VL-CDR1 comprising an amino acid sequence having at least 80%, 90% or 95% sequence identity to SEQ ID NO: 92; a VL-CDR2 comprising an amino acid sequence having at least 80%, 90% or 95% sequence identity to SEQ ID NO: 94; a VL-CDR3 comprising an amino acid sequence having at least 80%, 90% or 95% sequence identity to SEQ ID NO: 96; a VH-CDR1 comprising an amino acid sequence having at least 80%, 90% or 95% sequence identity to SEQ ID NO: 102; a VH-CDR2 comprising an amino acid sequence having at least 80%, 90% or 95% sequence identity to SEQ ID NO: 104; and a VH-CDR3 comprising an amino acid sequence having at least 80%, 90% or 95% sequence identity to SEQ ID NO: 106; or f) a VL-CDR1 comprising an amino acid sequence having at least 80%, 90% or 95% sequence identity to SEQ ID NO: 112; a VL-CDR2 comprising an amino acid sequence having at least 80%, 90% or 95% sequence identity to SEQ ID NO: 114; a VL-CDR3 comprising an amino acid sequence having at least 80%, 90% or 95% sequence identity to SEQ ID NO: 116; a VH-CDR1 comprising an amino acid sequence having at least 80%, 90% or 95% sequence identity to SEQ ID NO: 122; a VH-CDR2 comprising an amino acid sequence having at least 80%, 90% or 95% sequence identity to SEQ ID NO: 124; and a VH-CDR3 comprising an amino acid sequence having at least 80%, 90% or 95% sequence identity to SEQ ID NO: 126; or g) a VL-CDR1 comprising an amino acid sequence having at least 80%, 90% or 95% sequence identity to SEQ ID NO: 132; a VL-CDR2 comprising an amino acid sequence having at least 80%, 90% or 95% sequence identity to SEQ ID NO: 134; a VL-CDR3 comprising an amino acid sequence having at least 80%, 90% or 95% sequence identity to SEQ ID NO: 136; a VH-CDR1 comprising an amino acid sequence having at least 80%, 90% or 95% sequence identity to SEQ ID NO: 142; a VH-CDR2 comprising an amino acid sequence having at least 80%, 90% or 95% sequence identity to SEQ ID NO: 144; and a VH-CDR3 comprising an amino acid sequence having at least 80%, 90% or 95% sequence identity to SEQ ID NO: 146;

h) a VL-CDR1 comprising an amino acid sequence having at least 80%, 90% or 95% sequence identity to SEQ ID NO: 152; a VL-CDR2 comprising an amino acid sequence having at least 80%, 90% or 95% sequence identity to SEQ ID NO: 154; a VL-CDR3 comprising an amino acid sequence having at least 80%, 90% or 95% sequence identity to SEQ ID NO: 156; a VH-CDR1 comprising an amino acid sequence having at least 80%, 90% or 95% sequence identity to SEQ ID NO: 162; a VH-CDR2 comprising an amino acid sequence having at least 80%, 90% or 95% sequence identity to SEQ ID NO: 164; and a VH-CDR3 comprising an amino acid sequence having at least 80%, 90% or 95% sequence identity to SEQ ID NO: 166;

i) a VL-CDR1 comprising an amino acid sequence having at least 80%, 90% or 95% sequence identity to SEQ ID NO: 172; a VL-CDR2 comprising an amino acid sequence having at least 80%, 90% or 95% sequence identity to SEQ ID NO: 174; a VL-CDR3 comprising an amino acid sequence having at least 80%, 90% or 95% sequence identity to SEQ ID NO: 176; a VH-CDR1 comprising an amino acid sequence having at least 80%, 90% or 95% sequence identity to SEQ ID NO: 182; a VH-CDR2 comprising an amino acid sequence having at least 80%, 90% or 95% sequence identity to SEQ ID NO: 184; and a VH-CDR3 comprising an amino acid sequence having at least 80%, 90% or 95% sequence identity to SEQ ID NO: 186;

j) a VL-CDR1 comprising an amino acid sequence having at least 80%, 90% or 95% sequence identity to SEQ ID NO: 192; a VL-CDR2 comprising an amino acid sequence having at least 80%, 90% or 95% sequence identity to SEQ ID NO: 194; a VL-CDR3 comprising an amino acid sequence having at least 80%, 90% or 95% sequence identity to SEQ ID NO: 196; a VH-CDR1 comprising an amino acid sequence having at least 80%, 90% or 95% sequence identity to SEQ ID NO: 202; a VH-CDR2 comprising an amino acid sequence having at least 80%, 90% or 95% sequence identity to SEQ ID NO: 204; and a VH-CDR3 comprising an amino acid sequence having at least 80%, 90% or 95% sequence identity to SEQ ID NO: 206; or k) a VL-CDR1 comprising an amino acid sequence having at least 80%, 90% or 95% sequence identity to SEQ ID NO: 212; a VL-CDR2 comprising an amino acid sequence having at least 80%, 90% or 95% sequence identity to SEQ ID NO: 214; a VL-CDR3 comprising an amino acid sequence having at least 80%, 90% or 95% sequence identity to SEQ ID NO: 216; a VH-CDR1 comprising an amino acid sequence having at least 80%, 90% or 95% sequence identity to SEQ ID NO: 222; a VH-CDR2 comprising an amino acid sequence having at least 80%, 90% or 95% sequence identity to SEQ ID NO: 224; and a VH-CDR3 comprising an amino acid sequence having at least 80%, 90% or 95% sequence identity to SEQ ID NO: 226.

In some particular embodiments, the antibody comprises:

a) a Light Chain Variable Region (VL) comprising the sequence of SEQ ID NO: 10 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 10;

b) a Light Chain Variable Region (VL) comprising the sequence of SEQ ID NO: 30 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 30;

c) a Light Chain Variable Region (VL) comprising the sequence of SEQ ID NO: 50 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 50;

d) a Light Chain Variable Region (VL) comprising the sequence of SEQ ID NO: 90 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 90;

e) a Light Chain Variable Region (VL) comprising the sequence of SEQ ID NO: 110 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 110;

f) a Light Chain Variable Region (VL) comprising the sequence of SEQ ID NO: 130 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 130;

g) a Light Chain Variable Region (VL) comprising the sequence of SEQ ID NO: 150 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 150;

h) a Light Chain Variable Region (VL) comprising the sequence of SEQ ID NO: 170 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 170;

i) a Light Chain Variable Region (VL) comprising the sequence of SEQ ID NO: 190 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 190;

j) a Light Chain Variable Region (VL) comprising the sequence of SEQ ID NO: 230 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 230;

k) a Light Chain Variable Region (VL) comprising the sequence of SEQ ID NO: 234 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 234;

l) a Light Chain Variable Region (VL) comprising the sequence of SEQ ID NO: 238 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 238;

m) a Light Chain Variable Region (VL) comprising the sequence of SEQ ID NO: 246 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 246;

n) a Light Chain Variable Region (VL) comprising the sequence of SEQ ID NO: 250 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 250;

o) a Light Chain Variable Region (VL) comprising the sequence of SEQ ID NO: 254 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 254; or p) a Light Chain Variable Region (VL) comprising the sequence of SEQ ID NO: 258 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 258.

In some particular embodiments, the antibody comprises:

a) a Heavy Chain Variable Region (VH) comprising the sequence of SEQ ID NO: 20 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 20;

b) a Heavy Chain Variable Region (VH) comprising the sequence of SEQ ID NO: 40 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 40;

c) a Heavy Chain Variable Region (VH) comprising the sequence of SEQ ID NO: 60 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 60;

d) a Heavy Chain Variable Region (VH) comprising the sequence of SEQ ID NO: 100 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 100;

e) a Heavy Chain Variable Region (VH) comprising the sequence of SEQ ID NO: 120 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 120;

f) a Heavy Chain Variable Region (VH) comprising the sequence of SEQ ID NO: 140 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 140;

g) a Heavy Chain Variable Region (VH) comprising the sequence of SEQ ID NO:160 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 160;

h) a Heavy Chain Variable Region (VH) comprising the sequence of SEQ ID NO:180 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 180;

i) a Heavy Chain Variable Region (VH) comprising the sequence of SEQ ID NO:200 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 200;

j) a Heavy Chain Variable Region (VH) comprising the sequence of SEQ ID NO:232 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 232;

k) a Heavy Chain Variable Region (VH) comprising the sequence of SEQ ID NO:236 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 236;

l) a Heavy Chain Variable Region (VH) comprising the sequence of SEQ ID NO:240 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 240;

m) a Heavy Chain Variable Region (VH) comprising the sequence of SEQ ID NO:248 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 248;

n) a Heavy Chain Variable Region (VH) comprising the sequence of SEQ ID NO:252 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 252;

o) a Heavy Chain Variable Region (VH) comprising the sequence of SEQ ID NO:256 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 256; or p) a Heavy Chain Variable Region (VH) comprising the sequence of SEQ ID NO:260 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 260.

In some particular embodiments, the antibody comprises:

a) a Light Chain Variable Region (VL) comprising the sequence of SEQ ID NO: 10 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 10 and a Heavy Chain Variable Region (VH) comprising the sequence of SEQ ID NO: 20 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 20;

b) a Light Chain Variable Region (VL) comprising the sequence of SEQ ID NO: 30 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 30 and a Heavy Chain Variable Region (VH) comprising the sequence of SEQ ID NO: 40 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 40;

c) a Light Chain Variable Region (VL) comprising the sequence of SEQ ID NO: 50 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 50 and a Heavy Chain Variable Region (VH) comprising the sequence of SEQ ID NO: 60 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 60;

d) a Light Chain Variable Region (VL) comprising the sequence of SEQ ID NO: 90 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 90 and a Heavy Chain Variable Region (VH) comprising the sequence of SEQ ID NO: 100 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 100;

e) a Light Chain Variable Region (VL) comprising the sequence of SEQ ID NO: 110 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 110 and a Heavy Chain Variable Region (VH) comprising the sequence of SEQ ID NO: 120 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 120;

f) a Light Chain Variable Region (VL) comprising the sequence of SEQ ID NO: 130 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 130 and a Heavy Chain Variable Region (VH) comprising the sequence of SEQ ID NO: 140 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 140;

g) a Light Chain Variable Region (VL) comprising the sequence of SEQ ID NO: 150 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 150 and a Heavy Chain Variable Region (VH) comprising the sequence of SEQ ID NO: 160 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 160;

h) a Light Chain Variable Region (VL) comprising the sequence of SEQ ID NO: 170 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 170 and a Heavy Chain Variable Region (VH) comprising the sequence of SEQ ID NO: 180 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 180;

i) a Light Chain Variable Region (VL) comprising the sequence of SEQ ID NO: 190 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 190 and a Heavy Chain Variable Region (VH) comprising the sequence of SEQ ID NO: 200 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 200;

j) a Light Chain Variable Region (VL) comprising the sequence of SEQ ID NO: 230 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 230 and a Heavy Chain Variable Region (VH) comprising the sequence of SEQ ID NO: 232 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 232;

k) a Light Chain Variable Region (VL) comprising the sequence of SEQ ID NO: 234 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 234 and a Heavy Chain Variable Region (VH) comprising the sequence of SEQ ID NO: 236 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 236;

l) a Light Chain Variable Region (VL) comprising the sequence of SEQ ID NO: 238 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 238 and a Heavy Chain Variable Region (VH) comprising the sequence of SEQ ID NO: 240 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 240;

m) a Light Chain Variable Region (VL) comprising the sequence of SEQ ID NO: 246 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 246 and a Heavy Chain Variable Region (VH) comprising the sequence of SEQ ID NO: 248 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 248;

n) a Light Chain Variable Region (VL) comprising the sequence of SEQ ID NO: 250 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 250 and a Heavy Chain Variable Region (VH) comprising the sequence of SEQ ID NO: 252 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 252;
o) a Light Chain Variable Region (VL) comprising the sequence of SEQ ID NO: 254 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 254 and a Heavy Chain Variable Region (VH) comprising the sequence of SEQ ID NO: 256 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 256; or
p) a Light Chain Variable Region (VL) comprising the sequence of SEQ ID NO: 258 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 258 and a Heavy Chain Variable Region (VH) comprising the sequence of SEQ ID NO: 260 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 260.

In some particular embodiments, the antibody comprises:
a) VL-CDR1 comprising the amino acid sequence of SEQ ID NO: 12; VL-CDR2 comprising the amino acid sequence of SEQ ID NO: 14; and VL-CDR3 comprising the amino acid sequence of SEQ ID NO: 16 or a VL-CDR1 comprising an amino acid sequence having at least 80%, 90% or 95% sequence identity to SEQ ID NO: 12; a VL-CDR2 comprising an amino acid sequence having at least 80%, 90% or 95% sequence identity to SEQ ID NO: 14; and a VL-CDR3 comprising an amino acid sequence having at least 80%, 90% or 95% sequence identity to SEQ ID NO: 16; or
b) VL-CDR1 comprising the amino acid sequence of SEQ ID NO: 32; VL-CDR2 comprising the amino acid sequence of SEQ ID NO: 34; and VL-CDR3 comprising the amino acid sequence of SEQ ID NO: 36 or a VL-CDR1 comprising an amino acid sequence having at least 80%, 90% or 95% sequence identity to SEQ ID NO: 32; a VL-CDR2 comprising an amino acid sequence having at least 80%, 90% or 95% sequence identity to SEQ ID NO: 34; and a VL-CDR3 comprising an amino acid sequence having at least 80%, 90% or 95% sequence identity to SEQ ID NO: 36; or
c) VL-CDR1 comprising the amino acid sequence of SEQ ID NO: 52; VL-CDR2 comprising the amino acid sequence of SEQ ID NO: 54; and VL-CDR3 comprising the amino acid sequence of SEQ ID NO: 56 or a VL-CDR1 comprising an amino acid sequence having at least 80%, 90% or 95% sequence identity to SEQ ID NO: 52; a VL-CDR2 comprising an amino acid sequence having at least 80%, 90% or 95% sequence identity to SEQ ID NO: 54; and a VL-CDR3 comprising an amino acid sequence having at least 80%, 90% or 95% sequence identity to SEQ ID NO: 56; or
d) VL-CDR1 comprising the amino acid sequence of SEQ ID NO: 92; VL-CDR2 comprising the amino acid sequence of SEQ ID NO: 94; and VL-CDR3 comprising the amino acid sequence of SEQ ID NO: 96 or a VL-CDR1 comprising an amino acid sequence having at least 80%, 90% or 95% sequence identity to SEQ ID NO: 92; a VL-CDR2 comprising an amino acid sequence having at least 80%, 90% or 95% sequence identity to SEQ ID NO: 94; and a VL-CDR3 comprising an amino acid sequence having at least 80%, 90% or 95% sequence identity to SEQ ID NO: 96; or
e) VL-CDR1 comprising the amino acid sequence of SEQ ID NO: 112; VL-CDR2 comprising the amino acid sequence of SEQ ID NO: 114; and VL-CDR3 comprising the amino acid sequence of SEQ ID NO: 116 or a VL-CDR1 comprising an amino acid sequence having at least 80%, 90% or 95% sequence identity to SEQ ID NO: 112; a VL-CDR2 comprising an amino acid sequence having at least 80%, 90% or 95% sequence identity to SEQ ID NO: 114; and a VL-CDR3 comprising an amino acid sequence having at least 80%, 90% or 95% sequence identity to SEQ ID NO: 116; or
f) VL-CDR1 comprising the amino acid sequence of SEQ ID NO: 132; VL-CDR2 comprising the amino acid sequence of SEQ ID NO: 134; and VL-CDR3 comprising the amino acid sequence of SEQ ID NO: 136 or a VL-CDR1 comprising an amino acid sequence having at least 80%, 90% or 95% sequence identity to SEQ ID NO: 132; a VL-CDR2 comprising an amino acid sequence having at least 80%, 90% or 95% sequence identity to SEQ ID NO: 134; and a VL-CDR3 comprising an amino acid sequence having at least 80%, 90% or 95% sequence identity to SEQ ID NO: 136;
g) VL-CDR1 comprising the amino acid sequence of SEQ ID NO: 152; VL-CDR2 comprising the amino acid sequence of SEQ ID NO: 154; and VL-CDR3 comprising the amino acid sequence of SEQ ID NO: 156 or a VL-CDR1 comprising an amino acid sequence having at least 80%, 90% or 95% sequence identity to SEQ ID NO: 152; a VL-CDR2 comprising an amino acid sequence having at least 80%, 90% or 95% sequence identity to SEQ ID NO: 154; and a VL-CDR3 comprising an amino acid sequence having at least 80%, 90% or 95% sequence identity to SEQ ID NO: 156;
h) VL-CDR1 comprising the amino acid sequence of SEQ ID NO: 172; VL-CDR2 comprising the amino acid sequence of SEQ ID NO: 174; and VL-CDR3 comprising the amino acid sequence of SEQ ID NO: 176 or a VL-CDR1 comprising an amino acid sequence having at least 80%, 90% or 95% sequence identity to SEQ ID NO: 172; a VL-CDR2 comprising an amino acid sequence having at least 80%, 90% or 95% sequence identity to SEQ ID NO: 174; and a VL-CDR3 comprising an amino acid sequence having at least 80%, 90% or 95% sequence identity to SEQ ID NO: 176; or
i) VL-CDR1 comprising the amino acid sequence of SEQ ID NO: 192; VL-CDR2 comprising the amino acid sequence of SEQ ID NO: 194; and VL-CDR3 comprising the amino acid sequence of SEQ ID NO: 196 or a VL-CDR1 comprising an amino acid sequence having at least 80%, 90% or 95% sequence identity to SEQ ID NO: 192; a VL-CDR2 comprising an amino acid sequence having at least 80%, 90% or 95% sequence identity to SEQ ID NO: 194; and a VL-CDR3 comprising an amino acid sequence having at least 80%, 90% or 95% sequence identity to SEQ ID NO: 196.

In some particular embodiments, the antibody comprises:
a) VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26 or a VH-CDR1 comprising an amino acid sequence having at least 80%, 90% or 95% sequence identity to SEQ ID NO: 22; a VH-CDR2 comprising an amino acid sequence having at least 80%, 90% or 95% sequence identity to SEQ ID NO: 24; and a VH-CDR3 comprising an amino acid sequence having at least 80%, 90% or 95% sequence identity to SEQ ID NO: 26; or
b) VH-CDR1 comprising the amino acid sequence of SEQ ID NO: 42; VH-CDR2 comprising the amino acid sequence of SEQ ID NO: 44; and VH-CDR3 comprising the amino acid sequence of SEQ ID NO: 46 or a VH-CDR1 comprising an amino acid sequence having at least 80%, 90% or 95% sequence identity to SEQ ID NO: 42; a VH-CDR2 comprising an amino acid sequence having at least 80%, 90% or 95% sequence identity to SEQ ID NO: 44; and a VH-CDR3 comprising an amino acid sequence having at least 80%, 90% or 95% sequence identity to SEQ ID NO: 46; or
c) VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66 or a VH-CDR1 comprising an amino acid sequence having at least 80%, 90% or 95% sequence identity to SEQ ID NO: 62; a VH-CDR2 comprising an amino acid sequence having at least 80%, 90% or 95% sequence identity to SEQ ID NO: 64; and a VH-CDR3 comprising an amino acid sequence having at least 80%, 90% or 95% sequence identity to SEQ ID NO: 66; or
d) VH-CDR1 comprising the amino acid sequence of SEQ ID NO: 102; VH-CDR2 comprising the amino acid sequence of SEQ ID NO: 104; and VH-CDR3 comprising the amino acid sequence of SEQ ID NO: 106 or a VH-CDR1 comprising an amino acid sequence having at least 80%, 90% or 95% sequence identity to SEQ ID NO: 102; a VH-CDR2 comprising an amino acid sequence having at least 80%, 90% or 95% sequence identity to SEQ ID NO: 104; and a VH-CDR3 comprising an amino acid sequence having at least 80%, 90% or 95% sequence identity to SEQ ID NO: 106; or
e) VH-CDR1 comprising the amino acid sequence of SEQ ID NO: 122; VH-CDR2 comprising the amino acid sequence of SEQ ID NO: 124; and VH-CDR3 comprising the amino acid sequence of SEQ ID NO: 126 or a VH-CDR1 comprising an amino acid sequence having at least 80%, 90% or 95% sequence identity to SEQ ID NO: 122; a VH-CDR2 comprising an amino acid sequence having at least 80%, 90% or 95% sequence identity to SEQ ID NO: 124; and a VH-CDR3 comprising an amino acid sequence having at least 80%, 90% or 95% sequence identity to SEQ ID NO: 126; or
f) VH-CDR1 comprising the amino acid sequence of SEQ ID NO: 142; VH-CDR2 comprising the amino acid sequence of SEQ ID NO: 144; and VH-CDR3 comprising the amino acid sequence of SEQ ID NO: 146 or a VH-CDR1 comprising an amino acid sequence having at least 80%, 90% or 95% sequence identity to SEQ ID NO: 142; a VH-CDR2 comprising an amino acid sequence having at least 80%, 90% or 95% sequence identity to SEQ ID NO: 144; and a VH-CDR3 comprising an amino acid sequence having at least 80%, 90% or 95% sequence identity to SEQ ID NO: 146;
g) VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166 or a VH-CDR1 comprising an amino acid sequence having at least 80%, 90% or 95% sequence identity to SEQ ID NO: 162; a VH-CDR2 comprising an amino acid sequence having at least 80%, 90% or 95% sequence identity to SEQ ID NO: 164; and a VH-CDR3 comprising an amino acid sequence having at least 80%, 90% or 95% sequence identity to SEQ ID NO: 166;
h) VH-CDR1 comprising the amino acid sequence of SEQ ID NO: 182; VH-CDR2 comprising the amino acid sequence of SEQ ID NO: 184; and VH-CDR3 comprising the amino acid sequence of SEQ ID NO: 186 or a VH-CDR1 comprising an amino acid sequence having at least 80%, 90% or 95% sequence identity to SEQ ID NO: 182; a VH-CDR2 comprising an amino acid sequence having at least 80%, 90% or 95% sequence identity to SEQ ID NO: 184; and a VH-CDR3 comprising an amino acid sequence having at least 80%, 90% or 95% sequence identity to SEQ ID NO: 186; or
i) VH-CDR1 comprising the amino acid sequence of SEQ ID NO: 202; VH-CDR2 comprising the amino acid sequence of SEQ ID NO: 204; and VH-CDR3 comprising the amino acid sequence of SEQ ID NO: 206 or a VH-CDR1 comprising an amino acid sequence having at least 80%, 90% or 95% sequence identity to SEQ ID NO: 202; a VH-CDR2 comprising an amino acid sequence having at least 80%, 90% or 95% sequence identity to SEQ ID NO: 204; and a VH-CDR3 comprising an amino acid sequence having at least 80%, 90% or 95% sequence identity to SEQ ID NO: 206.

In some particular embodiments, the antibody comprises:
a) VL-CDR1 comprising the amino acid sequence of SEQ ID NO: 12; VL-CDR2 comprising the amino acid sequence of SEQ ID NO: 14; VL-CDR3 comprising the amino acid sequence of SEQ ID NO: 16; VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26; or
b) VL-CDR1 comprising the amino acid sequence of SEQ ID NO: 32; VL-CDR2 comprising the amino acid sequence of SEQ ID NO: 34; VL-CDR3 comprising the amino acid sequence of SEQ ID NO: 36; VH-CDR1 comprising the amino acid sequence of SEQ ID NO: 42; VH-CDR2 comprising the amino acid sequence of SEQ ID NO: 44; and VH-CDR3 comprising the amino acid sequence of SEQ ID NO: 46; or
c) VL-CDR1 comprising the amino acid sequence of SEQ ID NO: 52; VL-CDR2 comprising the amino acid sequence of SEQ ID NO: 54; VL-CDR3 comprising the amino acid sequence of SEQ ID NO: 56; VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66; or
d) VL-CDR1 comprising the amino acid sequence of SEQ ID NO: 92; VL-CDR2 comprising the amino acid sequence of SEQ ID NO: 94; VL-CDR3 comprising the amino acid sequence of SEQ ID NO: 96; VH-CDR1 comprising the amino acid sequence of SEQ ID NO: 102; VH-CDR2 comprising the amino acid sequence of SEQ ID NO: 104; and VH-CDR3 comprising the amino acid sequence of SEQ ID NO: 106; or
e) VL-CDR1 comprising the amino acid sequence of SEQ ID NO: 112; VL-CDR2 comprising the amino acid sequence of SEQ ID NO: 114; VL-CDR3 comprising the amino acid sequence of SEQ ID NO: 116; VH-CDR1 comprising the amino acid sequence of SEQ ID NO: 122; VH-CDR2 comprising the amino acid sequence of SEQ ID NO: 124; and VH-CDR3 comprising the amino acid sequence of SEQ ID NO: 126; or
f) VL-CDR1 comprising the amino acid sequence of SEQ ID NO: 132; VL-CDR2 comprising the amino acid sequence of SEQ ID NO: 134; VL-CDR3 comprising the amino acid sequence of SEQ ID NO: 136; VH-CDR1 comprising the amino acid sequence of SEQ ID NO: 142; VH-CDR2 comprising the amino acid sequence of SEQ ID NO: 144; and VH-CDR3 comprising the amino acid sequence of SEQ ID NO: 146;
g) VL-CDR1 comprising the amino acid sequence of SEQ ID NO: 152; VL-CDR2 comprising the amino acid sequence of SEQ ID NO: 154; VL-CDR3 comprising the amino acid sequence of SEQ ID NO: 156; VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166;
h) VL-CDR1 comprising the amino acid sequence of SEQ ID NO: 172; VL-CDR2 comprising the amino acid sequence of SEQ ID NO: 174; VL-CDR3 comprising the amino acid sequence of SEQ ID NO: 176; VH-CDR1 comprising the amino acid sequence of SEQ ID NO: 182; VH-CDR2 comprising the amino acid sequence of SEQ ID NO: 184; and VH-CDR3 comprising the amino acid sequence of SEQ ID NO: 186; or
i) VL-CDR1 comprising the amino acid sequence of SEQ ID NO: 192; VL-CDR2 comprising the amino acid sequence of SEQ ID NO: 194; VL-CDR3 comprising the amino acid sequence of SEQ ID NO: 196; VH-CDR1 comprising the amino acid sequence of SEQ ID NO: 202; VH-CDR2 comprising the amino acid sequence of SEQ ID NO: 204; and VH-CDR3 comprising the amino acid sequence of SEQ ID NO: 206.

In some particular embodiments, the antibody comprises:

a) a VL-CDR1 comprising an amino acid sequence having at least 80%, 90% or 95% sequence identity to SEQ ID NO: 12; a VL-CDR2 comprising an amino acid sequence having at least 80%, 90% or 95% sequence identity to SEQ ID NO: 14; a VL-CDR3 comprising an amino acid sequence having at least 80%, 90% or 95% sequence identity to SEQ ID NO: 16; a VH-CDR1 comprising an amino acid sequence having at least 80%, 90% or 95% sequence identity to SEQ ID NO: 22; a VH-CDR2 comprising an amino acid sequence having at least 80%, 90% or 95% sequence identity to SEQ ID NO: 24; and a VH-CDR3 comprising an amino acid sequence having at least 80%, 90% or 95% sequence identity to SEQ ID NO: 26; or
b) a VL-CDR1 comprising an amino acid sequence having at least 80%, 90% or 95% sequence identity to SEQ ID NO: 32; a VL-CDR2 comprising an amino acid sequence having at least 80%, 90% or 95% sequence identity to SEQ ID NO: 34; a VL-CDR3 comprising an amino acid sequence having at least 80%, 90% or 95% sequence identity to SEQ ID NO: 36; a VH-CDR1 comprising an amino acid sequence having at least 80%, 90% or 95% sequence identity to SEQ ID NO: 42; a VH-CDR2 comprising an amino acid sequence having at least 80%, 90% or 95% sequence identity to SEQ ID NO: 44; and a VH-CDR3 comprising an amino acid sequence having at least 80%, 90% or 95% sequence identity to SEQ ID NO: 46;
c) a VL-CDR1 comprising an amino acid sequence having at least 80%, 90% or 95% sequence identity to SEQ ID NO: 52; a VL-CDR2 comprising an amino acid sequence having at least 80%, 90% or 95% sequence identity to SEQ ID NO: 54; a VL-CDR3 comprising an amino acid sequence having at least 80%, 90% or 95% sequence identity to SEQ ID NO: 56; a VH-CDR1 comprising an amino acid sequence having at least 80%, 90% or 95% sequence identity to SEQ ID NO: 62; a VH-CDR2 comprising an amino acid sequence having at least 80%, 90% or 95% sequence identity to SEQ ID NO: 64; and a VH-CDR3 comprising an amino acid sequence having at least 80%, 90% or 95% sequence identity to SEQ ID NO: 66; or
d) a VL-CDR1 comprising an amino acid sequence having at least 80%, 90% or 95% sequence identity to SEQ ID NO: 92; a VL-CDR2 comprising an amino acid sequence having at least 80%, 90% or 95% sequence identity to SEQ ID NO: 94; a VL-CDR3 comprising an amino acid sequence having at least 80%, 90% or 95% sequence identity to SEQ ID NO: 96; a VH-CDR1 comprising an amino acid sequence having at least 80%, 90% or 95% sequence identity to SEQ ID NO: 102; a VH-CDR2 comprising an amino acid sequence having at least 80%, 90% or 95% sequence identity to SEQ ID NO: 104; and a VH-CDR3 comprising an amino acid sequence having at least 80%, 90% or 95% sequence identity to SEQ ID NO: 106; or
e) a VL-CDR1 comprising an amino acid sequence having at least 80%, 90% or 95% sequence identity to SEQ ID NO: 112; a VL-CDR2 comprising an amino acid sequence having at least 80%, 90% or 95% sequence identity to SEQ ID NO: 114; a VL-CDR3 comprising an amino acid sequence having at least 80%, 90% or 95% sequence identity to SEQ ID NO: 116; a VH-CDR1 comprising an amino acid sequence having at least 80%, 90% or 95% sequence identity to SEQ ID NO: 122; a VH-CDR2 comprising an amino acid sequence having at least 80%, 90% or 95% sequence identity to SEQ ID NO: 124; and a VH-CDR3 comprising an amino acid sequence having at least 80%, 90% or 95% sequence identity to SEQ ID NO: 126; or
f) a VL-CDR1 comprising an amino acid sequence having at least 80%, 90% or 95% sequence identity to SEQ ID NO: 132; a VL-CDR2 comprising an amino acid sequence having at least 80%, 90% or 95% sequence identity to SEQ ID NO: 134; a VL-CDR3 comprising an amino acid sequence having at least 80%, 90% or 95% sequence identity to SEQ ID NO: 136; a VH-CDR1 comprising an amino acid sequence having at least 80%, 90% or 95% sequence identity to SEQ ID NO: 142; a VH-CDR2 comprising an amino acid sequence having at least 80%, 90% or 95% sequence identity to SEQ ID NO: 144; and a VH-CDR3 comprising an amino acid sequence having at least 80%, 90% or 95% sequence identity to SEQ ID NO: 146;
g) a VL-CDR1 comprising an amino acid sequence having at least 80%, 90% or 95% sequence identity to SEQ ID NO: 152; a VL-CDR2 comprising an amino acid sequence having at least 80%, 90% or 95% sequence identity to SEQ ID NO: 154; a VL-CDR3 comprising an amino acid sequence having at least 80%, 90% or 95% sequence identity to SEQ ID NO: 156; a VH-CDR1 comprising an amino acid sequence having at least 80%, 90% or 95% sequence identity to SEQ ID NO: 162; a VH-CDR2 comprising an amino acid sequence having at least 80%, 90% or 95% sequence identity to SEQ ID NO: 164; and a VH-CDR3 comprising an amino acid sequence having at least 80%, 90% or 95% sequence identity to SEQ ID NO: 166;

h) a VL-CDR1 comprising an amino acid sequence having at least 80%, 90% or 95% sequence identity to SEQ ID NO: 172; a VL-CDR2 comprising an amino acid sequence having at least 80%, 90% or 95% sequence identity to SEQ ID NO: 174; a VL-CDR3 comprising an amino acid sequence having at least 80%, 90% or 95% sequence identity to SEQ ID NO: 176; a VH-CDR1 comprising an amino acid sequence having at least 80%, 90% or 95% sequence identity to SEQ ID NO: 182; a VH-CDR2 comprising an amino acid sequence having at least 80%, 90% or 95% sequence identity to SEQ ID NO: 184; and a VH-CDR3 comprising an amino acid sequence having at least 80%, 90% or 95% sequence identity to SEQ ID NO: 186; or i) a VL-CDR1 comprising an amino acid sequence having at least 80%, 90% or 95% sequence identity to SEQ ID NO: 192; a VL-CDR2 comprising an amino acid sequence having at least 80%, 90% or 95% sequence identity to SEQ ID NO: 194; a VL-CDR3 comprising an amino acid sequence having at least 80%, 90% or 95% sequence identity to SEQ ID NO: 196; a VH-CDR1 comprising an amino acid sequence having at least 80%, 90% or 95% sequence identity to SEQ ID NO: 202; a VH-CDR2 comprising an amino acid sequence having at least 80%, 90% or 95% sequence identity to SEQ ID NO: 204; and a VH-CDR3 comprising an amino acid sequence having at least 80%, 90% or 95% sequence identity to SEQ ID NO: 206.

In certain embodiments, a binding molecule or an antibody provided herein has a dissociation constant (KD) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M), in particular with respect to binding misfolded TDP-43, in particular misfolded monomeric TDP-43, misfolded aggregated TDP-43 and/or misfolded oligomeric TDP-43.

In one embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl) carbodiimide hydrochloride (EDC) and N-hydroxysuccinimide (NHS) according to the supplier's instructions. Antigen is diluted with 10 mM sodium acetate, pH 4.8, to 5 µg/ml (0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of antibody (0.58 nM to 200 nM) are injected in PBS with 0.05% polysorbate 20 (TWEEN-20™) surfactant (PEST) at 25° C. at a flow rate of approximately 25 µl/min. Association rates (kon) and dissociation rates (koff) are calculated using a simple one-to-one Langmuir binding model (BIACORE® T100 Evaluation Software) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

In some embodiments, an antibody, particularly an isolated antibody of the invention as described herein that binds human TDP-43 is provided, wherein the antibody binds each of misfolded monomeric TDP-43, misfolded aggregated TDP-43 and misfolded oligomeric TDP-43 with a KD of less than 100 nM, less than 10 nM, less than 1 nM, less than 200 pM, less than 100 pM, or less than 10 pM. Preferably, the antibody of the invention binds each of misfolded monomeric TDP-43, misfolded aggregated TDP-43, misfolded oligomeric TDP-43, wherein the TDP-43 is post-translationally modified, e.g. phosphorylated TDP-43, with a KD of less than 100 nM, less than 10 nM, less than 1 nM, less than 200 pM, less than 100 pM, or less than 10 pM.

The invention also relates to compositions comprising a binding molecule, particularly an antibody of the invention (including TDP-43-binding antibody fragments and derivatives) as described herein or TDP-43 agonists and cognate molecules, or alternately, antagonists of the same and to immunotherapeutic and immunodiagnostic methods using such compositions in the prevention, diagnosis or treatment of a TDP-43 proteinopathy, wherein an effective amount of the composition is administered to a patient in need thereof.

In some embodiments, the invention encompasses molecules, particularly antibodies of the invention as described herein that specifically bind TDP-43 and the use of these molecules to diagnose, prevent, alleviate or treat a disorder or abnormality associated with TDP-43 aggregates including but not limited to frontotemporal dementia (FTD), amyotrophic lateral sclerosis (ALS), Alzheimer's disease (AD) and Parkinson's disease (PD). The methods and compositions disclosed herein have applications in diagnosing, preventing, alleviating or treating a disorder or abnormality associated with TDP-43 aggregates including but not limited to frontotemporal dementia (FTD), amyotrophic lateral sclerosis (ALS).

In another embodiment, a binding molecule, particularly an antibody of the invention as described herein specific for TDP-43 is contacted with a sample to detect, diagnose or monitor a disorder or abnormality associated with TDP-43 aggregates selected from Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

In one embodiment, the invention encompasses molecules, particularly antibodies of the invention as described herein that specifically bind TDP-43 and the use of these molecules, particularly of these antibodies to detect the presence of TDP-43 in a sample. Accordingly, TDP-43 binding molecules of the invention, such as, anti-TDP43 antibodies as described herein, can be used to screen human blood, CSF, and urine for the presence of TDP-43 in samples, for example, by using ELISA-based or surface adapted assay. The methods and compositions of the invention also have applications in diagnosing presymptomatic disease and in monitoring disease progression and therapeutic efficacy. According to some embodiments, an antibody specific for TDP-43 (e.g., a full-length antibody or a TDP-43 binding fragment or derivative of an antibody) is contacted with a sample (e.g., blood, cerebrospinal fluid, or brain tissue) to detect, diagnose or monitor Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

In additional embodiments, the invention provides methods for preventing, alleviating or treating a disorder or abnormality associated with TDP-43 aggregates. According to one embodiment, the methods of the invention comprise administering an effective concentration of a binding molecule, particularly an antibody of the invention specific for TDP-43 (e.g., a full-length antibody or a TDP-43 binding fragment or derivative of an antibody) as described herein to a subject. In an additional embodiment, the invention provides a method for preventing, alleviating or treating a TDP-43 proteinopathies. According to some embodiments, a binding molecule, particularly an antibody of the invention as described herein specific for TDP-43 is administered to treat, alleviate or prevent frontotemporal degeneration (FTD) or amyotrophic lateral sclerosis (ALS). In another embodiment, a binding molecule, particularly an antibody of the invention as described herein specific for TDP-43 is administered to prevent, alleviate or treat a neurodegenerative disease selected from frontotemporal dementia (FTD), amyotrophic lateral sclerosis (ALS), Alzheimer's disease (AD, sporadic and familial), and Parkinson's disease (PD).

In another embodiment, a binding molecule, particularly an antibody of the invention as described herein specific for TDP-43 is administered to prevent, alleviate or treat a disease selected from: Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

DETAILED DESCRIPTION OF EMBODIMENTS OF THE INVENTION

X. Definitions

An "antigen binding molecule," as used herein, is any molecule that can specifically or selectively bind to an antigen. A binding molecule may include or be an antibody or a fragment thereof. An anti-misfolded TDP-43 binding molecule is a molecule that binds to the misfolded TDP-43 protein, such as an anti-TDP-43 antibody or fragment thereof, at a specific recognition site, epitope. That is, antigen-binding molecules of the invention bind to an epitope within the amino acid sequence of SEQ ID NO: 1, preferably within amino acids 215-222 thereof. Other anti-misfolded TDP-43 binding molecules may also include multivalent molecules, multi-specific molecules (e.g., diabodies), fusion molecules, aptamers, avimers, or other naturally occurring or recombinantly created molecules. Illustrative antigen-binding molecules useful in the present invention include antibody-like molecules. An antibody-like molecule is a molecule that can exhibit functions by binding to a target molecule (See, e.g., Current Opinion in Biotechnology 2006, 17:653-658; Current Opinion in Biotechnology 2007, 18:1-10; Current Opinion in Structural Biology 1997, 7:463-469; Protein Science 2006, 15:14-27), and includes, for example, DARPins (WO 2002/020565), Affibody (WO 1995/001937), Avimer (WO 2004/044011; WO 2005/040229), Adnectin (WO 2002/032925) and fynomers (WO 2013/135588).

The terms "anti misfolded TDP-43 antibody" and "an antibody that binds to misfolded TDP-43" or simply "antibody" as used herein refer to an antibody that is capable of binding misfolded TDP-43 with sufficient affinity such that the antibody is useful as a diagnostic and/or therapeutic agent in targeting TDP-43. In one embodiment, the extent of binding of an anti-TDP-43 antibody of the invention to an unrelated, non-TDP-43 protein or physiologically functional TDP-43 is less than about 10% of the binding of the antibody to misfolded TDP-43 as measured, e.g., by a radioimmunoassay (RIA). In certain embodiments, an anti-misfolded TDP-43 antibody binds to an epitope of TDP-43 that is not accessible in physiologically functional TDP-43. That is, upon misfolding, the epitope becomes accessible and is bound by the binding molecule, in particular antibody, of the invention. Such an epitope can be within amino acids 215-222 (SEQ ID NO:5) of human TDP-43. In this context, the term "physiologically functional" relates to a TDP-43 protein being in a status able to exhibit its desired function in an in vivo cellular environment. In contrast, upon misfolding, the TDP-43 protein will lose its ability to exhibit the same function, at least to an extent defined by more than 50% of the previous, physiologically relevant, function. In general, the term "antibody" is used herein in the broadest sense and encompasses various antibody structures, including but not limited to monoclonal antibodies, polyclonal antibodies, multispecific antibodies (e.g., bispecific antibodies), fully-human antibodies and antibody fragments so long as they exhibit the desired antigen-binding activity. Antibodies within the present invention may also be chimeric antibodies, recombinant antibodies, antigen-binding fragments of recombinant antibodies, humanized antibodies or antibodies displayed upon the surface of a phage or displayed upon the surface of a chimeric antigen receptor (CAR) T cell.

An "antigen-binding fragment" of an antibody refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to an epitope" within a defined region of a protein is an antibody that requires the presence of one or more of the amino acids within that region for binding to the protein.

In certain embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 20% of the binding to unaltered protein. In some embodiments, an "antibody that binds to an epitope" within a defined region of a protein is identified by mutation analysis, in which amino acids of the protein are mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. In certain embodiments, binding of the antibody is determined by FACS, WB or by a suitable binding assay such as ELISA. In some embodiments, the antibodies of the invention bind to an epitope which is not accessible in physiologically functional TDP-43 and which becomes accessible if TDP-43 is misfolded, i.e. in a different three dimensional conformation that does not allow the protein to exhibit its physiological function, preferably the epitope lies within amino acids 215-222 (SEQ ID NO:5) of SEQ ID NO:1.

The term "binding to" as used in the context of the present invention defines a binding (interaction) of at least two "antigen-interaction-sites" with each other. The term "antigen-interaction-site" defines, in accordance with the present invention, a motif of a polypeptide, i.e., a part of the antibody or antigen-binding fragment of the present invention, which shows the capacity of specific interaction with a specific antigen or a specific group of antigens of TDP-43. Said binding/interaction is also understood to define a "specific recognition". The term "specifically recognizing" means in accordance with this invention that the antibody is capable of specifically interacting with and/or binding to at least two amino acids of TDP-43 as defined herein, in particular interacting with/binding to at least two amino acids within residues 215-222 (SEQ ID NO:5) of SEQ ID NO:1.

The term "specific interaction" as used in accordance with the present invention means that the antibody or antigen-binding fragment thereof of the invention does not or does not essentially cross-react with (poly)peptides of similar structures. Accordingly, the antibody or antigen-binding fragment thereof of the invention specifically binds to/interacts with structures of TDP-43 formed by particular amino acid sequences within amino acids 215-222 (SEQ ID NO:5) of SEQ ID NO:1.

Cross-reactivity of antigen-binding molecules, in particular a panel of antibodies or antigen-binding fragments thereof under investigation may be tested, for example, by assessing binding of said panel of antibodies or antigen-binding fragments thereof under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, antigen-binding fragments thereof and the like) that bind to the certain structure of TDP-43 as defined herein, e.g., a specific epitope or (poly)peptide/protein of TDP-43 as defined herein but do not or do not essentially bind to any of the other epitope or (poly)peptides of the same TDP-43, are considered specific for the epitope or (poly)peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIACORE™), analytical ultracentrifugation, isothermal titration calorimetry, fluorescence anisotropy, fluorescence spectroscopy or by radiolabeled ligand binding assays.

Accordingly, specificity can be determined experimentally by methods known in the art and methods as described herein. Such methods comprise, but are not limited to Western Blots, ELISA-, RIA-, ECL-, IRMA-tests and peptide scans.

The term "monoclonal antibody" as used herein, refers to an antibody obtained from a population of substantially homogeneous antibodies, i.e., the individual antibodies comprising the population are identical except for possible naturally occurring mutations that may be present in minor amounts.

Monoclonal antibodies are highly specific, being directed against a single antigenic site. Monoclonal antibodies are advantageous in that they may be synthesized by a hybridoma culture, essentially uncontaminated by other immunoglobulins. The modified "monoclonal" indicates the character of the antibody as being amongst a substantially homogeneous population of antibodies, and is not to be construed as requiring production of the antibody by any particular method. As mentioned above, the monoclonal antibodies to be used in accordance with the present invention may be made by the hybridoma method described by Kohler, Nature 256 (1975), 495.

The term "polyclonal antibody" as used herein, refers to an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse/murine immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may also be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies", refers to an antibody which comprises a variable region of the present invention fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant (human) antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "heterohybrid antibody" refers to an antibody having light and heavy chains of different organismal origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: Jones et al., Nature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules (i.e., "antigen-binding fragment thereof"). Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fv, Fab', Fab'-SH, F(ab')2. The term antibody also comprises but is not limited to fully-human antibodies, chimeric antibodies, humanized antibodies, CDR-grafted antibodies and antibody constructs, like single chain Fvs (scFv) or antibody-fusion proteins.

"Single-chain Fv" or "scFv" antibody fragments have, in the context of the invention, the $V_H$ and $V_L$ domains of an antibody, wherein these domains are present in a single polypeptide chain. Generally, the scFv polypeptide further comprises a polypeptide linker between the VH and $V_L$ domains which enables the scFv to form the desired structure for antigen binding. Techniques described for the production of single chain antibodies are described, e.g., in Pluckthun in The Pharmacology of Monoclonal Antibodies, Rosenburg and Moore eds. Springer-Verlag, N.Y. (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')₂ molecule.

A "F(ab')₂ fragment" contains two light chains and two heavy chains containing a portion of the constant region between the $C_H1$ and $C_H2$ domains, such that an interchain disulfide bond is formed between the two heavy chains. A F(ab')₂ fragment thus is composed of two Fab' fragments that are held together by a disulfide bond between the two heavy chains.

The "Fv region" comprises the variable regions from both the heavy and light chains, but lacks the constant regions.

Antibodies, antibody constructs, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook et al., Molecular Cloning: A Laboratory Manual; Cold Spring Harbor Laboratory Press, 2$^{nd}$ edition (1989) and 3$^{rd}$ edition (2001). The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J., Mol. Biol. 196 (1987), 901-917 or Chothia, Nature 342 (1989), 877-883.

Accordingly, in the context of the present invention, the antibody molecule described herein above is selected from the group consisting of a full antibody (immunoglobulin, like an IgG1, an IgG2, an IgG2a, an IgG2b, an IgA1, an IgGA2, an IgG3, an IgG4, an IgA, an IgM, an IgD or an IgE), F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596.

Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art (see e.g. LoBuglio, Proceedings of the American Society of Clinical Oncology Abstract (1997), 1562 and Khor, Proceedings of the American Society of Clinical Oncology Abstract (1997), 847).

Accordingly, in the context of this invention, antibody molecules or antigen-binding fragments thereof are provided, which are humanized and can successfully be employed in pharmaceutical compositions.

The specificity of the antibody or antigen-binding fragment of the present invention may not only be expressed by the nature of the amino acid sequence of the antibody or the antigen-binding fragment as defined above but also by the epitope to which the antibody is capable of binding to. Thus, the present invention relates, in one embodiment, to an anti-misfolded TDP-43 antibody or an antigen-binding fragment thereof which recognizes the same epitope as an antibody of the invention.

It may be understood by a person skilled in the art that the epitopes may be comprised in the TDP-43 protein, but may also be comprised in a degradation product thereof or may be a chemically synthesized peptide. The amino acid positions are only indicated to demonstrate the position of the corresponding amino acid sequence in the sequence of the TDP-43 protein. The invention encompasses all peptides comprising the epitope. The peptide may be a part of a polypeptide of more than 100 amino acids in length or may be a small peptide of less than 100, preferably less than 50, more preferably less than 25 amino acids, even more preferably less than 16 amino acids. The amino acids of such peptide may be natural amino acids or nonnatural amino acids (e.g., beta-amino acids, gamma-amino acids, D-amino acids) or a combination thereof. Further, the present invention may encompass the respective retro-inverso peptides of the epitopes. The peptide may be unbound or bound. It may be bound, e.g., to a small molecule (e.g., a drug or a fluorophor), to a high-molecular weight polymer (e.g., polyethylene glycol (PEG), polyethylene imine (PEI), hydroxypropylmethacrylate (HPMA), etc.) or to a protein, a fatty acid, a sugar moiety or may be inserted in a membrane.

In order to test whether an antibody in question and the antibody of the present invention recognize the same epitope, the following competition study may be carried out: Vero cells infected with 3 MOI (multiplicity of infection) are incubated after 20 h with varying concentrations of the antibody in question as the competitor for 1 hour. In a second incubation step, the antibody of the present invention is applied in a constant concentration of 100 nM and its binding is flow-cytometrically detected using a fluorescence-labelled antibody directed against the constant domains of the antibody of the invention. Binding that conducts anti-proportional to the concentration of the antibody in question is indicative for that both antibodies recognize the same epitope. However, many other assays are known in the art which may be used.

The present invention also relates to the production of specific antibodies against native polypeptides and recombinant polypeptides of TDP-43 as long as these polypeptides represent the misfolded state of TDP-43. This production is based, for example, on the immunization of animals, like mice. However, also other animals for the production of antibody/antisera are envisaged within the present invention. For example, monoclonal and polyclonal antibodies can be produced by rabbit, mice, goats, donkeys and the like. The polynucleotide encoding a correspondingly chosen polypeptide of TDP-43 can be subcloned into an appropriated vector, wherein the recombinant polypeptide is to be expressed in an organism being able for an expression, for example in bacteria. Thus, the expressed recombinant protein can be intra-peritoneally injected into a mice and the resulting specific antibody can be, for example, obtained from the mice serum being provided by intra-cardiac blood puncture. The present invention also envisages the production of specific antibodies against native polypeptides and recombinant polypeptides by using a DNA vaccine strategy as exemplified in the appended examples. DNA vaccine strategies are well-known in the art and encompass liposome-mediated delivery, by gene gun or jet injection and intramuscular or intradermal injection. Thus, antibodies directed against a polypeptide or a protein or an epitope of TDP-43, in particular the epitope of the antibodies provided herein, can be obtained by directly immunizing the animal by directly injecting intramuscularly the vector expressing the desired polypeptide or a protein or an epitope of TDP-43, in particular the epitope of the antibodies of the invention, which lies within amino acid residues 215-222 of SEQ ID NO. 1. The amount of obtained specific antibody can be quantified using an ELISA, which is also described herein below. Further methods for the production of antibodies are well known in the art, see, e.g. Harlow and Lane, "Antibodies, A Laboratory Manual", CSH Press, Cold Spring Harbor, 1988.

Thus, under designated assay conditions, the specified antibodies and the corresponding epitope of TDP-43 bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Shepherd and Dean (2000), Monoclonal Antibodies: A Practical Approach, Oxford University Press and/or Howard and Bethell, (2000) Basic Methods in Antibody Production and Characterization, Crc. Pr. Inc. for a description of immunoassay formats and conditions that can be used to determine specific immunoreactivity. Typically a specific or selective reaction will be at least twice background signal to noise and more typically more than 10 to 100 times greater than background. The person skilled in the art is in a position to provide for and generate specific binding molecules directed against the novel polypeptides. For specific binding-assays it can be readily employed to avoid undesired cross-reactivity, for example polyclonal antibodies can easily be purified and selected by known methods (see Shepherd and Dean, loc. cit.).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, antibody variants having one or more amino acid substitutions are provided. Sites of interest for substitutional mutagenesis include the CDRs and FRs. Conservative substitutions are shown in Table 2 under the heading of "preferred substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |

TABLE 2-continued

| Original Residue | Exemplary Substitutions | Preferred Substitutions |
|---|---|---|
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244: 1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Bioteeh. Bioeng.* 87: 614 (2004); Kanda, Y. et al., *Bioteehnol. Bioeng.*, 94(4):680-688 (2006); and W02003/085 107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement activation and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes and microglia express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)).

Alternatively, non-radioactive assays methods may be employed (see, for example, ACTI™ non radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells.

Alternatively, or additionally, ADCC activity of the molecule of interest may be assessed in vivo, e.g., in a animal model such as that disclosed in Clynes et al., *Proc. Nat'l Acad. sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Alternatively, antibodies with reduced effector function include those with substitution of one or more of Fc region residues 234, 235 and 329, so-called "PG-LALA" Fc mutant with substitution of residues 234 and 235 to alanine and 329 to glycine (Lo, M. et al., Journal of Biochemistry, 292, 3900-3908).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises a Fc region with one or more amino acid substitutions which improve ADCC, e.g., substitutions at positions 298, 333, and/or 334 of the Fe region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kirn et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In certain embodiments, an antibody provided herein may be further modified to contain additional nonproteinaceous moieties that are known in the art and readily available. The moieties suitable for derivatization of the antibody include but are not limited to water soluble polymers. Nonlimiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Antibodies may be produced using recombinant methods and compositions, e.g., as described in U.S. Pat. No. 4,816,567. In one embodiment, isolated nucleic acid encoding an anti-misfolded TDP-43 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20). In one embodiment, a method of making an anti-misfolded TDP-43 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-misfolded TDP-43 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Val.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are macaque kidney CVI line transformed by SV40 (COS-7); human embryonic kidney line (293 or 293 cells as described, e.g., in Graham et al., *J. Gen Viral.* 36:59 (1977)); baby hamster kidney cells (BHK); mouse sertoli cells (TM4 cells as described, e.g., in Mather, *Biol. Reprod.* 23:243-251 (1980)); macaque kidney cells (CV 1); African green macaque kidney cells (VERO-76); human cervical carcinoma cells (HeLa); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y Aead. Sei.* 383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. cii. USA* 77:4216 (1980)); and myeloma cell lines such as YO, NSO and Sp2/0. For a review of certain mammalian host cell lines suitable for antibody production, see, e.g., Yazaki and Wu, *Methods in Molecular Biology*, Val. 248 (B. K. C. Lo, ed., Humana Press, Totowa, N.J.), pp. 255-268 (2003).

Anti-misfolded TDP-43 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, immunofluorescence or immunohistochemistry.

In another aspect, competition assays may be used to identify an antibody that competes with any of the antibodies described herein for binding to misfolded TDP-43. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized misfolded TDP-43 is incubated in a solution comprising a first labeled antibody that binds to misfolded TDP-43 (e.g., any of the antibodies described herein) and a second unlabeled antibody that is being tested for its ability to compete with the first antibody for binding to misfolded TDP-43. As a control, immobilized misfolded TDP-43 is incubated in a solution comprising the first labeled antibody but not the second unlabeled antibody. After incubation under conditions permissive for binding of the first antibody to misfolded TDP-43, excess unbound antibody is removed, and the amount of label associated with immobilized misfolded TDP-43 is measured. If the amount of label associated with immobilized misfolded TDP-43 is substantially reduced in the test sample relative to the control sample, then that indicates that the second antibody is competing with the first antibody for binding to misfolded TDP-43. See Harlow and Lane (1988) *Antibodies: A Laboratory Manual* ch. 14 (Cold Spring Harbor Laboratory, Cold Spring Harbor, N.Y.).

The invention also provides immunoconjugates comprising an anti-misfolded TDP-43 antibody provided herein conjugated to one or more therapeutic agents, such as chemotherapeutic agents or drugs, growth inhibitory agents, toxins (e.g., protein toxins, enzymatically active toxins of bacterial, fungal, plant, or animal origin, or fragments thereof), radioactive isotopes (i.e., a radioconjugate), blood brain barrier penetration moieties or detectable labels.

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, intravenous (IV) solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-TDP-43 antibody.

XI. Exemplary TDP-43 Specific Binding Molecules or Antibodies

In some embodiments, the antibody comprises VL-CDR1 comprising the amino acid sequence of SEQ ID NO: 12; VL-CDR2 comprising the amino acid sequence of SEQ ID NO: 14; VL-CDR3 comprising the amino acid sequence of SEQ ID NO: 16; VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26.

In some embodiments, the antibody comprises VL-CDR1 comprising the amino acid sequence of SEQ ID NO: 32; VL-CDR2 comprising the amino acid sequence of SEQ ID NO: 34; VL-CDR3 comprising the amino acid sequence of SEQ ID NO: 36; VH-CDR1 comprising the amino acid sequence of SEQ ID NO: 42; VH-CDR2 comprising the amino acid sequence of SEQ ID NO: 44; and VH-CDR3 comprising the amino acid sequence of SEQ ID NO: 46.

In some embodiments, the antibody comprises VL-CDR1 comprising the amino acid sequence of SEQ ID NO: 52; VL-CDR2 comprising the amino acid sequence of SEQ ID NO: 54; VL-CDR3 comprising the amino acid sequence of SEQ ID NO: 56; VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66.

In some embodiments, the antibody comprises VL-CDR1 comprising the amino acid sequence of SEQ ID NO: 72; VL-CDR2 comprising the amino acid sequence of SEQ ID NO: 74; VL-CDR3 comprising the amino acid sequence of SEQ ID NO: 76; VH-CDR1 comprising the amino acid sequence of SEQ ID NO: 82; VH-CDR2 comprising the amino acid sequence of SEQ ID NO: 84; and VH-CDR3 comprising the amino acid sequence of SEQ ID NO: 86.

In some embodiments, the antibody comprises VL-CDR1 comprising the amino acid sequence of SEQ ID NO: 92; VL-CDR2 comprising the amino acid sequence of SEQ ID NO: 94; VL-CDR3 comprising the amino acid sequence of SEQ ID NO: 96; VH-CDR1 comprising the amino acid sequence of SEQ ID NO: 102; VH-CDR2 comprising the amino acid sequence of SEQ ID NO: 104; and VH-CDR3 comprising the amino acid sequence of SEQ ID NO: 106.

In some embodiments, the antibody comprises VL-CDR1 comprising the amino acid sequence of SEQ ID NO: 112; VL-CDR2 comprising the amino acid sequence of SEQ ID NO: 114; VL-CDR3 comprising the amino acid sequence of SEQ ID NO: 116; VH-CDR1 comprising the amino acid sequence of SEQ ID NO: 122; VH-CDR2 comprising the amino acid sequence of SEQ ID NO: 124; and VH-CDR3 comprising the amino acid sequence of SEQ ID NO: 126.

In some embodiments, the antibody comprises VL-CDR1 comprising the amino acid sequence of SEQ ID NO: 132; VL-CDR2 comprising the amino acid sequence of SEQ ID NO: 134; VL-CDR3 comprising the amino acid sequence of SEQ ID NO: 136; VH-CDR1 comprising the amino acid sequence of SEQ ID NO: 142; VH-CDR2 comprising the amino acid sequence of SEQ ID NO: 144; and VH-CDR3 comprising the amino acid sequence of SEQ ID NO: 146.

In some embodiments, the antibody comprises VL-CDR1 comprising the amino acid sequence of SEQ ID NO: 152; VL-CDR2 comprising the amino acid sequence of SEQ ID NO: 154; VL-CDR3 comprising the amino acid sequence of SEQ ID NO: 156; VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166.

In some embodiments, the antibody comprises VL-CDR1 comprising the amino acid sequence of SEQ ID NO: 172; VL-CDR2 comprising the amino acid sequence of SEQ ID NO: 174; VL-CDR3 comprising the amino acid sequence of SEQ ID NO: 176; VH-CDR1 comprising the amino acid sequence of SEQ ID NO: 182; VH-CDR2 comprising the amino acid sequence of SEQ ID NO: 184; and VH-CDR3 comprising the amino acid sequence of SEQ ID NO: 186.

In some embodiments, the antibody comprises VL-CDR1 comprising the amino acid sequence of SEQ ID NO: 192; VL-CDR2 comprising the amino acid sequence of SEQ ID NO: 194; VL-CDR3 comprising the amino acid sequence of SEQ ID NO: 196; VH-CDR1 comprising the amino acid sequence of SEQ ID NO: 202; VH-CDR2 comprising the amino acid sequence of SEQ ID NO: 204; and VH-CDR3 comprising the amino acid sequence of SEQ ID NO: 206.

In some embodiments, the antibody comprises VL-CDR1 comprising the amino acid sequence of SEQ ID NO: 212; VL-CDR2 comprising the amino acid sequence of SEQ ID NO: 214; VL-CDR3 comprising the amino acid sequence of SEQ ID NO: 216; VH-CDR1 comprising the amino acid sequence of SEQ ID NO: 222; VH-CDR2 comprising the amino acid sequence of SEQ ID NO: 224; and VH-CDR3 comprising the amino acid sequence of SEQ ID NO: 226.

In some embodiments, the antibody comprises a Light Chain Variable Region (VL) comprising the sequence of SEQ ID NO: 10 and a Heavy Chain Variable Region (VH) comprising the sequence of SEQ ID NO: 20.

In some embodiments, the antibody comprises a Light Chain Variable Region (VL) comprising the sequence of SEQ ID NO: 30 and a Heavy Chain Variable Region (VH) comprising the sequence of SEQ ID NO: 40.

In some embodiments, the antibody comprises a Light Chain Variable Region (VL) comprising the sequence of SEQ ID NO: 50 and a Heavy Chain Variable Region (VH) comprising the sequence of SEQ ID NO: 60.

In some embodiments, the antibody comprises a Light Chain Variable Region (VL) comprising the sequence of SEQ ID NO: 70 and a Heavy Chain Variable Region (VH) comprising the sequence of SEQ ID NO: 80.

In some embodiments, the antibody comprises a Light Chain Variable Region (VL) comprising the sequence of SEQ ID NO: 90 and a Heavy Chain Variable Region (VH) comprising the sequence of SEQ ID NO: 100.

In some embodiments, the antibody comprises a Light Chain Variable Region (VL) comprising the sequence of SEQ ID NO: 110 and a Heavy Chain Variable Region (VH) comprising the sequence of SEQ ID NO: 120.

In some embodiments, the antibody comprises a Light Chain Variable Region (VL) comprising the sequence of SEQ ID NO: 130 and a Heavy Chain Variable Region (VH) comprising the sequence of SEQ ID NO: 140.

In some embodiments, the antibody comprises a Light Chain Variable Region (VL) comprising the sequence of SEQ ID NO: 150 and a Heavy Chain Variable Region (VH) comprising the sequence of SEQ ID NO: 160.

In some embodiments, the antibody comprises a Light Chain Variable Region (VL) comprising the sequence of SEQ ID NO: 170 and a Heavy Chain Variable Region (VH) comprising the sequence of SEQ ID NO: 180.

In some embodiments, the antibody comprises a Light Chain Variable Region (VL) comprising the sequence of SEQ ID NO: 190 and a Heavy Chain Variable Region (VH) comprising the sequence of SEQ ID NO: 200.

In some embodiments, the antibody comprises a Light Chain Variable Region (VL) comprising the sequence of SEQ ID NO: 210 and a Heavy Chain Variable Region (VH) comprising the sequence of SEQ ID NO: 220.

In some embodiments, the antibody comprises a Light Chain Variable Region (VL) comprising the sequence of SEQ ID NO: 230 and a Heavy Chain Variable Region (VH) comprising the sequence of SEQ ID NO: 232.

In some embodiments, the antibody comprises a Light Chain Variable Region (VL) comprising the sequence of SEQ ID NO: 234 and a Heavy Chain Variable Region (VH) comprising the sequence of SEQ ID NO: 236.

In some embodiments, the antibody comprises a Light Chain Variable Region (VL) comprising the sequence of SEQ ID NO: 238 and a Heavy Chain Variable Region (VH) comprising the sequence of SEQ ID NO: 240.

In some embodiments, the antibody comprises a Light Chain Variable Region (VL) comprising the sequence of SEQ ID NO: 242 and a Heavy Chain Variable Region (VH) comprising the sequence of SEQ ID NO: 244.

In some embodiments, the antibody comprises a Light Chain Variable Region (VL) comprising the sequence of SEQ ID NO: 246 and a Heavy Chain Variable Region (VH) comprising the sequence of SEQ ID NO: 248.

In some embodiments, the antibody comprises a Light Chain Variable Region (VL) comprising the sequence of SEQ ID NO: 250 and a Heavy Chain Variable Region (VH) comprising the sequence of SEQ ID NO: 252.

In some embodiments, the antibody comprises a Light Chain Variable Region (VL) comprising the sequence of SEQ ID NO: 254 and a Heavy Chain Variable Region (VH) comprising the sequence of SEQ ID NO: 256.

In some embodiments, the antibody comprises a Light Chain Variable Region (VL) comprising the sequence of SEQ ID NO: 258 and a Heavy Chain Variable Region (VH) comprising the sequence of SEQ ID NO: 260.

In some embodiments, an antibody is provided which binds to human TDP-43 within an epitope comprised in SEQ ID NO:4. In some particular embodiments, an isolated antibody that binds to human TDP-43 is provided, wherein the antibody binds an epitope within amino acids 215-222 (SEQ ID NO:5) of human TDP-43. In some embodiments an isolated antibody is provided that binds to misfolded TDP-43. In some embodiments, an isolated antibody that binds to human TDP-43 is provided, wherein the antibody binds extracellular or cytoplasmic TDP-43. In some embodiments an isolated antibody that binds to monomeric, oligomeric, or aggregated TDP-43. In some embodiments of the invention, the monomeric, oligomeric or aggregated TDP-43 is post-translationally modified, e.g. phosphorylated.

In some embodiments, the invention relates to an antibody selected from ACI-7062-401A2-Ab2, ACI-7062-404D6-Ab2, ACI-7062-406E3-Ab1, ACI-7062-406E3-Ab2, ACI-7062-410H3-Ab1, ACI-7062-412A7-Ab1, ACI-7062-412E12-Ab1, ACI-7062-414A5-Ab1, ACI-7062-415C4-Ab1, ACI-7062-415H10-Ab2, and ACI-7062-416A11-Ab1. In a preferred embodiment, the invention relates to an antibody selected from ACI-7062-401A2-Ab2, ACI-7062-406E3-Ab1, ACI-7062-406E3-Ab2, ACI-7062-410H3-Ab1, ACI-7062-412A7-Ab1, ACI-7062-412E12-Ab1, ACI-7062-414A5-Ab1, ACI-7062-415C4-Ab1 and ACI-7062-416A11-Ab1.

In some embodiments, an antibody generated by peptide sequence binds to the same epitope as an antibody selected from ACI-7062-401A2-Ab2, ACI-7062-404D6-Ab2, ACI-7062-406E3-Ab1, ACI-7062-406E3-Ab2, ACI-7062-410H3-Ab1, ACI-7062-412A7-Ab1, ACI-7062-412E12-Ab1, ACI-7062-414A5-Ab1, ACI-7062-415C4-Ab1, ACI-7062-415H10-Ab2, and ACI-7062-416A1 1-Ab1, preferably from ACI-7062-401A2-Ab2, ACI-7062-406E3-Ab1, ACI-7062-406E3-Ab2, ACI-7062-410H3-Ab1, ACI-7062-412A7-Ab1, ACI-7062-412E12-Ab1, ACI-7062-414A5-Ab1, ACI-7062-415C4-Ab1 and ACI-7062-416A11-Ab1. Antibodies binding the same epitope as any of the antibodies provided herein are also part of the invention.

In some embodiments, an isolated antibody is provided, wherein the isolated antibody has been generated with a peptide comprising SEQ ID NO: 2 and binds to the same epitope comprising the sequence SEQ ID NO: 4.

In some embodiments, an isolated antibody is provided, wherein the isolated antibody has been generated with a peptide comprising SEQ ID NO: 2 binds to the same epitope comprising the sequence SEQ ID NO: 5.

In some embodiments, an isolated nucleic acid is provided, wherein the isolated nucleic acid encodes an antibody described herein.

In some embodiments, an isolated nucleic acid is provided, wherein the isolated nucleic acid comprises SEQ ID NO:19 encoding an anti-TPD-43 antibody.

In some embodiments, an isolated nucleic acid is provided, wherein the isolated nucleic acid comprises SEQ ID NO:29 encoding an anti-TPD-43 antibody.

In some embodiments, an isolated nucleic acid is provided, wherein the isolated nucleic acid comprises SEQ ID NO:39 encoding an anti-TPD-43 antibody.

In some embodiments, an isolated nucleic acid is provided, wherein the isolated nucleic acid comprises SEQ ID NO:49 encoding an anti-TPD-43 antibody.

In some embodiments, an isolated nucleic acid is provided, wherein the isolated nucleic acid comprises SEQ ID NO:59 encoding an anti-TPD-43 antibody.

In some embodiments, an isolated nucleic acid is provided, wherein the isolated nucleic acid comprises SEQ ID NO:69 encoding an anti-TPD-43 antibody.

In some embodiments, an isolated nucleic acid is provided, wherein the isolated nucleic acid comprises SEQ ID NO:79 encoding an anti-TPD-43 antibody.

In some embodiments, an isolated nucleic acid is provided, wherein the isolated nucleic acid comprises SEQ ID NO:89 encoding an anti-TPD-43 antibody.

In some embodiments, an isolated nucleic acid is provided, wherein the isolated nucleic acid comprises SEQ ID NO:99 encoding an anti-TPD-43 antibody.

In some embodiments, an isolated nucleic acid is provided, wherein the isolated nucleic acid comprises SEQ ID NO:109 encoding an anti-TPD-43 antibody.

In some embodiments, an isolated nucleic acid is provided, wherein the isolated nucleic acid comprises SEQ ID NO:119 encoding an anti-TPD-43 antibody.

In some embodiments, an isolated nucleic acid is provided, wherein the isolated nucleic acid comprises SEQ ID NO:129 encoding an anti-TPD-43 antibody.

In some embodiments, an isolated nucleic acid is provided, wherein the isolated nucleic acid comprises SEQ ID NO:139 encoding an anti-TPD-43 antibody.

In some embodiments, an isolated nucleic acid is provided, wherein the isolated nucleic acid comprises SEQ ID NO:149 encoding an anti-TPD-43 antibody.

In some embodiments, an isolated nucleic acid is provided, wherein the isolated nucleic acid comprises SEQ ID NO:159 encoding an anti-TPD-43 antibody.

In some embodiments, an isolated nucleic acid is provided, wherein the isolated nucleic acid comprises SEQ ID NO:169 encoding an anti-TPD-43 antibody.

In some embodiments, an isolated nucleic acid is provided, wherein the isolated nucleic acid comprises SEQ ID NO:179 encoding an anti-TPD-43 antibody.

In some embodiments, an isolated nucleic acid is provided, wherein the isolated nucleic acid comprises SEQ ID NO:189 encoding an anti-TPD-43 antibody.

In some embodiments, an isolated nucleic acid is provided, wherein the isolated nucleic acid comprises SEQ ID NO:199 encoding an anti-TPD-43 antibody.

In some embodiments, an isolated nucleic acid is provided, wherein the isolated nucleic acid comprises SEQ ID NO:209 encoding an anti-TPD-43 antibody.

In some embodiments, an isolated nucleic acid is provided, wherein the isolated nucleic acid comprises SEQ ID NO:219 encoding an anti-TPD-43 antibody.

In some embodiments, an isolated nucleic acid is provided, wherein the isolated nucleic acid comprises SEQ ID NO:229 encoding an anti-TPD-43 antibody.

In some embodiments, an isolated nucleic acid is provided, wherein the isolated nucleic acid comprises SEQ ID NO:231 encoding an anti-TPD-43 antibody.

In some embodiments, an isolated nucleic acid is provided, wherein the isolated nucleic acid comprises SEQ ID NO:233 encoding an anti-TPD-43 antibody.

In some embodiments, an isolated nucleic acid is provided, wherein the isolated nucleic acid comprises SEQ ID NO:235 encoding an anti-TPD-43 antibody.

In some embodiments, an isolated nucleic acid is provided, wherein the isolated nucleic acid comprises SEQ ID NO:237 encoding an anti-TPD-43 antibody.

In some embodiments, an isolated nucleic acid is provided, wherein the isolated nucleic acid comprises SEQ ID NO:239 encoding an anti-TPD-43 antibody.

In some embodiments, an isolated nucleic acid is provided, wherein the isolated nucleic acid comprises SEQ ID NO:241 encoding an anti-TPD-43 antibody.

In some embodiments, an isolated nucleic acid is provided, wherein the isolated nucleic acid comprises SEQ ID NO:243 encoding an anti-TPD-43 antibody.

In some embodiments, an isolated nucleic acid is provided, wherein the isolated nucleic acid comprises SEQ ID NO:245 encoding an anti-TPD-43 antibody.

In some embodiments, an isolated nucleic acid is provided, wherein the isolated nucleic acid comprises SEQ ID NO:247 encoding an anti-TPD-43 antibody.

In some embodiments, an isolated nucleic acid is provided, wherein the isolated nucleic acid comprises SEQ ID NO:249 encoding an anti-TPD-43 antibody.

In some embodiments, an isolated nucleic acid is provided, wherein the isolated nucleic acid comprises SEQ ID NO:251 encoding an anti-TPD-43 antibody.

In some embodiments, an isolated nucleic acid is provided, wherein the isolated nucleic acid comprises SEQ ID NO:253 encoding an anti-TPD-43 antibody.

In some embodiments, an isolated nucleic acid is provided, wherein the isolated nucleic acid comprises SEQ ID NO:255 encoding an anti-TPD-43 antibody.

In some embodiments, an isolated nucleic acid is provided, wherein the isolated nucleic acid comprises SEQ ID NO:257 encoding an anti-TPD-43 antibody.

In some embodiments, an isolated nucleic acid is provided, wherein the isolated nucleic acid comprises SEQ ID NO:259 encoding an anti-TPD-43 antibody.

In some embodiments, an isolated nucleic acid is provided, wherein the isolated nucleic acid comprises SEQ ID NO:261 encoding an anti-TPD-43 antibody.

In some embodiments, a host cell is provided, wherein the host cell comprises an isolated nucleic acid that encodes an antibody described herein. In some embodiments, a method of producing an antibody is provided, comprising culturing the host cell under conditions suitable for producing the antibody.

In some embodiments the misfolded TDP-43 specific antibody comprises an amino acid sequence having a sequence homology of 70%, 80% 90%, 95%, 96%, 97% 98% or 99% with any of the antibodies provided herein.

In some embodiments the TDP-43 specific binding molecule has a sequence homology of 86% or more compared with the Light Chain Variable Region sequences (VL) comprising the sequence selected from the group of SEQ ID NO: 10; SEQ ID NO: 30; SEQ ID NO: 50; SEQ ID NO: 70; SEQ ID NO: 90; SEQ ID NO: 110; SEQ ID NO: 130; SEQ ID NO: 150; SEQ ID NO: 170; SEQ ID NO: 190; SEQ ID NO: 210; SEQ ID NO: 230; SEQ ID NO: 234; SEQ ID NO: 238; SEQ ID NO: 242; SEQ ID NO: 246; SEQ ID NO: 250; SEQ ID NO: 254; and SEQ ID NO: 258.

In some embodiments the TDP-43 specific binding molecule has a sequence homology of 86% or more compared with the Heavy Chain Variable Region (VH) comprising the sequence selected from the group of SEQ ID NO: 20; SEQ ID NO: 40; SEQ ID NO: 60; SEQ ID NO: 80; SEQ ID NO: 100; SEQ ID NO: 120; SEQ ID NO: 140; SEQ ID NO: 160; SEQ ID NO: 180; SEQ ID NO: 200; SEQ ID NO: 220; SEQ ID NO: 232; SEQ ID NO: 236; SEQ ID NO: 240; SEQ ID NO: 244; SEQ ID NO: 248; SEQ ID NO: 252; SEQ ID NO: 256; and SEQ ID NO: 260.

In some embodiments the TDP-43 specific binding molecule has a dissociation constant (KD) of ≥1 µM, ≥100 nM, ≥10 nM, ≥1 nM, ≥0.1 nM, ≥0.01 nM, or ≥0.001 nM (e.g. 10-8 M or less, e.g. from 10-8 M to 10-13 M, e.g., from 10-9 M to 10-13 M).

In some embodiments the TDP-43 specific binding molecule or the anti-TDP-43 antibody binds each of monomeric TDP-43, phosphorylated TDP-43, non-phosphorylated TDP-43, aggregated TDP-43, and oligomeric TDP-43 with a KD of less than 100 nM, less than 10 nM, less than 1 nM, less than 200 µM, less than 100 µM, or less than 10 µM.

XII. Compositions and Methods

In some embodiments, an immunoconjugate is provided, wherein the immunoconjugate comprises an isolated antibody described herein and a therapeutic agent. In some embodiments, a labeled antibody is provided, comprising an antibody described herein and a detectable label.

In some embodiments, a pharmaceutical composition is provided, comprising an isolated antibody described herein and a pharmaceutically acceptable carrier.

In some embodiments the TDP-43 specific binding molecule of the present invention is linked to a detectable label.

In some embodiments the TDP-43 specific binding molecule is part of an immunoconjugate wherein the TDP-43 specific binding molecule is covalently linked to another suitable therapeutic agent.

In some embodiments the TDP-43 specific binding molecule or the immunoconjugate comprising it is present as a composition comprising a TDP-43 specific binding molecule and a TDP-43 agonists and cognate molecules, or alternately, antagonists of the same.

In some embodiments the TDP-43 specific binding molecule is part of pharmaceutical composition comprising a TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same combined with a pharmaceutically acceptable carrier.

In some embodiments the TDP-43 specific binding molecule is part of a diagnostic kit comprising a TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same.

In some embodiments the TDP-43 specific binding molecule is used in an immunodiagnostic method for use in the prevention, diagnosis or treatment of a TDP-43 proteinopathy.

In some embodiments the TDP-43 specific binding molecule is part of an immunotherapeutic method for the prevention, or treatment of a TDP-43 proteinopathy, wherein an effective amount of the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof.

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof is used to diagnose, prevent, alleviate or treat a disorder or abnormality associated with TDP-43 aggregates including but not limited to frontotemporal dementia (FTD), amyotrophic lateral sclerosis (ALS), Alzheimer's disease (AD) and Parkinson's disease (PD).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof is used in a method for diagnosing or monitoring a disorder or abnormality associated with TDP-43 aggregates selected from Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

In some embodiments the TDP-43 specific binding molecule is used in a method for diagnosing presymptomatic disease or for monitoring disease progression and therapeutic efficacy, or for predicting responsiveness, or for selecting patients which are likely to respond to the treatment with a TDP-43 specific binding molecule. Said method is preferably performed using a sample of human blood or urine. Most preferably the method involves an ELISA-based or surface adapted assay.

In some embodiments the TDP-43 specific binding molecule is used in a method wherein a TDP-43 specific binding molecule of the present invention is contacted with a sample (e.g., blood, cerebrospinal fluid, or brain tissue) to detect, diagnose or monitor frontotemporal degeneration (FTD) or amyotrophic lateral sclerosis (ALS) Alzheimer's disease (AD) and Parkinson's disease (PD).

In some embodiments the TDP-43 specific binding molecule is used in a method wherein a TDP-43 specific binding molecule of the present invention is contacted with a sample (e.g., blood, cerebrospinal fluid, or brain tissue) to detect, diagnose or a disease selected from Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof is used for preventing, alleviating or treating a disorder or abnormality associated with TDP-43 aggregates or TDP-43 proteinopathies or frontotemporal degeneration (FTD) or amyotrophic lateral sclerosis (ALS), Alzheimer's disease (AD, sporadic and familial), and Parkinson's disease (PD).

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof is used for treating a disease selected from: Frontotemporal dementia (Sporadic or familial with or without motor-neuron disease (MND), with progranulin (GRN) mutation, with TARDBP mutation, with valosine-containing protein (VCP) mutation, linked to chromosome 9p, corticobasal degeneration, frontotemporal lobar degeneration with ubiquitin-positive inclusions, Argyrophilic grain disease, Pick's disease and the like), Amyotrophic lateral sclerosis (Sporadic ALS, with TARDBP mutation, with angiogenin (ANG) mutation), Alzheimer's disease (AD, sporadic and familial), Down syndrome, Familial British dementia, Polyglutamine diseases (Huntington's disease and spinocerebellar ataxia type 3 (SCA3; also known under Machado Joseph Disease)), Hippocampal sclerosis dementia and Myopathies (Sporadic inclusion body myositis, Inclusion body myopathy with a mutation in the valosin-containing protein (VCP; also Paget disease of bone and frontotemporal dementia), Oculo-pharyngeal muscular dystrophy with rimmed vacuoles, Myofibrillar myopathies with mutations in the myotilin (MYOT) gene or mutations in the gene coding for desmin (DES)). Preferably said disease treatment helps to retain or increase mental recognition and or reduces the level of TDP-43 aggregates in the brain.

In some embodiments the TDP-43 specific binding molecule, or an immunoconjugate wherein the TDP-43 specific binding molecule is covalently linked to another suitable therapeutic agent, or a composition comprising a TDP-43 specific binding molecule and a TDP-43 agonists and cognate molecules, or alternately, antagonists of the same is administered to a patient in need thereof is used for manufacturing a medicament for treating a disorder or abnormality associated with TDP-43 aggregates or TDP-43 proteinopathies or frontotemporal degeneration (FTD) or amyotrophic lateral sclerosis (ALS), Alzheimer's disease (AD, sporadic and familial), and Parkinson's disease (PD).

Pharmaceutical formulations of an anti-misfolded TDP-43 antibody or immunoconjugate as described herein are prepared by mixing such antibody or immunoconjugate having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules. The formulations to be used for in vivo administration are generally sterile. Sterility may be readily accomplished, e.g., by filtration through sterile filtration membranes.

Any of the antigen-binding molecules, anti-misfolded TDP-43 antibodies or immunoconjugates provided herein may be used in methods, e.g., therapeutic methods.

In another aspect, an anti-misfolded TDP-43 antibody or immunoconjugate for use as a medicament is provided. In further aspects, an anti-misfolded TDP-43 antibody or immunoconjugate for use in a method of treatment is provided. In certain embodiments, an anti-misfolded TDP-43 antibody or immunoconjugate for use in the prevention, diagnosis and/or treatment of a TDP-43 proteinopathy is provided. In a preferred embodiment of the invention, an anti-misfolded TDP-43 antibody or immunoconjugate is provided for use in the prevention, diagnosis and/or treatment of a TDP-43 associated disorder or abnormality associated with TDP-43 aggregates including but not limited to frontotemporal dementia (FTD), amyotrophic lateral sclerosis (ALS), Alzheimer's disease (AD) and/or Parkinson's disease (PD).

In a further aspect, the invention provides for the use of an anti-misfolded TDP-43 antibody or immunoconjugate in the manufacture or preparation of a medicament. In one such embodiment, the method further comprises administering to the individual an effective amount of at least one additional therapeutic agent, e.g., as described below.

A "subject" or an "individual" or a "patient" according to any of the above embodiments may be an animal, a mammal, preferably a human.

In a further aspect, the invention provides pharmaceutical formulations comprising any of the anti-misfolded TDP-43 antibodies or immunoconjugate provided herein, e.g., for use in any of the above therapeutic methods. In one embodiment, a pharmaceutical formulation comprises any of the anti-misfolded TDP-43 antibodies or immunoconjugates provided herein and a pharmaceutically acceptable carrier. In another embodiment, a pharmaceutical formulation comprises any of the anti-misfolded TDP-43 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-misfolded TDP-43 antibody.

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In a further embodiment, the invention relates to a method of retaining or increasing cognitive memory capacity, movement and language function or preventing and/or slowing decline of cognitive memory capacity, movement and language function in a subject, comprising administering the binding molecule of the invention, the immunoconjugate of the invention, the composition of the invention or the pharmaceutical composition of the invention.

In a further embodiment, the invention relates to a method of reducing the level of misfolded TDP-43, comprising administering the binding-molecule of the invention, the immunoconjugate of the invention, the composition of the invention or the pharmaceutical composition of the invention.

The methods of the invention may comprise administering at least one additional therapy, preferably wherein the additional therapy is selected from, but not limited to, neurological drugs, anti-abeta antibodies, anti-Tau antibodies, Tau aggregation inhibitors, beta-amyloid aggregation inhibitors, anti-BACE1 antibodies, and BACE1 inhibitors.

The invention furthermore relates to a method of detecting misfolded TDP-43, comprising contacting a sample with the binding molecule of the invention, preferably wherein the sample is a brain sample, a cerebrospinal fluid sample, urine sample or a blood sample.

EXAMPLES

Figure 1:
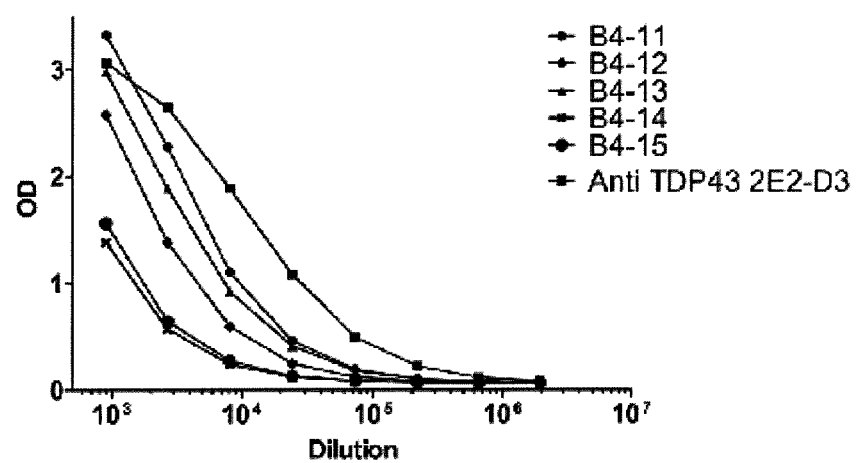
FIG. 1. Vaccine response measured in plasma. Binding to recombinant FL TDP-43 for the antibodies present in plasma from immunized mice at day 81 after first immunization was determined using an indirect ELISA. Serial dilution of plasma was used. Results are expressed in optical densities (O.D.). Each curve represents results from an individual mouse.
Figure 1:
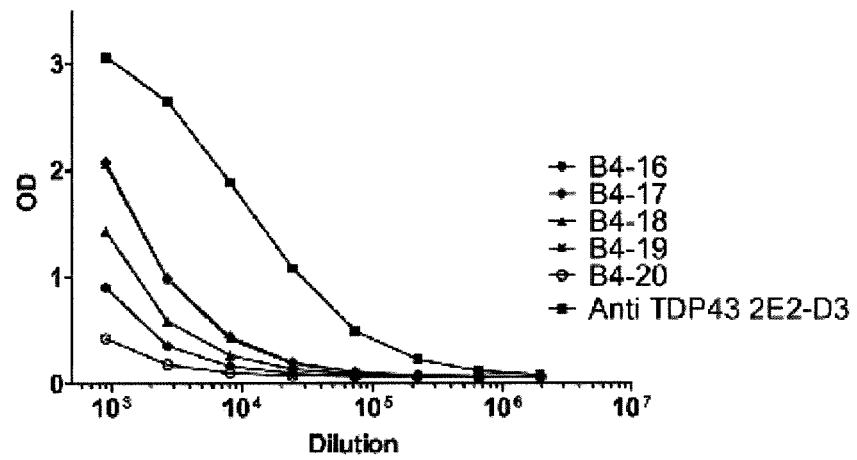

1. Example 1: Preparation of a TDP-43 Vaccine Composition

The liposome-based antigenic constructs were prepared according to the protocols published in WO2012/055933. The liposomal vaccine with TDP-1 peptide as antigen was used for antibody generation. Briefly, DMPC, DMPG lipids (both by Lipoid AG, Switzerland), cholesterol and monophosphoryl hexa-acyl Lipid A 3-deacyl synthetic (3D-(6-acyl) PHAD® (Avanti Polar Lipids, AL, USA) at a molar ratio 9:1:7:0.05, respectively, were solubilized in EtOH at 60° C. for 30 min. An identical batch was additionally manufactured but without adjuvant for boost vaccinations. Multilamellar liposomes were extruded (EmulsiFlex-C5, Avestin, Germany) through polycarbonate Whatman filters with a pore size of 0.08 µm. TDP-1 peptide used as the antigen was conjugated to liposomes using cysteine-maleimide coupling. The TDP-1 peptide was reduced with TCEP (Sigma-Aldrich, Switzerland) at a TCEP/peptide molar ratio of 100:1 for 30 min at room temperature. The TDP-1 was further coupled to DSPEPEG(2000)maleimide lipid (Avanti Polar Lipids) at a lipid/protein molar ratio of 30:1 at ambient temperature for 4 hours. The coupled product was incubated with preformed liposomes for 15 hours at 37° C. Liposomes were further subjected to ultrafiltration and diafiltration in PBS pH 7.4, sterile filtered by passing through 0.2 µm polyethersulfone (PES) membrane syringe filters, and stored at 5° C. until administration.

TABLE 3

TDP-43 protein and peptide antigen description

| SEQ ID NO | Definition | Amino acid sequence (1-letter code) |
|---|---|---|
| SEQ ID NO: 1 | Q13148<br>TADBP_HUMAN<br>TAR DNA-binding<br>protein 43<br>aa 1-414 | MSEYIRVTEDENDEPIEIPSEDDGTVLLSTVTAQFPGAC<br>GLRYRNPVSQCMRGVRLVEGILHAPDAGWGNLVYVV<br>NVPKDNKRKMDETDASSAVKVKRAVQKTSDLIVLGL<br>PWKTTEQDLKEYFSTFGEVLMVQVKKDLKTGHSKGF<br>GFVRFTEYETQVKVMSQRHMIDGRWCDCKLPNSKQS<br>QDEPLRSRKVFVGRCTEDMTEDELREFESQYGDVMDV<br>FIPKPFRAFAFVTFADDQIAQSLCGEDLIIKGISVHISNA<br>EPKHNSNRQLERSGRFGGNPGGFGNQGGFGNSRGGG<br>AGLGNNQGSNMGGGMNFGAFSINPAMMAAAQAALQ<br>SSWGMMGMLASQQNQSGPSGNNQNQGNMQREPNQA<br>FGSGNNSYSGSNSGAAIGWGSASNAGSGSGFNGGFGS<br>SMDSKSSGWGM |
| SEQ ID NO: 2 | TDP-1<br>aa 212-272 (61 aa) | SQYGDVMDVFIPKPFRAFAFVTFADDQIAQSLCGEDLII<br>KGISVHISNAEPKHNSNRQLER |
| SEQ ID NO: 3 | TDP-3<br>aa 310-370 (61 aa) | CGMNFGAFSINPAMMAAAQAALQSSWGMMGMLASQ<br>QNQSGPSGNNQNQGNMQREPNQAFGSG |

II. Example 2: Generation of Anti-TDP-43 Antibodies

A. Mouse Immunization

Female C57BL/6JOlaHsd (C57BL/6) and BALB/c OlaHsd (BALB/c) wild-type mice (Harlan, USA) were received at 9 weeks of age. Vaccinations started at 10 weeks. Mice were vaccinated with TDP-1 peptide (198 µg/ml) presented on the surface of liposomes in the presence of MPLA as adjuvant (97 µg/ml).

Mice were vaccinated by subcutaneous injection (s.c.) on days 0, 4, 8, 22, 36, and 62. Mice were bled and heparinized plasma prepared 7 days before immunization (pre-immune plasma) and on days 15, 29, 43 and 81 after first immunization. Mice used for myeloma fusion were additionally vaccinated with three daily booster injections of TDP-1 per i.p. injection without adjuvant.

TABLE 4

Mice and vaccination protocols

| Study group | Mouse strain | TDP-1 µg/injection | Adjuvant | Vaccination route |
|---|---|---|---|---|
| C | C57BL/6 | 39.6 | MPLA | s.c. |
| D | BALB/C | 39.6 | MPLA | s.c. |

B. Quantification of Antigen-Specific Antibodies after Immunization

Antigen-specific IgG responses were determined by ELISA. Briefly, plates were coated with 1 µg/mL of recombinant human full-length TDP-43 (recFL TDP-43) in carbonate buffer overnight at 4° C. After washing with PBS-0.05% Tween 20 and blocking with 1% BSA, serial dilutions of plasma were added to the plates and incubated at 37° C. for two hours. As a positive control a commercial mouse monoclonal antibody 2E2-D3 (Abcam) was used. After washing, plates were incubated with alkaline phosphatase (AP) conjugated anti-mouse IgG antibody (Jackson Immunoresearch, Lot 123565, diluted at 1/1000) for 1 hour at 37° C. After a final wash, plates were incubated for 30 min, 1 hour or 2 hours with AP substrate (p-nitrophenyl phosphate disodium hexahydrate; pNPP) and read at 405 nm using an ELISA plate reader. Results (FIG. 1) are expressed as optical density (O.D).

C. Generation of Hybridomas and Selection for Subcloning

Figure 2:
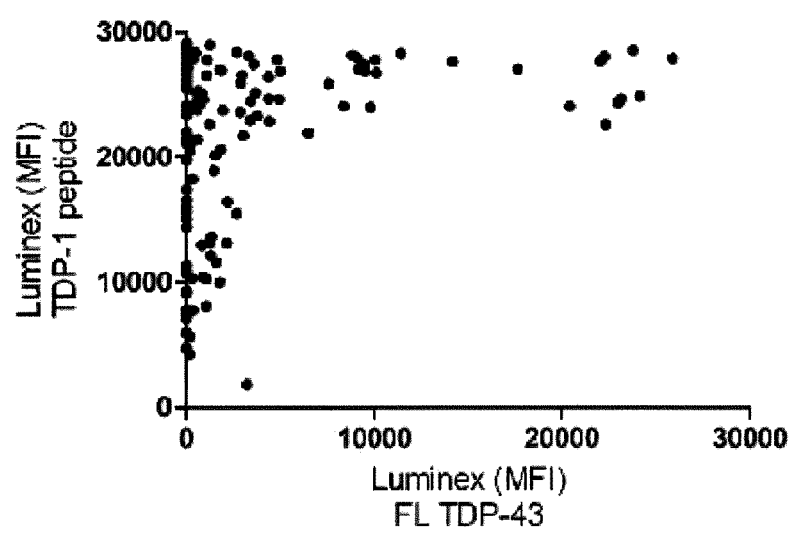
FIG. 2. Screening of hybridomas. Binding of antibodies from hybridomas from fusions of a BALB/c mouse was evaluated in Luminex multiplex assay on FL TDP-43 and on TDP-1 peptide. Data are presented as a correlation of binding of antibodies to two targets using a Luminex multiplex assay and shown as mean fluorescence intensity (MFI).

Mice were euthanized and fusion with myeloma cells was performed using splenocytes from two individual mice. For screening fusion products, a 1:32 supernatant dilution was analysed using Luminex bead-based multiplex assay (Luminex, The Netherlands). Luminex beads were conjugated to FL TDP-43, TDP-1 peptide, or TDP-3 peptide (irrelevant target), and with capturing IgGs with anti-mouse IgG-Fc antibodies specific for the IgG1, IgG2a, IgG2b, IgG2c, and IgG3 subclasses (Jackson Immunoresearch, USA). Binding to beads conjugated to FL TDP-43 and to TDP-1 peptide identified 153 hits derived from mouse from group D (BALB/C) (FIG. 2).

Viable hybridomas were grown using serum-containing selection media, and the best hybridomas binding to both targets were then selected for subcloning. Following limiting dilution, the clonal hybridomas were grown in low immunoglobin containing medium and stable colonies were selected for antibody screening and selection. Antibodies shown in table 4 were identified from this screen.

III. Example 3: Determination of Binding Affinity (EC50)

Figure 3:
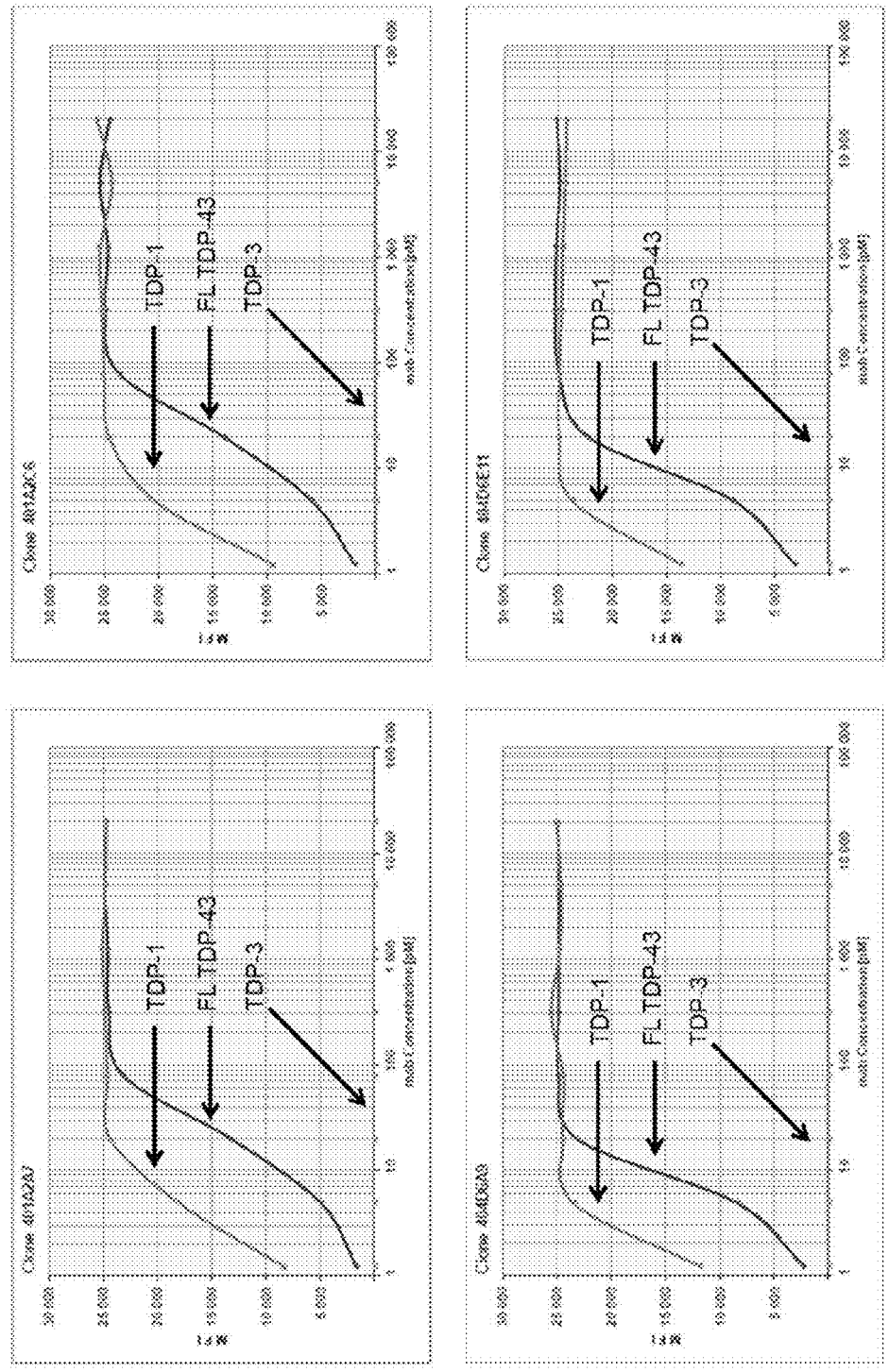
FIG. 3. Determination of binding affinity (EC50) for human FL TDP-43. Binding affinity (EC50) for human FL TDP-43, TDP-1 peptide and irrelevant TDP-3 peptide was determined in Luminex assay. Data are presented as mean fluorescence intensity (MFI).

Luminex assays with serial dilution of antibodies were performed as described before to determine half maximal effective concentration (EC50) of binding of antibodies to FL TDP-43, TDP-1 peptide or TDP-3 peptide (irrelevant target). Results for a subset of antibodies are shown in FIG. 3. EC50 values are shown in Table 5. All tested antibodies bind to full length TDP-43 and to TDP-1 peptide with high affinity (no binding was observed to unrelated TDP-3 peptide).

TABLE 5

EC50 values by Luminex Assay

Figure 5A:
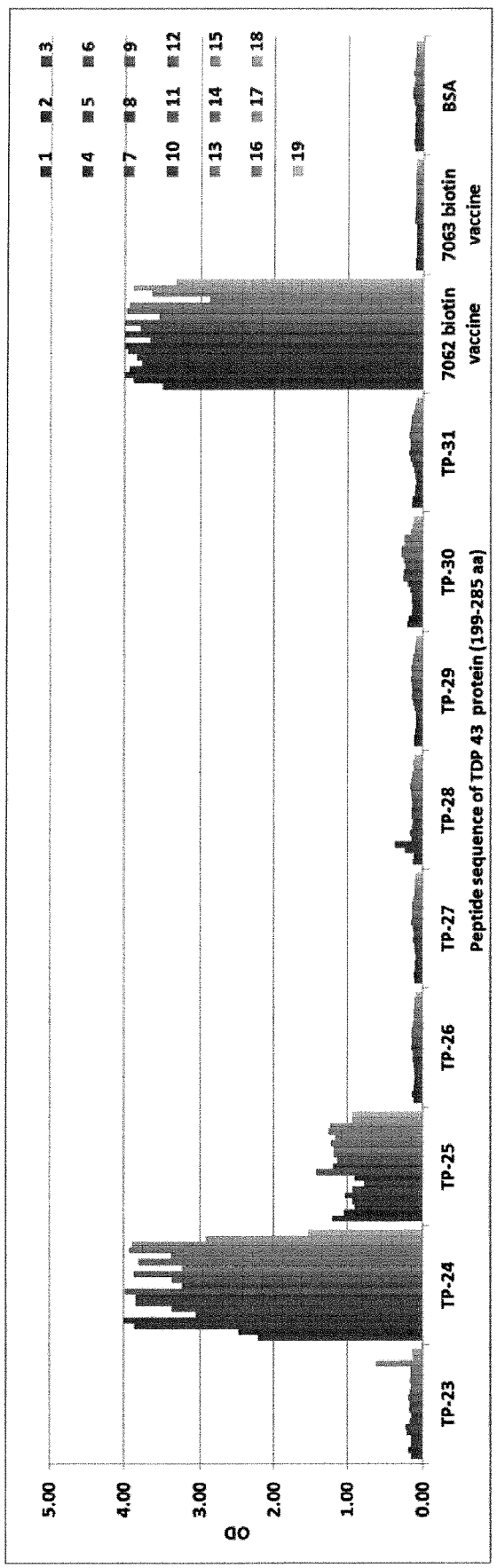
FIG. 5. Epitope mapping for the antibodies derived from stable hybridoma clones was determined using an indirect ELISA on a library of 15-mer peptides covering the sequence of human TDP-43 from 199 to 285 (A), and a library of 8-mer peptides covering the sequence of human TDP-43 from 210 to 231 (B). Results are expressed as optical density (O.D.). Each bar represents data for individual antibody. Same naming as in Table 5 is used. The 2E2-D3 antibody was used as a control.
Figure 5B:
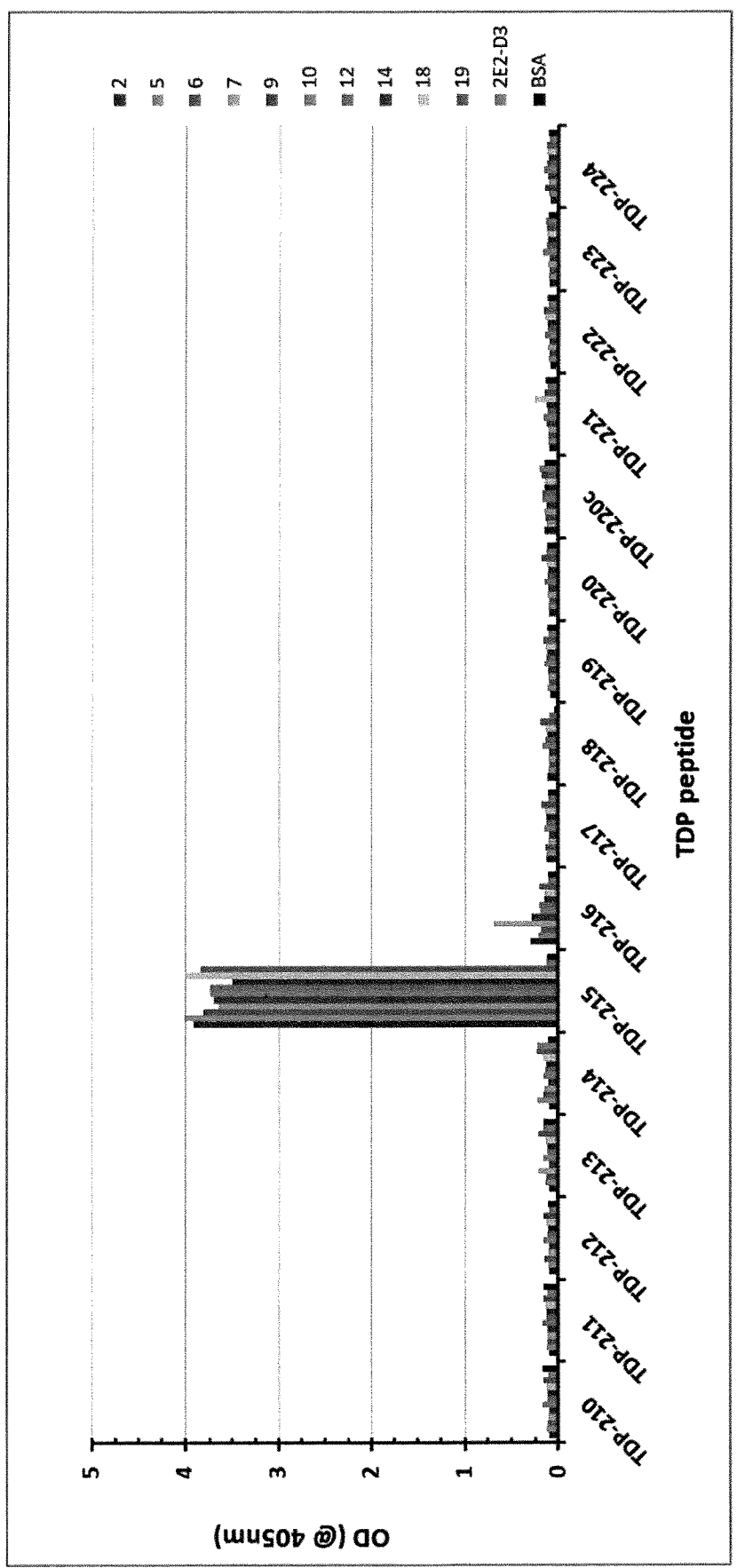
Figure 6:
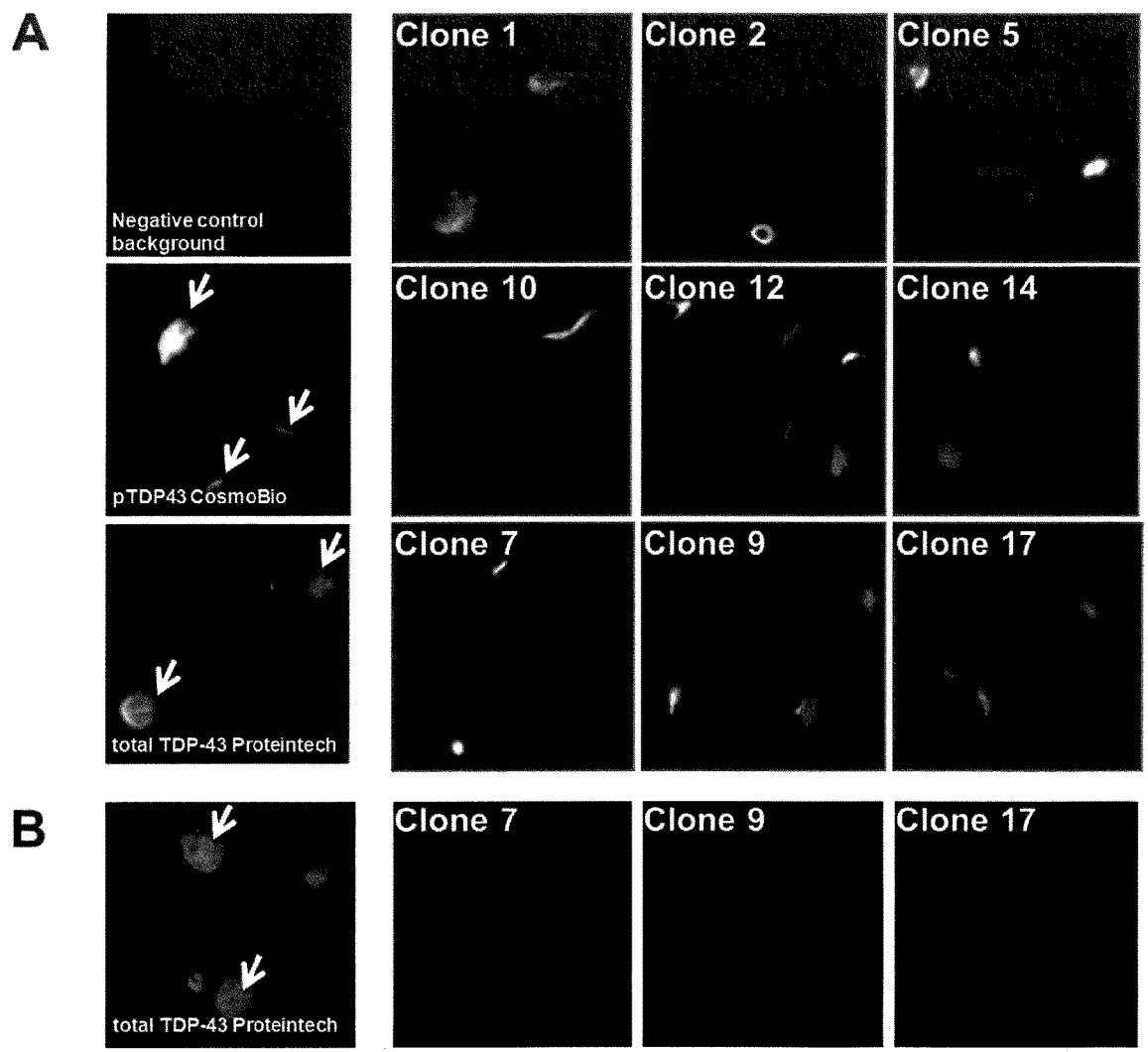
FIG. 6. Detection of TDP-43 in tissues from FTD type A/C patient. Immunohistochemistry was performed on 10 µm thick frozen sections from frontal cortex of an FTD patient with type A/C pathology (A) and on brain sections from an age-matched control donor (B) using fluorescent secondary antibody detection. Antibodies of the present invention specifically bind to misfolded, aggregated TDP-43 in the cytoplasm in Type A pathology and do not bind to physiological nuclear TDP-43 in patient nor in control brains. The following antibodies were used as controls: rabbit polyclonal pan TDP-43 antibody (Proteintech, 10782-2-AP) to detect pathological inclusions and physiological nuclear TDP-43; rabbit monoclonal phospho TDP-43 p409/410 antibody (Cosmobio, TIP-TD-P02) to detect pathological aggregated and phosphorylated TDP-43.

| Clone numbers used in FIGS. 5 and 6 | Hybridoma Clone | Antibody name | Isotype | EC50 (pM) TDP-43 protein | EC50 (pM) TDP-1 peptide | EC50 (pM) TDP-3 peptide |
|---|---|---|---|---|---|---|
| 1 | 401A2A7 | ACI-7062-401A2-Ab1 | IgG1, kappa | 20 | <10 | no binding |
| 2 | 401A2C6 | ACI-7062-401A2-Ab2 | IgG1, kappa | 15 | <10 | no binding |
| 3 | 404D6A9 | ACI-7062-404D6-Ab1 | IgG3, kappa | <10 | <10 | no binding |
| 4 | 404D6E11 | ACI-7062-404D6-Ab2 | IgG3, kappa | <10 | <10 | no binding |
| 5 | 406E3D5 | ACI-7062-406E3-Ab1 | IgG2a, kappa | <10 | <10 | no binding |
| 6 | 406E3G10 | ACI-7062-406E3-Ab2 | IgG2a, kappa | 10 | <10 | no binding |
| 7 | 410H3B9 | ACI-7062-410H3-Ab1 | IgG1, kappa | 30 | <10 | no binding |
| 8 | 410H3G7 | ACI-7062-410H3-Ab2 | IgG1, kappa | 25 | <10 | no binding |
| 9 | 412A7B7 | ACI-7062-412A7-Ab1 | IgG2b, kappa | 30 | <10 | no binding |
| 10 | 412E12A2 | ACI-7062-412E12-Ab1 | IgG1, kappa | 20 | <10 | no binding |
| 11 | 412E12F8 | ACI-7062-412E12-Ab2 | IgG1, kappa | 25 | <10 | no binding |
| 12 | 414A5D2 | ACI-7062-414A5-Ab1 | IgG2a, kappa | 100 | <10 | no binding |
| 13 | 414A5H4 | ACI-7062-414A5-Ab2 | IgG2a, kappa | 115 | <10 | no binding |
| 14 | 415C4C6 | ACI-7062-415C4-Ab1 | IgG1, kappa | <10 | <10 | no binding |
| 15 | 415C4F11 | ACI-7062-415C4-Ab2 | IgG1, kappa | <10 | <10 | no binding |
| 16 | 415H10A1 | ACI-7062-415H10-Ab1 | IgG3, kappa | 180 | <10 | no binding |
| 17 | 415H10B7 | ACI-7062-415H10-Ab2 | IgG3, kappa | 160 | <10 | no binding |
| 18 | 416A11B3 | ACI-7062-416A11-Ab1 | IgG2a, kappa | 15 | <10 | no binding |
| 19 | 416A11G11 | ACI-7062-416A11-Ab2 | IgG2a, kappa | 15 | <10 | no binding |

IV. Example 4: Antibody Binding to Human FL TDP-43

Figure 4:
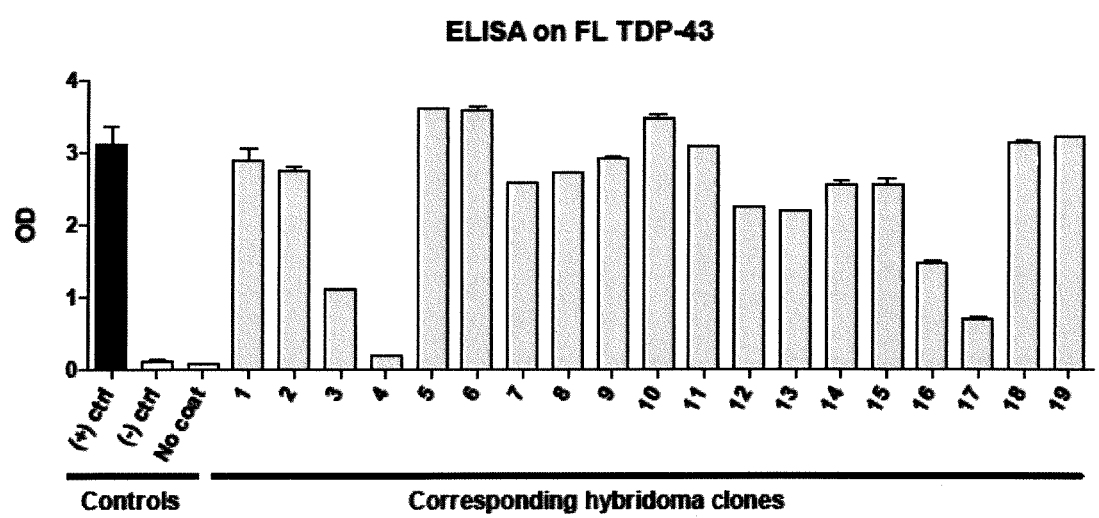
FIG. 4. Antibody binding to human FL TDP-43. Binding to recombinant FL TDP-43 for the antibodies derived from stable hybridoma clones was determined using an indirect ELISA. Results are expressed in optical densities (O.D.). Commercial antibody 2E2-D3 was used as a positive control (+); no sample was used as negative control (−). Same naming as in Table 5 is used.

Antibody binding to human FL TDP-43 was determined using an indirect ELISA. Coating was done overnight in carbonate buffer at 4° C. Plates were washed thoroughly with 0.05% Tween-20/PBS and then blocked with 1% bovine serum albumin (BSA) in 0.05% Tween-20/PBS for 1 hours at 37° C. The antibody contained in the hybridoma supernatant was then added at 1 µg/ml, and incubated for 2 hours at 37° C. after which the plates were washed as described previously. An AP-conjugated anti-mouse IgG secondary antibody (Jackson Immunoresearch Laboratories, United Kingdom) was added at 1/1000 dilution in 0.05% Tween-20/PBS for 1 hour at 37° C. After the final wash, plates were incubated with pNPP (Sigma-Aldrich, Switzerland) phosphatase substrate solution, and read at 405 nm using an ELISA plate reader (Tecan, Switzerland; FIG. 4). All tested clones bind to full length TDP-43 with different affinities.

V. Example 5: Epitope Mapping

Serum-free supernatants were harvested from stable hybridomas. The supernatants containing antibodies of interest were then screened by an indirect ELISA assay to determine epitopes. Epitopes were mapped using a library of TDP-43 15-mer peptides. Briefly, 96-well streptavidin-coated 96-well ELISA plates were incubated with 5 µg/mL of biotinylated 15-mer peptides spanning the amino acids (aa) 199-285 of human TDP-43 with 9 aa offset and 6 aa overlap. Peptide sequences are provided in Table 5. Plates were washed thoroughly with 0.05% Tween-20/PBS and then blocked with 1% bovine serum albumin (BSA) in 0.05% Tween-20/PBS for 1 hour at 37° C. The antibody contained in the hybridoma supernatant was then added at the indicated dilutions, and incubated for 2 hours at 37° C. after which the plates were washed as described previously. An AP-conjugated anti-mouse IgG secondary antibody (Jackson ImmunoResearch Laboratories, United Kingdom) was added at 1/1000 dilution in 0.05% Tween-20/PBS for 1 hour at 37° C. After the final wash, plates were incubated with pNPP (Sigma-Aldrich, Switzerland) an AP substrate solution, and read at 405 nm using an ELISA plate reader (Tecan). Results are shown in FIG. 5A and OD values for binding to TP-24 and TP-25 peptides are provided in Table 7. All 19 antibodies bind within the sequence SEQ ID NO: 4 REFFSQYGDVMDVFIPKPFRAFAF (TP-24 and TP-25 peptides as provided in Table 6).

TABLE 6

Sequences of 15-mer peptides for epitope mapping

| Peptide name | Sequence |
| --- | --- |
| TP-23 | TEDMTEDELREFFSQ |
| TP-24 | REFFSQYGDVMDVFI |
| TP-25 | VMDVFIPKPFRAFAF |
| TP-26 | FRAFAFVTFADDQIA |
| TP-27 | ADDQIAQSLCGEDLI |
| TP-28 | CGEDLIIKGISVHIS |
| TP-29 | ISVHISNAEPKHNSN |
| TP-30 | PKHNSNRQLERSGRF |
| TP-31 | ERSGRFGGNPGGFGN |

TABLE 7

OD values for binding to TP-24 and TP-25 peptides (defined in Table 6)

| Hybridoma Clone | TP-24 | TP-25 |
| --- | --- | --- |
| 401A2A7 | 2.2 | 1.2 |
| 401A2C6 | 2.5 | 1.0 |
| 404D6A9 | 3.9 | 0.9 |
| 404D6E11 | 4.0 | 0.9 |
| 406E3D5 | 3.0 | 1.0 |
| 406E3G10 | 3.4 | 0.9 |
| 410H3B9 | 3.8 | 0.8 |
| 410H3G7 | 3.8 | 0.9 |
| 412A7B7 | 4.0 | 1.4 |
| 412E12A2 | 3.2 | 1.2 |
| 412E12F8 | 3.4 | 1.1 |
| 414A5D2 | 3.9 | 1.2 |
| 414A5H4 | 3.2 | 1.2 |
| 415C4C6 | 3.8 | 1.2 |
| 415C4F11 | 3.4 | 1.2 |

TABLE 7-continued

OD values for binding to TP-24 and TP-25 peptides (defined in Table 6)

| Hybridoma Clone | TP-24 | TP-25 |
| --- | --- | --- |
| 415H10A1 | 3.9 | 1.3 |
| 415H10B7 | 3.9 | 1.2 |
| 416A11B3 | 2.9 | 0.9 |
| 416A11G11 | 1.5 | 0.9 |

Furthermore, antibodies were tested using an indirect ELISA on a peptide library of 8-mer peptides with 7 aa overlap covering the sequence of human TDP-43 from aa 210 to aa 231, using the same ELISA method as describe previously in this section. Peptide sequences are shown in Table 8 and the results of the ELISA are shown in FIG. 5B. The antibody 2E2-D3 (Abcam) with a reported epitope of 205-222 was used as control and did not bind to residues 215-222 of TDP-43 (Zhang et al. (2008) Neuroscience Letters 434, Issue 2, pp. 170-4). All antibodies tested bind within the sequence of the peptide GDVMDVFI (SEQ ID NO: 5, TDP-43 residues 215-222). The results also show that the control antibody does not bind any of the peptides indicating that it has a different epitope from the antibodies presented here.

TABLE 8

Sequences of 8-mer peptides for epitope mapping

| Peptide name | Sequence |
| --- | --- |
| TDP-208 | REFFSQYG |
| TDP-209 | EFFSQYGD |
| TDP-210 | FFSQYGDV |
| TDP-211 | FSQYGDVM |
| TDP-212 | SQYGDVMD |
| TDP-213 | QYGDVMDV |
| TDP-214 | YGDVMDVF |
| TDP-215 | GDVMDVFI |
| TDP-216 | DVMDVFIP |
| TDP-217 | VMDVFIPK |
| TDP-218 | MDVFIPKP |
| TDP-219 | DVFIPKPF |
| TDP-220 | VFIPKPFR |
| TDP-221 | FIPKPFRA |
| TDP-222 | IPKPFRAF |
| TDP-223 | PKPFRAFA |
| TDP-224 | KPFRAFAF |
| TDP-220 | VFIPKPFR |

VI. Example 6: Detection of TDP-43 in Brain Tissues from FD/ALS Patients

Target engagement was evaluated in immunohistochemistry experiments on tissues from FTD patient brains. The brain samples, human FTD tissues were obtained from The Netherlands Brain Bank (frontal cortex), Netherlands Institute for Neuroscience, Amsterdam (open access: www.brainbank.nl). All Material has been collected from donors from whom a written informed consent for brain autopsy and the use of the material and clinical information for research purposes has been obtained by the NBB. Also, human FTD tissues were obtained from the Department of Neuropathology, University Hospital Tübingen (frontal cortex and hippocampus). Immunohistochemistry was performed on 10 µm thick frozen sections using fluorescent secondary antibody detection or on 6 µm thick paraffin embedded sections using DAB detection. The following antibodies were used as controls: rabbit polyclonal pan TDP-43 antibody (Proteintech, 10782-2-AP) to detect pathological inclusions and physiological nuclear TDP-43; rabbit monoclonal phospho TDP-43 p409/410 antibody (Cosmobio, TIP-TD-P02) and rat monoclonal phospho TDP43 p409/410 antibody (Millipore, MAB N14) to detect pathological aggregated and phosphorylated TDP-43.

Figure 7:
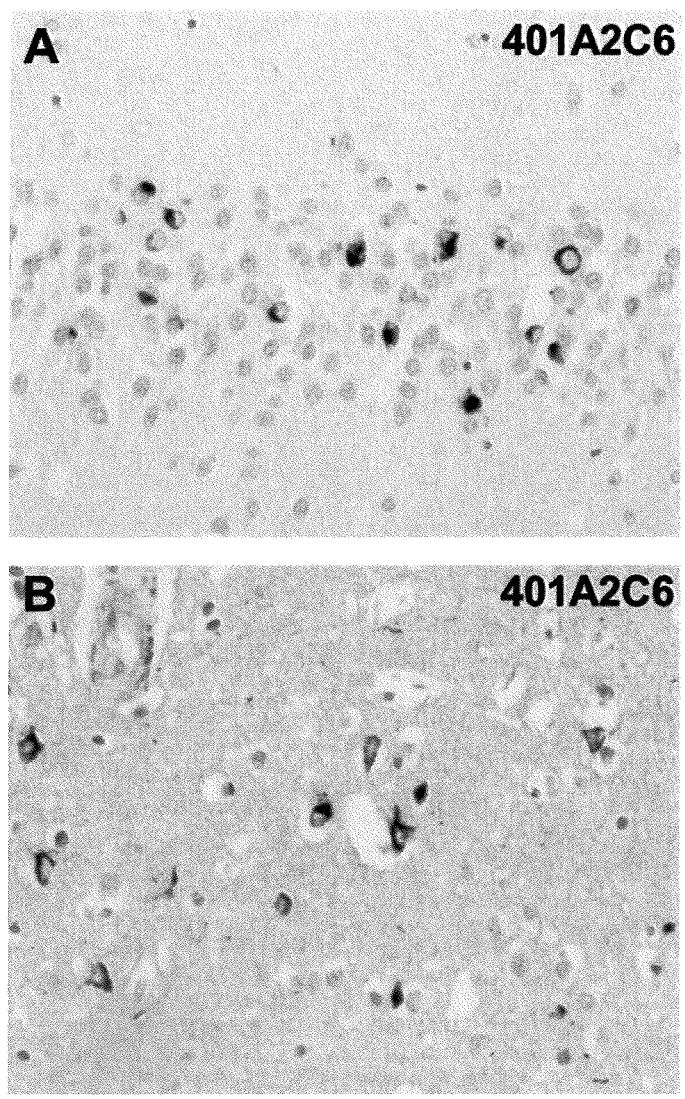
FIG. 7. Detection of TDP-43 in tissues from FTD type B patient. Immunohistochemistry was performed on 6 µm thick paraffin-embedded sections from hippocampus (A) and frontal cortex (B) of an FTD patient with type B pathology using DAB detection. Antibodies of the present invention specifically bind to aggregated TDP-43 in the cytoplasm in Type B pathology and do not bind to physiological nuclear TDP-43.

Antibodies in the present invention specifically bind to misfolded, aggregated TDP43 in the cytoplasm in Type A/C pathology (FIG. 6) and in Type B pathology (FIG. 7) and do not bind to physiological nuclear TDP-43 in patient nor in control brains. Evaluation of binding and signal to background ration is summarized in Table 9.

VII. Example 7: Affinity/Avidity Measurements Using SPR

Binding affinity to FL TDP-43 was evaluated by determining the dissociation constant (KD) using surface plasmon resonance (SPR; Biacore 8K, GE Healthcare Life Sciences). Anti-mouse IgG was immobilized on a CM5 Series S sensor chip (GE Healthcare Life Sciences) by amine coupling. Immobilization of anti-IgG was done at a concentration of 30 µg/ml in 10 mM sodium acetate (pH 5.5) with a flow rate of 10 µl/min for 500 s. The purified antibodies being tested, and the control antibody (2E2-D3), were injected at a concentration of 1 µg/ml at a flow rate of 10 µl/min for 500 s in 10 mM Na-acetate (pH 5.5). To evaluate KDs, recombinant human FL TDP-43 monomer analyte was injected at 2-fold dilutions starting from 400 nM and diluting down to 1.6 nM using single cycle kinetics. The protein analyte was injected at a flow rate of 20 µl/min for 600 s contact time and a 1200 s dissociation phase, without intermediate regeneration steps. Result obtained from kinetics was evaluated using a 1:1 binding model analysis. The affinities for 16 antibodies are shown in Table 10.

Figure 8A:
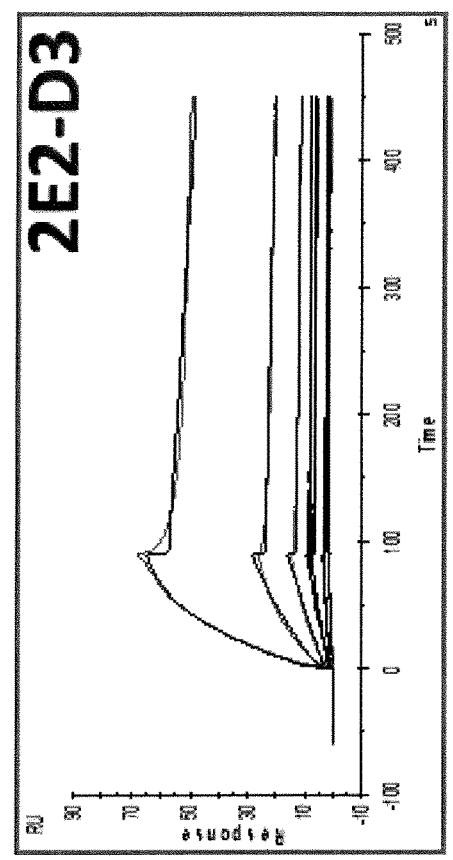
FIG. 8. Avidity evaluation by SPR. Sensorgram showing binding of clones 401A2A7 (FIG. 8A) and 401A2C6 (FIG. 8B) to human FL TDP-43 monomer covalently coupled to a Biacore sensor chip. Antibody 2E2-D3 was used as control. A 1:1 binding model was applied and is shown as an overlay. The x-axis indicates time (units=seconds). The y-axis indicated Resonance Units (RU).
Figure 8A:
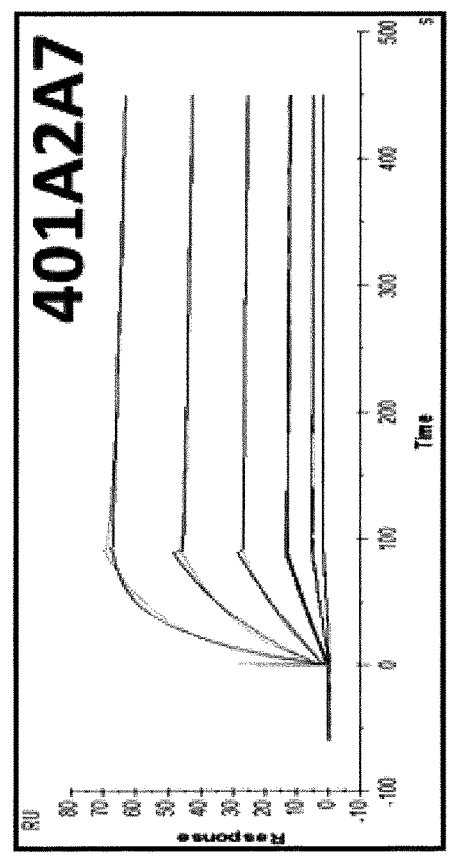
Figure 8B:
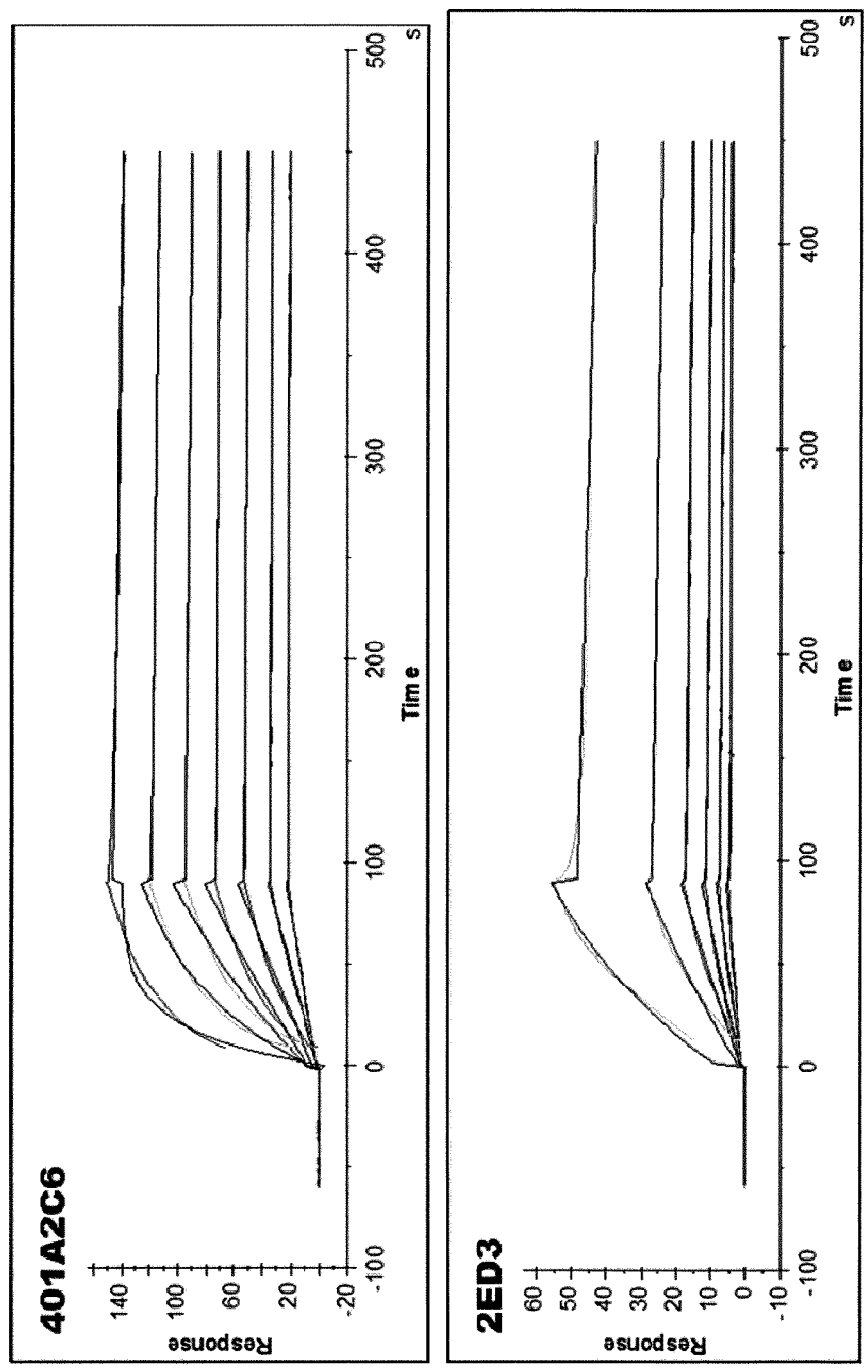

Avidity measurements were performed on an SPR instrument (Biacore T200, GE Healthcare Life Sciences) using CM5 Series S sensor chips. Recombinant human FL TDP-43 monomers or aggregated recombinant human FL TDP-43 was immobilized on a CM5 chip using amine coupling, injecting at a flow rate of 5 µl/min for 420 seconds. Conditions were optimized so that less than 200 RU protein was immobilized. Binding of the antibodies and the control antibody (2E2-D3) were obtained by injecting at: 1.37, 4.11, 12.33, 37, 111, and 333 nM in 1×PBS P+ at a flow rate of 50 µl/min for 90 s contact time and 600 s dissociation phase, with three regeneration cycles of the ligand surface by 10 mM Glycine-HCl (pH 1.7). Kinetics were analyzed using a 1:1 fitting model (see FIG. 8).

TABLE 9

| Detection of TDP-43 in brain tissues from FTD/ALS patients | | | |
|---|---|---|---|
| Hybridoma clone | IHC detection of misfolded aggregates - FTD Type A pathology | IHC detection of nuclear physiological TDP-43 - FTD type A pathology | IHC detection of misfolded aggregates - FTD Type B pathology |
| 401A2A7 | ++ | +/− | NA |
| 401A2C6 | +++ | +/− | +++ |
| 404D6A9 | ++ | − | NA |
| 404D6E11 | + | − | NA |
| 406E3D5 | + | − | + |
| 406E3G10 | ++ | − | NA |
| 410H3B9 | ++ | − | +++ |
| 410H3G7 | +++ | − | NA |
| 412A7B7 | +++ | − | +++ |
| 412E12A2 | +++ | − | ++ |
| 412E12F8 | +++ | − | NA |
| 414A5D2 | ++ | − | ++ |
| 414A5H4 | ++ | − | NA |
| 415C4C6 | ++ | − | ++ |
| 415C4F11 | ++ | − | NA |
| 415H10A1 | ++ | − | NA |
| 415H10B7 | +++ | − | NA |
| 416A11B3 | ++ | − | + |
| 416A11G11 | ++ | − | NA |

NA data not available;
− absent;
+/− not clear;
+ weak;
++ medium;
+++ abundant

TABLE 10

Affinity and avidity data

| Antibody | SPR affinity (single cycle kinetics): KD [nM] on TDP-43 monomer | SPR avidity: KD [nM] on TDP-43 monomer | SPR avidity: KD [nM] on TDP-43 aggregates |
|---|---|---|---|
| ACI-7062-401A2-Ab1 | 193 | 1.4 | 1.6 |
| ACI-7062-401A2-Ab2 | 149 | 2.1 | 0.3 |
| ACI-7062-404D6-Ab1 | NA | NA | NA |
| ACI-7062-404D6-Ab2 | NA | NA | NA |
| ACI-7062-406E3-Ab1 | 193 | 0.8 | 0.2 |
| ACI-7062-406E3-Ab2 | 101 | 0.3 | 0.4 |
| ACI-7062-410H3-Ab1 | 242 | 6.0 | 19.2 |
| ACI-7062-410H3-Ab2 | NA | 2.5 | 31.0 |
| ACI-7062-412A7-Ab1 | 66.1 | 1.0 | 0.3 |
| ACI-7062-412E12-Ab1 | 327 | 1.0 | 0.9 |
| ACI-7062-412E12-Ab2 | 184 | 1.3 | 0.4 |
| ACI-7062-414A5-Ab1 | 145 | 3.0 | NA |
| ACI-7062-414A5-Ab2 | 205 | 1.1 | 4.6 |
| ACI-7062-415C4-Ab1 | 379 | 2.7 | 0.7 |
| ACI-7062-415C4-Ab2 | NA | 1.1 | 1.2 |
| ACI-7062-415H10-Ab1 | NA | NA | NA |
| ACI-7062-415H10-Ab2 | NA | 1.1 | NA |
| ACI-7062-416A11-Ab1 | 307 | 2.4 | 1.2 |
| ACI-7062-416A11-Ab2 | 292 | 1.2 | 1.0 |

VIII. Example 8: Antibody Sequencing

Clonal hybridoma cell lysates were used for variable region gene sequencing. Mouse hybridomas were harvested and lysed using a lysis buffer containing guanidinium salts that deactivates RNases. Genomic DNA was then eliminated by RNase-free DNase, and RNA was purified with a silica-based affinity column using multiple washes and eluted from the column using RNase-free water. Once the RNA was extracted, its purity and concentration was measured spectrophotometrically. The integrity of the RNA was assessed on a denaturing agarose gel and RNA was reverse transcribed into cDNA using reverse transcriptase (RT). Before adding the reaction mixture, the RNA was heated to 70° C. for 10 min in order to disrupt RNA secondary structures. The RT products were directly used for PCR amplification. For high-fidelity PCR amplification of the cDNA, each of the variable region primers corresponding to the different gene families encoding for antibodies were individually mixed with the constant primer, for VH and VL separately in a total reaction volume of 50 µl. In first intention, a degenerate primer pool was used (12 for VH and 12 for VL) and, depending on the results, a second pool was used to obtain PCR products. After the PCR reaction, the products were analyzed by gel electrophoresis on 2% agarose gels stained with ethidium bromide. The PCR products for VL and VH were individually purified on an agarose gel using tris-acetate-EDTA (TAE). The purified fragments excised from the gel were then sequenced using the dye-terminator sequencing method. The same primers as those used for PCR were used for the sequencing reaction. Sequencing was carried out in both directions to provide overlap at both ends. The sequences were analyzed using multiple sequence alignment (Clustal tool). Sequences were annotated following the algorithm of IMGT Colliers de Perles as described in Pommié C et al., Journal of Molecular Recognition, 17, 17-32 (2004). Protein sequences for selected heavy (VH) and light (VL) chain variable domains, and their complementarity-determining regions (CDRs) are shown in Table 11.

TABLE 11

Antibody variable regions sequences

| SEQ ID NO: | Description including antibody name and the sequence information | Hybridoma clone | Sequence |
|---|---|---|---|
| 10 | ACI-7062-401A2-Ab2-VL Peptide sequence of the light chain variable domain with tail | 401A2C6 | DIVMTQSPSSLAMSVGQKVTMSCK SSQSLLNSGDQKNYLAWYQQKPGQ SPELLLYFASTRASGVPDRFIGSGSG TDFSLTISSVQAEDLADYFCQQHYSI PLTFGAGTKLELKRADAAPTVSIFP T |
| 11 | ACI-7062-401A2-Ab2-VL FR1 | | DIVMTQSPSSLAMSVGQKVTMSC |
| 12 | ACI-7062-401A2-Ab2-VL CDR1 | | KSSQSLLNSGDQKNYLA |
| 13 | ACI-7062-401A2-Ab2-VL FR2 | | WYQQKPGQSPELLLY |
| 14 | ACI-7062-401A2-Ab2-VL CDR2 | | FASTRAS |
| 15 | ACI-7062-401A2-Ab2-VL FR3 | | GVPDRFIGSGSGTDFSLTISSVQAED LADYFC |
| 16 | ACI-7062-401A2-Ab2-VL CDR3 | | QQHYSIPLT |

TABLE 11-continued

Antibody variable regions sequences

| SEQ ID NO: | Description including antibody name and the sequence information | Hybridoma clone | Sequence |
|---|---|---|---|
| 17 | ACI-7062-401A2-Ab2-VL FR4 | | FGAGTKLELKRA |
| 18 | ACI-7062-401A2-Ab2-VL Tail | | DAAPTVSIFPT |
| 19 | ACI-7062-401A2-Ab2-VL Nucleotide sequence of the light chain variable domain with tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCGATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCTCTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCTGATGCTGCA CCAACTGTATCCATCTTCCCTACC |
| 20 | ACI-7062-401A2-Ab2-VH Peptide sequence of the heavy chain variable domain with tail | | DVQLVESGGGLVQPGGSRRLSCAA SGFTFSRFGMHWVRQAPEKGLEWV AYIRSGSDIIYYADSVKGRFTISRDN PENTLFLQMTSLRSEDTAMYYCAR SGTTVPFDYWGQGTSLTVSSAKTTP PSVYPLAPGSAAQTNSMVTLGCLV KGYFP |
| 21 | ACI-7062-401A2-Ab2-VH FR1 | | DVQLVESGGGLVQPGGSRRLSCAA SGFTFS |
| 22 | ACI-7062-401A2-Ab2-VH CDR1 | | RFGMH |
| 23 | ACI-7062-401A2-Ab2-VH FR2 | | WVRQAPEKGLWVA |
| 24 | ACI-7062-401A2-Ab2-VH CDR2 | | YIRSGSDITYYADSVKG |
| 25 | ACI-7062-401A2-Ab2-VH FR3 | | RFTISRDNPENTLFLQMTSLRSEDTA MYYCAR |
| 26 | ACI-7062-401A2-Ab2-VH CDR3 | | SGTTVPFDY |
| 27 | ACI-7062-401A2-Ab2-VH FR4 | | WGQGTSLTVSS |
| 28 | ACI-7062-401A2-Ab2-VH Tail | | AKTTPPSVYPLAPGSAAQTNSMVTL GCLVKGYFP |
| 29 | ACI-7062-401A2-Ab2-VH Nucleotide sequence of the heavy chain variable domain with tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGGT TTGGAATGCACTGGGTTCGCCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA GCCAAAACGACACCCCCATCTGTC TATCCACTGGCCCCTGGATCTGCT GCCCAAACTAACTCCATGGTGACC CTGGGATGCCTGGTCAAGGGCTAT TTCCCT |
| 30 | ACI-7062-412A7-Ab1-VL Peptide sequence of the light chain variable domain with tail | 412A7B7 | DIVMTQSPSSLAMSVGQKVTMSCK SSQSLLNSGNQKNYLAWYQQKPGQ SPELLLYFASTRASGVPDRFIGSGSG TDFTLTISSVQAEDLADYFCQQHYS IPLTFGAGTKLELKRADAAPTVSTFP |
| 31 | ACI-7062-412A7-Ab1-VL FR1 | | DIVMTQSPSSLAMSVGQKVTMSC |
| 32 | ACI-7062-412A7-Ab1-VL CDR1 | | KSSQSLLNSGNQKNYLA |
| 33 | ACI-7062-412A7-Ab1-VL FR2 | | WYQQKPGQSPELLLY |
| 34 | ACI-7062-412A7-Ab1-VL CDR2 | | FASTRAS |
| 35 | ACI-7062-412A7-Ab1-VL FR3 | | GVPDRFIGSGSGTDFTLTISSVQAED LADYFC |

TABLE 11-continued

Antibody variable regions sequences

| SEQ ID NO: | Description including antibody name and the sequence information | Hybridoma clone | Sequence |
|---|---|---|---|
| 36 | ACI-7062-412A7-Ab1-VL CDR3 | | QQHYSIPLT |
| 37 | ACI-7062-412A7-Ab1-VL FR4 | | FGAGTKLELKRA |
| 38 | ACI-7062-412A7-Ab1-VL Tail | | DAAPTVSIFP |
| 39 | ACI-7062-412A7-Ab1-VL Nucleotide sequence of the light chain variable domain with tail | | GACATTGTGATGACACAGTCTCCATCCTCCCTGGCTATGTCAGTTGGACAGAAGGTCACTATGAGCTGCAAGTCCAGTCAGAGCCTTTTAAATAGTGGCAATCAAAAGAACTATTTGGCCTGGTACCAGCAGAAACCAGGACAGTCTCCTGAACTTCTATTATACTTTGCATCCACTAGGGCATCTGGGGTCCCTGATCGCTTCATAGGCAGTGGATCTGGGACAGATTTCACTCTTACCATCAGCAGTGTGCAGGCTGAAGACCTGGCAGATTACTTCTGTCAGCAACATTATAGTATTCCGCTCACGTTCGGTGCTGGGACCAAGCTGGAGCTGAAACGGGCTGATGCTGCACCAACTGTATCCATCTTCCCA |
| 40 | ACI-7062-412A7-Ab1-VH Peptide sequence of the heavy chain variable domain with tail | | DVQLVESGGGLVQPGGSRRLSCAASGFTFSSFGMHWVRQAPEKGLEWVAYIRSGSDIIYYADSVKGRFTISRDNPENTLFLQMTSLRSEDTAMYYCARSGTTVPFDYWGQGTSLTVSSAKTTPPSVYPLAPGCGDTTGSSVTLGC |
| 41 | ACI-7062-412A7-Ab1-VH FR1 | | DVQLVESGGGLVQPGGSRRLSCAASGFTFS |
| 42 | ACI-7062-412A7-Ab1-VH CDR1 | | SFGMH |
| 43 | ACI-7062-412A7-Ab1-VH FR2 | | WVRQAPEKGLEWVA |
| 44 | ACI-7062-412A7-Ab1-VH CDR2 | | YIRSGSDIWYADSVKG |
| 45 | ACI-7062-412A7-Ab1-VH FR3 | | RFTISRDNPENTLFLQMTSLRSEDTAMYYCAR |
| 46 | ACI-7062-412A7-Ab1-VH CDR3 | | SGTTVPFDY |
| 47 | ACI-7062-412A7-Ab1-VH FR4 | | WGQGTSLTVSS |
| 48 | ACI-7062-412A7-Ab1-VH Tail | | AKTTPPSVYPLAPGCGDTTGSSVTLGC |
| 49 | ACI-7062-412A7-Ab1-VH Nucleotide sequence of the heavy chain variable domain with tail | | GATGTGCAGCTGGTGGAGTCTGGGGGAGGCTTAGTGCAGCCTGGAGGGTCCCGGAGACTCTCCTGTGCAGCCTCTGGATTCACTTTCAGTAGCTTTGGAATGCACTGGGTTCGTCAGGCTCCAGAGAAGGGGCTGGAGTGGGTCGCATACATTAGGAGTGGCAGTGATATAATCTACTATGCAGACTCAGTGAAGGGCCGATTCACCATCTCCAGAGACAATCCCGAGAACACCCTGTTCCTGCAAATGACCAGTCTAAGGTCTGAGGACACGGCCATGTATTACTGTGCAAGATCAGGGACTACGGTCCCCTTTGACTACTGGGGCCAAGGCACCAGTCTCACAGTCTCTTCAGCCAAAACAACACCCCCATCAGTCTATCCACTGGCCCCTGGGTGTGGAGATACAACTGGTTCCTCCGTGACTCTGGGATGC |
| 50 | ACI-7062-406E3-Ab1-VL Peptide sequence of the light chain variable domain with tail | 406E3D5 | DVLMTQTPLSLPVSLGDRASISCRSSQSIVHRSGNTYLEWYLQKPGQSPKLLIYKVSNRFSGVPDRFSGSGSGTDFTLKISRVEAEDLGVYYCFQGSHVPTPFGAGTKLELKRADAAPTVSIFPPSSE |
| 51 | ACI-7062-406E3-Ab1-VL FR1 | | DVLMTQTPLSLPVSLGDRASISC |
| 52 | ACI-7062-406E3-Ab1-VL CDR1 | | RSSQSIVHRSGNTYLE |
| 53 | ACI-7062-406E3-Ab1-VL FR2 | | WYLQKPGQSPKLLIY |
| 54 | ACI-7062-406E3-Ab1-VL CDR2 | | KVSNRFS |
| 55 | ACI-7062-406E3-Ab1-VL FR3 | | GVPDRFSGSGSGTDFTLKISRVEAEDLGVYYC |

TABLE 11-continued

Antibody variable regions sequences

| SEQ ID NO: | Description including antibody name and the sequence information | Hybridoma clone | Sequence |
|---|---|---|---|
| 56 | ACI-7062-406E3-Ab1-VL CDR3 | | FQGSHVPT |
| 57 | ACI-7062-406E3-Ab1-VL FR4 | | FGAGTKLELKRA |
| 58 | ACI-7062-406E3-Ab1-VL Tail | | DAAPTVSIFPPSSE |
| 59 | ACI-7062-406E3-Ab1-VL Nucleotide sequence of the light chain variable domain with tail | | GATGTTTTGATGACCCAAACTCCA CTCTCCCTGCCTGTCAGTCTTGGA GATCGAGCCTCCATCTCTTGCAGA TCTAGTCAGAGCATTGTACATCGT AGTGGAAACACCTATTTAGAGTG GTACCTGCAGAAACCAGGCCAGT CTCCAAAGCTCCTGATCTACAAAG TTTCCAACCGATTTTCTGGGGTCC CAGACAGGTTCAGTGGCAGTGGA TCAGGGACAGATTTCACACTCAA GATCAGCAGAGTGGAGGCTGAGG ATCTGGGAGTTTATTACTGCTTTC AAGGTTCACATGTTCCCACGTTCG GTGCTGGGACCAAGCTGGAGCTG AAACGGGCTGATGCTGCACCAAC TGTATCCATCTTCCCACCATCCAG TGAG |
| 60 | ACI-7062-406E3-Ab1-VH Peptide sequence of the heavy chain variable domain with tail | | QVTLKESGPAILQPSQTLSLTCSFSG FSLTTYGIGVGWIRQPSGKGLEWLA HIWWNDNKYYNTALKSRLTVSKD TSNNQVFLKIASVDTADTATYYCA RVYGNLYYFAYWGQGTTLTVSSA KTTAPSVYPLAPVCGDTTGSSVTLG CLVKGY |
| 61 | ACI-7062-406E3-Ab1-VH FR1 | | QVTLKESGPAILQPSQTLSLTCSFSG FSLT |
| 62 | ACI-7062-406E3-Ab1-VH CDR1 | | TYGIGVG |
| 63 | ACI-7062-406E3-Ab1-VH FR2 | | WIRQPSGKGLEWLA |
| 64 | ACI-7062-406E3-Ab1-VH CDR2 | | HIWWNDNKYYNTALKS |
| 65 | ACI-7062-406E3-Ab1-VH FR3 | | RLTVSKDTSNNQVFLKIASVDTADT ATYYCAR |
| 66 | ACI-7062-406E3-Ab1-VH CDR3 | | VYGNLYYFAY |
| 67 | ACI-7062-406E3-Ab1-VH FR4 | | WGQGTTLTVSS |
| 68 | ACI-7062-406E3-Ab1-VH Tail | | AKTTAPSVYPLAPVCGDTTGSSVTL GCLVKGY |
| 69 | ACI-7062-406E3-Ab1-VH Nucleotide sequence of the heavy chain variable domain with tail | | CAGGTTACTCTGAAAGAGTCTGGC CCTGCGATATTGCAGCCCTCCCAG ACCCTCAGTCTGACTTGTTCTTTCT CTGGGTTTTCACTGACCACTTATG GTATAGGAGTAGGCTGGATTCGTC AGCCTTCAGGGAAGGGTCTGGAG TGGCTGGCACACATTTGGTGGAAT GATAATAAGTACTATAACACAGC CCTGAAGAGCCGGCTCACTGTCTC CAAGGATACCTCCAACAACCAGG TATTCCTCAAGATCGCCAGTGTAG ACACTGCAGATACTGCCACATACT ACTGTGCTCGAGTCTATGGTAACC TGTACTACTTTGCCTACTGGGGCC AAGGCACCACTCTCACAGTCTCCT CAGCCAAAACAACAGCCCCATCG GTCTATCCACTGGCCCCTGTGTGT GGAGATACAACTGGCTCCTCGGT GACTCTAGGATGCCTGGTCAAGG GTTAT |
| 70 | ACI-7062-404D6-Ab2-VL Peptide sequence of the light chain variable domain with tail | 404D6E11 | DVLMTQTPLSLPVSLGDQASISCRS SQSIVHGSGNTYLEWYLQKPGQSP KLLIYKVSNRFSGVPDRFSGSGSGT DFTLRISRVEAEDLGVYYCFQGSHV PTFGAGTKLELKRADAAPTVSIFPPS S |
| 71 | ACI-7062-404D6-Ab2-VL FR1 | | DVLMTQTPLSLPVSLGDQASISC |
| 72 | ACI-7062-404D6-Ab2-VL CDR1 | | RSSQSIVHGSGNTYLE |

TABLE 11-continued

Antibody variable regions sequences

| SEQ ID NO: | Description including antibody name and the sequence information | Hybridoma clone | Sequence |
|---|---|---|---|
| 73 | ACI-7062-404D6-Ab2-VL FR2 | | WYLQKPGQSPKLLIY |
| 74 | ACI-7062-404D6-Ab2-VL CDR2 | | KVSNRFS |
| 75 | ACI-7062-404D6-Ab2-VL FR3 | | GVPDRFSGSGSGTDFTLRISRVEAE DLGVYYC |
| 76 | ACI-7062-404D6-Ab2-VL CDR3 | | FQGSHVPT |
| 77 | ACI-7062-404D6-Ab2-VL FR4 | | FGAGTKLELKRA |
| 78 | ACI-7062-404D6-Ab2-VL Tail | | DAAPTVSIFPPSS |
| 79 | ACI-7062-404D6-Ab2-VL Nucleotide sequence of the light chain variable domain with tail | | GATGTTTTGATGACCCAAACTCCA CTCTCCCTGCCTGTCAGTCTTGGA GATCAAGCCTCCATCTCTTGCAGA TCTAGTCAGAGCATTGTACATGGT TCTGGAAACACCTATTTAGAATGG TACCTGCAGAAACCAGGCCAGTC TCCAAAGCTCCTGATCTACAAAGT TTCCAACCGATTTTCTGGGGTCCC AGACAGGTTCAGTGGCAGTGGAT CAGGGACAGATTTCACACTCAGG ATCAGCAGAGTGGAGGCTGAGGA TCTGGGAGTTTATTACTGCTTTCA AGGTTCACATGTTCCCACGTTCGG TGCTGGGACCAAGCTGGAGCTGA AACGGGCTGATGCTGCACCAACT GTATCCATCTTCCCACCATCCAGT |
| 80 | ACI-7062-404D6-Ab2-VH Peptide sequence of the heavy chain variable domain with tail | | QVTLKESGPGILQPSQTLSLTCSFSG FSLSTYGIGVGWIRQPSGKGLEWLA HIWWNDYKYYNTALKSRLTISKDT SNNRVFLKIASVDTADTATYYCAR VYGNLYYFDYWGQGTTLTVSSATT TAPSWS |
| 81 | ACI-7062-404D6-Ab2-VH FR1 | | QVTLKESGPGILQPSQTLSLTCSFSG FSLS |
| 82 | ACI-7062-404D6-Ab2-VH CDR1 | | TYGIGVG |
| 83 | ACI-7062-404D6-Ab2-VH FR2 | | WIRQPSGKGLEWLA |
| 84 | ACI-7062-404D6-Ab2-VH CDR2 | | HIWWNDYKYYNTALKS |
| 85 | ACI-7062-404D6-Ab2-VH FR3 | | RLTISKDTSNNRVFLKIASVDTADT ATYYCAR |
| 86 | ACI-7062-404D6-Ab2-VH CDR3 | | VYGNLYYFDY |
| 87 | ACI-7062-404D6-Ab2-VH FR4 | | WGQGTTLTVSS |
| 88 | ACI-7062-404D6-Ab2-VH Tail | | ATTTAPSWS |
| 89 | ACI-7062-404D6-Ab2-VH Nucleotide sequence of the heavy chain variable domain with tail | | CAGGTTACTCTGAAAGAGTCTGGC CCTGGGATATTGCAGCCCTCCCAG ACCCTCAGTCTGACTTGTTCTTTCT CTGGGTTTTCACTGAGCACTTATG GTATAGGAGTAGGCTGGATTCGTC AGCCTTCAGGGAAGGGTCTGGAG TGGCTGGCACACATTTGGTGGAAT GATTATAAGTACTATAACACAGCC CTGAAGAGCCGGCTCACAATCTCC AAGGATACCTCCAACAACCGGGT ATTCCTCAAGATCGCCAGTGTGGA CACTGCAGATACTGCCACATACTA CTGTGCTCGAGTCTATGGTAACCT GTACTACTTTGACTACTGGGGCCA AGGCACCACTCTCACAGTCTCCTC AGCTACAACAACAGCCCCATCTTG GTCC |
| 90 | ACI-7062-410H3-Ab1-VL Peptide sequence of the light chain variable domain with tail | 410H3B9 | DIVMTQSPSSLAMSVGQKVTMSCK SSQSLLNSGNQKNYLAWYQQKPGQ SPELLLYFASTRASGVPDRFIGSGSG TDFTLTISSVQAEDLADYFCQQHYS IPLTFGAGTKLELKRADAAPTVSIFP T |
| 91 | ACI-7062-410H3-Ab1-VL FR1 | | DIVMTQSPSSLAMSVGQKVTMSC |
| 92 | ACI-7062-410H3-Ab1-VL CDR1 | | KSSQSLLNSGNQKNYLA |
| 93 | ACI-7062-410H3-Ab1-VL FR2 | | WYQQKPGQSPELLLY |
| 94 | ACI-7062-410H3-Ab1-VL CDR2 | | FASTRAS |

TABLE 11-continued

Antibody variable regions sequences

| SEQ ID NO: | Description including antibody name and the sequence information | Hybridoma clone | Sequence |
|---|---|---|---|
| 95 | ACI-7062-410H3-Ab1-VL FR3 | | GVPDRFIGSGSGTDFTLTISSVQAED LADYFC |
| 96 | ACI-7062-410H3-Ab1-VL CDR3 | | QQHYSIPLT |
| 97 | ACI-7062-410H3-Ab1-VL FR4 | | FGAGTKLELKRA |
| 98 | ACI-7062-410H3-Ab1-VL Tail | | DAAPTVSIFPT |
| 99 | ACI-7062-410H3-Ab1-VL Nucleotide sequence of the light chain variable domain with tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCAATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCACTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCTGATGCTGCA CCAACTGTATCCATCTTCCCTACC |
| 100 | ACI-7062-410H3-Ab1-VH Peptide sequence of the heavy chain variable domain with tail | | DVQLVESGGGLVQPGGSRRLSCAA SGFTFSSFGMHWVRQAPEKGLEWV AYIRSGSDIIYYADSVKGRFTISRDN PENTLFLQMTSLRSEDTAMYYCAR SGTTVPFDYWGQGTSLTVSSAKTTP PSVYPLAPGSAAQTNSMVTLGCLV KGYFP |
| 101 | ACI-7062-410H3-Ab1-VH FR1 | | DVQLVESGGGLVQPGGSRRLSCAA SGFTFS |
| 102 | ACI-7062-410H3-Ab1-VH CDR1 | | SFGMH |
| 103 | ACI-7062-410H3-Ab1-VH FR2 | | WVRQAPEKGLEWVA |
| 104 | ACI-7062-410H3-Ab1-VH CDR2 | | YIRSGSDIIYYADSVKG |
| 105 | ACI-7062-410H3-Ab1-VH FR3 | | RFTISRDNPENTLFLQMTSLRSEDTA MYYCAR |
| 106 | ACI-7062-410H3-Ab1-VH CDR3 | | SGTTVPFDY |
| 107 | ACI-7062-410H3-Ab1-VH FR4 | | WGQGTSLTVSS |
| 108 | ACI-7062-410H3-Ab1-VH Tail | | AKTTPPSVYPLAPGSAAQTNSMVTL GCLVKGYFP |
| 109 | ACI-7062-410H3-Ab1-VH Nucleotide sequence of the heavy chain variable domain with tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGCT TTGGAATGCACTGGGTTCGTCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GCCAAAACGACACCCCATCTGTC TATCCACTGGCCCCTGGATCTGCT GCCCAAACTAACTCCATGGTGACC CTGGGATGCCTGGTCAAGGGCTAT TTCCCT |
| 110 | ACI-7062-414A5-Ab1-VL Peptide sequence of the light chain variable domain with tail | 414A5D2 | DIVMTQSPSSLAMSVGQKVTMSCK SSQSLLNSSNQKNYLAWYQQKPGQ SPKLLVYFASTRESGVPDRFIGSGSG TDFTLTLNSVQAEDLADYFCQQHYS IPLTFGAGTKLELKRADAAPTVSIFP T |
| 111 | ACI-7062-414A5-Ab1-VL FR1 | | DIVMTQSPSSLAMSVGQKVTMSC |
| 112 | ACI-7062-414A5-Ab1-VL CDR1 | | KSSQSLLNSSNQKNYLA |

TABLE 11-continued

Antibody variable regions sequences

| SEQ ID NO: | Description including antibody name and the sequence information | Hybridoma clone | Sequence |
|---|---|---|---|
| 113 | ACI-7062-414A5-Ab1-VL FR2 | | WYQQKPGQSPKLLVY |
| 114 | ACI-7062-414A5-Ab1-VL CDR2 | | FASTRES |
| 115 | ACI-7062-414A5-Ab1-VL FR3 | | GVPDRFIGSGSGTDFTLTINSVQAED LADYFC |
| 116 | ACI-7062-414A5-Ab1-VL CDR3 | | QQHYSIPLT |
| 117 | ACI-7062-414A5-Ab1-VL FR4 | | FGAGTKLELKRA |
| 118 | ACI-7062-414A5-Ab1-VL Tail | | DAAPTVSIFPT |
| 119 | ACI-7062-414A5-Ab1-VL Nucleotide sequence of the light chain variable domain with tail | | GACATTGTGATGACACAGTCTCCA TCCTCCCTGGCTATGTCAGTAGGA CAGAAGGTCACTATGAGCTGCAA GTCCAGTCAGAGCCTTTTAAATAG TAGCAATCAAAAGAACTATTTGG CCTGGTACCAGCAGAAACCAGGA CAGTCTCCTAAACTTCTGGTATAC TTTGCATCCACTAGGGAATCTGGG GTCCCTGATCGCTTCATAGGCAGT GGATCTGGGACAGATTTCACTCTT ACCATCAACAGTGTGCAGGCTGA AGACCTGGCAGATTACTTCTGTCA GCAACATTATAGTATTCCGCTCAC GTTCGGTGCTGGGACCAAGCTGG AGCTGAAACGGGCTGATGCTGCA CCAACTGTATCCATCTTCCCTACC |
| 120 | ACI-7062-414A5-Ab1-VH Peptide sequence of the heavy chain variable domain with tail | | DVQLVESGGGLVQPGGSRRLSCAA SGFTFSSFGMHWVRQAPEKGLEWV AYIRSGSDIIYYADTVKGRFTISRDN PENTLFLEMTRLRSEDTAMYYCAR SGTTVPFDYWGQGTSLTVSSAKTT APSVYPLAPVCGDTTGSSVTLGCLV KGYFP |
| 121 | ACI-7062-414A5-Ab1-VH FR1 | | DVQLVESGGGLVQPGGSRRLSCAA SGFTFS |
| 122 | ACI-7062-414A5-Ab1-VH CDR1 | | SFGMH |
| 123 | ACI-7062-414A5-Ab1-VH FR2 | | WVRQAPEKGLEWVA |
| 124 | ACI-7062-414A5-Ab1-VH CDR2 | | YIRSGSDIFYYADTVKG |
| 125 | ACI-7062-414A5-Ab1-VH FR3 | | RFTISRDNPENTLFLEMTRLRSEDTA MYYCAR |
| 126 | ACI-7062-414A5-Ab1-VH CDR3 | | SGTTVPFDY |
| 127 | ACI-7062-414A5-Ab1-VH FR4 | | WGQGTSLTVSS |
| 128 | ACI-7062-414A5-Ab1-VH Tail | | AKTTAPSVYPLAPVCGDTTGSSVTL GCLVKGYFP |
| 129 | ACI-7062-414A5-Ab1-VH Nucleotide sequence of the heavy chain variable domain with tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGCT TTGGAATGCACTGGGTTCGTCAGG CTCCAGAGAAGGGGCTGGAGTGG GTCGCATACATTAGGAGTGGCAG TGATATAATCTACTATGCAGACAC AGTGAAGGGCCGATTCACCATCTC CAGAGACAATCCCGAGAACACCC TGTTTTTGGAAATGACCAGACTAA GGTCTGAGGACACGGCCATGTATT ACTGTGCAAGATCAGGGACTACG GTCCCCTTTGACTACTGGGGCCAA GGCACCAGTCTCACAGTCTCTTCA GCCAAAACAACAGCCCCATCGGT CTATCCACTGGCCCCTGTGTGTGG AGATACAACTGGCTCCTCGGTGAC TCTAGGATGCCTGGTCAAGGGTTA TTTCCCTGA |
| 130 | ACI-7062-412E12-Ab1-VL Peptide sequence of the light chain variable domain with tail | 412E12A2 | DIVMTQSPSSLAMSVGQKVTMSCK SSQSLLNSGDQKNYLAWYQQKPGQ SPELLLYFASTRASGVPDRFIGSGSG TDFSLTISSVQAEDLADYFCQQHYSI PLTFGAGTKLELKRADAAPTVSIFP |
| 131 | ACI-7062-412E12-Ab1-VL FR1 | | DIVMTQSPSSLAMSVGQKVTMSC |

TABLE 11-continued

Antibody variable regions sequences

| SEQ ID NO: | Description including antibody name and the sequence information | Hybridoma clone | Sequence |
|---|---|---|---|
| 132 | ACI-7062-412E12-Ab1-VL CDR1 | | KSSQSLLNSGDQKNYLA |
| 133 | ACI-7062-412E12-Ab1-VL FR2 | | WYQQKPGQSPELLLY |
| 134 | ACI-7062-412E12-Ab1-VL CDR2 | | FASTRAS |
| 135 | ACI-7062-412E12-Ab1-VL FR3 | | GVPDRFIGSGSGTDFSLTISSVQAED LADYFC |
| 136 | ACI-7062-412E12-Ab1-VL CDR3 | | QQHYSIPLT |
| 137 | ACI-7062-412E12-Ab1-VL FR4 | | FGAGTKLELKRA |
| 138 | ACI-7062-412E12-Ab1-VL Tail | | DAAPTVSIFF |
| 139 | ACI-7062-412E12-Ab1-VL Nucleotide sequence of the light chain variable domain with tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCGATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCTCTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCTGATGCTGCA CCAACTGTATCCATCTTCCCA |
| 140 | ACI-7062-412E12-Ab1-VH Peptide sequence of the heavy chain variable domain with tail | | DVQLVESGGGLVQPGGSRRLSCAA SGFTFSRFGMHWVRQAPEKGLEWV AYIRSGSDHYYADSVKGRFTISRDN PENTLFLQMTSLRSEDTAMYYCAR SGYLVPFDYWGQGTSLTVSSAKTTP PSVYP |
| 141 | ACI-7062-412E12-Ab1-VH FR1 | | DVQLVESGGGLVQPGGSRRLSCAA SGFTFS |
| 142 | ACI-7062-412E12-Ab1-VH CDR1 | | RFGMH |
| 143 | ACI-7062-412E12-Ab1-VH FR2 | | WVRQAPEKGLEWVA |
| 144 | ACI-7062-412E12-Ab1-VH CDR2 | | YIRSGSDHYYADSVKG |
| 145 | ACI-7062-412E12-Ab1-VH FR3 | | RFTISRDNPENTLFLQMTSLRSEDTA MYYCAR |
| 146 | ACI-7062-412E12-Ab1-VH CDR3 | | SGTTVPFDY |
| 147 | ACI-7062-412E12-Ab1-VH FR4 | | WGQGTSLTVSS |
| 148 | ACI-7062-412E12-Ab1-VH Tail | | AKTTPPSVYP |
| 149 | ACI-7062-412E12-Ab1-VH Nucleotide sequence of the heavy chain variable domain with tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGGT TTGGAATGCACTGGGTTCGCCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA GCCAAAACGACACCCCCATCTGTC TATCCA |
| 150 | ACI-7062-416A11-Ab1-VL Peptide sequence of the light chain variable domain with tail | 416A11B3 | DVLMTQTPLSLPVSLGDRASISCRSS QSIVHSSGNTYLEWYLQKPGQSPKL LIYKVSNRFSGVPDRFSGSGSGTDF TLKISRVEAEDLGVYYCFQGSRVPT FGAGTKLELKRADAAPTVSI |

TABLE 11-continued

Antibody variable regions sequences

| SEQ ID NO: | Description including antibody name and the sequence information | Hybridoma clone | Sequence |
|---|---|---|---|
| 151 | ACI-7062-416A11-Ab1-VL FR1 | | DVLMTQTPLSLPVSLGDRASISC |
| 152 | ACI-7062-416A11-Ab1-VL CDR1 | | RSSQSIVHSSGNTYLE |
| 153 | ACI-7062-416A11-Ab1-VL FR2 | | WYLQKPGQSPKLLIY |
| 154 | ACI-7062-416A11-Ab1-VL CDR2 | | KVSNRFS |
| 155 | ACI-7062-416A11-Ab1-VL FR3 | | GVPDRFSGSGSGTDFTLKISRVEAEDLGVYYC |
| 156 | ACI-7062-416A11-Ab1-VL CDR3 | | FQGSRVPT |
| 157 | ACI-7062-416A11-Ab1-VL FR4 | | FGAGTKLELKRA |
| 158 | ACI-7062-416A11-Ab1-VH Tail | | DAAPTVSI |
| 159 | ACI-7062-416A11-Ab1-VL Nucleotide Sequence of the light chain variable domain with tail | | GATGTTTTGATGACCCAAACTCCACTCTCCCTGCCTGTCAGTCTTGGAGATCGAGCCTCCATCTCTTGCAGATCTAGTCAGAGCATTGTACATAGTAGTGGAAACACCTATTTAGAATGGTACCTGCAGAAGCCAGGCCAGTCTCCAAAGCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTACTGCTTTCAAGGTTCACGTGTTCCCACGTTCGGTGCTGGGACCAAGCTGGAGCTGAAACGGGCTGATGCTGCACCAACTGTATCCATCT |
| 160 | ACI-7062-416A11-Ab1-VH Peptide sequence of the heavy chain variable domain with tail | | QVTLKESGPGILQSSQTLSLTCSFSGFSLSTYGIGVGWIRQPSGKGLEWLAHIWWNDNKYYNTALKSRLTISKDTSNNQVFLKIASVDTADAATYYCARVYGNLYYFGYWGQGTTLTVSSAKTTAPSVYPLAPVCGDTTGSSVT |
| 161 | ACI-7062-416A11-Ab1-VH FR1 | | QVTLKESGPGILQSSQTLSLTCSFSGFSLS |
| 162 | ACI-7062-416A11-Ab1-VH CDR1 | | TYGIGVG |
| 163 | ACI-7062-416A11-Ab1-VH FR2 | | WIRQPSGKGLEWLA |
| 164 | ACI-7062-416A11-Ab1-VH CDR2 | | HIWWNDNKYYNTALKS |
| 165 | ACI-7062-416A11-Ab1-VH FR3 | | RLTISKDTSNNQVFLKIASVDTADAATYYCAR |
| 166 | ACI-7062-416A11-Ab1-VH CDR3 | | VYGNLYYFGY |
| 167 | ACI-7062-416A11-Ab1-VH FR4 | | WGQGTTLTVSS |
| 168 | ACI-7062-416A11-Ab1-VH Tail | | AKTTAPSVYPLAPVCGDTTGSSVT |
| 169 | ACI-7062-416A11-Ab1-VH Nucleotide sequence of the heavy chain variable domain with tail | | CAGGTTACTCTGAAAGAGTCTGGCCCTGGGATATTGCAGTCCTCCCAGACCCTCAGTCTGACTTGTTCTTTCTCTGGATTTTCACTGAGCACTTATGGTATAGGAGTAGGCTGGATTCGTCAGCCTTCAGGGAAGGGTCTGGAGTGGCTGGCACACATTTGGTGGAATGATAATAAGTACTATAACACAGCCCTGAAGAGCCGACTCACAATCTCCAAGGATACCTCCAACAACCAGGTATTCCTCAAGATCGCCAGTGTGGACACTGCAGATGCTGCCACATACTACTGTGCTCGAGTCTATGGTAACCTATACTACTTTGGCTACTGGGGCCAAGGCACCACTCTCACAGTCTCCTCAGCCAAAACAACAGCCCCATCGGTCTATCCACTGGCCCCTGTGTGTGGAGATACAACTGGCTCCTCGGTGACTC |

TABLE 11-continued

Antibody variable regions sequences

| SEQ ID NO: | Description including antibody name and the sequence information | Hybridoma clone | Sequence |
|---|---|---|---|
| 170 | ACI-7062-406E3-Ab2-VL Peptide sequence of the light chain variable domain without tail | 406E3G10 | DVLMTQTPLSLPVSLGDRASISCRSS QSIVHRSGNTYLEWYLQKPGQSPK LLIYKVSNRFSGVPDRFSGSGSGTD FTLKISRVEAEDLGVYYCFQGSHVP TFGAGTKLELKRA |
| 171 | ACI-7062-406E3-Ab2-VL-FR1 | | DVLMTQTPLSLPVSLGDRASISC |
| 172 | ACI-7062-406E3-Ab2-VL-CDR1 | | RSSQSIVHRSGNTYLE |
| 173 | ACI-7062-406E3-Ab2-VL-FR2 | | WYLQKPGQSPKLLIY |
| 174 | ACI-7062-406E3-Ab2-VL-CDR2 | | KVSNRFS |
| 175 | ACI-7062-406E3-Ab2-VL-FR3 | | GVPDRFSGSGSGTDFTLKISRVEAE DLGVYYC |
| 176 | ACI-7062-406E3-Ab2-VL-CDR3 | | FQGSHVPT |
| 177 | ACI-7062-406E3-Ab2-VL-FR4 | | FGAGTKLELKRA |
| 178 | ACI-7062-406E3-Ab2-VL-Tail | | DAAPTVSIFPPSSEQ |
| 179 | ACI-7062-406E3-Ab2-VL Nucleotide sequence of the light chain variable domain without tail | | GATGTTTTGATGACCCAAACTCCA CTCTCCCTGCCTGTCAGTCTTGGA GATCGAGCCTCCATCTCTTGCAGA TCTAGTCAGAGCATTGTACATCGT AGTGGAAACACCTATTTAGAGTG GTACCTGCAGAAACCAGGCCAGT CTCCAAAGCTCCTGATCTACAAAG TTTCCAACCGATTTTCTGGGGTCC CAGACAGGTTCAGTGGCAGTGGA TCAGGGACAGATTTCACACTCAA GATCAGCAGAGTGGAGGCTGAGG ATCTGGGAGTTTATTACTGCTTTC AAGGTTCACATGTTCCCACGTTCG GTGCTGGGACCAAGCTGGAGCTG AAACGGGCT |
| 180 | ACI-7062-406E3-Ab2-VH Peptide sequence of the heavy chain variable domain without tail | | QVTLKESGPAILQPSQTLSLTCSFSG FSLTTYGIGVGWIRQPSGKGLEWLA HIWWNDNKYYNTALKSRLTVSKD TSNNQVFLKIASVDTADTATYYCA RVYGNLYYFAYWGQGTTLTVSS |
| 181 | ACI-7062-406E3-Ab2-VH-FR1 | | QVTLKESGPAILQPSQTLSLTCSFSG FSLT |
| 182 | ACI-7062-406E3-Ab2-VH-CDR1 | | TYGIGVG |
| 183 | ACI-7062-406E3-Ab2-VH-FR2 | | WIRQPSGKGLEWLA |
| 184 | ACI-7062-406E3-Ab2-VH-CDR2 | | HIWWNDNKYYNTALKS |
| 185 | ACI-7062-406E3-Ab2-VH-FR3 | | RLTVSKDTSNNQVFLKIASVDTADT ATYYCAR |
| 186 | ACI-7062-406E3-Ab2-VH-CDR3 | | VYGNLYYFAY |
| 187 | ACI-7062-406E3-Ab2-VH-FR4 | | WGQGTTLTVSS |
| 188 | ACI-7062-406E3-Ab2-VH-Tail | | AKTTAPSVYPLAPVCGDTTGSSVTL |
| 189 | ACI-7062-406E3-Ab2-VH Nucleotide sequence of the heavy chain variable domain without tail | | CAGGTTACTCTGAAAGAGTCTGGC CCTGCGATATTGCAGCCCTCCCAG ACCCTCAGTCTGACTTGTTCTTTCT CTGGGTTTTCACTGACCACTTATG GTATAGGAGTAGGCTGGATTCGTC AGCCTTCAGGGAAGGGTCTGGAG TGGCTGGCACACATTTGGTGGAAT GATAATAAGTACTATAACACAGC CCTGAAGAGCCGGCTCACTGTCTC CAAGGATACCTCCAACAACCAGG TATTCCTCAAGATCGCCAGTGTAG ACACTGCAGATACTGCCACATACT ACTGTGCTCGAGTCTATGGTAACC TGTACTACTTTGCCTACTGGGCC AAGGCACCACTCTCACAGTCTCCT CA |
| 190 | ACI-7062-415C4-Ab1-VL Peptide sequence of the light chain variable domain without tail | 415C4C6 | DVLMTQTPLSLPVSLGDQASISCRS SQSIVHSTGNTYLEWYLQKPGQSPK LLIYKVSNRFSGVPDRFSGSGSGTD FTLKISRVEAEDLGVYYCFQGSRVP TFGAGTKLELKRA |

TABLE 11-continued

Antibody variable regions sequences

| SEQ ID NO: | Description including antibody name and the sequence information | Hybridoma clone | Sequence |
|---|---|---|---|
| 191 | ACI-7062-415C4-Ab1-VL-FR1 | | DVLMTQTPLSLPVSLGDQASISC |
| 192 | ACI-7062-415C4-Ab1-VL-CDR1 | | RSSQSIVHSTGNTYLE |
| 193 | ACI-7062-415C4-Ab1-VL-FR2 | | WYLQKPGQSPKLLIY |
| 194 | ACI-7062-415C4-Ab1-VL-CDR2 | | KVSNRFS |
| 195 | ACI-7062-415C4-Ab1-VL-FR3 | | GVPDRFSGSGSGTDFTLKISRVEAE DLGVYYC |
| 196 | ACI-7062-415C4-Ab1-VL-CDR3 | | FQGSRVPT |
| 197 | ACI-7062-415C4-Ab1-VL-FR4 | | FGAGTKLELKRA |
| 198 | ACI-7062-415C4-Ab1-VL-Tail | | DAAPTVSIFPPSSEQLTSGGASVVCF LNNFYPKDINVKWKIDGSERQNGV L |
| 199 | ACI-7062-415C4-Ab1-VL Nucleotide sequence of the light chain variable domain without tail | | GATGTTTTGATGACCCAAACTCCA CTCTCCCTGCCTGTCAGTCTTGGA GATCAAGCCTCCATCTCTTGCAGA TCTAGTCAGAGCATTGTACATAGT ACTGGAAACACCTATTTGGAATG GTACCTGCAGAAACCAGGCCAGT CTCCAAAGCTCCTGATCTACAAAG TTTCCAACCGATTTTCTGGGGTCC CAGACAGGTTCAGTGGCAGTGGA TCAGGGACAGATTTCACACTCAA GATCAGCAGAGTGGAGGCTGAGG ATCTGGGAGTTTATTACTGCTTTC AAGGTTCACGTGTTCCCACGTTCG GTGCTGGGACCAAGCTGGAGCTG AAACGGGCT |
| 200 | ACI-7062-415C4-Ab1-VH Peptide sequence of the heavy chain variable domain without tail | | QVTLKESGPGILQPSQTLSLTCSFSG FSLSTYGIGVGWIRQPSGKGLEWLA HIWWDNKYYKTALKSRLTISKDT SNNQVFLKIASVDTADSATYYCAR VYGNLYYFGYWGQGTTLTVSS |
| 201 | ACI-7062-415C4-Ab1-VH-FR1 | | QVTLKESGPGILQPSQTLSLTCSFSG FSLS |
| 202 | ACI-7062-415C4-Ab1-VH-CDR1 | | TYGIGVG |
| 203 | ACI-7062-415C4-Ab1-VH-FR2 | | WIRQPSGKGLEWLA |
| 204 | ACI-7062-415C4-Ab1-VH-CDR2 | | HIWWDNKYYKTALKS |
| 205 | ACI-7062-415C4-Ab1-VH-FR3 | | RLTISKDTSNNQVFLKIASVDTADS ATYYCAR |
| 206 | ACI-7062-415C4-Ab1-VH-CDR3 | | VYGNLYYFGY |
| 207 | ACI-7062-415C4-Ab1-VH-FR4 | | WGQGTTLTVSS |
| 208 | ACI-7062-415C4-Ab1-VH-Tail | | AKTIIPPSVYPLAPGSAAQTNSMVTL GCLVKGY |
| 209 | ACI-7062-415C4-Ab1-VH Nucleotide sequence of the heavy chain variable domain without tail | | CAGGTTACTCTGAAAGAGTCTGGC CCTGGGATATTGCAGCCCTCCCAG ACCCTCAGTCTGACTTGTTCTTTCT CTGGGTTTTCACTGAGCACTTATG GTATAGGAGTAGGCTGGATTCGTC AGCCCTCAGGGAAGGGTCTGGAG TGGCTGGCACACATTTGGTGGAAT GATAATAAGTACTATAAGACAGC CCTGAAGAGCCGGCTCACAATCTC CAAGGACACCTCCAACAACCAGG TTTTCCTCAAGATCGCCAGTGTGG ACACTGCAGATTCTGCCACATACT ACTGTGCTCGAGTCTATGGTAACC TGTACTACTTTGGCTACTGGGGCC AAGGCACCACTCTCACAGTCTCCT CA |
| 210 | ACI-7062-415H10-Ab2-VL Peptide sequence of the light chain variable domain without tail | 415H10B7 | DIVMTQSPSSLAMSVGQKVTMSCK SSQSLLNSSNQKNYLAWYQQKPGQ SPKLLIYFASTRESGVPDRFIGSGSG TDFTLTISSVQAEDLADYFCQQHYG IPLTFGAGTKLELKRA |
| 211 | ACI-7062-415H10-Ab2-VL-FR1 | | DIVMTQSPSSLAMSVGQKVTMSC |
| 212 | ACI-7062-4151H0-Ab2-VL-CDR1 | | KSSQSLLNSSNQKNYLA |

TABLE 11-continued

Antibody variable regions sequences

| SEQ ID NO: | Description including antibody name and the sequence information | Hybridoma clone | Sequence |
|---|---|---|---|
| 213 | ACI-7062-4151H0-Ab2-VL-FR2 | | WYQQKPGQSPKLLIY |
| 214 | ACI-7062-415H10-Ab2-VL-CDR2 | | FASTRES |
| 215 | ACI-7062-415H10-Ab2-VL-FR3 | | GVPDRFIGSGSGTDFTLTISSVQAEDLADYFC |
| 216 | ACI-7062-4151H0-Ab2-VL-CDR3 | | QQHYGIPLT |
| 217 | ACI-7062-415H10-Ab2-VL-FR4 | | FGAGTKLELKRA |
| 218 | ACI-7062-415H10-Ab2-VL-Tail | | DAAPTVSIFP |
| 219 | ACI-7062-415H10-Ab2-VL Nucleotide sequence of the light chain variable domain without tail | | GACATTGTGATGACACAGTCTCCATCCTCCCTGGCTATGTCAGTAGGACAGAAGGTCACTATGAGCTGCAAGTCCAGTCAGAGCCTTTTAAATAGTAGCAATCAAAAGAACTATTTGGCCTGGTACCAGCAGAAACCAGGACAGTCTCCTAAACTTCTAATATACTTTGCATCCACTAGGGAATCTGGGGTCCCTGATCGCTTCATAGGCAGTGGATCTGGGACAGATTTCACTCTTACCATCAGCAGTGTGCAGGCTGAAGACCTGGCAGATTACTTCTGTCAGCAACATTATGGCATTCCGCTCACGTTCGGTGCTGGGACCAAGCTGGAACTGAAACGGGCT |
| 220 | ACI-7062-415H10-Ab2-VH Peptide sequence of the heavy chain variable domain without tail | | DVQLVESGGGLVQPGGSRKLSCAASGFTFSSFGMHWVRQAPEKGLEWVAYISSGSSNIYYTDTVKGRFTISRDNPKNTLFLQMTSLRSEDTAIYYCARSGTTVPFDYWGQGTTLTVSS |
| 221 | ACI-7062-415H10-Ab2-VH-FR1 | | DVQLVESGGGLVQPGGSRKLSCAASGFTFS |
| 222 | ACI-7062-415H10-Ab2-VH-CDR1 | | SFGMH |
| 223 | ACI-7062-415H10-Ab2-VH-FR2 | | WVRQAPEKGLEWVA |
| 224 | ACI-7062-415H10-Ab2-VH-CDR2 | | YISSGSSNIYYTDTVKG |
| 225 | ACI-7062-415H10-Ab2-VH-FR3 | | RFTISRDNPKNTLFLQMTSLRSEDTAIYYCAR |
| 226 | ACI-7062-415H10-Ab2-VH-CDR3 | | SGTTVPFDY |
| 227 | ACI-7062-415H10-Ab2-VH-FR4 | | WGQGTTLTVSS |
| 228 | ACI-7062-415H10-Ab2-VH-Tail | | ATTTAPSVYPLVPGCSDTSGSSVTLG |
| 229 | ACI-7062-415H10-Ab2-VH Nucleotide sequence of the heavy chain variable domain without tail | | GATGTGCAGCTGGTGGAGTCGGGGGGAGGCTTAGTGCAGCCTGGAGGGTCCCGGAAACTCTCCTGTGCAGCCTCTGGATTCACTTTCAGTAGCTTTGGAATGCACTGGGTTCGTCAGGCTCCAGAGAAGGGGCTGGAGTGGGTCGCATACATTAGTAGTGGCAGTAGTAACATCTACTATACAGACACAGTGAAGGGCCGATTCACCATCTCTAGAGACAATCCCAAGAACACCCTGTTCCTGCAAATGACCAGTCTAAGGTCTGAGGACACGGCCATATATTACTGTGCAAGATCAGGGACTACGGTCCCCTTTGACTACTGGGGCCAAGGCACCACTCTCACAGTCTCCTCA |
| 230 | ACI-7062-401A2-Ab2-VL Peptide sequence of the light chain variable domain without tail | 401A2C6 | DIVMTQSPSSLAMSVGQKVTMSCKSSQSLLNSGDQKNYLAWYQQKPGQSPELLLYFASTRASGVPDRFIGSGSGTDFSLTISSVQAEDLADYFCQQHYSIPLTFGAGTKLELKRA |

TABLE 11-continued

Antibody variable regions sequences

| SEQ ID NO: | Description including antibody name and the sequence information | Hybridoma clone | Sequence |
|---|---|---|---|
| 231 | ACI-7062-401A2-Ab2-VL Nucleotide sequence of the light chain variable domain without tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCGATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCTCTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCT |
| 232 | ACI-7062-401A2-Ab2-VH Peptide sequence of the heavy chain variable domain without tail | | DVQLVESGGGLVQPGGSRRLSCAA SGETFSRFGMHWVRQAPEKGLEWV AYIRSGSDIIYYADSVKGRFTISRDN PENTLFLQMTSLRSEDTAMYYCAR SGTTVPFDYWGQGTSLTVSS |
| 233 | ACI-7062-401A2-Ab2-VH Nucleotide sequence of the heavy chain variable domain without tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGGT TTGGAATGCACTGGGTTCGCCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA |
| 234 | ACI-7062-412A7-Ab1-VL Peptide sequence of the light chain variable domain without tail | 412A7B7 | DIVMTQSPSSLAMSVGQKVTMSCK SSQSLLNSGNQKNYLAWYQQKPGQ SPELLLYFASTRASGVPDRFIGSGSG TDFTLTISSVQAEDLADYFCQQHYS IPLTFGAGTKLELKRA |
| 235 | ACI-7062-412A7-Ab1-VL Nucleotide sequence of the light chain variable domain without tail | | GACATTGTGATGACACAGTCTCCA TCCTCCCTGGCTATGTCAGTTGGA CAGAAGGTCACTATGAGCTGCAA GTCCAGTCAGAGCCTTITAAATAG TGGCAATCAAAAGAACTATTTGG CCTGGTACCAGCAGAAACCAGGA CAGTCTCCTGAACTTCTATTATAC TTTGCATCCACTAGGGCATCTGGG GTCCCTGATCGCTTCATAGGCAGT GGATCTGGGACAGATTTCACTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCT |
| 236 | ACI-7062-412A7-Ab1-VH Peptide sequence of the heavy chain variable domain without tail | | DVQLVESGGGLVQPGGSRRLSCAA SGFTFSSFGMHWVRQAPEKGLEWV AYIRSGSDIIYYADSVKGRFTISRDN PENTLFLQMTSLRSEDTAMYYCAR |

TABLE 11-continued

Antibody variable regions sequences

| SEQ ID NO: | Description including antibody name and the sequence information | Hybridoma clone | Sequence |
|---|---|---|---|
| 237 | ACI-7062-412A7-Ab1-VH Nucleotide sequence of the heavy chain variable domain without tail | | SGTTVPFDYWGQGTSLTVSS GATGTGCAGCTGGTGGAGTCTGG GGGAGGCTTAGTGCAGCCTGGAG GGTCCCGGAGACTCTCCTGTGCAG CCTCTGGATTCACTTTCAGTAGCT TTGGAATGCACTGGGTTCGTCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA |
| 238 | ACI-7062-406E3-Ab1-VL Peptide sequence of the light chain variable domain without tail | 406E3D5 | DVLMTQTPLSLPVSLGDRASISCRSS QSIVHRSGNTYLEWYLQKPGQSPK LLIYKVSNRFSGVPDRFSGSGSGTD FTLKISRVEAEDLGVYYCFQGSHVP TFGAGTKLELKRA |
| 239 | ACI-7062-406E3-Ab1-VL Nucleotide sequence of the light chain variable domain without tail | | GATGTTTTGATGACCCAAACTCCA CTCTCCCTGCCTGTCAGTCTTGGA GATCGAGCCTCCATCTCTTGCAGA TCTAGTCAGAGCATTGTACATCGT AGTGGAAACACCTATTTAGAGTG GTACCTGCAGAAACCAGGCCAGT CTCCAAAGCTCCTGATCTACAAAG TTTCCAACCGATTTTCTGGGGTCC CAGACAGGTTCAGTGGCAGTGGA TCAGGGACAGATTTCACACTCAA GATCAGCAGAGTGGAGGCTGAGG ATCTGGGAGTTTATTACTGCTTTC AAGGTTCACATGTTCCCACGTTCG GTGCTGGGACCAAGCTGGAGCTG AAACGGGCT |
| 240 | ACI-7062-406E3-Ab1-VH Peptide sequence of the heavy chain variable domain without tail | | QVTLKESGPAILQPSQTLSLTCSFSG FSLTTYGIGVGWIRQPSGKGLEWLA HIWWNDNKYYNTALKSRLTVSKD TSNNQVFLKIASVDTADTATYYCA RVYGNLYYFAYWGQGTLTVSS |
| 241 | ACI-7062-406E3-Ab1-VH Nucleotide sequence of the heavy chain variable domain without tail | | CAGGTTACTCTGAAAGAGTCTGGC CCTGCGATATTGCAGCCCTCCCAG ACCCTCAGTCTGACTTGTTCTTTCT CTGGGTTTTCACTGACCACTTATG GTATAGGAGTAGGCTGGATTCGTC AGCCTTCAGGGAAGGGTCTGGAG TGGCTGGCACACATTTGGTGGAAT GATAATAAGTACTATAACACAGC CCTGAAGAGCCGGCTCACTGTCTC CAAGGATACCTCCAACAACCAGG TATTCCTCAAGATCGCCAGTGTAG ACACTGCAGATACTGCCACATACT ACTGTGCTCGAGTCTATGGTAACC TGTACTACTTTGCCTACTGGGGCC AAGGCACCACTCTCACAGTCTCCT CA |
| 242 | ACI-7062-404D6-Ab2-VL Peptide sequence of the light chain variable domain without tail | 404D6E11 | DVLMTQTPLSLPVSLGDQASISCRS SQSIVHGSGNTYLEWYLQKPGQSP KLLIYKVSNRFSGVPDRFSGSGSGT DFTLRISRVEAEDLGVYYCFQGSHV PTFGAGTKLELKRA |
| 243 | ACI-7062-404D6-Ab2-VL Nucleotide sequence of the light chain variable domain without tail | | GATGITITGATGACCCAAACTCCA CTCTCCCTGCCTGTCAGTCTTGGA GATCAAGCCTCCATCTCTTGCAGA TCTAGTCAGAGCATTGTACATGGT TCTGGAAACACCTATTTAGAATGG TACCTGCAGAAACCAGGCCAGTC TCCAAAGCTCCTGATCTACAAAGT TTCCAACCGATTTTCTGGGGTCCC AGACAGGTTCAGTGGCAGTGGAT CAGGGACAGATTTCACACTCAGG |

TABLE 11-continued

Antibody variable regions sequences

| SEQ ID NO: | Description including antibody name and the sequence information | Hybridoma clone | Sequence |
|---|---|---|---|
| | | | ATCAGCAGAGTGGAGGCTGAGGA TCTGGGAGTTTATTACTGCTTTCA AGGTTCACATGTTCCCACGTTCGG TGCTGGGACCAAGCTGGAGCTGA AACGGGCT |
| 244 | ACI-7062-404D6-Ab2-VH Peptide sequence of the heavy chain variable domain without tail | | QVTLKESGPGILQPSQTLSLTCSFSG FSLSTYGIGVGWIRQPSGKGLEWLA HIWWNDYKYYNTALKSRLTISKDT SNNRVFLKIASVDTADTATYYCAR VYGNLYYFDYWGQGTTLTVSS |
| 245 | ACI-7062-404D6-Ab2-VH Nucleotide sequence of the heavy chain variable domain without tail | | CAGGTTACTCTGAAAGAGTCTGGC CCTGGGATATTGCAGCCCTCCCAG ACCCTCAGTCTGACTTGTTCTTTCT CTGGGTTTTCACTGAGCACTTATG GTATAGGAGTAGGCTGGATTCGTC AGCCTTCAGGGAAGGGTCTGGAG TGGCTGGCACACATTTGGTGGAAT GATTATAAGTACTATAACACAGCC CTGAAGAGCCGGCTCACAATCTCC AAGGATACCTCCAACAACCGGGT ATTCCTCAAGATCGCCAGTGTGGA CACTGCAGATACTGCCACATACTA CTGTGCTCGAGTCTATGGTAACCT GTACTACTTTGACTACTGGGGCCA AGGCACCACTCTCACAGTCTCCTC A |
| 246 | ACI-7062-410H3-Ab1-VL Peptide sequence of the light chain variable domain without tail | 410H3B9 | DIVMTQSPSSLAMSVGQKVTMSCK SSQSLLNSGNQKNYLAWYQQKPGQ SPELLLYFASTRASGVPDRFIGSGSG TDFTLTISSVQAEDLADYFCQQHYS IPLTFGAGTKLELKRA |
| 247 | ACI-7062-410H3-Ab1-VL Nucleotide sequence of the light chain variable domain without tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCAATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCACTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCT |
| 248 | ACI-7062-410H3-Ab1-VH Peptide sequence of the heavy chain variable domain without tail | | DVQLVESGGGLVQPGGSRRLSCAA SGFTFSSFGMHWVRQAPEKGLEWV AYIRSGSDIWYADSVKGRFTISRDN PENTLFLQMTSLRSEDTAMYYCAR SGTTVPFDYWGQGTSLTVSS |
| 249 | ACI-7062-410H3-Ab1-VH Nucleotide sequence of the heavy chain variable domain without tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGCT TTGGAATGCACTGGGTTCGTCAGG CTCCAGAGAAGGGGCTGGAGTGG GTCGCATACATTAGGAGTGGCAG TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA |

TABLE 11-continued

Antibody variable regions sequences

| SEQ ID NO: | Description including antibody name and the sequence information | Hybridoma clone | Sequence |
|---|---|---|---|
| 250 | ACI-7062-414A5-Ab1-VL Peptide sequence of the light chain variable domain without tail | 414A5D2 | DIVMTQSPSSLAMSVGQKVTMSCK SSQSLLNSSNQKNYLAWYQQKPGQ SPKLLVYFASTRESGVPDRFIGSGSG TDFTLTINSVQAEDLADYFCQQHYS IPLTFGAGTKLELKRA |
| 251 | ACI-7062-414A5-Ab1-VL Nucleotide sequence of the light chain variable domain without tail | | GACATTGTGATGACACAGTCTCCA TCCTCCCTGGCTATGTCAGTAGGA CAGAAGGTCACTATGAGCTGCAA GTCCAGTCAGAGCCTTTTAAATAG TAGCAATCAAAAGAACTATTTGG CCTGGTACCAGCAGAAACCAGGA CAGTCTCCTAAACTTCTGGTATAC TTTGCATCCACTAGGGAATCTGGG GTCCCTGATCGCTTCATAGGCAGT GGATCTGGGACAGATTTCACTCTT ACCATCAACAGTGTGCAGGCTGA AGACCTGGCAGATTACTTCTGTCA GCAACATTATAGTATTCCGCTCAC GTTCGGTGCTGGGACCAAGCTGG AGCTGAAACGGGCT |
| 252 | ACI-7062-414A5-Ab1-VH Peptide sequence of the heavy chain variable domain without tail | | DVQLVESGGGLVQPGGSRRLSCAA SGFTFSSFGMHWVRQAPEKGLEWV AYIRSGSDIWYADTVKGRFTISRDN PENTLFLEMTRLRSEDTAMYYCAR SGTTVPFDYWGQGTSLTVSS |
| 253 | ACI-7062-414A5-Ab1-VH Nucleotide sequence of the heavy chain variable domain without tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGCT TTGGAATGCACTGGGTTCGTCAGG CTCCAGAGAAGGGGCTGGAGTGG GTCGCATACATTAGGAGTGGCAG TGATATAATCTACTATGCAGACAC AGTGAAGGGCCGATTCACCATCTC CAGAGACAATCCCGAGAACACCC TGTTTTTGGAAATGACCAGACTAA GGTCTGAGGACACGGCCATGTATT ACTGTGCAAGATCAGGGACTACG GTCCCCTTTGACTACTGGGGCCAA GGCACCAGTCTCACAGTCTCTTCA |
| 254 | ACI-7062-412E12-Ab1-VL Peptide sequence of the light chain variable domain without tail | 412E12A2 | DIVMTQSPSSLAMSVGQKVTMSCK SSQSLLNSGDQKNYLAWYQQKPGQ SPELLLYFASTRASGVPDRFIGSGSG TDFSLTISSVQAEDLADYFCQQHYSI PLTFGAGTKLELKRA |
| 255 | ACI-7062-412E12-Ab1-VL Nucleotide sequence of the light chain variable domain without tail | | GACATTGTGATGACACAGTCTCCA TCCTCCCTGGCTATGTCAGTTGGA CAGAAGGTCACTATGAGCTGCAA GTCCAGTCAGAGCCTTTTAAATAG TGGCGATCAAAAGAACTATTTGG CCTGGTACCAGCAGAAACCAGGA CAGTCTCCTGAACTTCTGTTATAC TTTGCATCCACTAGGGCATCTGGG GTCCCTGATCGCTTCATAGGCAGT GGATCTGGGACAGATTTCTCTCTT ACCATCAGCAGTGTGCAGGCTGA AGACCTGGCAGATTACTTCTGTCA GCAACATTATAGTATTCCGCTCAC GTTCGGTGCTGGGACCAAGCTGG AGCTGAAACGGGCT |
| 256 | ACI-7062-412E12-Ab1-VH Peptide sequence of the heavy chain variable domain without tail | | DVQLVESGGGLVQPGGSRRLSCAA SGFTESREGMHWVRQAPEKGLEWV AYIRSGSDIIYYADSVKGRFTISRDN PENTLFLQMTSLRSEDTAMYYCAR SGTTVPFDYWGQGTSLTVSS |
| 257 | ACI-7062-412E12-Ab1-VH Nucleotide sequence of the heavy chain variable domain without tail | | GATGTGCAGCTGGTGGAGTCTGG GGGAGGCTTAGTGCAGCCTGGAG GGTCCCGGAGACTCTCCTGTGCAG CCTCTGGATTCACTTTCAGTAGGT TTGGAATGCACTGGGTTCGCCAGG CTCCAGAGAAGGGGCTGGAGTGG GTCGCATACATTAGGAGTGGCAG |

TABLE 11-continued

Antibody variable regions sequences

| SEQ ID NO: | Description including antibody name and the sequence information | Hybridoma clone | Sequence |
|---|---|---|---|
| | | | TGATATAATCTACTATGCAGACTC AGTGAAGGGCCGATTCACCATCTC CAGAGACAATCCCGAGAACACCC TGTTCCTGCAAATGACCAGTCTAA GGTCTGAGGACACGGCCATGTATT ACTGTGCAAGATCAGGGACTACG GTCCCCTTTGACTACTGGGGCCAA GGCACCAGTCTCACAGTCTCTTCA |
| 258 | ACI-7062-416A11-Ab1-VL Peptide sequence of the light chain variable domain without tail | 416A11B3 | DVLMTQTPLSLPVSLGDRASISCRSS QSIVHSSGNTYLEWYLQKPGQSPKL LIYKVSNRFSGVPDRFSGSGSGTDF TLKISRVEAEDLGVYYCFQGSRVPT FGAGTKLELKRA |
| 259 | ACI-7062-416A11-Ab1-VL Nucleotide Sequence of the light chain variable domain without tail | | GATGTTTTGATGACCCAAACTCCA CTCTCCCTGCCTGTCAGTCTTGGA GATCGAGCCTCCATCTCTTGCAGA TCTAGTCAGAGCATTGTACATAGT AGTGGAAACACCTATTTAGAATG GTACCTGCAGAAGCCAGGCCAGT CTCCAAAGCTCCTGATCTACAAAG TTTCCAACCGATTTTCTGGGGTCC CAGACAGGTTCAGTGGCAGTGGA TCAGGGACAGATTTCACACTCAA GATCAGCAGAGTGGAGGCTGAGG ATCTGGGAGTTTATTACTGCTTTC AAGGTTCACGTGTTCCCACGTTCG GTGCTGGGACCAAGCTGGAGCTG AAACGGGCT |
| 260 | ACI-7062-416A11-Ab1-VH Peptide sequence of the heavy chain variable domain without tail | | QVTLKESGPGILQSSQTLSLTCSFSG FSLSTYGIGVGWIRQPSGKGLEWLA HIWWNDNKYYNTALKSRLTISKDT SNNQVFLKIASVDTADAATYYCAR VYGNLYYFGYWGQGTTLTVSS |
| 261 | ACI-7062-416A11-Ab1-VH Nucleotide sequence of the heavy chain variable domain without tail | | CAGGTTACTCTGAAAGAGTCTGGC CCTGGGATATTGCAGTCCTCCCAG ACCCTCAGTCTGACTTGTTCTTTCT CTGGATTTTCACTGAGCACTTATG GTATAGGAGTAGGCTGGATTCGTC AGCCTTCAGGGAAGGGTCTGGAG TGGCTGGCACACATTTGGTGGAAT GATAATAAGTACTATAACACAGC CCTGAAGAGCCGACTCACAATCTC CAAGGATACCTCCAACAACCAGG TATTCCTCAAGATCGCCAGTGTGG ACACTGCAGATGCTGCCACATACT ACTGTGCTCGAGTCTATGGTAACC TATACTACTTTGGCTACTGGGGCC AAGGCACCACTCTCACAGTCTCCT CA |

REFERENCES

Arai et al., TDP-43 is a component of ubiquitin-positive tau-negative inclusions in frontotemporal lobar degeneration and amyotrophic lateral sclerosis, Biochemical and Biophysical Research Communications 351 (2006) 602-611.

Buratti and Baralle, Nuclear factor TDP-43 can affect selected microRNA levels, FEBS Journal 277 (2010) 2268-2281.

Brettschneider J et al., Spreading of pathology in neurodegenerative diseases: a focus on human studies, Nature Rev. Neuroscience, 2015, 109.

Brettschneider et al., Stages of pTDP-43 pathology in amyotrophic lateral sclerosis, Ann Neurol. 2013 July; 74(1): 20-38.

Charlton, Methods in Molecular Biology, Val. 248 (B. K. C. Lo, ed., Humana Press, Totowa, N.J., 2003), pp. 245-254.

Chen et al. Selection and analysis of an optimized anti-VEGF antibody: crystal structure of an affinity-matured Fab in complex with antigen, J. Mol. Biol. 293:865-881 (1999).

Chothia J., Canonical structures for the hypervariable regions of immunoglobulins Mol. Biol. 196 (1987), 901-917.

Chothia, Conformations of immunoglobulin hypervariable regions Nature 342 (1989), 877-883.

Chowdhury, Methods Mol. Biol. 207:179-196 (2008)

Clynes et al., Fc receptors are required in passive and active immunity to melanoma Proc. Nat'l Acad. sci. USA 95:652-656 (1998)

Cohen et al., An acetylation switch controls TDP-43 function and aggregation propensity, Nat Commun. 6: 5845, 2015.

Cragg, M. S. et al., Complement-mediated lysis by anti-CD20 mAb correlates with segregation into lipid rafts, Blood 101:1045-1052 (2003)

Cragg, M. S. and M. J. Glennie, Antibody specificity controls in vivo effector mechanisms of anti-CD20 reagents, Blood 103:2738-2743 (2004)).

Cunningham and Wells, High-resolution epitope mapping of hGH-receptor interactions by alanine-scanning mutagenesis, (1989) Science, 244: 1081-1085.

Duncan & Winter, The binding site for C1q on IgG, Nature 322:738-40 (1988)

Feiler et al., TDP-43 is intercellularly transmitted across axon Terminals, J. Cell Biol. Vol. 211 No. 4 897-911.

Gazzano-Santoro et al., Engineered Antibodies with Increased Activity to Recruit Complement, J. Immunol. Methods 202:163 (1996)

Gerngross, Advances in the production of human therapeutic proteins in yeasts and filamentous fungi, Nat. Biotech. 22:1409-1414 (2004).

Gerhardt et al., Methods for General and Molecular Bacteriology, ASM Press (1994).

Golemis, Protein-Protein Interactions: A Molecular Cloning Manual, Cold Spring Harbor Laboratory Press (2002).

Graham et al., Characteristics of a human cell line transformed by DNA from human adenovirus type 5, J. Gen Viral. 36:59 (1977)

Guyer et al., Immunoglobulin binding by mouse intestinal epithelial cell receptors, J. Immunol. 117:587 (1976).

Harlow and Lane, Antibodies: A Laboratory Manual, Cold Spring Harbor Laboratory Press, (1988).

Harlow and Lane, Using Antibodies: A Laboratory Manual, Cold Spring Harbor Laboratory Press, (1999).

Hasegawa et al., Phosphorylated TDP-143 in frontotemporal lobar degeneration and amyotrophic lateral sclerosis, (2008) Annals of Neurology Vol 64 No 1, 60-70.

Hasegawa et al., Prion-like mechanisms and potential therapeutic targets in neurodegenerative disorders, Pharmacol Ther. 2017 April; 172:22-33.

Hellstrom, I. et al. Proc. Nat'l Acad. Sci. USA 83:7059-7063 (1986).

Hellstrom, I. et al. Proc. Nat'l Acad. Sci. USA 83:7059-7063 (1986).

Hellstrom, I et al., Proc. Nat'l Acad. Sci. USA 82:1499-1502 (1985).

Hoogenboom et al., Methods in Molecular Biology 178:1-37 (O'Brien et al., ed., Human Press, Totowa, N.J., (2001).

Howard and Bethell. (2000) Basic Methods in Antibody Production and Characterization, Crc. Pr. Inc. Idusogie et al., J. Immunol. 164: 4178-4184 (2000).

Ishii et al., Formation and spreading of TDP-43 aggregates in cultured neuronal and glial cells demonstrated by time-lapse imaging, PLoS ONE 12(6): e0179375, 2017.

Jones et al., Replacing the complementarity-determining regions in a human antibody with those from a mouse, Nature 321 (1986), 522-525.

K A et al., TDP-43 is a key player in the clinical features associated with Alzheimer's disease, Acta Neuropathol. 2014; 127(6): 811-824.

K A et al., Staging TDP-43 pathology in Alzheimer's disease Acta Neuropathol. 2014; 127(3): 441-450.

Kam et al., Proc. Natl. Acad. Sci. USA 102: 11600-11605 (2005).

Kanda Y. et al., Bioteehnol. Bioeng., 94(4):680-688 (2006).

Kabat "Sequences of Proteins of Immunological Interest", 5th edit. NIH Publication no. 91-3242 U.S. Department of Health and Human Services (1991).

Kim et al., J. Immunol. 24:249 (1994).

Kohler, Nature 256 (1975), 495.

Khor, Proceedings of the American Society of Clinical Oncology Abstract (1997), 847.

Lagier-Tourenne et al., TDP-43 and FUS/TLS: emerging roles in RNA processing and neurodegeneration, Human Molecular Genetics, 2010, Vol. 19, Review Issue 1 R46-R64.

Lagier-Tourenne and Cleveland, Rethinking ALS: the FUS about TDP-43, Cell 136, 2009, 1001-1004.

Le Ber, Genetics of frontotemporal lobar degeneration: an up-date and diagnosis algorithm, Revue Neurologique 169 (2013) 811-819.

Lefkovits, Immunology Methods Manual: The Comprehensive Sourcebook of Techniques; Academic Press (1997).

Lo M. et al., Effector-attenuating Substitutions That Maintain Antibody Stability and Reduce Toxicity in Mice Journal of Biochemistry, 292, 3900-3908.

LoBuglio, Proceedings of the American Society of Clinical Oncology Abstract (1997), 1562.

Li et al., Optimization of humanized IgGs in glycoengineered *Pichia pastoris*, Nat. Biotech. 24:210-215 (2006).

Mackenzie and Neumann, Molecular neuropathology of frontotemporal dementia: insights into disease mechanisms from postmortem studies, J. Neurochem. (2016) 138 (Suppl. 1), 54-70.

Mather, Establishment and characterization of two distinct mouse testicular epithelial cell lines, Biol. Reprod. 23:243-251 (1980)

Mather et al., Culture of testicular cells in hormone-supplemented serum-free medium, Annals N. Y Aead. Sei. 383:44-68 (1982)

McAleese et al., TDP-43 pathology in Alzheimer's disease, dementia with Lewy bodies and ageing, Brain Pathol. 2017 July; 27(4): 472-479.

Morris, Epitope Mapping Protocols, Methods in Molecular Biology vol. 66(1996) (Humana Press, Totowa, N.J.).

Nonaka et al., Prion-like Properties of Pathological TDP-43 Aggregates from Diseased Brains, Cell Reports 4 (2013), 124-134.

Neumann et al., Ubiquitinated TDP-43 in frontotemporal lobar degeneration and amyotrophic lateral sclerosis, Science 314, (2006), 130-133.

Neumann et al., Phosphorylation of S409/410 of TDP-43 is a consistent feature in all sporadic and familial forms of TDP-43 proteinopathies, Acta Neuropathol. (2009) 117: 137-149.

Petkova, S. B. et al., Int'l. Immunol. 18(12):1759-1769 (2006).

Plückthun, The Pharmacology of Monoclonal Antibodies, Rosenburg and Moore eds. Springer-Verlag, N.Y. (1994), 269-315.

Porta S. et al., Patient-derived frontotemporal lobar degeneration brain extracts induce formation and spreading of TDP-43 pathology in vivo Nat. Comm., 2018

Okazaki et al., Fucose depletion from human IgG1 oligosaccharide enhances binding enthalpy and association rate between IgG1 and FcgammaRIIIa. J. Mol. Biol. 336: 1239-1249 (2004).

Presta L G., Antibody engineering, Curr Op Struct Biol 2 (1992), 593-596.

Reichmann, Reshaping human antibodies for therapy, Nature 332(1998), 323-327.

Remington's Pharmaceutical Sciences 16th edition, Osol, A. Ed. (1980)

Ripka et al., Two Chinese hamster ovary glycosylation mutants affected in the conversion of GDP-mannose to GDP-fucose. Arch. Biochem. Biophys. 249:533-545 (1986).

Sambrook et al., Molecular Cloning: A Laboratory Manual; Cold Spring Harbor Laboratory Press, 2nd edition (1989) and 3rd edition (2001).

Shepherd and Dean (2000), Monoclonal Antibodies: A Practical Approach, Oxford University Press Shields et al., High Resolution Mapping of the Binding Site on Human IgG1 for FcγRI, FcγRII, FcγRIII, and FcRn and Design of IgG1 Variants with Improved Binding to the FcγR, J. Biol. Chem. 9(2): 6591-6604 (2001).

Ticozzi et al., Protein Aggregation and Defective RNA Metabolism as Mechanisms for Motor Neuron Damage, 9(3): 285-296 CNS Neurol. Disord. Drug Targets. 2010, 9(3), 285-296.

Urlaub et al., Isolation of Chinese hamster cell mutants deficient in dihydrofolate reductase activity, Proc. Natl. Acad. cii. USA 77:4216 (1980)

Verhoeyen et al., Reshaping human antibodies: Grafting an antilysozyme activity, Science 239 (1988), 1534-1536.

Wang et al., TDP-43: an emerging new player in neurodegenerative diseases Trends in Molecular Medicine Vol. 14 No. 11, 2008, 479-485.

Waraich et al., TDP-43: a DNA and RNA binding protein with roles in neurodegenerative diseases, The International Journal of Biochemistry & Cell Biology 42 (2010) 1606-1609.

Wright et al., Effect of glycosylation on antibody function. TIBTECH 15:26-32 (1997).

Yamane-Ohnuki et al., Establishment of FUT8 knockout Chinese hamster ovary cells: An ideal host cell line for producing completely defucosylated antibodies with enhanced antibody-dependent cellular cytotoxicity. Biotech. Bioeng. 87: 614 (2004).

Yazaki and Wu, Methods in Molecular Biology, Val. 248 (B. K. C. Lo, ed., Humana Press, Totowa, N.J.), pp. 255-268 (2003).

The invention claimed is:

1. A binding molecule which specifically recognizes misfolded TDP-43, wherein the binding molecule specifically binds to an epitope within amino acids 215-222 of mature human TDP-43, and wherein the binding molecule comprises CDR sequences selected from the group consisting of:
  (a) VL-CDR1 comprising the amino acid sequence of SEQ ID NO: 12; VL-CDR2 comprising the amino acid sequence of SEQ ID NO: 14; VL-CDR3 comprising the amino acid sequence of SEQ ID NO: 16; VH-CDR1 comprising the amino acid sequence of SEQ ID NO: 22; VH-CDR2 comprising the amino acid sequence of SEQ ID NO: 24; and VH-CDR3 comprising the amino acid sequence of SEQ ID NO: 26;
  (b) VL-CDR1 comprising the amino acid sequence of SEQ ID NO: 32; VL-CDR2 comprising the amino acid sequence of SEQ ID NO: 34; VL-CDR3 comprising the amino acid sequence of SEQ ID NO: 36; VH-CDR1 comprising the amino acid sequence of SEQ ID NO: 42; VH-CDR2 comprising the amino acid sequence of SEQ ID NO: 24; and VH-CDR3 comprising the amino acid sequence of SEQ ID NO: 46;
  (c) VL-CDR1 comprising the amino acid sequence of SEQ ID NO: 52; VL-CDR2 comprising the amino acid sequence of SEQ ID NO: 54; VL-CDR3 comprising the amino acid sequence of SEQ ID NO: 56; VH-CDR1 comprising the amino acid sequence of SEQ ID NO: 62; VH-CDR2 comprising the amino acid sequence of SEQ ID NO: 64; and VH-CDR3 comprising the amino acid sequence of SEQ ID NO: 66;
  (d) VL-CDR1 comprising the amino acid sequence of SEQ ID NO: 72; VL-CDR2 comprising the amino acid sequence of SEQ ID NO: 74; VL-CDR3 comprising the amino acid sequence of SEQ ID NO: 76; VH-CDR1 comprising the amino acid sequence of SEQ ID NO: 82; VH-CDR2 comprising the amino acid sequence of SEQ ID NO: 84; and VH-CDR3 comprising the amino acid sequence of SEQ ID NO: 86;
  (e) VL-CDR1 comprising the amino acid sequence of SEQ ID NO: 92; VL-CDR2 comprising the amino acid sequence of SEQ ID NO: 94; VL-CDR3 comprising the amino acid sequence of SEQ ID NO: 96; VH-CDR1 comprising the amino acid sequence of SEQ ID NO: 102;
  VH-CDR2 comprising the amino acid sequence of SEQ ID NO: 104; and VH-CDR3 comprising the amino acid sequence of SEQ ID NO: 106;
  (f) VL-CDR1 comprising the amino acid sequence of SEQ ID NO: 112; VL-CDR2 comprising the amino acid sequence of SEQ ID NO: 114; VL-CDR3 comprising the amino acid sequence of SEQ ID NO: 116; VH-CDR1 comprising the amino acid sequence of SEQ ID NO: 122;
  VH-CDR2 comprising the amino acid sequence of SEQ ID NO: 124; and VH-CDR3 comprising the amino acid sequence of SEQ ID NO: 126;
  (g) VL-CDR1 comprising the amino acid sequence of SEQ ID NO: 132; VL-CDR2 comprising the amino acid sequence of SEQ ID NO: 134; VL-CDR3 comprising the amino acid sequence of SEQ ID NO: 136; VH-CDR1 comprising the amino acid sequence of SEQ ID NO: 142;
  VH-CDR2 comprising the amino acid sequence of SEQ ID NO: 24; and VH-CDR3 comprising the amino acid sequence of SEQ ID NO: 146;

(h) VL-CDR1 comprising the amino acid sequence of SEQ ID NO: 152; VL-CDR2 comprising the amino acid sequence of SEQ ID NO: 154; VL-CDR3 comprising the amino acid sequence of SEQ ID NO: 156; VH-CDR1 comprising the amino acid sequence of SEQ ID NO: 162; VH-CDR2 comprising the amino acid sequence of SEQ ID NO: 164; and VH-CDR3 comprising the amino acid sequence of SEQ ID NO: 166;

(i) VL-CDR1 comprising the amino acid sequence of SEQ ID NO: 192; VL-CDR2 comprising the amino acid sequence of SEQ ID NO: 194; VL-CDR3 comprising the amino acid sequence of SEQ ID NO: 196; VH-CDR1 comprising the amino acid sequence of SEQ ID NO: 202; VH-CDR2 comprising the amino acid sequence of SEQ ID NO: 64; and VH-CDR3 comprising the amino acid sequence of SEQ ID NO: 206; and (j) VL-CDR1 comprising the amino acid sequence of SEQ ID NO: 212; VL-CDR2 comprising the amino acid sequence of SEQ ID NO: 214; VL-CDR3 comprising the amino acid sequence of SEQ ID NO: 216; VH-CDR1 comprising the amino acid sequence of SEQ ID NO: 222; VH-CDR2 comprising the amino acid sequence of SEQ ID NO: 224; and VH-CDR3 comprising the amino acid sequence of SEQ ID NO: 226.

2. The binding molecule of claim 1, which specifically binds to cytoplasmic misfolded and/or extracellular misfolded TDP 43.

3. The binding molecule of claim 1, which blocks TDP-43 cell-to-cell spreading, and/or disaggregates TDP-43 aggregates and/or inhibits the aggregation of TDP-43 protein or fragments thereof.

4. The binding molecule of claim 1, which is an antibody or an antigen-binding fragment thereof.

5. The binding molecule of claim 4, wherein the antibody is:
 (a) a monoclonal antibody; and/or
 (b) a murine antibody; or
 (c) a humanized antibody; or
 (d) a chimeric antibody.

6. The binding molecule of claim 4, wherein the antibody comprises:
 (a) a Light Chain Variable Region (VL) comprising the sequence of SEQ ID NO: 10 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 10 and a Heavy Chain Variable Region (VH) comprising the sequence of SEQ ID NO: 20 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 20;
 (b) a Light Chain Variable Region (VL) comprising the sequence of SEQ ID NO: 30 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 30 and a Heavy Chain Variable Region (VH) comprising the sequence of SEQ ID NO: 40 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 40;
 (c) a Light Chain Variable Region (VL) comprising the sequence of SEQ ID NO: 50 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 50 and a Heavy Chain Variable Region (VH) comprising the sequence of SEQ ID NO: 60 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 60;
 (d) a Light Chain Variable Region (VL) comprising the sequence of SEQ ID NO: 70 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 70 and a Heavy Chain Variable Region (VH) comprising the sequence of SEQ ID NO: 80 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 80;
 (e) a Light Chain Variable Region (VL) comprising the sequence of SEQ ID NO: 90 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 90 and a Heavy Chain Variable Region (VH) comprising the sequence of SEQ ID NO: 100 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 100;
 (f) a Light Chain Variable Region (VL) comprising the sequence of SEQ ID NO: 110 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 110 and a Heavy Chain Variable Region (VH) comprising the sequence of SEQ ID NO: 120 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 120;
 (g) a Light Chain Variable Region (VL) comprising the sequence of SEQ ID NO: 130 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 130 and a Heavy Chain Variable Region (VH) comprising the sequence of SEQ ID NO: 140 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 140;
 (h) a Light Chain Variable Region (VL) comprising the sequence of SEQ ID NO: 150 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 150 and a Heavy Chain Variable Region (VH) comprising the sequence of SEQ ID NO: 160 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 160;

(i) a Light Chain Variable Region (VL) comprising the sequence of SEQ ID NO: 170 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 170 and a Heavy Chain Variable Region (VH) comprising the sequence of SEQ ID NO: 180 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 180;

(j) a Light Chain Variable Region (VL) comprising the sequence of SEQ ID NO: 190 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 190 and a Heavy Chain Variable Region (VH) comprising the sequence of SEQ ID NO: 200 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 200;

(k) a Light Chain Variable Region (VL) comprising the sequence of SEQ ID NO: 210 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 210 and a Heavy Chain Variable Region (VH) comprising the sequence of SEQ ID NO: 220 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 220;

(l) a Light Chain Variable Region (VL) comprising the sequence of SEQ ID NO: 230 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 230 and a Heavy Chain Variable Region (VH) comprising the sequence of SEQ ID NO: 232 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 232;

(m) a Light Chain Variable Region (VL) comprising the sequence of SEQ ID NO: 234 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 234 and a Heavy Chain Variable Region (VH) comprising the sequence of SEQ ID NO: 236 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 236;

(n) a Light Chain Variable Region (VL) comprising the sequence of SEQ ID NO: 238 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 238 and a Heavy Chain Variable Region (VH) comprising the sequence of SEQ ID NO: 240 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 240;

(o) a Light Chain Variable Region (VL) comprising the sequence of SEQ ID NO: 242 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 242 and a Heavy Chain Variable Region (VH) comprising the sequence of SEQ ID NO: 244 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 244;

(p) a Light Chain Variable Region (VL) comprising the sequence of SEQ ID NO: 246 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 246 and a Heavy Chain Variable Region (VH) comprising the sequence of SEQ ID NO: 248 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 248;

(q) a Light Chain Variable Region (VL) comprising the sequence of SEQ ID NO: 250 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 250 and a Heavy Chain Variable Region (VH) comprising the sequence of SEQ ID NO: 252 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 252;

(r) a Light Chain Variable Region (VL) comprising the sequence of SEQ ID NO: 254 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 254 and a Heavy Chain Variable Region (VH) comprising the sequence of SEQ ID NO: 256 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 256; or (s) a Light Chain Variable Region (VL) comprising the sequence of SEQ ID NO: 258 or a light chain variable region (VL) having at least 70%, 75%, 80%, 85%, 90%, 91%, 92%, 93%, 94%, 95%, 96%, 97%, 98%, 99%, or 100% sequence identity to the amino acid sequence of SEQ ID NO: 258 and a Heavy Chain Variable Region (VH) comprising the sequence of SEQ ID NO: 260 or a heavy chain variable region (VH) having at least 70%, 75%, 80%, 85%, 90%, 91%, 92%, 93%, 94%, 95%, 96%, 97%, 98%, 99%, or 100% sequence identity to the amino acid sequence of SEQ ID NO: 260.

7. The binding molecule of claim 1, wherein mature human TDP-43 is represented by SEQ ID NO:1.

8. The binding molecule of claim 1, which specifically binds to cytoplasmic aggregated and/or extracellular aggregated TDP-43.

9. The binding molecule of claim 1, which comprises
(a) the variable regions VL and/or VH of the amino acid sequence set forth in SEQ ID NO: 10 and SEQ ID NO: 20; SEQ ID NO: 30 and SEQ ID NO: 40; SEQ ID NO: 50 and SEQ ID NO: 60; SEQ ID NO: 70 and SEQ ID NO: 80; SEQ ID NO: 90 and SEQ ID NO: 100; SEQ ID NO: 110 and SEQ ID NO: 120; SEQ ID NO: 130 and SEQ ID NO: 140; or SEQ ID NO: 150 and SEQ ID NO: 160; SEQ ID NO: 170 and SEQ ID NO: 180; SEQ ID NO: 190 and SEQ ID NO: 200; SEQ ID NO: 210 and SEQ ID NO: 220; SEQ ID NO: 230 and SEQ ID NO: 232; SEQ ID NO: 234 and SEQ ID NO: 236; SEQ ID NO: 238 and SEQ ID NO: 240; SEQ ID NO: 242 and SEQ ID NO: 244; SEQ ID NO: 246 and SEQ ID NO: 248; SEQ ID NO: 250 and SEQ ID NO: 252; SEQ ID NO: 254 and SEQ ID NO: 256 or SEQ ID NO: 258 and SEQ ID NO: 260, respectively; or
(b) amino acid sequences of the variable regions VL and/or VH having at least 70%, 80%, 90% or 95% sequence homology to the amino acid sequence set forth in SEQ ID NO: 10 and SEQ ID NO: 20; SEQ ID NO: 30 and SEQ ID NO: 40; SEQ ID NO: 50 and SEQ ID NO: 60; SEQ ID NO: 70 and SEQ ID NO: 80; SEQ ID NO: 90 and SEQ ID NO: 100; SEQ ID NO: 110 and SEQ ID NO: 120; SEQ ID NO: 130 and SEQ ID NO: 140; or SEQ ID NO: 150 and SEQ ID NO: 160; SEQ ID NO: 170 and SEQ ID NO: 180; SEQ ID NO: 190 and SEQ ID NO: 200; SEQ ID NO: 210 and SEQ ID NO: 220; SEQ ID NO: 230 and SEQ ID NO: 232; SEQ ID NO: 234 and SEQ ID NO: 236; SEQ ID NO: 238 and SEQ ID NO: 240; SEQ ID NO: 242 and SEQ ID NO: 244; SEQ ID NO: 246 and SEQ ID NO: 248; SEQ ID NO: 250 and SEQ ID NO: 252; SEQ ID NO: 254 and SEQ ID NO: 256 or SEQ ID NO: 258 and SEQ ID NO: 260, respectively.

10. The binding molecule of claim 1, having:
(a) a Light Chain Variable Region (VL) comprising an amino acid sequence selected from the group of SEQ ID NO: 10; SEQ ID NO: 30; SEQ ID NO: 50; SEQ ID NO: 70; SEQ ID NO: 90; SEQ ID NO: 110; SEQ ID NO: 130; SEQ ID NO: 150; SEQ ID NO: 170; SEQ ID NO: 190; SEQ ID NO: 210; SEQ ID NO: 230; SEQ ID NO: 234; SEQ ID NO: 238; SEQ ID NO: 242; SEQ ID NO: 246; SEQ ID NO: 250; SEQ ID NO: 254; and SEQ ID NO: 258; or
(b) a Heavy Chain Variable Region (VH) comprising an amino acid sequence selected from the group of SEQ ID NO: 20; SEQ ID NO: 40; SEQ ID NO: 60; SEQ ID NO: 80; SEQ ID NO: 100; SEQ ID NO: 120; SEQ ID NO: 140; SEQ ID NO: 160; SEQ ID NO: 180; SEQ ID NO: 200; SEQ ID NO: 220; SEQ ID NO: 232; SEQ ID NO: 236; SEQ ID NO: 240; SEQ ID NO: 244; SEQ ID NO: 248; SEQ ID NO: 252; SEQ ID NO: 256; and SEQ ID NO: 260.

11. The binding molecule of claim 1, wherein the binding molecule has a dissociation constant (KD) of ≤1 µM, ≤100 nM, ≤10 nM, ≤1 nM, ≤0.1 nM, ≤0.01 nM, or ≤0.001 nM.

12. The binding molecule of claim 1, wherein the binding molecule is linked to a detectable label.

13. A nucleic acid encoding the binding molecule of claim 1.

14. A host cell comprising a nucleic acid of claim 13.

15. A method for producing a binding molecule of claim 1, wherein the method comprises culturing a host cell comprising a nucleic acid encoding the binding molecule of claim 1 under conditions suitable for producing the binding molecule.

16. A method of retaining or increasing cognitive memory capacity, movement and language function or slowing decline of cognitive memory capacity, movement and language function in a subject in need thereof, comprising administering to the subject an effective amount of the binding molecule of claim 1.

17. A method of reducing the level of misfolded TDP-43, comprising administering an effective amount of the binding-molecule of claim 1.

18. The method of claim 16 or 17, wherein the method comprises administering at least one additional therapy.

19. The method of claim 18, wherein the additional therapy is selected from the group consisting of: neurological drugs, anti-abeta antibodies, anti-Tau antibodies, Tau aggregation inhibitors, beta-amyloid aggregation inhibitors, anti-BACE1 antibodies, and BACE1 inhibitors.

20. The binding molecule of claim 1, wherein the binding molecule does not bind to physiologically functional TDP-43.

21. The binding molecule of claim 1, wherein the misfolded TDP-43 is:
(a) monomeric;
(b) oligomeric;
(c) aggregated; and/or
(d) post-translationally modified TDP-43.

22. The binding molecule of claim 21, wherein the post-translationally modified TDP-43 is phosphorylated TDP-43.

23. An immunoconjugate comprising the binding molecule of claim 1, wherein the binding molecule is covalently linked to a therapeutic agent.

24. A pharmaceutical composition comprising the binding molecule of claim 1 or the immunoconjugate of claim 23 and a pharmaceutically acceptable carrier and/or diluent and/or adjuvant.

25. A method of detecting misfolded TDP-43, comprising contacting a sample with the binding molecule of claim 1 or the immunoconjugate of claim 23.

26. An immunodiagnostic method, the method comprising: contacting the binding molecule of claim 1 or the immunoconjugate of claim 23 with a sample obtained from a subject to diagnose a TDP-43 proteinopathy in a subject.

27. The method of claim 26, wherein the sample is a blood sample, CSF sample, brain tissue sample or urine sample.

28. A method for treating a TDP-43 proteinopathy comprising administering an effective amount of the binding molecule of claim 1 or the immunoconjugate of claim 23, to a subject in need thereof.

29. The method of claim 28, which reduces the level of TDP-43 aggregates in the brain.

30. The method of claim 28, wherein the TDP-43 proteinopathy is Frontotemporal dementia (FTD), Sporadic or familial FTD with or without motor-neuron disease (MND), FTD with progranulin (GRN) mutation, FTD with TARDBP mutation, FTD with valosine-containing protein (VCP) mutation, FTD linked to chromosome 9p, corticobasal degeneration, frontotemporal lobar degeneration with ubiquitin-positive inclusions, Argyrophilic grain disease, Pick's disease, Amyotrophic lateral sclerosis (ALS), Sporadic ALS, ALS with TARDBP mutation, ALS with angiogenin (ANG) mutation), Alzheimer's disease (AD), sporadic AD, familial AD, Down syndrome, Familial British dementia, a Polyglutamine disease, Huntington's disease, spinocerebellar ataxia type 3 (SCA3), Hippocampal sclerosis dementia, Hippocampal sclerosis myopathy, Sporadic inclusion body myositis, Inclusion body myopathy with a mutation in the valosin-containing protein (VCP) Paget disease of bone and frontotemporal dementia, Oculo-pharyngeal muscular dystrophy with rimmed vacuoles, Myofibrillar myopathies with mutations in the myotilin (MYOT) gene, Myofibrillar myopathies with mutations in the gene coding for desmin (DES), or Parkinson's disease (PD).

31. The method of claim 28, wherein the TDP-43 proteinopathy is a disorder or abnormality associated with TDP-43 aggregates selected from the group consisting of: frontotemporal dementia (FTD), amyotrophic lateral sclerosis (ALS), Alzheimer's disease (AD), and Parkinson's disease (PD).

* * * * *

SEQUENCE LISTING

```
<160> NUMBER OF SEQ ID NOS: 287

<210> SEQ ID NO 1
<211> LENGTH: 414
<212> TYPE: PRT
<213> ORGANISM: Homo sapiens
<220> FEATURE:
<223> OTHER INFORMATION: Q13148 TADBP_HUMAN TAR DNA-binding protein 43
      aa 1-414

<400> SEQUENCE: 1

Met Ser Glu Tyr Ile Arg Val Thr Glu Asp Glu Asn Asp Glu Pro Ile
1               5                   10                  15

Glu Ile Pro Ser Glu Asp Asp Gly Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190

Val Phe Val Gly Arg Cys Thr Glu Asp Met Thr Glu Asp Glu Leu Arg
        195                 200                 205

Glu Phe Phe Ser Gln Tyr Gly Asp Val Met Asp Val Phe Ile Pro Lys
```

```
                  210                 215                 220
Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
            245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
            290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
            370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 2
<211> LENGTH: 61
<212> TYPE: PRT
<213> ORGANISM: Homo sapiens
<220> FEATURE:
<223> OTHER INFORMATION: Peptide TDP-1 aa 212-272 (61aa)

<400> SEQUENCE: 2

Ser Gln Tyr Gly Asp Val Met Asp Val Phe Ile Pro Lys Pro Phe Arg
1               5                   10                  15

Ala Phe Ala Phe Val Thr Phe Ala Asp Asp Gln Ile Ala Gln Ser Leu
                20                  25                  30

Cys Gly Glu Asp Leu Ile Ile Lys Gly Ile Ser Val His Ile Ser Asn
            35                  40                  45

Ala Glu Pro Lys His Asn Ser Asn Arg Gln Leu Glu Arg
        50                  55                  60

<210> SEQ ID NO 3
<211> LENGTH: 62
<212> TYPE: PRT
<213> ORGANISM: Homo sapiens
<220> FEATURE:
<223> OTHER INFORMATION: Peptide TDP-3 aa 310-370 (62aa)

<400> SEQUENCE: 3

Cys Gly Met Asn Phe Gly Ala Phe Ser Ile Asn Pro Ala Met Met Ala
1               5                   10                  15

Ala Ala Gln Ala Ala Leu Gln Ser Ser Trp Gly Met Met Gly Met Leu
                20                  25                  30

Ala Ser Gln Gln Asn Gln Ser Gly Pro Ser Gly Asn Asn Gln Asn Gln
            35                  40                  45
```

```
Gly Asn Met Gln Arg Glu Pro Asn Gln Ala Phe Gly Ser Gly
        50                  55                  60

<210> SEQ ID NO 4
<211> LENGTH: 24
<212> TYPE: PRT
<213> ORGANISM: Homo sapiens
<220> FEATURE:
<223> OTHER INFORMATION: TP24-25

<400> SEQUENCE: 4

Arg Glu Phe Phe Ser Gln Tyr Gly Asp Val Met Asp Val Phe Ile Pro
1               5                   10                  15

Lys Pro Phe Arg Ala Phe Ala Phe
            20

<210> SEQ ID NO 5
<211> LENGTH: 8
<212> TYPE: PRT
<213> ORGANISM: Homo sapiens
<220> FEATURE:
<223> OTHER INFORMATION: Epitope

<400> SEQUENCE: 5

Gly Asp Val Met Asp Val Phe Ile
1               5

<210> SEQ ID NO 6
<211> LENGTH: 414
<212> TYPE: PRT
<213> ORGANISM: Homo sapiens
<220> FEATURE:
<223> OTHER INFORMATION: Q13148 TADBP_HUMAN TAR DNA-binding protein 43
      aa 1-414

<400> SEQUENCE: 6

Met Ser Glu Tyr Ile Arg Val Thr Glu Pro Ser Glu Asp Gly Thr
1               5                   10                  15

Val Leu Leu Ser Thr Val Thr Ala Thr Val Leu Leu Ser Thr Val Thr
                20                  25                  30

Ala Gln Phe Pro Gly Ala Cys Gly Leu Arg Tyr Arg Asn Pro Val Ser
                35                  40                  45

Gln Cys Met Arg Gly Val Arg Leu Val Glu Gly Ile Leu His Ala Pro
        50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100                 105                 110

Trp Lys Thr Thr Glu Gln Asp Leu Lys Glu Tyr Phe Ser Thr Phe Gly
        115                 120                 125

Glu Val Leu Met Val Gln Val Lys Lys Asp Leu Lys Thr Gly His Ser
    130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
            180                 185                 190
```

```
Val Phe Val Gly Arg Cys Thr Glu Asp Met Thr Glu Asp Glu Leu Arg
            195                 200                 205

Glu Phe Phe Ser Gln Tyr Gly Asp Val Met Asp Val Phe Ile Pro Lys
        210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
            245                 250                 255

Ile Ser Asn Ala Glu Pro Lys His Asn Ser Asn Arg Gln Leu Glu Arg
        260                 265                 270

Ser Gly Arg Phe Gly Gly Asn Pro Gly Gly Phe Gly Asn Gln Gly Gly
            275                 280                 285

Phe Gly Asn Ser Arg Gly Gly Gly Ala Gly Leu Gly Asn Asn Gln Gly
        290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
            325                 330                 335

Met Gly Met Leu Ala Ser Gln Gln Asn Gln Ser Gly Pro Ser Gly Asn
        340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
        370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
            405                 410

<210> SEQ ID NO 7
<211> LENGTH: 414
<212> TYPE: PRT
<213> ORGANISM: Homo sapiens
<220> FEATURE:
<223> OTHER INFORMATION: Q13148 TADBP_HUMAN TAR DNA-binding protein 43
      aa 1-414

<400> SEQUENCE: 7

Met Ser Glu Tyr Ile Arg Val Thr Glu Pro Ser Glu Asp Asp Gly Thr
1               5                   10                  15

Val Leu Leu Ser Thr Val Thr Ala Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Asn Tyr Pro Lys Asp
65                  70                  75                  80

Asn Lys Arg Lys Met Asp Glu Thr Asp Ala Ser Ser Ala Val Lys Val
            85                  90                  95

Lys Arg Ala Val Gln Lys Thr Ser Asp Leu Ile Val Leu Gly Leu Pro
        100                 105                 110

Trp Lys Thr Thr Glu Gln Asp Leu Lys Glu Tyr Phe Ser Thr Phe Gly
    115                 120                 125

Glu Val Leu Met Val Gln Val Lys Lys Asp Leu Lys Thr Gly His Ser
            130                 135                 140
```

```
Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
            165                 170                 175

Leu Pro Asn Ser Lys Gln Ser Gln Asp Glu Pro Leu Arg Ser Arg Lys
        180                 185                 190

Val Phe Val Gly Arg Cys Thr Glu Asp Met Thr Glu Asp Glu Leu Arg
    195                 200                 205

Glu Phe Phe Ser Gln Tyr Gly Asp Val Met Asp Val Phe Ile Pro Lys
210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
            260                 265                 270

Ser Gly Arg Phe Gly Gly Asn Pro Gly Gly Phe Gly Asn Gln Gly Gly
        275                 280                 285

Phe Gly Asn Ser Arg Gly Gly Gly Ala Gly Leu Gly Asn Asn Gln Gly
    290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
            340                 345                 350

Asn Gln Asn Gln Gly Asn Met Gln Arg Glu Pro Asn Gln Ala Phe Gly
        355                 360                 365

Ser Gly Asn Asn Ser Tyr Ser Gly Ser Asn Ser Gly Ala Ala Ile Gly
    370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410

<210> SEQ ID NO 8
<211> LENGTH: 414
<212> TYPE: PRT
<213> ORGANISM: Homo sapiens
<220> FEATURE:
<223> OTHER INFORMATION: Q13148 TADBP_HUMAN TAR DNA-binding protein 43
      aa 1-414

<400> SEQUENCE: 8

Met Ser Glu Tyr Ile Arg Val Thr Glu Pro Ser Glu Asp Asp Gly Thr
1               5                   10                  15

Val Leu Leu Ser Thr Val Thr Ala Thr Val Leu Leu Ser Thr Val Thr
            20                  25                  30

Ala Gln Phe Pro Gly Ala Cys Gly Leu Arg Tyr Arg Asn Pro Val Ser
        35                  40                  45

Gln Cys Met Arg Gly Val Arg Leu Val Glu Gly Ile Leu His Ala Pro
    50                  55                  60

Asp Ala Gly Trp Gly Asn Leu Val Tyr Val Val Asn Tyr Pro Lys Asp
65                  70                  75                  80

Asn Lys Arg Lys Met Asp Glu Thr Asp Ala Ser Ser Ala Val Lys Val
```

-continued

```
                    85                  90                  95
Lys Arg Ala Val Gln Lys Thr Ser Asp Leu Ile Val Leu Gly Leu Pro
                100                 105                 110
Trp Lys Thr Thr Glu Gln Asp Leu Lys Glu Tyr Phe Ser Thr Phe Gly
                115                 120                 125
Glu Val Leu Met Val Gln Val Lys Lys Asp Leu Lys Thr Gly His Ser
            130                 135                 140
Lys Gly Phe Gly Phe Val Arg Phe Thr Glu Tyr Glu Thr Gln Val Lys
145                 150                 155                 160
Val Met Ser Gln Arg His Met Ile Asp Gly Arg Trp Cys Asp Cys Lys
                165                 170                 175
Leu Pro Asn Ser Lys Gln Ser Gln Asp Glu Pro Leu Arg Ser Arg Lys
                180                 185                 190
Val Phe Val Gly Arg Cys Thr Glu Asp Met Thr Glu Asp Glu Leu Arg
                195                 200                 205
Glu Phe Phe Ser Gln Tyr Gly Asp Val Met Asp Val Phe Ile Pro Lys
            210                 215                 220
Pro Phe Arg Ala Phe Ala Phe Val Thr Phe Ala Asp Asp Gln Ile Ala
225                 230                 235                 240
Gln Ser Leu Cys Gly Glu Asp Leu Ile Ile Lys Gly Ile Ser Val His
                245                 250                 255
Ile Ser Asn Ala Glu Pro Lys His Asn Ser Asn Arg Gln Leu Glu Arg
                260                 265                 270
Ser Gly Arg Phe Gly Gly Asn Pro Gly Gly Phe Gly Asn Gln Gly Gly
                275                 280                 285
Phe Gly Asn Ser Arg Gly Gly Gly Ala Gly Leu Gly Asn Asn Gln Gly
            290                 295                 300
Ser Asn Met Gly Gly Gly Met Asn Phe Gly Ala Phe Ser Ile Asn Pro
305                 310                 315                 320
Ala Met Met Ala Ala Ala Gln Ala Ala Leu Gln Ser Ser Trp Gly Met
                325                 330                 335
Met Gly Met Leu Ala Ser Gln Gln Asn Gln Ser Gly Pro Ser Gly Asn
                340                 345                 350
Asn Gln Asn Gln Gly Asn Met Gln Arg Glu Pro Asn Gln Ala Phe Gly
            355                 360                 365
Ser Gly Asn Asn Ser Tyr Ser Gly Ser Asn Ser Gly Ala Ala Ile Gly
            370                 375                 380
Trp Gly Ser Ala Ser Asn Ala Gly Ser Gly Ser Gly Phe Asn Gly Gly
385                 390                 395                 400
Phe Gly Ser Ser Met Asp Ser Lys Ser Ser Gly Trp Gly Met
                405                 410
```

<210> SEQ ID NO 9
<211> LENGTH: 414
<212> TYPE: PRT
<213> ORGANISM: Homo sapiens
<220> FEATURE:
<223> OTHER INFORMATION: Q13148 TADBP_HUMAN TAR DNA-binding protein 43
    aa 1-414

<400> SEQUENCE: 9

```
Met Ser Glu Tyr Ile Arg Val Thr Glu Pro Ser Glu Asp Asp Gly Thr
1               5                   10                  15
Val Leu Leu Ser Thr Val Thr Ala Thr Val Leu Leu Ser Thr Val Thr
            20                  25                  30
```

```
Ala Gln Phe Pro Gly Ala Cys Gly Leu Arg Tyr Arg Asn Pro Val Ser
         35                  40                  45

Gln Cys Met Arg Gly Val Arg Leu Val Glu Gly Ile Leu His Ala Pro
 50                  55                  60

Asp Ala Gly Trp Gly Asn Leu Val Tyr Val Asn Tyr Pro Lys Asp
 65                  70                  75                  80

Asn Lys Arg Lys Met Asp Glu Thr Asp Ala Ser Ser Ala Val Lys Val
                 85                  90                  95

Lys Arg Ala Val Gln Lys Thr Ser Asp Leu Ile Val Leu Gly Leu Pro
                100                 105                 110

Trp Lys Thr Thr Glu Gln Asp Leu Lys Glu Tyr Phe Ser Thr Phe Gly
            115                 120                 125

Glu Val Leu Met Val Gln Val Lys Asp Leu Lys Thr Gly His Ser
        130                 135                 140

Lys Gly Phe Gly Phe Val Arg Phe Thr Glu Tyr Glu Thr Gln Val Lys
145                 150                 155                 160

Val Met Ser Gln Arg His Met Ile Asp Gly Arg Trp Cys Asp Cys Lys
                165                 170                 175

Leu Pro Asn Ser Lys Gln Ser Gln Asp Glu Pro Leu Arg Ser Arg Lys
                180                 185                 190

Val Phe Val Gly Arg Cys Thr Glu Asp Met Thr Glu Asp Glu Leu Arg
            195                 200                 205

Glu Phe Phe Ser Gln Tyr Gly Asp Val Met Asp Val Phe Ile Pro Lys
        210                 215                 220

Pro Phe Arg Ala Phe Ala Phe Val Thr Phe Ala Asp Asp Gln Ile Ala
225                 230                 235                 240

Gln Ser Leu Cys Gly Glu Asp Leu Ile Ile Lys Gly Ile Ser Val His
                245                 250                 255

Ile Ser Asn Ala Glu Pro Lys His Asn Ser Asn Arg Gln Leu Glu Arg
                260                 265                 270

Ser Gly Arg Phe Gly Gly Asn Pro Gly Gly Phe Gly Asn Gln Gly Gly
            275                 280                 285

Phe Gly Asn Ser Arg Gly Gly Ala Gly Leu Gly Asn Asn Gln Gly
        290                 295                 300

Ser Asn Met Gly Gly Gly Met Asn Phe Gly Ala Phe Ser Ile Asn Pro
305                 310                 315                 320

Ala Met Met Ala Ala Ala Gln Ala Ala Leu Gln Ser Ser Trp Gly Met
                325                 330                 335

Met Gly Met Leu Ala Ser Gln Gln Asn Gln Ser Gly Pro Ser Gly Asn
                340                 345                 350

Asn Gln Asn Gln Gly Asn Met Gln Arg Glu Pro Asn Gln Ala Phe Gly
            355                 360                 365

Ser Gly Asn Asn Ser Tyr Ser Gly Ser Asn Ser Gly Ala Ala Ile Gly
        370                 375                 380

Trp Gly Ser Ala Ser Asn Ala Gly Ser Gly Ser Gly Phe Asn Gly Gly
385                 390                 395                 400

Phe Gly Ser Ser Met Asp Ser Lys Ser Ser Gly Trp Gly Met
                405                 410
```

<210> SEQ ID NO 10
<211> LENGTH: 126
<212> TYPE: PRT
<213> ORGANISM: Artificial Sequence
<220> FEATURE:
<223> OTHER INFORMATION: ACI-7062-401A2-Ab2-VL Peptidic sequence of the light chain variable domain

<400> SEQUENCE: 10

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asp Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Ser Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala Asp Ala Ala Pro Thr Val Ser Ile Phe Pro Thr
            115                 120                 125

<210> SEQ ID NO 11
<211> LENGTH: 23
<212> TYPE: PRT
<213> ORGANISM: Artificial Sequence
<220> FEATURE:
<223> OTHER INFORMATION: ACI-7062-401A2-Ab2-VL FR1

<400> SEQUENCE: 11

Asp Ile Val Met Thr Gln Ser Pro Ser Ser Leu Ala Met Ser Val Gly
1               5                   10                  15

Gln Lys Val Thr Met Ser Cys
            20

<210> SEQ ID NO 12
<211> LENGTH: 17
<212> TYPE: PRT
<213> ORGANISM: Artificial Sequence
<220> FEATURE:
<223> OTHER INFORMATION: ACI-7062-401A2-Ab2-VL CDR1

<400> SEQUENCE: 12

Lys Ser Ser Gln Ser Leu Leu Asn Ser Gly Asp Gln Lys Asn Tyr Leu
1               5                   10                  15

Ala

<210> SEQ ID NO 13
<211> LENGTH: 15
<212> TYPE: PRT
<213> ORGANISM: Artificial Sequence
<220> FEATURE:
<223> OTHER INFORMATION: ACI-7062-401A2-Ab2-VL FR2

<400> SEQUENCE: 13

Trp Tyr Gln Gln Lys Pro Gly Gln Ser Pro Glu Leu Leu Leu Tyr
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: ACI-7062-401A2-Ab2-VL CDR2

<400> SEQUENCE: 14

Phe Ala Ser Thr Arg Ala Ser
1               5

<210> SEQ ID NO 15
<211> LENGTH: 32
<212> TYPE: PRT
<213> ORGANISM: Artificial Sequence
<220> FEATURE:
<223> OTHER INFORMATION: ACI-7062-401A2-Ab2-VL FR3

<400> SEQUENCE: 15

Gly Val Pro Asp Arg Phe Ile Gly Ser Gly Ser Gly Thr Asp Phe Ser
1               5                   10                  15

Leu Thr Ile Ser Ser Val Gln Ala Glu Asp Leu Ala Asp Tyr Phe Cys
            20                  25                  30

<210> SEQ ID NO 16
<211> LENGTH: 9
<212> TYPE: PRT
<213> ORGANISM: Artificial Sequence
<220> FEATURE:
<223> OTHER INFORMATION: ACI-7062-401A2-Ab2-VL CDR3

<400> SEQUENCE: 16

Gln Gln His Tyr Ser Ile Pro Leu Thr
1               5

<210> SEQ ID NO 17
<211> LENGTH: 12
<212> TYPE: PRT
<213> ORGANISM: Artificial Sequence
<220> FEATURE:
<223> OTHER INFORMATION: ACI-7062-401A2-Ab2-VL FR4

<400> SEQUENCE: 17

Phe Gly Ala Gly Thr Lys Leu Glu Leu Lys Arg Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: ACI-7062-401A2-Ab2-VL Tail

<400> SEQUENCE: 18

Asp Ala Ala Pro Thr Val Ser Ile Phe Pro Thr
1               5                   10

<210> SEQ ID NO 19
<211> LENGTH: 378
<212> TYPE: DNA
<213> ORGANISM: Artificial Sequence
<220> FEATURE:
<223> OTHER INFORMATION: ACI-7062-401A2-Ab2-VL Nucleotidic sequence of
      the light chain variable domain

<400> SEQUENCE: 19
gacattgtga tgacacagtc tccatcctcc ctggctatgt cagttggaca gaaggtcact      60
atgagctgca agtccagtca gagccttta aatagtggcg atcaaaagaa ctatttggcc     120
tggtaccagc agaaaccagg acagtctcct gaacttctgt tatactttgc atccactagg    180
gcatctgggg tccctgatcg cttcataggc agtggatctg ggacagattt ctctcttacc    240

-continued

```
atcagcagtg tgcaggctga agacctggca gattacttct gtcagcaaca ttatagtatt    300
ccgctcacgt tcggtgctgg gaccaagctg gagctgaaac gggctgatgc tgcaccaact    360
gtatccatct tccctacc                                                  378
```

<210> SEQ ID NO 20
<211> LENGTH: 152
<212> TYPE: PRT
<213> ORGANISM: Artificial Sequence
<220> FEATURE:
<223> OTHER INFORMATION: ACI-7062-401A2-Ab2-VH Peptide sequence of the
      heavy chain variable domain

<400> SEQUENCE: 20

```
Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Arg Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro
145                 150
```

<210> SEQ ID NO 21
<211> LENGTH: 30
<212> TYPE: PRT
<213> ORGANISM: Artificial Sequence
<220> FEATURE:
<223> OTHER INFORMATION: ACI-7062-401A2-Ab2-VH FR1

<400> SEQUENCE: 21

```
Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser
            20                  25                  30
```

<210> SEQ ID NO 22
<211> LENGTH: 5
<212> TYPE: PRT
<213> ORGANISM: Artificial Sequence
<220> FEATURE:
<223> OTHER INFORMATION: ACI-7062-401A2-Ab2-VH CDR1

<400> SEQUENCE: 22

```
Arg Phe Gly Met His
1               5
```

<210> SEQ ID NO 23

```
<211> LENGTH: 14
<212> TYPE: PRT
<213> ORGANISM: Artificial Sequence
<220> FEATURE:
<223> OTHER INFORMATION: ACI-7062-401A2-Ab2-VH FR2

<400> SEQUENCE: 23

Trp Val Arg Gln Ala Pro Glu Lys Gly Leu Glu Trp Val Ala
1               5                   10

<210> SEQ ID NO 24
<211> LENGTH: 17
<212> TYPE: PRT
<213> ORGANISM: Artificial Sequence
<220> FEATURE:
<223> OTHER INFORMATION: ACI-7062-401A2-Ab2-VH CDR2

<400> SEQUENCE: 24

Tyr Ile Arg Ser Gly Ser Asp Ile Ile Tyr Tyr Ala Asp Ser Val Lys
1               5                   10                  15

Gly

<210> SEQ ID NO 25
<211> LENGTH: 32
<212> TYPE: PRT
<213> ORGANISM: Artificial Sequence
<220> FEATURE:
<223> OTHER INFORMATION: ACI-7062-401A2-Ab2-VH FR3

<400> SEQUENCE: 25

Arg Phe Thr Ile Ser Arg Asp Asn Pro Glu Asn Thr Leu Phe Leu Gln
1               5                   10                  15

Met Thr Ser Leu Arg Ser Glu Asp Thr Ala Met Tyr Tyr Cys Ala Arg
            20                  25                  30

<210> SEQ ID NO 26
<211> LENGTH: 9
<212> TYPE: PRT
<213> ORGANISM: Artificial Sequence
<220> FEATURE:
<223> OTHER INFORMATION: ACI-7062-401A2-Ab2-VH CDR3

<400> SEQUENCE: 26

Ser Gly Thr Thr Val Pro Phe Asp Tyr
1               5

<210> SEQ ID NO 27
<211> LENGTH: 11
<212> TYPE: PRT
<213> ORGANISM: Artificial Sequence
<220> FEATURE:
<223> OTHER INFORMATION: ACI-7062-401A2-Ab2-VH FR4

<400> SEQUENCE: 27

Trp Gly Gln Gly Thr Ser Leu Thr Val Ser Ser
1               5                   10

<210> SEQ ID NO 28
<211> LENGTH: 34
<212> TYPE: PRT
<213> ORGANISM: Artificial Sequence
<220> FEATURE:
<223> OTHER INFORMATION: ACI-7062-401A2-Ab2-VH Tail

<400> SEQUENCE: 28

Ala Lys Thr Thr Pro Pro Ser Val Tyr Pro Leu Ala Pro Gly Ser Ala
```

```
                1               5                    10                   15
Ala Gln Thr Asn Ser Met Val Thr Leu Gly Cys Leu Val Lys Gly Tyr
                            20                   25                   30

Phe Pro

<210> SEQ ID NO 29
<211> LENGTH: 456
<212> TYPE: DNA
<213> ORGANISM: Artificial Sequence
<220> FEATURE:
<223> OTHER INFORMATION: ACI-7062-401A2-Ab2-VH Nucleotide sequence of
      the heavy chain variable domain

<400> SEQUENCE: 29
gatgtgcagc tggtggagtc tgggggaggc ttagtgcagc ctggagggtc ccggagactc      60
tcctgtgcag cctctggatt cactttcagt aggtttggaa tgcactgggt tcgccaggct     120
ccagagaagg ggctggagtg ggtcgcatac attaggagtg gcagtgatat aatctactat     180
gcagactcag tgaagggccg attcaccatc tccagagaca tcccgagaa cacccctgttc     240 ctgcaaatga ccagtctaag gtctgaggac acggccatgt attactgtgc aagatcaggg     300
actacggtcc cctttgacta ctggggccaa ggcaccagtc tcacagtctc ttcagccaaa     360
acgacacccc catctgtcta tccactggcc cctggatctg ctgcccaaac taactccatg     420
gtgaccctgg gatgcctggt caagggctat ttccct                                456

<210> SEQ ID NO 30
<211> LENGTH: 125
<212> TYPE: PRT
<213> ORGANISM: Artificial Sequence
<220> FEATURE:
<223> OTHER INFORMATION: ACI-7062-412A7-Ab1-VL Peptide sequence of the
      light chain variable domain

<400> SEQUENCE: 30

Asp Ile Val Met Thr Gln Ser Pro Ser Ser Leu Ala Met Ser Val Gly
1               5                    10                   15

Gln Lys Val Thr Met Ser Cys Lys Ser Ser Gln Ser Leu Leu Asn Ser
                            20                   25                   30

Gly Asn Gln Lys Asn Tyr Leu Ala Trp Tyr Gln Gln Lys Pro Gly Gln
            35                   40                   45

Ser Pro Glu Leu Leu Leu Tyr Phe Ala Ser Thr Arg Ala Ser Gly Val
        50                   55                   60

Pro Asp Arg Phe Ile Gly Ser Gly Ser Gly Thr Asp Phe Thr Leu Thr
65                   70                   75                   80

Ile Ser Ser Val Gln Ala Glu Asp Leu Ala Asp Tyr Phe Cys Gln Gln
                    85                   90                   95

His Tyr Ser Ile Pro Leu Thr Phe Gly Ala Gly Thr Lys Leu Glu Leu
            100                  105                  110

Lys Arg Ala Asp Ala Ala Pro Thr Val Ser Ile Phe Pro
        115                  120                  125

<210> SEQ ID NO 31
<211> LENGTH: 23
<212> TYPE: PRT
<213> ORGANISM: Artificial Sequence
<220> FEATURE:
<223> OTHER INFORMATION: ACI-7062-412A7-Ab1-VL FR1

<400> SEQUENCE: 31
```

```
Asp Ile Val Met Thr Gln Ser Pro Ser Ser Leu Ala Met Ser Val Gly
1               5                   10                  15

Gln Lys Val Thr Met Ser Cys
            20
```

<210> SEQ ID NO 32
<211> LENGTH: 17
<212> TYPE: PRT
<213> ORGANISM: Artificial Sequence
<220> FEATURE:
<223> OTHER INFORMATION: ACI-7062-412A7-Ab1-VL CDR1

<400> SEQUENCE: 32

```
Lys Ser Ser Gln Ser Leu Leu Asn Ser Gly Asn Gln Lys Asn Tyr Leu
1               5                   10                  15

Ala
```

<210> SEQ ID NO 33
<211> LENGTH: 15
<212> TYPE: PRT
<213> ORGANISM: Artificial Sequence
<220> FEATURE:
<223> OTHER INFORMATION: ACI-7062-412A7-Ab1-VL FR2

<400> SEQUENCE: 33

```
Trp Tyr Gln Gln Lys Pro Gly Gln Ser Pro Glu Leu Leu Leu Tyr
1               5                   10                  15
```

<210> SEQ ID NO 34
<211> LENGTH: 7
<212> TYPE: PRT
<213> ORGANISM: Artificial Sequence
<220> FEATURE:
<223> OTHER INFORMATION: ACI-7062-412A7-Ab1-VL CDR2

<400> SEQUENCE: 34

```
Phe Ala Ser Thr Arg Ala Ser
1               5
```

<210> SEQ ID NO 35
<211> LENGTH: 32
<212> TYPE: PRT
<213> ORGANISM: Artificial Sequence
<220> FEATURE:
<223> OTHER INFORMATION: ACI-7062-412A7-Ab1-VL FR3

<400> SEQUENCE: 35

```
Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Phe Cys
            20                  25                  30
```

<210> SEQ ID NO 36
<211> LENGTH: 9
<212> TYPE: PRT
<213> ORGANISM: Artificial Sequence
<220> FEATURE:
<223> OTHER INFORMATION: ACI-7062-412A7-Ab1-VL CDR3

<400> SEQUENCE: 36

```
Gln Gln His Tyr Ser Ile Pro Leu Thr
1               5
```

<210> SEQ ID NO 37
<211> LENGTH: 12

```
<212> TYPE: PRT
<213> ORGANISM: Artificial Sequence
<220> FEATURE:
<223> OTHER INFORMATION: ACI-7062-412A7-Ab1-VL FR4

<400> SEQUENCE: 37

Phe Gly Ala Gly Thr Lys Leu Glu Leu Lys Arg Ala
1               5                   10

<210> SEQ ID NO 38
<211> LENGTH: 10
<212> TYPE: PRT
<213> ORGANISM: Artificial Sequence
<220> FEATURE:
<223> OTHER INFORMATION: ACI-7062-412A7-Ab1-VL Tail

<400> SEQUENCE: 38

Asp Ala Ala Pro Thr Val Ser Ile Phe Pro
1               5                   10

<210> SEQ ID NO 39
<211> LENGTH: 375
<212> TYPE: DNA
<213> ORGANISM: Artificial Sequence
<220> FEATURE:
<223> OTHER INFORMATION: ACI-7062-412A7-Ab1-VL Nucleotide sequence of
      the light chain variable domain

<400> SEQUENCE: 39
gacattgtga tgacacagtc tccatcctcc ctggctatgt cagttggaca gaaggtcact    60
atgagctgca gtccagtca gagcctttta aatagtggca atcaaaagaa ctatttggcc   120
tggtaccagc agaaaccagg acagtctcct gaacttctat tatactttgc atccactagg   180
gcatctgggg tccctgatcg cttcataggc agtggatctg ggacagattt cactcttacc   240
atcagcagtg tgcaggctga agacctggca gattacttct gtcagcaaca ttatagtatt   300
ccgctcacgt tcggtgctgg gaccaagctg gagctgaaac gggctgatgc tgcaccaact   360
gtatccatct tccca                                                    375

<210> SEQ ID NO 40
<211> LENGTH: 145
<212> TYPE: PRT
<213> ORGANISM: Artificial Sequence
<220> FEATURE:
<223> OTHER INFORMATION: ACI-7062-412A7-Ab1-VH Peptidic sequence of the
      heavy chain variable domain

<400> SEQUENCE: 40

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110
```

```
Ser Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys
145

<210> SEQ ID NO 41
<211> LENGTH: 30
<212> TYPE: PRT
<213> ORGANISM: Artificial Sequence
<220> FEATURE:
<223> OTHER INFORMATION: ACI-7062-412A7-Ab1-VH FR1

<400> SEQUENCE: 41

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser
            20                  25                  30

<210> SEQ ID NO 42
<211> LENGTH: 5
<212> TYPE: PRT
<213> ORGANISM: Artificial Sequence
<220> FEATURE:
<223> OTHER INFORMATION: ACI-7062-412A7-Ab1-VH CDR1

<400> SEQUENCE: 42

Ser Phe Gly Met His
1               5

<210> SEQ ID NO 43
<211> LENGTH: 14
<212> TYPE: PRT
<213> ORGANISM: Artificial Sequence
<220> FEATURE:
<223> OTHER INFORMATION: ACI-7062-412A7-Ab1-VH FR2

<400> SEQUENCE: 43

Trp Val Arg Gln Ala Pro Glu Lys Gly Leu Glu Trp Val Ala
1               5                   10

<210> SEQ ID NO 44
<211> LENGTH: 17
<212> TYPE: PRT
<213> ORGANISM: Artificial Sequence
<220> FEATURE:
<223> OTHER INFORMATION: ACI-7062-412A7-Ab1-VH CDR2

<400> SEQUENCE: 44

Tyr Ile Arg Ser Gly Ser Asp Ile Ile Tyr Tyr Ala Asp Ser Val Lys
1               5                   10                  15

Gly

<210> SEQ ID NO 45
<211> LENGTH: 32
<212> TYPE: PRT
<213> ORGANISM: Artificial Sequence
<220> FEATURE:
<223> OTHER INFORMATION: ACI-7062-412A7-Ab1-VH FR3

<400> SEQUENCE: 45

Arg Phe Thr Ile Ser Arg Asp Asn Pro Glu Asn Thr Leu Phe Leu Gln
1               5                   10                  15
```

Met Thr Ser Leu Arg Ser Glu Asp Thr Ala Met Tyr Tyr Cys Ala Arg
            20                  25                  30

<210> SEQ ID NO 46
<211> LENGTH: 9
<212> TYPE: PRT
<213> ORGANISM: Artificial Sequence
<220> FEATURE:
<223> OTHER INFORMATION: ACI-7062-412A7-Ab1-VH CDR3

<400> SEQUENCE: 46

Ser Gly Thr Thr Val Pro Phe Asp Tyr
1               5

<210> SEQ ID NO 47
<211> LENGTH: 11
<212> TYPE: PRT
<213> ORGANISM: Artificial Sequence
<220> FEATURE:
<223> OTHER INFORMATION: ACI-7062-412A7-Ab1-VH FR4

<400> SEQUENCE: 47

Trp Gly Gln Gly Thr Ser Leu Thr Val Ser Ser
1               5                   10

<210> SEQ ID NO 48
<211> LENGTH: 27
<212> TYPE: PRT
<213> ORGANISM: Artificial Sequence
<220> FEATURE:
<223> OTHER INFORMATION: ACI-7062-412A7-Ab1-VH Tail

<400> SEQUENCE: 48

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys
            20                  25

<210> SEQ ID NO 49
<211> LENGTH: 435
<212> TYPE: DNA
<213> ORGANISM: Artificial Sequence
<220> FEATURE:
<223> OTHER INFORMATION: ACI-7062-412A7-Ab1-VH Nucleotidic sequence of
      the heavy chain variable domain

<400> SEQUENCE: 49
gatgtgcagc tggtggagtc tgggggaggc ttagtgcagc ctggagggtc ccggagactc       60
tcctgtgcag cctctggatt cactttcagt agctttggaa tgcactgggt cgtcaggct      120 ccagagaagg ggctggagtg ggtcgcatac attaggagtg cagtgatat aatctactat      180 gcagactcag tgaagggccg attcaccatc tccagagaca atcccgagaa caccctgttc      240
ctgcaaatga ccagtctaag gtctgaggac acggccatgt attactgtgc aagatcaggg      300
actacggtcc cctttgacta ctggggccaa ggcaccagtc tcacagtctc ttcagccaaa      360
acaacacccc catcagtcta tccactggcc cctgggtgtg gagatacaac tggttcctcc      420
gtgactctgg gatgc                                                      435

<210> SEQ ID NO 50
<211> LENGTH: 127
<212> TYPE: PRT
<213> ORGANISM: Artificial Sequence
<220> FEATURE:

<223> OTHER INFORMATION: ACI-7062-406E3-Ab1-VL Peptidic sequence of the
      light chain variable domain

<400> SEQUENCE: 50

Asp Val Leu Met Thr Gln Thr Pro Leu Ser Leu Pro Val Ser Leu Gly
1               5                   10                  15

Asp Arg Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Thr Phe Gly Ala Gly Thr Lys Leu Glu Leu Lys Arg
            100                 105                 110

Ala Asp Ala Ala Pro Thr Val Ser Ile Phe Pro Pro Ser Glu
        115                 120                 125

<210> SEQ ID NO 51
<211> LENGTH: 23
<212> TYPE: PRT
<213> ORGANISM: Artificial Sequence
<220> FEATURE:
<223> OTHER INFORMATION: ACI-7062-406E3-Ab1-VL FR1

<400> SEQUENCE: 51

Asp Val Leu Met Thr Gln Thr Pro Leu Ser Leu Pro Val Ser Leu Gly
1               5                   10                  15

Asp Arg Ala Ser Ile Ser Cys
            20

<210> SEQ ID NO 52
<211> LENGTH: 16
<212> TYPE: PRT
<213> ORGANISM: Artificial Sequence
<220> FEATURE:
<223> OTHER INFORMATION: ACI-7062-406E3-Ab1-VL CDR1

<400> SEQUENCE: 52

Arg Ser Ser Gln Ser Ile Val His Arg Ser Gly Asn Thr Tyr Leu Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: ACI-7062-406E3-Ab1-VL FR2

<400> SEQUENCE: 53

Trp Tyr Leu Gln Lys Pro Gly Gln Ser Pro Lys Leu Leu Ile Tyr
1               5                   10                  15

<210> SEQ ID NO 54
<211> LENGTH: 7
<212> TYPE: PRT
<213> ORGANISM: Artificial Sequence
<220> FEATURE:
<223> OTHER INFORMATION: ACI-7062-406E3-Ab1-VL CDR2

<400> SEQUENCE: 54

Lys Val Ser Asn Arg Phe Ser
1               5

<210> SEQ ID NO 55
<211> LENGTH: 32
<212> TYPE: PRT
<213> ORGANISM: Artificial Sequence
<220> FEATURE:
<223> OTHER INFORMATION: ACI-7062-406E3-Ab1-VL FR3

<400> SEQUENCE: 55

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 56
<211> LENGTH: 8
<212> TYPE: PRT
<213> ORGANISM: Artificial Sequence
<220> FEATURE:
<223> OTHER INFORMATION: ACI-7062-406E3-Ab1-VL CDR3

<400> SEQUENCE: 56

Phe Gln Gly Ser His Val Pro Thr
1               5

<210> SEQ ID NO 57
<211> LENGTH: 12
<212> TYPE: PRT
<213> ORGANISM: Artificial Sequence
<220> FEATURE:
<223> OTHER INFORMATION: ACI-7062-406E3-Ab1-VL FR4

<400> SEQUENCE: 57

Phe Gly Ala Gly Thr Lys Leu Glu Leu Lys Arg Ala
1               5                   10

<210> SEQ ID NO 58
<211> LENGTH: 14
<212> TYPE: PRT
<213> ORGANISM: Artificial Sequence
<220> FEATURE:
<223> OTHER INFORMATION: ACI-7062-406E3-Ab1-VL Tail

<400> SEQUENCE: 58

Asp Ala Ala Pro Thr Val Ser Ile Phe Pro Pro Ser Ser Glu
1               5                   10

<210> SEQ ID NO 59
<211> LENGTH: 381
<212> TYPE: DNA
<213> ORGANISM: Artificial Sequence
<220> FEATURE:
<223> OTHER INFORMATION: ACI-7062-406E3-Ab1-VL Nucleotidic sequence of
      the light chain variable domain

<400> SEQUENCE: 59
gatgttttga tgacccaaac tccactctcc ctgcctgtca gtcttggaga tcgagcctcc      60
atctcttgca gatctagtca gagcattgta catcgtagtg aaacacccta tttagagtgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240

```
agcagagtgg aggctgagga tctgggagtt tattactgct ttcaaggttc acatgttccc      300
acgttcggtg ctgggaccaa gctggagctg aaacgggctg atgctgcacc aactgtatcc      360
atcttcccac catccagtga g                                                 381
```

<210> SEQ ID NO 60
<211> LENGTH: 152
<212> TYPE: PRT
<213> ORGANISM: Artificial Sequence
<220> FEATURE:
<223> OTHER INFORMATION: ACI-7062-406E3-Ab1-VH Peptidic sequence of the
      heavy chain variable domain

<400> SEQUENCE: 60

Gln Val Thr Leu Lys Glu Ser Gly Pro Ala Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Val Tyr Gly Asn Leu Tyr Tyr Phe Ala Tyr Trp Gly Gln
            100                 105                 110

Gly Thr Thr Leu Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr
145                 150

<210> SEQ ID NO 61
<211> LENGTH: 30
<212> TYPE: PRT
<213> ORGANISM: Artificial Sequence
<220> FEATURE:
<223> OTHER INFORMATION: ACI-7062-406E3-Ab1-VH FR1

<400> SEQUENCE: 61

Gln Val Thr Leu Lys Glu Ser Gly Pro Ala Ile Leu Gln Pro Ser Gln
1               5                   10                  15

Thr Leu Ser Leu Thr Cys Ser Phe Ser Gly Phe Ser Leu Thr
            20                  25                  30

<210> SEQ ID NO 62
<211> LENGTH: 7
<212> TYPE: PRT
<213> ORGANISM: Artificial Sequence
<220> FEATURE:
<223> OTHER INFORMATION: ACI-7062-406E3-Ab1-VH CDR1

<400> SEQUENCE: 62

Thr Tyr Gly Ile Gly Val Gly
1               5

<210> SEQ ID NO 63
<211> LENGTH: 14

```
<212> TYPE: PRT
<213> ORGANISM: Artificial Sequence
<220> FEATURE:
<223> OTHER INFORMATION: ACI-7062-406E3-Ab1-VH FR2

<400> SEQUENCE: 63

Trp Ile Arg Gln Pro Ser Gly Lys Gly Leu Glu Trp Leu Ala
1               5                   10

<210> SEQ ID NO 64
<211> LENGTH: 16
<212> TYPE: PRT
<213> ORGANISM: Artificial Sequence
<220> FEATURE:
<223> OTHER INFORMATION: ACI-7062-406E3-Ab1-VH CDR2

<400> SEQUENCE: 64

His Ile Trp Trp Asn Asp Asn Lys Tyr Tyr Asn Thr Ala Leu Lys Ser
1               5                   10                  15

<210> SEQ ID NO 65
<211> LENGTH: 32
<212> TYPE: PRT
<213> ORGANISM: Artificial Sequence
<220> FEATURE:
<223> OTHER INFORMATION: ACI-7062-406E3-Ab1-VH FR3

<400> SEQUENCE: 65

Arg Leu Thr Val Ser Lys Asp Thr Ser Asn Asn Gln Val Phe Leu Lys
1               5                   10                  15

Ile Ala Ser Val Asp Thr Ala Asp Thr Ala Thr Tyr Tyr Cys Ala Arg
            20                  25                  30

<210> SEQ ID NO 66
<211> LENGTH: 10
<212> TYPE: PRT
<213> ORGANISM: Artificial Sequence
<220> FEATURE:
<223> OTHER INFORMATION: ACI-7062-406E3-Ab1-VH CDR3

<400> SEQUENCE: 66

Val Tyr Gly Asn Leu Tyr Tyr Phe Ala Tyr
1               5                   10

<210> SEQ ID NO 67
<211> LENGTH: 11
<212> TYPE: PRT
<213> ORGANISM: Artificial Sequence
<220> FEATURE:
<223> OTHER INFORMATION: ACI-7062-406E3-Ab1-VH FR4

<400> SEQUENCE: 67

Trp Gly Gln Gly Thr Thr Leu Thr Val Ser Ser
1               5                   10

<210> SEQ ID NO 68
<211> LENGTH: 32
<212> TYPE: PRT
<213> ORGANISM: Artificial Sequence
<220> FEATURE:
<223> OTHER INFORMATION: ACI-7062-406E3-Ab1-VH Tail

<400> SEQUENCE: 68

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
```

-continued

```
                 20                  25                  30
```

<210> SEQ ID NO 69
<211> LENGTH: 456
<212> TYPE: DNA
<213> ORGANISM: Artificial Sequence
<220> FEATURE:
<223> OTHER INFORMATION: ACI-7062-406E3-Ab1-VH Nucleotidic sequence of
      the heavy chain variable domain

<400> SEQUENCE: 69

```
caggttactc tgaaagagtc tggccctgcg atattgcagc cctcccagac cctcagtctg      60
acttgttctt tctctgggtt ttcactgacc acttatggta taggagtagg ctggattcgt     120
cagccttcag ggaagggtct ggagtggctg gcacacattt ggtggaatga taataagtac     180
tataacacag ccctgaagag ccggctcact gtctccaagg atacctccaa caaccaggta     240
ttcctcaaga tcgccagtgt agacactgca gatactgcca catactactg tgctcgagtc     300
tatggtaacc tgtactactt tgcctactgg ggccaaggca ccactctcac agtctcctca     360
gccaaaacaa cagcccccatc ggtctatcca ctggcccctg tgtgtggaga tacaactggc     420
tcctcggtga ctctaggatg cctggtcaag ggttat                               456
```

<210> SEQ ID NO 70
<211> LENGTH: 126
<212> TYPE: PRT
<213> ORGANISM: Artificial Sequence
<220> FEATURE:
<223> OTHER INFORMATION: ACI-7062-404D6-Ab2-VL Peptidic sequence of the
      light chain variable domain

<400> SEQUENCE: 70

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Gly
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Thr Phe Gly Ala Gly Thr Lys Leu Glu Leu Lys Arg
            100                 105                 110

Ala Asp Ala Ala Pro Thr Val Ser Ile Phe Pro Pro Ser Ser
        115                 120                 125
```

<210> SEQ ID NO 71
<211> LENGTH: 23
<212> TYPE: PRT
<213> ORGANISM: Artificial Sequence
<220> FEATURE:
<223> OTHER INFORMATION: ACI-7062-404D6-Ab2-VL FR1

<400> SEQUENCE: 71

```
Asp Val Leu Met Thr Gln Thr Pro Leu Ser Leu Pro Val Ser Leu Gly
1               5                   10                  15

Asp Gln Ala Ser Ile Ser Cys
            20
```

<210> SEQ ID NO 72
<211> LENGTH: 16
<212> TYPE: PRT
<213> ORGANISM: Artificial Sequence
<220> FEATURE:
<223> OTHER INFORMATION: ACI-7062-404D6-Ab2-VL CDR1

<400> SEQUENCE: 72

Arg Ser Ser Gln Ser Ile Val His Gly Ser Gly Asn Thr Tyr Leu Glu
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: ACI-7062-404D6-Ab2-VL FR2

<400> SEQUENCE: 73

Trp Tyr Leu Gln Lys Pro Gly Gln Ser Pro Lys Leu Leu Ile Tyr
1               5                   10                  15

<210> SEQ ID NO 74
<211> LENGTH: 7
<212> TYPE: PRT
<213> ORGANISM: Artificial Sequence
<220> FEATURE:
<223> OTHER INFORMATION: ACI-7062-404D6-Ab2-VL CDR2

<400> SEQUENCE: 74

Lys Val Ser Asn Arg Phe Ser
1               5

<210> SEQ ID NO 75
<211> LENGTH: 32
<212> TYPE: PRT
<213> ORGANISM: Artificial Sequence
<220> FEATURE:
<223> OTHER INFORMATION: ACI-7062-404D6-Ab2-VL FR3

<400> SEQUENCE: 75

Gly Val Pro Asp Arg Phe Ser Gly Ser Gly Ser Gly Thr Asp Phe Thr
1               5                   10                  15

Leu Arg Ile Ser Arg Val Glu Ala Glu Asp Leu Gly Val Tyr Tyr Cys
            20                  25                  30

<210> SEQ ID NO 76
<211> LENGTH: 8
<212> TYPE: PRT
<213> ORGANISM: Artificial Sequence
<220> FEATURE:
<223> OTHER INFORMATION: ACI-7062-404D6-Ab2-VL CDR3

<400> SEQUENCE: 76

Phe Gln Gly Ser His Val Pro Thr
1               5

<210> SEQ ID NO 77
<211> LENGTH: 12
<212> TYPE: PRT
<213> ORGANISM: Artificial Sequence
<220> FEATURE:
<223> OTHER INFORMATION: ACI-7062-404D6-Ab2-VL FR4

<400> SEQUENCE: 77

Phe Gly Ala Gly Thr Lys Leu Glu Leu Lys Arg Ala
1               5                   10

<210> SEQ ID NO 78
<211> LENGTH: 13
<212> TYPE: PRT
<213> ORGANISM: Artificial Sequence
<220> FEATURE:
<223> OTHER INFORMATION: ACI-7062-404D6-Ab2-VL Tail

<400> SEQUENCE: 78

Asp Ala Ala Pro Thr Val Ser Ile Phe Pro Pro Ser Ser
1               5                   10

<210> SEQ ID NO 79
<211> LENGTH: 378
<212> TYPE: DNA
<213> ORGANISM: Artificial Sequence
<220> FEATURE:
<223> OTHER INFORMATION: ACI-7062-404D6-Ab2-VL Nucleotidic sequence of
      the light chain variable domain

<400> SEQUENCE: 79
gatgttttga tgacccaaac tccactctcc ctgcctgtca gtcttggaga tcaagcctcc    60
atctcttgca gatctagtca gagcattgta catggttctg aaacaccta tttagaatgg    120 tacctgcaga aaccaggcca gtctccaaag ctcctgatct acaaagtttc caaccgattt    180
tctggggtcc cagacaggtt cagtggcagt ggatcaggga cagatttcac actcaggatc    240
agcagagtgg aggctgagga tctgggagtt tattactgct ttcaaggttc acatgttccc    300
acgttcggtg ctgggaccaa gctggagctg aaacgggctg atgctgcacc aactgtatcc    360
atcttcccac catccagt                                                  378

<210> SEQ ID NO 80
<211> LENGTH: 129
<212> TYPE: PRT
<213> ORGANISM: Artificial Sequence
<220> FEATURE:
<223> OTHER INFORMATION: ACI-7062-404D6-Ab2-VH Peptide sequence of the
      heavy chain variable domain

<400> SEQUENCE: 80

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
                20                  25                  30

Gly Ile Gly Val Gly Trp Ile Arg Gln Pro Ser Gly Lys Gly Leu Glu
            35                  40                  45

Trp Leu Ala His Ile Trp Trp Asn Asp Tyr Lys Tyr Tyr Asn Thr Ala
        50                  55                  60

Leu Lys Ser Arg Leu Thr Ile Ser Lys Asp Thr Ser Asn Asn Arg Val
65                  70                  75                  80

Phe Leu Lys Ile Ala Ser Val Asp Thr Ala Asp Thr Ala Thr Tyr Tyr
                85                  90                  95

Cys Ala Arg Val Tyr Gly Asn Leu Tyr Tyr Phe Asp Tyr Trp Gly Gln
            100                 105                 110

Gly Thr Thr Leu Thr Val Ser Ser Ala Thr Thr Ala Pro Ser Trp
        115                 120                 125

Ser

```
<210> SEQ ID NO 81
<211> LENGTH: 30
<212> TYPE: PRT
<213> ORGANISM: Artificial Sequence
<220> FEATURE:
<223> OTHER INFORMATION: ACI-7062-404D6-Ab2-VH FR1

<400> SEQUENCE: 81

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30

<210> SEQ ID NO 82
<211> LENGTH: 7
<212> TYPE: PRT
<213> ORGANISM: Artificial Sequence
<220> FEATURE:
<223> OTHER INFORMATION: ACI-7062-404D6-Ab2-VH CDR1

<400> SEQUENCE: 82

Thr Tyr Gly Ile Gly Val Gly
1               5

<210> SEQ ID NO 83
<211> LENGTH: 14
<212> TYPE: PRT
<213> ORGANISM: Artificial Sequence
<220> FEATURE:
<223> OTHER INFORMATION: ACI-7062-404D6-Ab2-VH FR2

<400> SEQUENCE: 83

Trp Ile Arg Gln Pro Ser Gly Lys Gly Leu Glu Trp Leu Ala
1               5                   10

<210> SEQ ID NO 84
<211> LENGTH: 16
<212> TYPE: PRT
<213> ORGANISM: Artificial Sequence
<220> FEATURE:
<223> OTHER INFORMATION: ACI-7062-404D6-Ab2-VH CDR2

<400> SEQUENCE: 84

His Ile Trp Trp Asn Asp Tyr Lys Tyr Tyr Asn Thr Ala Leu Lys Ser
1               5                   10                  15

<210> SEQ ID NO 85
<211> LENGTH: 32
<212> TYPE: PRT
<213> ORGANISM: Artificial Sequence
<220> FEATURE:
<223> OTHER INFORMATION: ACI-7062-404D6-Ab2-VH FR3

<400> SEQUENCE: 85

Arg Leu Thr Ile Ser Lys Asp Thr Ser Asn Asn Arg Val Phe Leu Lys
1               5                   10                  15

Ile Ala Ser Val Asp Thr Ala Asp Thr Ala Thr Tyr Tyr Cys Ala Arg
            20                  25                  30

<210> SEQ ID NO 86
<211> LENGTH: 10
<212> TYPE: PRT
<213> ORGANISM: Artificial Sequence
<220> FEATURE:
<223> OTHER INFORMATION: ACI-7062-404D6-Ab2-VH CDR3

<400> SEQUENCE: 86
```

Val Tyr Gly Asn Leu Tyr Tyr Phe Asp Tyr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: ACI-7062-404D6-Ab2-VH FR4

<400> SEQUENCE: 87

Trp Gly Gln Gly Thr Thr Leu Thr Val Ser Ser
1               5                   10

<210> SEQ ID NO 88
<211> LENGTH: 9
<212> TYPE: PRT
<213> ORGANISM: Artificial Sequence
<220> FEATURE:
<223> OTHER INFORMATION: ACI-7062-404D6-Ab2-VH Tail

<400> SEQUENCE: 88

Ala Thr Thr Thr Ala Pro Ser Trp Ser
1               5

<210> SEQ ID NO 89
<211> LENGTH: 387
<212> TYPE: DNA
<213> ORGANISM: Artificial Sequence
<220> FEATURE:
<223> OTHER INFORMATION: ACI-7062-404D6-Ab2-VH Nucleotide sequence of
      the heavy chain variable domain

<400> SEQUENCE: 89
caggttactc tgaaagagtc tggccctggg atattgcagc cctcccagac cctcagtctg      60
acttgttctt tctctgggtt ttcactgagc acttatggta taggagtagg ctggattcgt     120
cagccttcag ggaagggtct ggagtggctg gcacacattt ggtggaatga ttataagtac     180
tataacacag ccctgaagag ccggctcaca atctccaagg atacctccaa caaccgggta     240
ttcctcaaga tcgccagtgt ggacactgca gatactgcca catactactg tgctcgagtc     300
tatggtaacc tgtactactt tgactactgg ggccaaggca ccactctcac agtctcctca     360
gctacaacaa cagccccatc ttggtcc                                         387

<210> SEQ ID NO 90
<211> LENGTH: 126
<212> TYPE: PRT
<213> ORGANISM: Artificial Sequence
<220> FEATURE:
<223> OTHER INFORMATION: ACI-7062-410H3-Ab1-VL Peptide sequence of the
      light chain variable domain

<400> SEQUENCE: 90

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Thr Leu Thr

```
                65                  70                  75                  80
Ile Ser Ser Val Gln Ala Glu Asp Leu Ala Asp Tyr Phe Cys Gln Gln
                    85                  90                  95

His Tyr Ser Ile Pro Leu Thr Phe Gly Ala Gly Thr Lys Leu Glu Leu
            100                 105                 110

Lys Arg Ala Asp Ala Ala Pro Thr Val Ser Ile Phe Pro Thr
        115                 120                 125
```

<210> SEQ ID NO 91
<211> LENGTH: 23
<212> TYPE: PRT
<213> ORGANISM: Artificial Sequence
<220> FEATURE:
<223> OTHER INFORMATION: ACI-7062-410H3-Ab1-VL FR1

<400> SEQUENCE: 91

```
Asp Ile Val Met Thr Gln Ser Pro Ser Ser Leu Ala Met Ser Val Gly
1               5                   10                  15

Gln Lys Val Thr Met Ser Cys
            20
```

<210> SEQ ID NO 92
<211> LENGTH: 17
<212> TYPE: PRT
<213> ORGANISM: Artificial Sequence
<220> FEATURE:
<223> OTHER INFORMATION: ACI-7062-410H3-Ab1-VL CDR1

<400> SEQUENCE: 92

```
Lys Ser Ser Gln Ser Leu Leu Asn Ser Gly Asn Gln Lys Asn Tyr Leu
1               5                   10                  15

Ala
```

<210> SEQ ID NO 93
<211> LENGTH: 15
<212> TYPE: PRT
<213> ORGANISM: Artificial Sequence
<220> FEATURE:
<223> OTHER INFORMATION: ACI-7062-410H3-Ab1-VL FR2

<400> SEQUENCE: 93

```
Trp Tyr Gln Gln Lys Pro Gly Gln Ser Pro Glu Leu Leu Leu Tyr
1               5                   10                  15
```

<210> SEQ ID NO 94
<211> LENGTH: 7
<212> TYPE: PRT
<213> ORGANISM: Artificial Sequence
<220> FEATURE:
<223> OTHER INFORMATION: ACI-7062-410H3-Ab1-VL CDR2

<400> SEQUENCE: 94

```
Phe Ala Ser Thr Arg Ala Ser
1               5
```

<210> SEQ ID NO 95
<211> LENGTH: 32
<212> TYPE: PRT
<213> ORGANISM: Artificial Sequence
<220> FEATURE:
<223> OTHER INFORMATION: ACI-7062-410H3-Ab1-VL FR3

<400> SEQUENCE: 95

```
Gly Val Pro Asp Arg Phe Ile Gly Ser Gly Ser Gly Thr Asp Phe Thr
```

```
                1               5                  10                  15
Leu Thr Ile Ser Ser Val Gln Ala Glu Asp Leu Ala Asp Tyr Phe Cys
                20                  25                  30
```

<210> SEQ ID NO 96
<211> LENGTH: 9
<212> TYPE: PRT
<213> ORGANISM: Artificial Sequence
<220> FEATURE:
<223> OTHER INFORMATION: ACI-7062-410H3-Ab1-VL CDR3

<400> SEQUENCE: 96

```
Gln Gln His Tyr Ser Ile Pro Leu Thr
1               5
```

<210> SEQ ID NO 97
<211> LENGTH: 12
<212> TYPE: PRT
<213> ORGANISM: Artificial Sequence
<220> FEATURE:
<223> OTHER INFORMATION: ACI-7062-410H3-Ab1-VL FR4

<400> SEQUENCE: 97

```
Phe Gly Ala Gly Thr Lys Leu Glu Leu Lys Arg Ala
1               5                  10
```

<210> SEQ ID NO 98
<211> LENGTH: 11
<212> TYPE: PRT
<213> ORGANISM: Artificial Sequence
<220> FEATURE:
<223> OTHER INFORMATION: ACI-7062-410H3-Ab1-VL Tail

<400> SEQUENCE: 98

```
Asp Ala Ala Pro Thr Val Ser Ile Phe Pro Thr
1               5                  10
```

<210> SEQ ID NO 99
<211> LENGTH: 378
<212> TYPE: DNA
<213> ORGANISM: Artificial Sequence
<220> FEATURE:
<223> OTHER INFORMATION: ACI-7062-410H3-Ab1-VL Nucleotide sequence of
      the light chain variable domain

<400> SEQUENCE: 99

```
gacattgtga tgacacagtc tccatcctcc ctggctatgt cagttggaca gaaggtcact      60
atgagctgca gtccagtca gagccttta aatagtggca atcaaaagaa ctatttggcc     120
tggtaccagc agaaaccagg acagtctcct gaacttctgt tatactttgc atccactagg     180
gcatctgggg tccctgatcg cttcataggc agtggatctg ggacagattt cactcttacc     240
atcagcagtg tgcaggctga agacctggca gattacttct gtcagcaaca ttatagtatt     300
ccgctcacgt tcggtgctgg gaccaagctg gagctgaaac gggctgatgc tgcaccaact     360
gtatccatct tccctacc                                                   378
```

<210> SEQ ID NO 100
<211> LENGTH: 152
<212> TYPE: PRT
<213> ORGANISM: Artificial Sequence
<220> FEATURE:
<223> OTHER INFORMATION: ACI-7062-410H3-Ab1-VH Peptidic sequence of the
      heavy chain variable domain

<400> SEQUENCE: 100

```
Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65              70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro
145                 150

<210> SEQ ID NO 101
<211> LENGTH: 30
<212> TYPE: PRT
<213> ORGANISM: Artificial Sequence
<220> FEATURE:
<223> OTHER INFORMATION: ACI-7062-410H3-Ab1-VH FR1

<400> SEQUENCE: 101

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser
            20                  25                  30

<210> SEQ ID NO 102
<211> LENGTH: 5
<212> TYPE: PRT
<213> ORGANISM: Artificial Sequence
<220> FEATURE:
<223> OTHER INFORMATION: ACI-7062-410H3-Ab1-VH CDR1

<400> SEQUENCE: 102

Ser Phe Gly Met His
1               5

<210> SEQ ID NO 103
<211> LENGTH: 14
<212> TYPE: PRT
<213> ORGANISM: Artificial Sequence
<220> FEATURE:
<223> OTHER INFORMATION: ACI-7062-410H3-Ab1-VH FR2

<400> SEQUENCE: 103

Trp Val Arg Gln Ala Pro Glu Lys Gly Leu Glu Trp Val Ala
1               5                   10

<210> SEQ ID NO 104
<211> LENGTH: 17
<212> TYPE: PRT
<213> ORGANISM: Artificial Sequence
<220> FEATURE:
```

<223> OTHER INFORMATION: ACI-7062-410H3-Ab1-VH CDR2

<400> SEQUENCE: 104

Tyr Ile Arg Ser Gly Ser Asp Ile Ile Tyr Tyr Ala Asp Ser Val Lys
1               5                   10                  15

Gly

<210> SEQ ID NO 105
<211> LENGTH: 32
<212> TYPE: PRT
<213> ORGANISM: Artificial Sequence
<220> FEATURE:
<223> OTHER INFORMATION: ACI-7062-410H3-Ab1-VH FR3

<400> SEQUENCE: 105

Arg Phe Thr Ile Ser Arg Asp Asn Pro Glu Asn Thr Leu Phe Leu Gln
1               5                   10                  15

Met Thr Ser Leu Arg Ser Glu Asp Thr Ala Met Tyr Tyr Cys Ala Arg
            20                  25                  30

<210> SEQ ID NO 106
<211> LENGTH: 9
<212> TYPE: PRT
<213> ORGANISM: Artificial Sequence
<220> FEATURE:
<223> OTHER INFORMATION: ACI-7062-410H3-Ab1-VH CDR3

<400> SEQUENCE: 106

Ser Gly Thr Thr Val Pro Phe Asp Tyr
1               5

<210> SEQ ID NO 107
<211> LENGTH: 11
<212> TYPE: PRT
<213> ORGANISM: Artificial Sequence
<220> FEATURE:
<223> OTHER INFORMATION: ACI-7062-410H3-Ab1-VH FR4

<400> SEQUENCE: 107

Trp Gly Gln Gly Thr Ser Leu Thr Val Ser Ser
1               5                   10

<210> SEQ ID NO 108
<211> LENGTH: 34
<212> TYPE: PRT
<213> ORGANISM: Artificial Sequence
<220> FEATURE:
<223> OTHER INFORMATION: ACI-7062-410H3-Ab1-VH Tail

<400> SEQUENCE: 108

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro

<210> SEQ ID NO 109
<211> LENGTH: 456
<212> TYPE: DNA
<213> ORGANISM: Artificial Sequence
<220> FEATURE:
<223> OTHER INFORMATION: ACI-7062-410H3-Ab1-VH Nucleotide sequence of
      the heavy chain variable domain

<400> SEQUENCE: 109

```
gatgtgcagc tggtggagtc tgggggaggc ttagtgcagc ctggagggtc ccggagactc    60
tcctgtgcag cctctggatt cactttcagt agctttggaa tgcactgggt tcgtcaggct   120
ccagagaagg ggctggagtg ggtcgcatac attaggagtg gcagtgatat aatctactat   180
gcagactcag tgaagggccg attcaccatc tccagagaca tcccgagaa caccctgttc    240 ctgcaaatga ccagtctaag gtctgaggac acggccatgt attactgtgc aagatcaggg   300
actacggtcc cctttgacta ctggggccaa ggcaccagtc tcacagtctc ttcagccaaa   360
acgacacccc catctgtcta tccactggcc cctggatctg ctgcccaaac taactccatg   420
gtgaccctgg gatgcctggt caagggctat ttccct                             456
```

<210> SEQ ID NO 110
<211> LENGTH: 126
<212> TYPE: PRT
<213> ORGANISM: Artificial Sequence
<220> FEATURE:
<223> OTHER INFORMATION: ACI-7062-414A5-Ab1-VL Peptide sequence of the
      light chain variable domain

<400> SEQUENCE: 110

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala Asp Ala Ala Pro Thr Val Ser Ile Phe Pro Thr
        115                 120                 125
```

<210> SEQ ID NO 111
<211> LENGTH: 23
<212> TYPE: PRT
<213> ORGANISM: Artificial Sequence
<220> FEATURE:
<223> OTHER INFORMATION: ACI-7062-414A5-Ab1-VL FR1

<400> SEQUENCE: 111

```
Asp Ile Val Met Thr Gln Ser Pro Ser Ser Leu Ala Met Ser Val Gly
1               5                   10                  15

Gln Lys Val Thr Met Ser Cys
            20
```

<210> SEQ ID NO 112
<211> LENGTH: 17
<212> TYPE: PRT
<213> ORGANISM: Artificial Sequence
<220> FEATURE:
<223> OTHER INFORMATION: ACI-7062-414A5-Ab1-VL CDR1

<400> SEQUENCE: 112

Lys Ser Ser Gln Ser Leu Leu Asn Ser Ser Asn Gln Lys Asn Tyr Leu

Ala

<210> SEQ ID NO 113
<211> LENGTH: 15
<212> TYPE: PRT
<213> ORGANISM: Artificial Sequence
<220> FEATURE:
<223> OTHER INFORMATION: ACI-7062-414A5-Ab1-VL FR2

<400> SEQUENCE: 113

Trp Tyr Gln Gln Lys Pro Gly Gln Ser Pro Lys Leu Leu Val Tyr
1               5                   10                  15

<210> SEQ ID NO 114
<211> LENGTH: 7
<212> TYPE: PRT
<213> ORGANISM: Artificial Sequence
<220> FEATURE:
<223> OTHER INFORMATION: ACI-7062-414A5-Ab1-VL CDR2

<400> SEQUENCE: 114

Phe Ala Ser Thr Arg Glu Ser
1               5

<210> SEQ ID NO 115
<211> LENGTH: 32
<212> TYPE: PRT
<213> ORGANISM: Artificial Sequence
<220> FEATURE:
<223> OTHER INFORMATION: ACI-7062-414A5-Ab1-VL FR3

<400> SEQUENCE: 115

Gly Val Pro Asp Arg Phe Ile Gly Ser Gly Ser Gly Thr Asp Phe Thr
1               5                   10                  15

Leu Thr Ile Asn Ser Val Gln Ala Glu Asp Leu Ala Asp Tyr Phe Cys
            20                  25                  30

<210> SEQ ID NO 116
<211> LENGTH: 9
<212> TYPE: PRT
<213> ORGANISM: Artificial Sequence
<220> FEATURE:
<223> OTHER INFORMATION: ACI-7062-414A5-Ab1-VL CDR3

<400> SEQUENCE: 116

Gln Gln His Tyr Ser Ile Pro Leu Thr
1               5

<210> SEQ ID NO 117
<211> LENGTH: 12
<212> TYPE: PRT
<213> ORGANISM: Artificial Sequence
<220> FEATURE:
<223> OTHER INFORMATION: ACI-7062-414A5-Ab1-VL FR4

<400> SEQUENCE: 117

Phe Gly Ala Gly Thr Lys Leu Glu Leu Lys Arg Ala
1               5                   10

<210> SEQ ID NO 118
<211> LENGTH: 11
<212> TYPE: PRT
<213> ORGANISM: Artificial Sequence
<220> FEATURE:
<223> OTHER INFORMATION: ACI-7062-414A5-Ab1-VL Tail

<400> SEQUENCE: 118

Asp Ala Ala Pro Thr Val Ser Ile Phe Pro Thr
1               5                   10

<210> SEQ ID NO 119
<211> LENGTH: 378
<212> TYPE: DNA
<213> ORGANISM: Artificial Sequence
<220> FEATURE:
<223> OTHER INFORMATION: ACI-7062-414A5-Ab1-VL Nucleotide sequence of
      the light chain variable domain

<400> SEQUENCE: 119

```
gacattgtga tgacacagtc tccatcctcc ctggctatgt cagtaggaca gaaggtcact    60
atgagctgca agtccagtca gagccttttta aatagtagca atcaaaagaa ctatttggcc   120
tggtaccagc agaaaccagg acagtctcct aaacttctgg tatactttgc atccactagg   180
gaatctgggg tccctgatcg cttcataggc agtggatctg gacagattt cactcttacc    240
atcaacagtg tgcaggctga agacctggca gattacttct gtcagcaaca ttatagtatt    300
ccgctcacgt tcggtgctgg gaccaagctg gagctgaaac gggctgatgc tgcaccaact    360
gtatccatct tccctacc                                                  378
```

<210> SEQ ID NO 120
<211> LENGTH: 152
<212> TYPE: PRT
<213> ORGANISM: Artificial Sequence
<220> FEATURE:
<223> OTHER INFORMATION: ACI-7062-414A5-Ab1-VH Peptide sequence of the
      heavy chain variable domain

<400> SEQUENCE: 120

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Thr Val
    50                  55                  60

Lys Gly Arg Phe Thr Ile Ser Arg Asp Asn Pro Glu Asn Thr Leu Phe
65                  70                  75                  80

Leu Glu Met Thr Arg Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro
145                 150

<210> SEQ ID NO 121
<211> LENGTH: 30
<212> TYPE: PRT
<213> ORGANISM: Artificial Sequence
<220> FEATURE:
<223> OTHER INFORMATION: ACI-7062-414A5-Ab1-VH FR1

<400> SEQUENCE: 121

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser
            20                  25                  30

<210> SEQ ID NO 122
<211> LENGTH: 5
<212> TYPE: PRT
<213> ORGANISM: Artificial Sequence
<220> FEATURE:
<223> OTHER INFORMATION: ACI-7062-414A5-Ab1-VH CDR1

<400> SEQUENCE: 122

Ser Phe Gly Met His
1               5

<210> SEQ ID NO 123
<211> LENGTH: 14
<212> TYPE: PRT
<213> ORGANISM: Artificial Sequence
<220> FEATURE:
<223> OTHER INFORMATION: ACI-7062-414A5-Ab1-VH FR2

<400> SEQUENCE: 123

Trp Val Arg Gln Ala Pro Glu Lys Gly Leu Glu Trp Val Ala
1               5                   10

<210> SEQ ID NO 124
<211> LENGTH: 17
<212> TYPE: PRT
<213> ORGANISM: Artificial Sequence
<220> FEATURE:
<223> OTHER INFORMATION: ACI-7062-414A5-Ab1-VH CDR2

<400> SEQUENCE: 124

Tyr Ile Arg Ser Gly Ser Asp Ile Ile Tyr Tyr Ala Asp Thr Val Lys
1               5                   10                  15

Gly

<210> SEQ ID NO 125
<211> LENGTH: 32
<212> TYPE: PRT
<213> ORGANISM: Artificial Sequence
<220> FEATURE:
<223> OTHER INFORMATION: ACI-7062-414A5-Ab1-VH FR3

<400> SEQUENCE: 125

Arg Phe Thr Ile Ser Arg Asp Asn Pro Glu Asn Thr Leu Phe Leu Glu
1               5                   10                  15

Met Thr Arg Leu Arg Ser Glu Asp Thr Ala Met Tyr Tyr Cys Ala Arg
            20                  25                  30

<210> SEQ ID NO 126
<211> LENGTH: 9
<212> TYPE: PRT
<213> ORGANISM: Artificial Sequence
<220> FEATURE:
<223> OTHER INFORMATION: ACI-7062-414A5-Ab1-VH CDR3

<400> SEQUENCE: 126

Ser Gly Thr Thr Val Pro Phe Asp Tyr
1               5

<210> SEQ ID NO 127
<211> LENGTH: 11
<212> TYPE: PRT
<213> ORGANISM: Artificial Sequence
<220> FEATURE:
<223> OTHER INFORMATION: ACI-7062-414A5-Ab1-VH FR4

<400> SEQUENCE: 127

Trp Gly Gln Gly Thr Ser Leu Thr Val Ser Ser
1               5                   10

<210> SEQ ID NO 128
<211> LENGTH: 34
<212> TYPE: PRT
<213> ORGANISM: Artificial Sequence
<220> FEATURE:
<223> OTHER INFORMATION: ACI-7062-414A5-Ab1-VH Tail

<400> SEQUENCE: 128

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro

<210> SEQ ID NO 129
<211> LENGTH: 458
<212> TYPE: DNA
<213> ORGANISM: Artificial Sequence
<220> FEATURE:
<223> OTHER INFORMATION: ACI-7062-414A5-Ab1-VH Nucleotide sequence of
      the heavy chain variable domain

<400> SEQUENCE: 129
gatgtgcagc tggtggagtc tgggggaggc ttagtgcagc ctggagggtc ccggagactc      60
tcctgtgcag cctctggatt cactttcagt agctttggaa tgcactgggt cgtcaggct     120 ccagagaagg ggctggagtg ggtcgcatac attaggagtg cagtgatat aatctactat      180 gcagacacag tgaagggccg attcaccatc tccagagaca atcccgagaa caccctgttt     240
ttggaaatga ccagactaag gtctgaggac acggccatgt attactgtgc aagatcaggg     300
actacggtcc cctttgacta ctggggccaa ggcaccagtc tcacagtctc ttcagccaaa     360
acaacagccc catcggtcta tccactggcc cctgtgtgtg gagatacaac tggctcctcg     420
gtgactctag gatgcctggt caagggttat ttccctga                             458

<210> SEQ ID NO 130
<211> LENGTH: 125
<212> TYPE: PRT
<213> ORGANISM: Artificial Sequence
<220> FEATURE:
<223> OTHER INFORMATION: ACI-7062-412E12-Ab1-VL Peptide sequence of the
      light chain variable domain

<400> SEQUENCE: 130

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asp Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val

-continued

```
                    50                  55                  60
Pro Asp Arg Phe Ile Gly Ser Gly Ser Gly Thr Asp Phe Ser Leu Thr
 65                  70                  75                  80

Ile Ser Ser Val Gln Ala Glu Asp Leu Ala Asp Tyr Phe Cys Gln Gln
                 85                  90                  95

His Tyr Ser Ile Pro Leu Thr Phe Gly Ala Gly Thr Lys Leu Glu Leu
            100                 105                 110

Lys Arg Ala Asp Ala Ala Pro Thr Val Ser Ile Phe Pro
        115                 120                 125

<210> SEQ ID NO 131
<211> LENGTH: 23
<212> TYPE: PRT
<213> ORGANISM: Artificial Sequence
<220> FEATURE:
<223> OTHER INFORMATION: ACI-7062-412E12-Ab1-VL FR1

<400> SEQUENCE: 131

Asp Ile Val Met Thr Gln Ser Pro Ser Ser Leu Ala Met Ser Val Gly
 1               5                  10                  15

Gln Lys Val Thr Met Ser Cys
             20

<210> SEQ ID NO 132
<211> LENGTH: 17
<212> TYPE: PRT
<213> ORGANISM: Artificial Sequence
<220> FEATURE:
<223> OTHER INFORMATION: ACI-7062-412E12-Ab1-VL CDR1

<400> SEQUENCE: 132

Lys Ser Ser Gln Ser Leu Leu Asn Ser Gly Asp Gln Lys Asn Tyr Leu
 1               5                  10                  15

Ala

<210> SEQ ID NO 133
<211> LENGTH: 15
<212> TYPE: PRT
<213> ORGANISM: Artificial Sequence
<220> FEATURE:
<223> OTHER INFORMATION: ACI-7062-412E12-Ab1-VL FR2

<400> SEQUENCE: 133

Trp Tyr Gln Gln Lys Pro Gly Gln Ser Pro Glu Leu Leu Leu Tyr
 1               5                  10                  15

<210> SEQ ID NO 134
<211> LENGTH: 7
<212> TYPE: PRT
<213> ORGANISM: Artificial Sequence
<220> FEATURE:
<223> OTHER INFORMATION: ACI-7062-412E12-Ab1-VL CDR2

<400> SEQUENCE: 134

Phe Ala Ser Thr Arg Ala Ser
 1               5

<210> SEQ ID NO 135
<211> LENGTH: 32
<212> TYPE: PRT
<213> ORGANISM: Artificial Sequence
<220> FEATURE:
<223> OTHER INFORMATION: ACI-7062-412E12-Ab1-VL FR3
```

```
<400> SEQUENCE: 135

Gly Val Pro Asp Arg Phe Ile Gly Ser Gly Ser Gly Thr Asp Phe Ser
1               5                   10                  15

Leu Thr Ile Ser Ser Val Gln Ala Glu Asp Leu Ala Asp Tyr Phe Cys
            20                  25                  30

<210> SEQ ID NO 136
<211> LENGTH: 9
<212> TYPE: PRT
<213> ORGANISM: Artificial Sequence
<220> FEATURE:
<223> OTHER INFORMATION: ACI-7062-412E12-Ab1-VL CDR3

<400> SEQUENCE: 136

Gln Gln His Tyr Ser Ile Pro Leu Thr
1               5

<210> SEQ ID NO 137
<211> LENGTH: 12
<212> TYPE: PRT
<213> ORGANISM: Artificial Sequence
<220> FEATURE:
<223> OTHER INFORMATION: ACI-7062-412E12-Ab1-VL FR4

<400> SEQUENCE: 137

Phe Gly Ala Gly Thr Lys Leu Glu Leu Lys Arg Ala
1               5                   10

<210> SEQ ID NO 138
<211> LENGTH: 10
<212> TYPE: PRT
<213> ORGANISM: Artificial Sequence
<220> FEATURE:
<223> OTHER INFORMATION: ACI-7062-412E12-Ab1-VL Tail

<400> SEQUENCE: 138

Asp Ala Ala Pro Thr Val Ser Ile Phe Pro
1               5                   10

<210> SEQ ID NO 139
<211> LENGTH: 375
<212> TYPE: DNA
<213> ORGANISM: Artificial Sequence
<220> FEATURE:
<223> OTHER INFORMATION: ACI-7062-412E12-Ab1-VL Nucleotidic sequence of
      the light chain variable domain

<400> SEQUENCE: 139
gacattgtga tgacacagtc tccatcctcc ctggctatgt cagttggaca gaaggtcact    60
atgagctgca gtccagtca gagccttta aatagtggcg atcaaaagaa ctatttggcc    120
tggtaccagc agaaaccagg acagtctcct gaacttctgt tatactttgc atccactagg   180
gcatctgggg tccctgatcg cttcataggc agtggatctg gacagatttt ctctcttacc   240
atcagcagtg tgcaggctga agacctggca gattacttct gtcagcaaca ttatagtatt   300
ccgctcacgt tcggtgctgg gaccaagctg gagctgaaac gggctgatgc tgcaccaact   360
gtatccatct tccca                                                    375

<210> SEQ ID NO 140
<211> LENGTH: 128
<212> TYPE: PRT
<213> ORGANISM: Artificial Sequence
<220> FEATURE:
<223> OTHER INFORMATION: ACI-7062-412E12-Ab1-VH Peptidic sequence of the
``` heavy chain variable domain

<400> SEQUENCE: 140

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Arg Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser Ala Lys Thr Thr Pro Pro Ser Val Tyr Pro
        115                 120                 125

<210> SEQ ID NO 141
<211> LENGTH: 30
<212> TYPE: PRT
<213> ORGANISM: Artificial Sequence
<220> FEATURE:
<223> OTHER INFORMATION: ACI-7062-412E12-Ab1-VH FR1

<400> SEQUENCE: 141

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser
            20                  25                  30

<210> SEQ ID NO 142
<211> LENGTH: 5
<212> TYPE: PRT
<213> ORGANISM: Artificial Sequence
<220> FEATURE:
<223> OTHER INFORMATION: ACI-7062-412E12-Ab1-VH CDR1

<400> SEQUENCE: 142

Arg Phe Gly Met His
1               5

<210> SEQ ID NO 143
<211> LENGTH: 14
<212> TYPE: PRT
<213> ORGANISM: Artificial Sequence
<220> FEATURE:
<223> OTHER INFORMATION: ACI-7062-412E12-Ab1-VH FR2

<400> SEQUENCE: 143

Trp Val Arg Gln Ala Pro Glu Lys Gly Leu Glu Trp Val Ala
1               5                   10

<210> SEQ ID NO 144
<211> LENGTH: 17
<212> TYPE: PRT
<213> ORGANISM: Artificial Sequence
<220> FEATURE:
<223> OTHER INFORMATION: ACI-7062-412E12-Ab1-VH CDR2

<400> SEQUENCE: 144

-continued

Tyr Ile Arg Ser Gly Ser Asp Ile Ile Tyr Tyr Ala Asp Ser Val Lys
1               5                   10                  15

Gly

<210> SEQ ID NO 145
<211> LENGTH: 32
<212> TYPE: PRT
<213> ORGANISM: Artificial Sequence
<220> FEATURE:
<223> OTHER INFORMATION: ACI-7062-412E12-Ab1-VH FR3

<400> SEQUENCE: 145

Arg Phe Thr Ile Ser Arg Asp Asn Pro Glu Asn Thr Leu Phe Leu Gln
1               5                   10                  15

Met Thr Ser Leu Arg Ser Glu Asp Thr Ala Met Tyr Tyr Cys Ala Arg
            20                  25                  30

<210> SEQ ID NO 146
<211> LENGTH: 9
<212> TYPE: PRT
<213> ORGANISM: Artificial Sequence
<220> FEATURE:
<223> OTHER INFORMATION: ACI-7062-412E12-Ab1-VH CDR3

<400> SEQUENCE: 146

Ser Gly Thr Thr Val Pro Phe Asp Tyr
1               5

<210> SEQ ID NO 147
<211> LENGTH: 11
<212> TYPE: PRT
<213> ORGANISM: Artificial Sequence
<220> FEATURE:
<223> OTHER INFORMATION: ACI-7062-412E12-Ab1-VH FR4

<400> SEQUENCE: 147

Trp Gly Gln Gly Thr Ser Leu Thr Val Ser Ser
1               5                   10

<210> SEQ ID NO 148
<211> LENGTH: 10
<212> TYPE: PRT
<213> ORGANISM: Artificial Sequence
<220> FEATURE:
<223> OTHER INFORMATION: ACI-7062-412E12-Ab1-VH Tail

<400> SEQUENCE: 148

Ala Lys Thr Thr Pro Pro Ser Val Tyr Pro
1               5                   10

<210> SEQ ID NO 149
<211> LENGTH: 384
<212> TYPE: DNA
<213> ORGANISM: Artificial Sequence
<220> FEATURE:
<223> OTHER INFORMATION: ACI-7062-412E12-Ab1-VH Nucleotidic sequence of
      the heavy chain variable domain

<400> SEQUENCE: 149
gatgtgcagc tggtggagtc tgggggaggc ttagtgcagc ctggagggtc ccggagactc      60
tcctgtgcag cctctggatt cactttcagt aggtttggaa tgcactgggt tcgccaggct     120
ccagagaagg ggctggagtg ggtcgcatac attaggagtg gcagtgatat aatctactat     180
gcagactcag tgaagggccg attcaccatc tccagagaca atcccgagaa caccctgttc     240

```
ctgcaaatga ccagtctaag gtctgaggac acggccatgt attactgtgc aagatcaggg    300
actacggtcc cctttgacta ctggggccaa ggcaccagtc tcacagtctc ttcagccaaa    360
acgacacccc catctgtcta tcca                                           384
```

<210> SEQ ID NO 150
<211> LENGTH: 121
<212> TYPE: PRT
<213> ORGANISM: Artificial Sequence
<220> FEATURE:
<223> OTHER INFORMATION: ACI-7062-416A11-Ab1-VL Peptidic sequence of the
      light chain variable domain

<400> SEQUENCE: 150

```
Asp Val Leu Met Thr Gln Thr Pro Leu Ser Leu Pro Val Ser Leu Gly
1               5                   10                  15

Asp Arg Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Arg Val Pro Thr Phe Gly Ala Gly Thr Lys Leu Glu Leu Lys Arg
            100                 105                 110

Ala Asp Ala Ala Pro Thr Val Ser Ile
        115                 120
```

<210> SEQ ID NO 151
<211> LENGTH: 23
<212> TYPE: PRT
<213> ORGANISM: Artificial Sequence
<220> FEATURE:
<223> OTHER INFORMATION: ACI-7062-416A11-Ab1-VL FR1

<400> SEQUENCE: 151

```
Asp Val Leu Met Thr Gln Thr Pro Leu Ser Leu Pro Val Ser Leu Gly
1               5                   10                  15

Asp Arg Ala Ser Ile Ser Cys
            20
```

<210> SEQ ID NO 152
<211> LENGTH: 16
<212> TYPE: PRT
<213> ORGANISM: Artificial Sequence
<220> FEATURE:
<223> OTHER INFORMATION: ACI-7062-416A11-Ab1-VL CDR1

<400> SEQUENCE: 152

```
Arg Ser Ser Gln Ser Ile Val His Ser Ser Gly Asn Thr Tyr Leu Glu
1               5                   10                  15
```

<210> SEQ ID NO 153
<211> LENGTH: 15
<212> TYPE: PRT
<213> ORGANISM: Artificial Sequence
<220> FEATURE:
<223> OTHER INFORMATION: ACI-7062-416A11-Ab1-VL FR2

```
<400> SEQUENCE: 153

Trp Tyr Leu Gln Lys Pro Gly Gln Ser Pro Lys Leu Leu Ile Tyr
1               5                   10                  15

<210> SEQ ID NO 154
<211> LENGTH: 7
<212> TYPE: PRT
<213> ORGANISM: Artificial Sequence
<220> FEATURE:
<223> OTHER INFORMATION: ACI-7062-416A11-Ab1-VL CDR2

<400> SEQUENCE: 154

Lys Val Ser Asn Arg Phe Ser
1               5

<210> SEQ ID NO 155
<211> LENGTH: 32
<212> TYPE: PRT
<213> ORGANISM: Artificial Sequence
<220> FEATURE:
<223> OTHER INFORMATION: ACI-7062-416A11-Ab1-VL FR3

<400> SEQUENCE: 155

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 156
<211> LENGTH: 8
<212> TYPE: PRT
<213> ORGANISM: Artificial Sequence
<220> FEATURE:
<223> OTHER INFORMATION: ACI-7062-416A11-Ab1-VL CDR3

<400> SEQUENCE: 156

Phe Gln Gly Ser Arg Val Pro Thr
1               5

<210> SEQ ID NO 157
<211> LENGTH: 12
<212> TYPE: PRT
<213> ORGANISM: Artificial Sequence
<220> FEATURE:
<223> OTHER INFORMATION: ACI-7062-416A11-Ab1-VL FR4

<400> SEQUENCE: 157

Phe Gly Ala Gly Thr Lys Leu Glu Leu Lys Arg Ala
1               5                   10

<210> SEQ ID NO 158
<211> LENGTH: 8
<212> TYPE: PRT
<213> ORGANISM: Artificial Sequence
<220> FEATURE:
<223> OTHER INFORMATION: ACI-7062-416A11-Ab1-VH Tail

<400> SEQUENCE: 158

Asp Ala Ala Pro Thr Val Ser Ile
1               5

<210> SEQ ID NO 159
<211> LENGTH: 364
<212> TYPE: DNA
<213> ORGANISM: Artificial Sequence
<220> FEATURE:
```

<223> OTHER INFORMATION: ACI-7062-416A11-Ab1-VL Nucleotidic Sequence of
      the light chain variable domain

<400> SEQUENCE: 159

```
gatgttttga tgacccaaac tccactctcc ctgcctgtca gtcttggaga tcgagcctcc      60
atctcttgca gatctagtca gagcattgta catagtagtg aaacaccta tttagaatgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acgtgttccc     300
acgttcggtg ctgggaccaa gctggagctg aaacgggctg atgctgcacc aactgtatcc     360
atct                                                                  364
```

<210> SEQ ID NO 160
<211> LENGTH: 144
<212> TYPE: PRT
<213> ORGANISM: Artificial Sequence
<220> FEATURE:
<223> OTHER INFORMATION: ACI-7062-416A11-Ab1-VH Peptidic sequence of the
      heavy chain variable domain

<400> SEQUENCE: 160

```
Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Ala Ala Thr Tyr Tyr
                85                  90                  95

Cys Ala Arg Val Tyr Gly Asn Leu Tyr Tyr Phe Gly Tyr Trp Gly Gln
            100                 105                 110

Gly Thr Thr Leu Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140
```

<210> SEQ ID NO 161
<211> LENGTH: 30
<212> TYPE: PRT
<213> ORGANISM: Artificial Sequence
<220> FEATURE:
<223> OTHER INFORMATION: ACI-7062-416A11-Ab1-VH FR1

<400> SEQUENCE: 161

```
Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser
            20                  25                  30
```

<210> SEQ ID NO 162
<211> LENGTH: 7
<212> TYPE: PRT
<213> ORGANISM: Artificial Sequence
<220> FEATURE:

<223> OTHER INFORMATION: ACI-7062-416A11-Ab1-VH CDR1

<400> SEQUENCE: 162

Thr Tyr Gly Ile Gly Val Gly
1               5

<210> SEQ ID NO 163
<211> LENGTH: 14
<212> TYPE: PRT
<213> ORGANISM: Artificial Sequence
<220> FEATURE:
<223> OTHER INFORMATION: ACI-7062-416A11-Ab1-VH FR2

<400> SEQUENCE: 163

Trp Ile Arg Gln Pro Ser Gly Lys Gly Leu Glu Trp Leu Ala
1               5                   10

<210> SEQ ID NO 164
<211> LENGTH: 16
<212> TYPE: PRT
<213> ORGANISM: Artificial Sequence
<220> FEATURE:
<223> OTHER INFORMATION: ACI-7062-416A11-Ab1-VH CDR2

<400> SEQUENCE: 164

His Ile Trp Trp Asn Asp Asn Lys Tyr Tyr Asn Thr Ala Leu Lys Ser
1               5                   10                  15

<210> SEQ ID NO 165
<211> LENGTH: 32
<212> TYPE: PRT
<213> ORGANISM: Artificial Sequence
<220> FEATURE:
<223> OTHER INFORMATION: ACI-7062-416A11-Ab1-VH FR3

<400> SEQUENCE: 165

Arg Leu Thr Ile Ser Lys Asp Thr Ser Asn Asn Gln Val Phe Leu Lys
1               5                   10                  15

Ile Ala Ser Val Asp Thr Ala Asp Ala Ala Thr Tyr Tyr Cys Ala Arg
            20                  25                  30

<210> SEQ ID NO 166
<211> LENGTH: 10
<212> TYPE: PRT
<213> ORGANISM: Artificial Sequence
<220> FEATURE:
<223> OTHER INFORMATION: ACI-7062-416A11-Ab1-VH CDR3

<400> SEQUENCE: 166

Val Tyr Gly Asn Leu Tyr Tyr Phe Gly Tyr
1               5                   10

<210> SEQ ID NO 167
<211> LENGTH: 11
<212> TYPE: PRT
<213> ORGANISM: Artificial Sequence
<220> FEATURE:
<223> OTHER INFORMATION: ACI-7062-416A11-Ab1-VH FR4

<400> SEQUENCE: 167

Trp Gly Gln Gly Thr Thr Leu Thr Val Ser Ser
1               5                   10

<210> SEQ ID NO 168
<211> LENGTH: 24
<212> TYPE: PRT

```
<213> ORGANISM: Artificial Sequence
<220> FEATURE:
<223> OTHER INFORMATION: ACI-7062-416A11-Ab1-VH Tail

<400> SEQUENCE: 168

Ala Lys Thr Thr Ala Pro Ser Val Tyr Pro Leu Ala Pro Val Cys Gly
1               5                   10                  15

Asp Thr Thr Gly Ser Ser Val Thr
            20

<210> SEQ ID NO 169
<211> LENGTH: 433
<212> TYPE: DNA
<213> ORGANISM: Artificial Sequence
<220> FEATURE:
<223> OTHER INFORMATION: ACI-7062-416A11-Ab1-VH Nucleotide sequence of
      the heavy chain variable domain

<400> SEQUENCE: 169
caggttactc tgaaagagtc tggccctggg atattgcagt cctcccagac cctcagtctg    60
acttgttctt tctctggatt ttcactgagc acttatggta taggagtagg ctggattcgt   120
cagccttcag ggaagggtct ggagtggctg gcacacattt ggtggaatga taataagtac   180
tataacacag ccctgaagag ccgactcaca atctccaagg atacctccaa caaccaggta   240
ttcctcaaga tcgccagtgt ggacactgca gatgctgcca catactactg tgctcgagtc   300
tatggtaacc tatactactt tggctactgg ggccaaggca ccactctcac agtctcctca   360
gccaaaacaa cagccccatc ggtctatcca ctggcccctg tgtgtggaga tacaactggc   420
tcctcggtga ctc                                                      433

<210> SEQ ID NO 170
<211> LENGTH: 113
<212> TYPE: PRT
<213> ORGANISM: Artificial Sequence
<220> FEATURE:
<223> OTHER INFORMATION: ACI-7062-406E3-Ab2-VL Peptide sequence of the
      light chain variable domain

<400> SEQUENCE: 170

Asp Val Leu Met Thr Gln Thr Pro Leu Ser Leu Pro Val Ser Leu Gly
1               5                   10                  15

Asp Arg Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Thr Phe Gly Ala Gly Thr Lys Leu Glu Leu Lys Arg
            100                 105                 110

Ala

<210> SEQ ID NO 171
<211> LENGTH: 23
<212> TYPE: PRT
<213> ORGANISM: Artificial Sequence
<220> FEATURE:
```

<223> OTHER INFORMATION: ACI-7062-406E3-Ab2-VL-FR1

<400> SEQUENCE: 171

Asp Val Leu Met Thr Gln Thr Pro Leu Ser Leu Pro Val Ser Leu Gly
1               5                   10                  15

Asp Arg Ala Ser Ile Ser Cys
            20

<210> SEQ ID NO 172
<211> LENGTH: 16
<212> TYPE: PRT
<213> ORGANISM: Artificial Sequence
<220> FEATURE:
<223> OTHER INFORMATION: ACI-7062-406E3-Ab2-VL-CDR1

<400> SEQUENCE: 172

Arg Ser Ser Gln Ser Ile Val His Arg Ser Gly Asn Thr Tyr Leu Glu
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: ACI-7062-406E3-Ab2-VL-FR2

<400> SEQUENCE: 173

Trp Tyr Leu Gln Lys Pro Gly Gln Ser Pro Lys Leu Leu Ile Tyr
1               5                   10                  15

<210> SEQ ID NO 174
<211> LENGTH: 7
<212> TYPE: PRT
<213> ORGANISM: Artificial Sequence
<220> FEATURE:
<223> OTHER INFORMATION: ACI-7062-406E3-Ab2-VL-CDR2

<400> SEQUENCE: 174

Lys Val Ser Asn Arg Phe Ser
1               5

<210> SEQ ID NO 175
<211> LENGTH: 32
<212> TYPE: PRT
<213> ORGANISM: Artificial Sequence
<220> FEATURE:
<223> OTHER INFORMATION: ACI-7062-406E3-Ab2-VL-FR3

<400> SEQUENCE: 175

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 176
<211> LENGTH: 8
<212> TYPE: PRT
<213> ORGANISM: Artificial Sequence
<220> FEATURE:
<223> OTHER INFORMATION: ACI-7062-406E3-Ab2-VL-CDR3

<400> SEQUENCE: 176

Phe Gln Gly Ser His Val Pro Thr
1               5

```
<210> SEQ ID NO 177
<211> LENGTH: 12
<212> TYPE: PRT
<213> ORGANISM: Artificial Sequence
<220> FEATURE:
<223> OTHER INFORMATION: ACI-7062-406E3-Ab2-VL-FR4

<400> SEQUENCE: 177

Phe Gly Ala Gly Thr Lys Leu Glu Leu Lys Arg Ala
1               5                   10

<210> SEQ ID NO 178
<211> LENGTH: 15
<212> TYPE: PRT
<213> ORGANISM: Artificial Sequence
<220> FEATURE:
<223> OTHER INFORMATION: ACI-7062-406E3-Ab2-VL-Tail

<400> SEQUENCE: 178

Asp Ala Ala Pro Thr Val Ser Ile Phe Pro Pro Ser Ser Glu Gln
1               5                   10                  15

<210> SEQ ID NO 179
<211> LENGTH: 339
<212> TYPE: DNA
<213> ORGANISM: Artificial Sequence
<220> FEATURE:
<223> OTHER INFORMATION: ACI-7062-406E3-Ab2-VL Nucleotide sequence of
      the light chain variable domain without tail

<400> SEQUENCE: 179
gatgttttga tgacccaaac tccactctcc ctgcctgtca gtcttggaga tcgagcctcc      60
atctcttgca gatctagtca gagcattgta catcgtagtg aaacacctta tttagagtgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccc     300
acgttcggtg ctgggaccaa gctggagctg aaacgggct                            339

<210> SEQ ID NO 180
<211> LENGTH: 120
<212> TYPE: PRT
<213> ORGANISM: Artificial Sequence
<220> FEATURE:
<223> OTHER INFORMATION: ACI-7062-406E3-Ab2-VH Peptide sequence of the
      heavy chain variable domain

<400> SEQUENCE: 180

Gln Val Thr Leu Lys Glu Ser Gly Pro Ala Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Val Tyr Gly Asn Leu Tyr Tyr Phe Ala Tyr Trp Gly Gln
            100                 105                 110
```

Gly Thr Thr Leu Thr Val Ser Ser
        115                 120

<210> SEQ ID NO 181
<211> LENGTH: 30
<212> TYPE: PRT
<213> ORGANISM: Artificial Sequence
<220> FEATURE:
<223> OTHER INFORMATION: ACI-7062-406E3-Ab2-VH-FR1

<400> SEQUENCE: 181

Gln Val Thr Leu Lys Glu Ser Gly Pro Ala Ile Leu Gln Pro Ser Gln
1               5                   10                  15

Thr Leu Ser Leu Thr Cys Ser Phe Ser Gly Phe Ser Leu Thr
            20                  25                  30

<210> SEQ ID NO 182
<211> LENGTH: 7
<212> TYPE: PRT
<213> ORGANISM: Artificial Sequence
<220> FEATURE:
<223> OTHER INFORMATION: ACI-7062-406E3-Ab2-VH-CDR1

<400> SEQUENCE: 182

Thr Tyr Gly Ile Gly Val Gly
1               5

<210> SEQ ID NO 183
<211> LENGTH: 14
<212> TYPE: PRT
<213> ORGANISM: Artificial Sequence
<220> FEATURE:
<223> OTHER INFORMATION: ACI-7062-406E3-Ab2-VH-FR2

<400> SEQUENCE: 183

Trp Ile Arg Gln Pro Ser Gly Lys Gly Leu Glu Trp Leu Ala
1               5                   10

<210> SEQ ID NO 184
<211> LENGTH: 16
<212> TYPE: PRT
<213> ORGANISM: Artificial Sequence
<220> FEATURE:
<223> OTHER INFORMATION: ACI-7062-406E3-Ab2-VH-CDR2

<400> SEQUENCE: 184

His Ile Trp Trp Asn Asp Asn Lys Tyr Tyr Asn Thr Ala Leu Lys Ser
1               5                   10                  15

<210> SEQ ID NO 185
<211> LENGTH: 32
<212> TYPE: PRT
<213> ORGANISM: Artificial Sequence
<220> FEATURE:
<223> OTHER INFORMATION: ACI-7062-406E3-Ab2-VH-FR3

<400> SEQUENCE: 185

Arg Leu Thr Val Ser Lys Asp Thr Ser Asn Asn Gln Val Phe Leu Lys
1               5                   10                  15

Ile Ala Ser Val Asp Thr Ala Asp Thr Ala Thr Tyr Tyr Cys Ala Arg
            20                  25                  30

<210> SEQ ID NO 186
<211> LENGTH: 10
<212> TYPE: PRT

<213> ORGANISM: Artificial Sequence
<220> FEATURE:
<223> OTHER INFORMATION: ACI-7062-406E3-Ab2-VH-CDR3

<400> SEQUENCE: 186

Val Tyr Gly Asn Leu Tyr Tyr Phe Ala Tyr
1               5                   10

<210> SEQ ID NO 187
<211> LENGTH: 11
<212> TYPE: PRT
<213> ORGANISM: Artificial Sequence
<220> FEATURE:
<223> OTHER INFORMATION: ACI-7062-406E3-Ab2-VH-FR4

<400> SEQUENCE: 187

Trp Gly Gln Gly Thr Thr Leu Thr Val Ser Ser
1               5                   10

<210> SEQ ID NO 188
<211> LENGTH: 25
<212> TYPE: PRT
<213> ORGANISM: Artificial Sequence
<220> FEATURE:
<223> OTHER INFORMATION: ACI-7062-406E3-Ab2-VH-Tail

<400> SEQUENCE: 188

Ala Lys Thr Thr Ala Pro Ser Val Tyr Pro Leu Ala Pro Val Cys Gly
1               5                   10                  15

Asp Thr Thr Gly Ser Ser Val Thr Leu
            20                  25

<210> SEQ ID NO 189
<211> LENGTH: 360
<212> TYPE: DNA
<213> ORGANISM: Artificial Sequence
<220> FEATURE:
<223> OTHER INFORMATION: ACI-7062-406E3-Ab2-VH Nucleotide sequence of
      the heavy chain variable domain without tail

<400> SEQUENCE: 189
caggttactc tgaaagagtc tggccctgcg atattgcagc cctcccagac cctcagtctg      60
acttgttctt tctctgggtt ttcactgacc acttatggta taggagtagg ctggattcgt     120
cagccttcag ggaagggtct ggagtggctg gcacacattt ggtggaatga ataagtac       180 tataacacag ccctgaagag ccggctcact gtctccaagg atacctccaa caaccaggta     240
ttcctcaaga tcgccagtgt agacactgca gatactgcca catactactg tgctcgagtc     300
tatggtaacc tgtactactt tgcctactgg ggccaaggca ccactctcac agtctcctca     360

<210> SEQ ID NO 190
<211> LENGTH: 113
<212> TYPE: PRT
<213> ORGANISM: Artificial Sequence
<220> FEATURE:
<223> OTHER INFORMATION: ACI-7062-415C4-Ab1-VL Peptide sequence of the
      light chain variable domain

<400> SEQUENCE: 190

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser

```
                35                  40                  45
Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Arg Val Pro Thr Phe Gly Ala Gly Thr Lys Leu Glu Leu Lys Arg
            100                 105                 110

Ala

<210> SEQ ID NO 191
<211> LENGTH: 23
<212> TYPE: PRT
<213> ORGANISM: Artificial Sequence
<220> FEATURE:
<223> OTHER INFORMATION: ACI-7062-415C4-Ab1-VL-FR1

<400> SEQUENCE: 191

Asp Val Leu Met Thr Gln Thr Pro Leu Ser Leu Pro Val Ser Leu Gly
 1               5                  10                  15

Asp Gln Ala Ser Ile Ser Cys
             20

<210> SEQ ID NO 192
<211> LENGTH: 16
<212> TYPE: PRT
<213> ORGANISM: Artificial Sequence
<220> FEATURE:
<223> OTHER INFORMATION: ACI-7062-415C4-Ab1-VL-CDR1

<400> SEQUENCE: 192

Arg Ser Ser Gln Ser Ile Val His Ser Thr Gly Asn Thr Tyr Leu Glu
 1               5                  10                  15

<210> SEQ ID NO 193
<211> LENGTH: 15
<212> TYPE: PRT
<213> ORGANISM: Artificial Sequence
<220> FEATURE:
<223> OTHER INFORMATION: ACI-7062-415C4-Ab1-VL-FR2

<400> SEQUENCE: 193

Trp Tyr Leu Gln Lys Pro Gly Gln Ser Pro Lys Leu Leu Ile Tyr
 1               5                  10                  15

<210> SEQ ID NO 194
<211> LENGTH: 7
<212> TYPE: PRT
<213> ORGANISM: Artificial Sequence
<220> FEATURE:
<223> OTHER INFORMATION: ACI-7062-415C4-Ab1-VL-CDR2

<400> SEQUENCE: 194

Lys Val Ser Asn Arg Phe Ser
 1               5

<210> SEQ ID NO 195
<211> LENGTH: 32
<212> TYPE: PRT
<213> ORGANISM: Artificial Sequence
<220> FEATURE:
<223> OTHER INFORMATION: ACI-7062-415C4-Ab1-VL-FR3
```

```
<400> SEQUENCE: 195

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 196
<211> LENGTH: 8
<212> TYPE: PRT
<213> ORGANISM: Artificial Sequence
<220> FEATURE:
<223> OTHER INFORMATION: ACI-7062-415C4-Ab1-VL-CDR3

<400> SEQUENCE: 196

Phe Gln Gly Ser Arg Val Pro Thr
1               5

<210> SEQ ID NO 197
<211> LENGTH: 12
<212> TYPE: PRT
<213> ORGANISM: Artificial Sequence
<220> FEATURE:
<223> OTHER INFORMATION: ACI-7062-415C4-Ab1-VL-FR4

<400> SEQUENCE: 197

Phe Gly Ala Gly Thr Lys Leu Glu Leu Lys Arg Ala
1               5                   10

<210> SEQ ID NO 198
<211> LENGTH: 51
<212> TYPE: PRT
<213> ORGANISM: Artificial Sequence
<220> FEATURE:
<223> OTHER INFORMATION: ACI-7062-415C4-Ab1-VL-Tail

<400> SEQUENCE: 198

Asp Ala Ala Pro Thr Val Ser Ile Phe Pro Pro Ser Ser Glu Gln Leu
1               5                   10                  15

Thr Ser Gly Gly Ala Ser Val Val Cys Phe Leu Asn Asn Phe Tyr Pro
            20                  25                  30

Lys Asp Ile Asn Val Lys Trp Lys Ile Asp Gly Ser Glu Arg Gln Asn
        35                  40                  45

Gly Val Leu
    50

<210> SEQ ID NO 199
<211> LENGTH: 339
<212> TYPE: DNA
<213> ORGANISM: Artificial Sequence
<220> FEATURE:
<223> OTHER INFORMATION: ACI-7062-415C4-Ab1-VL Nucleotide sequence of
      the light chain variable domain without tail

<400> SEQUENCE: 199
gatgttttga tgacccaaac tccactctcc ctgcctgtca gtcttggaga tcaagcctcc      60
atctcttgca gatctagtca gagcattgta catagtactg gaaacaccta tttggaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acgtgttccc     300
acgttcggtg ctgggaccaa gctggagctg aaacgggct                            339
```

<210> SEQ ID NO 200
<211> LENGTH: 120
<212> TYPE: PRT
<213> ORGANISM: Artificial Sequence
<220> FEATURE:
<223> OTHER INFORMATION: ACI-7062-415C4-Ab1-VH Peptide sequence of the heavy chain variable domain

<400> SEQUENCE: 200

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Lys Thr Ala
    50                  55                  60

Leu Lys Ser Arg Leu Thr Ile Ser Lys Asp Thr Ser Asn Asn Gln Val
65                  70                  75                  80

Phe Leu Lys Ile Ala Ser Val Asp Thr Ala Asp Ser Ala Thr Tyr Tyr
                85                  90                  95

Cys Ala Arg Val Tyr Gly Asn Leu Tyr Tyr Phe Gly Tyr Trp Gly Gln
            100                 105                 110

Gly Thr Thr Leu Thr Val Ser Ser
        115                 120
```

<210> SEQ ID NO 201
<211> LENGTH: 30
<212> TYPE: PRT
<213> ORGANISM: Artificial Sequence
<220> FEATURE:
<223> OTHER INFORMATION: ACI-7062-415C4-Ab1-VH-FR1

<400> SEQUENCE: 201

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30
```

<210> SEQ ID NO 202
<211> LENGTH: 7
<212> TYPE: PRT
<213> ORGANISM: Artificial Sequence
<220> FEATURE:
<223> OTHER INFORMATION: ACI-7062-415C4-Ab1-VH-CDR1

<400> SEQUENCE: 202

```
Thr Tyr Gly Ile Gly Val Gly
1               5
```

<210> SEQ ID NO 203
<211> LENGTH: 14
<212> TYPE: PRT
<213> ORGANISM: Artificial Sequence
<220> FEATURE:
<223> OTHER INFORMATION: ACI-7062-415C4-Ab1-VH-FR2

<400> SEQUENCE: 203

```
Trp Ile Arg Gln Pro Ser Gly Lys Gly Leu Glu Trp Leu Ala
1               5                   10
```

<210> SEQ ID NO 204

```
<211> LENGTH: 16
<212> TYPE: PRT
<213> ORGANISM: Artificial Sequence
<220> FEATURE:
<223> OTHER INFORMATION: ACI-7062-415C4-Ab1-VH-CDR2

<400> SEQUENCE: 204

His Ile Trp Trp Asn Asp Asn Lys Tyr Tyr Lys Thr Ala Leu Lys Ser
1               5                   10                  15

<210> SEQ ID NO 205
<211> LENGTH: 32
<212> TYPE: PRT
<213> ORGANISM: Artificial Sequence
<220> FEATURE:
<223> OTHER INFORMATION: ACI-7062-415C4-Ab1-VH-FR3

<400> SEQUENCE: 205

Arg Leu Thr Ile Ser Lys Asp Thr Ser Asn Asn Gln Val Phe Leu Lys
1               5                   10                  15

Ile Ala Ser Val Asp Thr Ala Asp Ser Ala Thr Tyr Tyr Cys Ala Arg
            20                  25                  30

<210> SEQ ID NO 206
<211> LENGTH: 10
<212> TYPE: PRT
<213> ORGANISM: Artificial Sequence
<220> FEATURE:
<223> OTHER INFORMATION: ACI-7062-415C4-Ab1-VH-CDR3

<400> SEQUENCE: 206

Val Tyr Gly Asn Leu Tyr Tyr Phe Gly Tyr
1               5                   10

<210> SEQ ID NO 207
<211> LENGTH: 11
<212> TYPE: PRT
<213> ORGANISM: Artificial Sequence
<220> FEATURE:
<223> OTHER INFORMATION: ACI-7062-415C4-Ab1-VH-FR4

<400> SEQUENCE: 207

Trp Gly Gln Gly Thr Thr Leu Thr Val Ser Ser
1               5                   10

<210> SEQ ID NO 208
<211> LENGTH: 32
<212> TYPE: PRT
<213> ORGANISM: Artificial Sequence
<220> FEATURE:
<223> OTHER INFORMATION: ACI-7062-415C4-Ab1-VH-Tail

<400> SEQUENCE: 208

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

<210> SEQ ID NO 209
<211> LENGTH: 360
<212> TYPE: DNA
<213> ORGANISM: Artificial Sequence
<220> FEATURE:
<223> OTHER INFORMATION: ACI-7062-415C4-Ab1-VH Nucleotide sequence of
      the heavy chain variable domain without tail

<400> SEQUENCE: 209
```

```
caggttactc tgaaagagtc tggccctggg atattgcagc cctcccagac cctcagtctg    60
acttgttctt tctctgggtt ttcactgagc acttatggta taggagtagg ctggattcgt   120
cagccctcag ggaagggtct ggagtggctg gcacacattt ggtggaatga taataagtac   180
tataagacag ccctgaagag ccggctcaca atctccaagg acacctccaa caaccaggtt   240
ttcctcaaga tcgccagtgt ggacactgca gattctgcca catactactg tgctcgagtc   300
tatggtaacc tgtactactt tggctactgg ggccaaggca ccactctcac agtctcctca   360
```

<210> SEQ ID NO 210
<211> LENGTH: 115
<212> TYPE: PRT
<213> ORGANISM: Artificial Sequence
<220> FEATURE:
<223> OTHER INFORMATION: ACI-7062-415H10-Ab2-VL Peptide sequence of the
      light chain variable domain

<400> SEQUENCE: 210

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Gly Ile Pro Leu Thr Phe Gly Ala Gly Thr Lys Leu Glu Leu
            100                 105                 110

Lys Arg Ala
        115

<210> SEQ ID NO 211
<211> LENGTH: 23
<212> TYPE: PRT
<213> ORGANISM: Artificial Sequence
<220> FEATURE:
<223> OTHER INFORMATION: ACI-7062-415H10-Ab2-VL-FR1

<400> SEQUENCE: 211

Asp Ile Val Met Thr Gln Ser Pro Ser Ser Leu Ala Met Ser Val Gly
1               5                   10                  15

Gln Lys Val Thr Met Ser Cys
            20

<210> SEQ ID NO 212
<211> LENGTH: 17
<212> TYPE: PRT
<213> ORGANISM: Artificial Sequence
<220> FEATURE:
<223> OTHER INFORMATION: ACI-7062-415H10-Ab2-VL-CDR1

<400> SEQUENCE: 212

Lys Ser Ser Gln Ser Leu Leu Asn Ser Ser Asn Gln Lys Asn Tyr Leu
1               5                   10                  15

Ala

<210> SEQ ID NO 213
<211> LENGTH: 15
<212> TYPE: PRT
<213> ORGANISM: Artificial Sequence
<220> FEATURE:
<223> OTHER INFORMATION: ACI-7062-415H10-Ab2-VL-FR2

<400> SEQUENCE: 213

Trp Tyr Gln Gln Lys Pro Gly Gln Ser Pro Lys Leu Leu Ile Tyr
1               5                   10                  15

<210> SEQ ID NO 214
<211> LENGTH: 7
<212> TYPE: PRT
<213> ORGANISM: Artificial Sequence
<220> FEATURE:
<223> OTHER INFORMATION: ACI-7062-415H10-Ab2-VL-CDR2

<400> SEQUENCE: 214

Phe Ala Ser Thr Arg Glu Ser
1               5

<210> SEQ ID NO 215
<211> LENGTH: 32
<212> TYPE: PRT
<213> ORGANISM: Artificial Sequence
<220> FEATURE:
<223> OTHER INFORMATION: ACI-7062-415H10-Ab2-VL-FR3

<400> SEQUENCE: 215

Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Phe Cys
            20                  25                  30

<210> SEQ ID NO 216
<211> LENGTH: 9
<212> TYPE: PRT
<213> ORGANISM: Artificial Sequence
<220> FEATURE:
<223> OTHER INFORMATION: ACI-7062-415H10-Ab2-VL-CDR3

<400> SEQUENCE: 216

Gln Gln His Tyr Gly Ile Pro Leu Thr
1               5

<210> SEQ ID NO 217
<211> LENGTH: 12
<212> TYPE: PRT
<213> ORGANISM: Artificial Sequence
<220> FEATURE:
<223> OTHER INFORMATION: ACI-7062-415H10-Ab2-VL-FR4

<400> SEQUENCE: 217

Phe Gly Ala Gly Thr Lys Leu Glu Leu Lys Arg Ala
1               5                   10

<210> SEQ ID NO 218
<211> LENGTH: 10
<212> TYPE: PRT
<213> ORGANISM: Artificial Sequence
<220> FEATURE:
<223> OTHER INFORMATION: ACI-7062-415H10-Ab2-VL-Tail

<400> SEQUENCE: 218

Asp Ala Ala Pro Thr Val Ser Ile Phe Pro

<210> SEQ ID NO 219
<211> LENGTH: 345
<212> TYPE: DNA
<213> ORGANISM: Artificial Sequence
<220> FEATURE:
<223> OTHER INFORMATION: ACI-7062-415H10-Ab2-VL Nucleotide sequence of the light chain variable domain without tail

<400> SEQUENCE: 219

```
gacattgtga tgacacagtc tccatcctcc ctggctatgt cagtaggaca gaaggtcact    60
atgagctgca agtccagtca gagccttta aatagtagca tcaaaagaa ctatttggcc    120
tggtaccagc agaaaccagg acagtctcct aaacttctaa tatactttgc atccactagg    180
gaatctgggg tccctgatcg cttcataggc agtggatctg ggacagattt cactcttacc    240
atcagcagtg tgcaggctga agacctggca gattacttct gtcagcaaca ttatggcatt    300
ccgctcacgt tcggtgctgg gaccaagctg gaactgaaac gggct    345
```

<210> SEQ ID NO 220
<211> LENGTH: 118
<212> TYPE: PRT
<213> ORGANISM: Artificial Sequence
<220> FEATURE:
<223> OTHER INFORMATION: ACI-7062-415H10-Ab2-VH Peptide sequence of the heavy chain variable domain

<400> SEQUENCE: 220

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Asn Ile Tyr Tyr Thr Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Ile Tyr Tyr Cys
                85                  90                  95

Ala Arg Ser Gly Thr Thr Val Pro Phe Asp Tyr Trp Gly Gln Gly Thr
            100                 105                 110

Thr Leu Thr Val Ser Ser
        115

<210> SEQ ID NO 221
<211> LENGTH: 30
<212> TYPE: PRT
<213> ORGANISM: Artificial Sequence
<220> FEATURE:
<223> OTHER INFORMATION: ACI-7062-415H10-Ab2-VH-FR1

<400> SEQUENCE: 221

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser
            20                  25                  30

<210> SEQ ID NO 222
<211> LENGTH: 5

```
<212> TYPE: PRT
<213> ORGANISM: Artificial Sequence
<220> FEATURE:
<223> OTHER INFORMATION: ACI-7062-415H10-Ab2-VH-CDR1

<400> SEQUENCE: 222

Ser Phe Gly Met His
1               5

<210> SEQ ID NO 223
<211> LENGTH: 14
<212> TYPE: PRT
<213> ORGANISM: Artificial Sequence
<220> FEATURE:
<223> OTHER INFORMATION: ACI-7062-415H10-Ab2-VH-FR2

<400> SEQUENCE: 223

Trp Val Arg Gln Ala Pro Glu Lys Gly Leu Glu Trp Val Ala
1               5                   10

<210> SEQ ID NO 224
<211> LENGTH: 17
<212> TYPE: PRT
<213> ORGANISM: Artificial Sequence
<220> FEATURE:
<223> OTHER INFORMATION: ACI-7062-415H10-Ab2-VH-CDR2

<400> SEQUENCE: 224

Tyr Ile Ser Ser Gly Ser Ser Asn Ile Tyr Tyr Thr Asp Thr Val Lys
1               5                   10                  15

Gly

<210> SEQ ID NO 225
<211> LENGTH: 32
<212> TYPE: PRT
<213> ORGANISM: Artificial Sequence
<220> FEATURE:
<223> OTHER INFORMATION: ACI-7062-415H10-Ab2-VH-FR3

<400> SEQUENCE: 225

Arg Phe Thr Ile Ser Arg Asp Asn Pro Lys Asn Thr Leu Phe Leu Gln
1               5                   10                  15

Met Thr Ser Leu Arg Ser Glu Asp Thr Ala Ile Tyr Tyr Cys Ala Arg
                20                  25                  30

<210> SEQ ID NO 226
<211> LENGTH: 9
<212> TYPE: PRT
<213> ORGANISM: Artificial Sequence
<220> FEATURE:
<223> OTHER INFORMATION: ACI-7062-415H10-Ab2-VH-CDR3

<400> SEQUENCE: 226

Ser Gly Thr Thr Val Pro Phe Asp Tyr
1               5

<210> SEQ ID NO 227
<211> LENGTH: 11
<212> TYPE: PRT
<213> ORGANISM: Artificial Sequence
<220> FEATURE:
<223> OTHER INFORMATION: ACI-7062-415H10-Ab2-VH-FR4

<400> SEQUENCE: 227

Trp Gly Gln Gly Thr Thr Leu Thr Val Ser Ser
1               5                   10
```

<210> SEQ ID NO 228
<211> LENGTH: 26
<212> TYPE: PRT
<213> ORGANISM: Artificial Sequence
<220> FEATURE:
<223> OTHER INFORMATION: ACI-7062-415H10-Ab2-VH-Tail

<400> SEQUENCE: 228

Ala Thr Thr Thr Ala Pro Ser Val Tyr Pro Leu Val Pro Gly Cys Ser
1               5                   10                  15

Asp Thr Ser Gly Ser Ser Val Thr Leu Gly
            20                  25

<210> SEQ ID NO 229
<211> LENGTH: 354
<212> TYPE: DNA
<213> ORGANISM: Artificial Sequence
<220> FEATURE:
<223> OTHER INFORMATION: ACI-7062-415H10-Ab2-VH Nucleotide sequence of
      the heavy chain variable domain without tail

<400> SEQUENCE: 229
gatgtgcagc tggtggagtc gggggggaggc ttagtgcagc ctggagggtc ccggaaactc       60
tcctgtgcag cctctggatt cactttcagt agctttggaa tgcactgggt tcgtcaggct      120
ccagagaagg ggctggagtg ggtcgcatac attagtagtg gcagtagtaa catctactat      180
acagacacag tgaagggccg attcaccatc tctagagaca atcccaagaa caccctgttc      240
ctgcaaatga ccagtctaag gtctgaggac acggccatat attactgtgc aagatcaggg      300
actacggtcc cctttgacta ctggggccaa ggcaccactc tcacagtctc ctca            354

<210> SEQ ID NO 230
<211> LENGTH: 115
<212> TYPE: PRT
<213> ORGANISM: Artificial Sequence
<220> FEATURE:
<223> OTHER INFORMATION: ACI-7062-401A2-Ab2-VL Peptide sequence of the
      light chain variable domain without tail

<400> SEQUENCE: 230

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asp Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Ser Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala
        115

<210> SEQ ID NO 231
<211> LENGTH: 345
<212> TYPE: DNA

<213> ORGANISM: Artificial Sequence
<220> FEATURE:
<223> OTHER INFORMATION: ACI-7062-401A2-Ab2-VL Nucleotide sequence of
     the light chain variable domain without tail

<400> SEQUENCE: 231

```
gacattgtga tgacacagtc tccatcctcc ctggctatgt cagttggaca gaaggtcact      60
atgagctgca agtccagtca gagccttttta aatagtggcg atcaaaagaa ctatttggcc    120
tggtaccagc agaaaccagg acagtctcct gaacttctgt tatactttgc atccactagg    180
gcatctgggg tccctgatcg cttcataggc agtggatctg ggacagattt ctctcttacc    240
atcagcagtg tgcaggctga agacctggca gattacttct gtcagcaaca ttatagtatt    300
ccgctcacgt tcggtgctgg gaccaagctg gagctgaaac gggct                    345
```

<210> SEQ ID NO 232
<211> LENGTH: 118
<212> TYPE: PRT
<213> ORGANISM: Artificial Sequence
<220> FEATURE:
<223> OTHER INFORMATION: ACI-7062-401A2-Ab2-VH Peptide sequence of the
     heavy chain variable domain without tail

<400> SEQUENCE: 232

```
Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Arg Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser
        115
```

<210> SEQ ID NO 233
<211> LENGTH: 354
<212> TYPE: DNA
<213> ORGANISM: Artificial Sequence
<220> FEATURE:
<223> OTHER INFORMATION: ACI-7062-401A2-Ab2-VH Nucleotide sequence of
     the heavy chain variable domain without tail

<400> SEQUENCE: 233

```
gatgtgcagc tggtggagtc tgggggaggc ttagtgcagc ctggagggtc ccggagactc      60
tcctgtgcag cctctggatt cactttcagt aggtttggaa tgcactgggt tcgccaggct    120
ccagagaagg ggctggagtg ggtcgcatac attaggagtg gcagtgatat aatctactat    180
gcagactcag tgaagggccg attcaccatc tccagagaca tcccagaaa cacccctgttc    240 ctgcaaatga ccagtctaag gtctgaggac acggccatgt attactgtgc aagatcaggg    300
actacggtcc ccttgacta ctggggccaa ggcaccagtc tcacagtctc ttca            354
```

<210> SEQ ID NO 234

```
<211> LENGTH: 115
<212> TYPE: PRT
<213> ORGANISM: Artificial Sequence
<220> FEATURE:
<223> OTHER INFORMATION: ACI-7062-412A7-Ab1-VL Peptide sequence of the
      light chain variable domain without tail

<400> SEQUENCE: 234

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala
        115

<210> SEQ ID NO 235
<211> LENGTH: 345
<212> TYPE: DNA
<213> ORGANISM: Artificial Sequence
<220> FEATURE:
<223> OTHER INFORMATION: ACI-7062-412A7-Ab1-VL Nucleotide sequence of
      the light chain variable domain without tail

<400> SEQUENCE: 235
gacattgtga tgacacagtc tccatcctcc ctggctatgt cagttggaca gaaggtcact      60
atgagctgca agtccagtca gagccttta aatagtggca atcaaaagaa ctatttggcc     120
tggtaccagc agaaaccagg acagtctcct gaacttctat tatactttgc atccactagg    180
gcatctgggg tccctgatcg cttcataggc agtggatctg gacagatttt cactcttacc    240
atcagcagtg tgcaggctga agacctggca gattacttct gtcagcaaca ttatagtatt    300
ccgctcacgt tcggtgctgg gaccaagctg gagctgaaac gggct                    345

<210> SEQ ID NO 236
<211> LENGTH: 118
<212> TYPE: PRT
<213> ORGANISM: Artificial Sequence
<220> FEATURE:
<223> OTHER INFORMATION: ACI-7062-412A7-Ab1-VH Peptide sequence of the
      heavy chain variable domain without tail

<400> SEQUENCE: 236

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60
```

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser
        115

<210> SEQ ID NO 237
<211> LENGTH: 354
<212> TYPE: DNA
<213> ORGANISM: Artificial Sequence
<220> FEATURE:
<223> OTHER INFORMATION: ACI-7062-412A7-Ab1-VH Nucleotide sequence of
      the heavy chain variable domain without tail

<400> SEQUENCE: 237
gatgtgcagc tggtggagtc tgggggaggc ttagtgcagc ctggagggtc ccggagactc      60
tcctgtgcag cctctggatt cactttcagt agctttggaa tgcactgggt tcgtcaggct     120
ccagagaagg ggctggagtg ggtcgcatac attaggagtg gcagtgatat aatctactat     180
gcagactcag tgaagggccg attcaccatc tccagagaca atcccgagaa caccctgttc     240
ctgcaaatga ccagtctaag gtctgaggac acggccatgt attactgtgc aagatcaggg     300
actacggtcc cctttgacta ctggggccaa ggcaccagtc tcacagtctc ttca           354

<210> SEQ ID NO 238
<211> LENGTH: 113
<212> TYPE: PRT
<213> ORGANISM: Artificial Sequence
<220> FEATURE:
<223> OTHER INFORMATION: ACI-7062-406E3-Ab1-VL Peptide sequence of the
      light chain variable domain without tail

<400> SEQUENCE: 238

Asp Val Leu Met Thr Gln Thr Pro Leu Ser Leu Pro Val Ser Leu Gly
1               5                   10                  15

Asp Arg Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Thr Phe Gly Ala Gly Thr Lys Leu Glu Leu Lys Arg
            100                 105                 110

Ala

<210> SEQ ID NO 239
<211> LENGTH: 339
<212> TYPE: DNA
<213> ORGANISM: Artificial Sequence
<220> FEATURE:
<223> OTHER INFORMATION: ACI-7062-406E3-Ab1-VL Nucleotide sequence of
      the light chain variable domain without tail

<400> SEQUENCE: 239

```
gatgttttga tgacccaaac tccactctcc ctgcctgtca gtcttggaga tcgagcctcc      60
atctcttgca gatctagtca gagcattgta catcgtagtg aaacaccta tttagagtgg     120 tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttccc    300
acgttcggtg ctgggaccaa gctggagctg aaacgggct                           339

<210> SEQ ID NO 240
<211> LENGTH: 120
<212> TYPE: PRT
<213> ORGANISM: Artificial Sequence
<220> FEATURE:
<223> OTHER INFORMATION: ACI-7062-406E3-Ab1-VH Peptide sequence of the
      heavy chain variable domain without tail

<400> SEQUENCE: 240

Gln Val Thr Leu Lys Glu Ser Gly Pro Ala Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Asn Lys Tyr Tyr Asn Thr Ala
    50                  55                  60

Leu Lys Ser Arg Leu Thr Val Ser Lys Asp Thr Ser Asn Asn Gln Val
65                  70                  75                  80

Phe Leu Lys Ile Ala Ser Val Asp Thr Ala Asp Thr Ala Thr Tyr Tyr
                85                  90                  95

Cys Ala Arg Val Tyr Gly Asn Leu Tyr Tyr Phe Ala Tyr Trp Gly Gln
            100                 105                 110

Gly Thr Thr Leu Thr Val Ser Ser
        115                 120

<210> SEQ ID NO 241
<211> LENGTH: 360
<212> TYPE: DNA
<213> ORGANISM: Artificial Sequence
<220> FEATURE:
<223> OTHER INFORMATION: ACI-7062-406E3-Ab1-VH Nucleotide sequence of
      the heavy chain variable domain without tail

<400> SEQUENCE: 241
caggttactc tgaaagagtc tggccctgcg atattgcagc cctcccagac cctcagtctg      60
acttgttctt tctctgggtt ttcactgacc acttatggta taggagtagg ctggattcgt    120
cagccttcag ggaagggtct ggagtggctg gcacacattt ggtggaatga taataagtac    180
tataacacag ccctgaagag ccggctcact gtctccaagg atacctccaa caaccaggta    240
ttcctcaaga tcgccagtgt agacactgca gatactgcca catactactg tgctcgagtc    300
tatggtaacc tgtactactt tgcctactgg ggccaaggca ccactctcac agtctcctca    360

<210> SEQ ID NO 242
<211> LENGTH: 113
<212> TYPE: PRT
<213> ORGANISM: Artificial Sequence
<220> FEATURE:
<223> OTHER INFORMATION: ACI-7062-404D6-Ab2-VL Peptide sequence of the
      light chain variable domain without tail
```

<400> SEQUENCE: 242

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Gly
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Tyr Cys Phe Gln Gly
                85                  90                  95

Ser His Val Pro Thr Phe Gly Ala Gly Thr Lys Leu Glu Leu Lys Arg
            100                 105                 110

Ala

<210> SEQ ID NO 243
<211> LENGTH: 339
<212> TYPE: DNA
<213> ORGANISM: Artificial Sequence
<220> FEATURE:
<223> OTHER INFORMATION: ACI-7062-404D6-Ab2-VL Nucleotide sequence of
      the light chain variable domain without tail

<400> SEQUENCE: 243
gatgttttga tgacccaaac tccactctcc ctgcctgtca gtcttggaga tcaagcctcc      60
atctcttgca gatctagtca gagcattgta catggttctg aaacacccta tttagaatgg     120
tacctgcaga accaggcca gtctccaaag ctcctgatct acaaagtttc caaccgattt     180
tctggggtcc cagacaggtt cagtggcagt ggatcaggga cagatttcac actcaggatc    240
agcagagtgg aggctgagga tctgggagtt tattactgct ttcaaggttc acatgttccc    300
acgttcggtg ctgggaccaa gctggagctg aaacgggct                           339

<210> SEQ ID NO 244
<211> LENGTH: 120
<212> TYPE: PRT
<213> ORGANISM: Artificial Sequence
<220> FEATURE:
<223> OTHER INFORMATION: ACI-7062-404D6-Ab2-VH Peptide sequence of the
      heavy chain variable domain without tail

<400> SEQUENCE: 244

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Ile Gly Val Gly Trp Ile Arg Gln Pro Ser Gly Lys Gly Leu Glu
        35                  40                  45

Trp Leu Ala His Ile Trp Trp Asn Asp Tyr Lys Tyr Tyr Asn Thr Ala
    50                  55                  60

Leu Lys Ser Arg Leu Thr Ile Ser Lys Asp Thr Ser Asn Asn Arg Val
65                  70                  75                  80

Phe Leu Lys Ile Ala Ser Val Asp Thr Ala Asp Thr Ala Thr Tyr Tyr
                85                  90                  95

Cys Ala Arg Val Tyr Gly Asn Leu Tyr Tyr Phe Asp Tyr Trp Gly Gln

```
                  100               105                 110
Gly Thr Thr Leu Thr Val Ser Ser
        115                 120

<210> SEQ ID NO 245
<211> LENGTH: 360
<212> TYPE: DNA
<213> ORGANISM: Artificial Sequence
<220> FEATURE:
<223> OTHER INFORMATION: ACI-7062-404D6-Ab2-VH Nucleotide sequence of
      the heavy chain variable domain without tail

<400> SEQUENCE: 245
caggttactc tgaaagagtc tggccctggg atattgcagc cctcccagac cctcagtctg    60
acttgttctt tctctgggtt ttcactgagc acttatggta taggagtagg ctggattcgt   120
cagccttcag ggaagggtct ggagtggctg gcacacattt ggtggaatga ttataagtac   180
tataacacag ccctgaagag ccggctcaca atctccaagg atacctccaa caaccgggta   240
ttcctcaaga tcgccagtgt ggacactgca gatactgcca catactactg tgctcgagtc   300
tatggtaacc tgtactactt tgactactgg ggccaaggca ccactctcac agtctcctca   360

<210> SEQ ID NO 246
<211> LENGTH: 115
<212> TYPE: PRT
<213> ORGANISM: Artificial Sequence
<220> FEATURE:
<223> OTHER INFORMATION: ACI-7062-410H3-Ab1-VL Peptide sequence of the
      light chain variable domain without tail

<400> SEQUENCE: 246

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asn Gln Lys Asn Tyr Leu Ala Trp Tyr Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala
        115

<210> SEQ ID NO 247
<211> LENGTH: 345
<212> TYPE: DNA
<213> ORGANISM: Artificial Sequence
<220> FEATURE:
<223> OTHER INFORMATION: ACI-7062-410H3-Ab1-VL Nucleotide sequence of
      the light chain variable domain without tail

<400> SEQUENCE: 247
gacattgtga tgacacagtc tccatcctcc ctggctatgt cagttggaca gaaggtcact    60
atgagctgca agtccagtca gagccttta aatagtggaa tcaaaagaa ctatttggcc   120 tggtaccagc agaaaccagg acagtctcct gaacttctgt tatactttgc atccactagg   180
```

```
gcatctgggg tccctgatcg cttcataggc agtggatctg ggacagattt cactcttacc    240
atcagcagtg tgcaggctga agacctggca gattacttct gtcagcaaca ttatagtatt    300
ccgctcacgt tcggtgctgg gaccaagctg gagctgaaac gggct                    345
```

```
<210> SEQ ID NO 248
<211> LENGTH: 118
<212> TYPE: PRT
<213> ORGANISM: Artificial Sequence
<220> FEATURE:
<223> OTHER INFORMATION: ACI-7062-410H3-Ab1-VH Peptide sequence of the
      heavy chain variable domain without tail

<400> SEQUENCE: 248

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser
        115
```

```
<210> SEQ ID NO 249
<211> LENGTH: 354
<212> TYPE: DNA
<213> ORGANISM: Artificial Sequence
<220> FEATURE:
<223> OTHER INFORMATION: ACI-7062-410H3-Ab1-VH Nucleotide sequence of
      the heavy chain variable domain without tail

<400> SEQUENCE: 249
gatgtgcagc tggtggagtc tgggggaggc ttagtgcagc ctggagggtc ccggagactc     60
tcctgtgcag cctctggatt cactttcagt agctttggaa tgcactgggt tcgtcaggct    120
ccagagaagg gctggagtg gtcgcatac attaggagtg gcagtgatat aatctactat     180
gcagactcag tgaagggccg attcaccatc tccagagaca atcccgagaa caccctgttc    240
ctgcaaatga ccagtctaag gtctgaggac acggccatgt attactgtgc aagatcaggg    300
actacggtcc cctttgacta ctggggccaa ggcaccagtc tcacagtctc ttca          354
```

```
<210> SEQ ID NO 250
<211> LENGTH: 115
<212> TYPE: PRT
<213> ORGANISM: Artificial Sequence
<220> FEATURE:
<223> OTHER INFORMATION: ACI-7062-414A5-Ab1-VL Peptide sequence of the
      light chain variable domain without tail

<400> SEQUENCE: 250

Asp Ile Val Met Thr Gln Ser Pro Ser Ser Leu Ala Met Ser Val Gly
1               5                   10                  15
```

```
Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Lys Pro Gly Gln
        35                  40                  45

Ser Pro Lys Leu Leu Val Tyr Phe Ala Ser Thr Arg Glu Ser Gly Val
50                  55                  60

Pro Asp Arg Phe Ile Gly Ser Gly Ser Gly Thr Asp Phe Thr Leu Thr
65                  70                  75                  80

Ile Asn Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
                100                 105                 110

Lys Arg Ala
        115

<210> SEQ ID NO 251
<211> LENGTH: 345
<212> TYPE: DNA
<213> ORGANISM: Artificial Sequence
<220> FEATURE:
<223> OTHER INFORMATION: ACI-7062-414A5-Ab1-VL Nucleotide sequence of
      the light chain variable domain without tail

<400> SEQUENCE: 251
gacattgtga tgacacagtc tccatcctcc ctggctatgt cagtaggaca gaaggtcact      60
atgagctgca agtccagtca gagccttttta aatagtagca atcaaaagaa ctatttggcc    120
tggtaccagc agaaaccagg acagtctcct aaacttctgg tatactttgc atccactagg    180
gaatctgggg tccctgatcg cttcataggc agtggatctg gacagattt cactcttacc     240 atcaacagtg tgcaggctga agacctggca gattacttct gtcagcaaca ttatagtatt    300
ccgctcacgt tcggtgctgg gaccaagctg gagctgaaac gggct                    345

<210> SEQ ID NO 252
<211> LENGTH: 118
<212> TYPE: PRT
<213> ORGANISM: Artificial Sequence
<220> FEATURE:
<223> OTHER INFORMATION: ACI-7062-414A5-Ab1-VH Peptide sequence of the
      heavy chain variable domain without tail

<400> SEQUENCE: 252

Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Thr Val
50                  55                  60

Lys Gly Arg Phe Thr Ile Ser Arg Asp Asn Pro Glu Asn Thr Leu Phe
65                  70                  75                  80

Leu Glu Met Thr Arg Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
                100                 105                 110

Ser Leu Thr Val Ser Ser
        115
```

<210> SEQ ID NO 253
<211> LENGTH: 354
<212> TYPE: DNA
<213> ORGANISM: Artificial Sequence
<220> FEATURE:
<223> OTHER INFORMATION: ACI-7062-414A5-Ab1-VH Nucleotide sequence of the heavy chain variable domain without tail

<400> SEQUENCE: 253

```
gatgtgcagc tggtggagtc tgggggaggc ttagtgcagc ctggagggtc ccggagactc      60
tcctgtgcag cctctggatt cactttcagt agctttggaa tgcactgggt tcgtcaggct     120
ccagagaagg ggctggagtg ggtcgcatac attaggagtg gcagtgatat aatctactat     180
gcagacacag tgaagggccg attcaccatc tccagagaca atcccgagaa caccctgttt     240
ttggaaatga ccagactaag gtctgaggac acggccatgt attactgtgc aagatcaggg     300
actacggtcc cctttgacta ctggggccaa ggcaccagtc tcacagtctc ttca           354
```

<210> SEQ ID NO 254
<211> LENGTH: 115
<212> TYPE: PRT
<213> ORGANISM: Artificial Sequence
<220> FEATURE:
<223> OTHER INFORMATION: ACI-7062-412E12-Ab1-VL Peptide sequence of the light chain variable domain without tail

<400> SEQUENCE: 254

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Gly Asp Gln Lys Asn Tyr Leu Ala Trp Tyr Gln Gln Lys Pro Gly Gln
        35                  40                  45

Ser Pro Glu Leu Leu Leu Tyr Phe Ala Ser Thr Arg Ala Ser Gly Val
    50                  55                  60

Pro Asp Arg Phe Ile Gly Ser Gly Ser Gly Thr Asp Phe Ser Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
            100                 105                 110

Lys Arg Ala
        115
```

<210> SEQ ID NO 255
<211> LENGTH: 345
<212> TYPE: DNA
<213> ORGANISM: Artificial Sequence
<220> FEATURE:
<223> OTHER INFORMATION: ACI-7062-412E12-Ab1-VL Nucleotide sequence of the light chain variable domain without tail

<400> SEQUENCE: 255

```
gacattgtga tgacacagtc tccatcctcc ctggctatgt cagttggaca gaaggtcact      60
atgagctgca agtccagtca gagccttta aatagtggcg atcaaaagaa ctatttggcc     120
tggtaccagc agaaaccagg acagtctcct gaacttctgt tatactttgc atccactagg     180
gcatctgggg tccctgatcg cttcataggc agtggatctg gaacagattt ctctcttacc     240
atcagcagtg tgcaggctga agacctggca gattacttct gtcagcaaca ttatagtatt     300
```

```
ccgctcacgt tcggtgctgg gaccaagctg gagctgaaac gggct          345
```

<210> SEQ ID NO 256
<211> LENGTH: 118
<212> TYPE: PRT
<213> ORGANISM: Artificial Sequence
<220> FEATURE:
<223> OTHER INFORMATION: ACI-7062-412E12-Ab1-VH Peptide sequence of the
      heavy chain variable domain without tail

<400> SEQUENCE: 256

```
Asp Val Gln Leu Val Glu Ser Gly Gly Gly Leu Val Gln Pro Gly Gly
1               5                   10                  15

Ser Arg Arg Leu Ser Cys Ala Ala Ser Gly Phe Thr Phe Ser Arg Phe
            20                  25                  30

Gly Met His Trp Val Arg Gln Ala Pro Glu Lys Gly Leu Glu Trp Val
        35                  40                  45

Ala Tyr Ile Arg Ser Gly Ser Asp Ile Ile Tyr Tyr Ala Asp Ser Val
    50                  55                  60

Lys Gly Arg Phe Thr Ile Ser Arg Asp Asn Pro Glu Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Thr Thr Val Pro Phe Asp Tyr Trp Gly Gln Gly Thr
            100                 105                 110

Ser Leu Thr Val Ser Ser
        115
```

<210> SEQ ID NO 257
<211> LENGTH: 354
<212> TYPE: DNA
<213> ORGANISM: Artificial Sequence
<220> FEATURE:
<223> OTHER INFORMATION: ACI-7062-412E12-Ab1-VH Nucleotide sequence of
      the heavy chain variable domain without tail

<400> SEQUENCE: 257

```
gatgtgcagc tggtggagtc tgggggaggc ttagtgcagc ctggagggtc ccggagactc    60
tcctgtgcag cctctggatt cactttcagt aggtttggaa tgcactgggt tcgccaggct   120
ccagagaagg ggctggagtg ggtcgcatac attaggagtg gcagtgatat aatctactat   180
gcagactcag tgaagggccg attcaccatc tccagagaca atcccgagaa caccctgttc   240
ctgcaaatga ccagtctaag gtctgaggac acggccatgt attactgtgc aagatcaggg   300
actacggtcc cctttgacta ctggggccaa ggcaccagtc tcacagtctc ttca         354
```

<210> SEQ ID NO 258
<211> LENGTH: 113
<212> TYPE: PRT
<213> ORGANISM: Artificial Sequence
<220> FEATURE:
<223> OTHER INFORMATION: ACI-7062-416A11-Ab1-VL Peptide sequence of the
      light chain variable domain without tail

<400> SEQUENCE: 258

```
Asp Val Leu Met Thr Gln Thr Pro Leu Ser Leu Pro Val Ser Leu Gly
1               5                   10                  15

Asp Arg Ala Ser Ile Ser Cys Arg Ser Ser Gln Ser Ile Val His Ser
            20                  25                  30

Ser Gly Asn Thr Tyr Leu Glu Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Arg Val Pro Thr Phe Gly Ala Gly Thr Lys Leu Glu Leu Lys Arg
            100                 105                 110

Ala
```

```
<210> SEQ ID NO 259
<211> LENGTH: 339
<212> TYPE: DNA
<213> ORGANISM: Artificial Sequence
<220> FEATURE:
<223> OTHER INFORMATION: ACI-7062-416A11-Ab1-VL Nucleotide Sequence of
      the light chain variable domain without tail

<400> SEQUENCE: 259
gatgttttga tgacccaaac tccactctcc ctgcctgtca gtcttggaga tcgagcctcc      60
atctcttgca gatctagtca gagcattgta catagtagtg aaacaccta tttagaatgg     120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acgtgttccc    300
acgttcggtg ctgggaccaa gctggagctg aaacgggct                           339
```

```
<210> SEQ ID NO 260
<211> LENGTH: 120
<212> TYPE: PRT
<213> ORGANISM: Artificial Sequence
<220> FEATURE:
<223> OTHER INFORMATION: ACI-7062-416A11-Ab1-VH Peptide sequence of the
      heavy chain variable domain without tail

<400> SEQUENCE: 260

Gln Val Thr Leu Lys Glu Ser Gly Pro Gly Ile Leu Gln Ser Ser Gln
 1               5                  10                  15

Thr Leu Ser Leu Thr Cys Ser Phe Ser Gly Phe Ser Leu Ser Thr Tyr
             20                  25                  30

Gly Ile Gly Val Gly Trp Ile Arg Gln Pro Ser Gly Lys Gly Leu Glu
         35                  40                  45

Trp Leu Ala His Ile Trp Trp Asn Asp Asn Lys Tyr Tyr Asn Thr Ala
 50                  55                  60

Leu Lys Ser Arg Leu Thr Ile Ser Lys Asp Thr Ser Asn Asn Gln Val
 65                  70                  75                  80

Phe Leu Lys Ile Ala Ser Val Asp Thr Ala Asp Ala Ala Thr Tyr Tyr
                 85                  90                  95

Cys Ala Arg Val Tyr Gly Asn Leu Tyr Tyr Phe Gly Tyr Trp Gly Gln
            100                 105                 110

Gly Thr Thr Leu Thr Val Ser Ser
        115                 120
```

```
<210> SEQ ID NO 261
<211> LENGTH: 360
<212> TYPE: DNA
<213> ORGANISM: Artificial Sequence
<220> FEATURE:
```

<223> OTHER INFORMATION: ACI-7062-416A11-Ab1-VH Nucleotide sequence of
the heavy chain variable domain without tail

<400> SEQUENCE: 261

```
caggttactc tgaaagagtc tggccctggg atattgcagt cctcccagac cctcagtctg      60
acttgttctt tctctggatt ttcactgagc acttatggta taggagtagg ctggattcgt     120
cagccttcag ggaagggtct ggagtggctg gcacacattt ggtggaatga taataagtac     180
tataacacag ccctgaagag ccgactcaca atctccaagg atacctccaa caaccaggta     240
ttcctcaaga tcgccagtgt ggacactgca gatgctgcca catactactg tgctcgagtc     300
tatggtaacc tatactactt tggctactgg ggccaaggca ccactctcac agtctcctca     360
```

<210> SEQ ID NO 262
<211> LENGTH: 15
<212> TYPE: PRT
<213> ORGANISM: Unknown
<220> FEATURE:
<223> OTHER INFORMATION: Mammalia; TP-23

<400> SEQUENCE: 262

Thr Glu Asp Met Thr Glu Asp Glu Leu Arg Glu Phe Phe Ser Gln
1               5                   10                  15

<210> SEQ ID NO 263
<211> LENGTH: 15
<212> TYPE: PRT
<213> ORGANISM: Unknown
<220> FEATURE:
<223> OTHER INFORMATION: Mammalia; TP-24

<400> SEQUENCE: 263

Arg Glu Phe Phe Ser Gln Tyr Gly Asp Val Met Asp Val Phe Ile
1               5                   10                  15

<210> SEQ ID NO 264
<211> LENGTH: 15
<212> TYPE: PRT
<213> ORGANISM: Unknown
<220> FEATURE:
<223> OTHER INFORMATION: Mammalia; TP-25

<400> SEQUENCE: 264

Val Met Asp Val Phe Ile Pro Lys Pro Phe Arg Ala Phe Ala Phe
1               5                   10                  15

<210> SEQ ID NO 265
<211> LENGTH: 15
<212> TYPE: PRT
<213> ORGANISM: Unknown
<220> FEATURE:
<223> OTHER INFORMATION: Mammalia; TP-26

<400> SEQUENCE: 265

Phe Arg Ala Phe Ala Phe Val Thr Phe Ala Asp Asp Gln Ile Ala
1               5                   10                  15

<210> SEQ ID NO 266
<211> LENGTH: 15
<212> TYPE: PRT
<213> ORGANISM: Unknown
<220> FEATURE:
<223> OTHER INFORMATION: Mammalia; TP-27

<400> SEQUENCE: 266

```
Ala Asp Asp Gln Ile Ala Gln Ser Leu Cys Gly Glu Asp Leu Ile
1               5                   10                  15

<210> SEQ ID NO 267
<211> LENGTH: 15
<212> TYPE: PRT
<213> ORGANISM: Unknown
<220> FEATURE:
<223> OTHER INFORMATION: Mammalia; TP-28

<400> SEQUENCE: 267

Cys Gly Glu Asp Leu Ile Ile Lys Gly Ile Ser Val His Ile Ser
1               5                   10                  15

<210> SEQ ID NO 268
<211> LENGTH: 15
<212> TYPE: PRT
<213> ORGANISM: Unknown
<220> FEATURE:
<223> OTHER INFORMATION: Mammalia; TP-29

<400> SEQUENCE: 268

Ile Ser Val His Ile Ser Asn Ala Glu Pro Lys His Asn Ser Asn
1               5                   10                  15

<210> SEQ ID NO 269
<211> LENGTH: 15
<212> TYPE: PRT
<213> ORGANISM: Unknown
<220> FEATURE:
<223> OTHER INFORMATION: Mammalia; TP-30

<400> SEQUENCE: 269

Pro Lys His Asn Ser Asn Arg Gln Leu Glu Arg Ser Gly Arg Phe
1               5                   10                  15

<210> SEQ ID NO 270
<211> LENGTH: 15
<212> TYPE: PRT
<213> ORGANISM: Unknown
<220> FEATURE:
<223> OTHER INFORMATION: Mammalia; TP-31

<400> SEQUENCE: 270

Glu Arg Ser Gly Arg Phe Gly Gly Asn Pro Gly Gly Phe Gly Asn
1               5                   10                  15

<210> SEQ ID NO 271
<211> LENGTH: 8
<212> TYPE: PRT
<213> ORGANISM: Unknown
<220> FEATURE:
<223> OTHER INFORMATION: Mammalia; TDP-208

<400> SEQUENCE: 271

Arg Glu Phe Phe Ser Gln Tyr Gly
1               5

<210> SEQ ID NO 272
<211> LENGTH: 8
<212> TYPE: PRT
<213> ORGANISM: Unknown
<220> FEATURE:
<223> OTHER INFORMATION: Mammalia; TDP-209

<400> SEQUENCE: 272

Glu Phe Phe Ser Gln Tyr Gly Asp
```

```
1               5

<210> SEQ ID NO 273
<211> LENGTH: 8
<212> TYPE: PRT
<213> ORGANISM: Unknown
<220> FEATURE:
<223> OTHER INFORMATION: Mammalia; TDP-210

<400> SEQUENCE: 273

Phe Phe Ser Gln Tyr Gly Asp Val
1               5

<210> SEQ ID NO 274
<211> LENGTH: 8
<212> TYPE: PRT
<213> ORGANISM: Unknown
<220> FEATURE:
<223> OTHER INFORMATION: Mammalia; TDP-211

<400> SEQUENCE: 274

Phe Ser Gln Tyr Gly Asp Val Met
1               5

<210> SEQ ID NO 275
<211> LENGTH: 8
<212> TYPE: PRT
<213> ORGANISM: Unknown
<220> FEATURE:
<223> OTHER INFORMATION: Mammalia; TDP-212

<400> SEQUENCE: 275

Ser Gln Tyr Gly Asp Val Met Asp
1               5

<210> SEQ ID NO 276
<211> LENGTH: 8
<212> TYPE: PRT
<213> ORGANISM: Unknown
<220> FEATURE:
<223> OTHER INFORMATION: Mammalia; TDP-213

<400> SEQUENCE: 276

Gln Tyr Gly Asp Val Met Asp Val
1               5

<210> SEQ ID NO 277
<211> LENGTH: 8
<212> TYPE: PRT
<213> ORGANISM: Unknown
<220> FEATURE:
<223> OTHER INFORMATION: Mammalia; TDP-214

<400> SEQUENCE: 277

Tyr Gly Asp Val Met Asp Val Phe
1               5

<210> SEQ ID NO 278
<211> LENGTH: 8
<212> TYPE: PRT
<213> ORGANISM: Unknown
<220> FEATURE:
<223> OTHER INFORMATION: Mammalia; TDP-215

<400> SEQUENCE: 278

Gly Asp Val Met Asp Val Phe Ile
1               5
```

<210> SEQ ID NO 279
<211> LENGTH: 8
<212> TYPE: PRT
<213> ORGANISM: Unknown
<220> FEATURE:
<223> OTHER INFORMATION: Mammalia; TDP-216

<400> SEQUENCE: 279

Asp Val Met Asp Val Phe Ile Pro
1               5

<210> SEQ ID NO 280
<211> LENGTH: 8
<212> TYPE: PRT
<213> ORGANISM: Unknown
<220> FEATURE:
<223> OTHER INFORMATION: Mammalia; TDP-217

<400> SEQUENCE: 280

Val Met Asp Val Phe Ile Pro Lys
1               5

<210> SEQ ID NO 281
<211> LENGTH: 8
<212> TYPE: PRT
<213> ORGANISM: Unknown
<220> FEATURE:
<223> OTHER INFORMATION: Mammalia; TDP-218

<400> SEQUENCE: 281

Met Asp Val Phe Ile Pro Lys Pro
1               5

<210> SEQ ID NO 282
<211> LENGTH: 8
<212> TYPE: PRT
<213> ORGANISM: Unknown
<220> FEATURE:
<223> OTHER INFORMATION: Mammalia; TDP-219

<400> SEQUENCE: 282

Asp Val Phe Ile Pro Lys Pro Phe
1               5

<210> SEQ ID NO 283
<211> LENGTH: 8
<212> TYPE: PRT
<213> ORGANISM: Unknown
<220> FEATURE:
<223> OTHER INFORMATION: Mammalia; TDP-220

<400> SEQUENCE: 283

Val Phe Ile Pro Lys Pro Phe Arg
1               5

<210> SEQ ID NO 284
<211> LENGTH: 8
<212> TYPE: PRT
<213> ORGANISM: Unknown
<220> FEATURE:
<223> OTHER INFORMATION: Mammalia; TDP-221

<400> SEQUENCE: 284

Phe Ile Pro Lys Pro Phe Arg Ala
1               5

-continued

```
<210> SEQ ID NO 285
<211> LENGTH: 8
<212> TYPE: PRT
<213> ORGANISM: Unknown
<220> FEATURE:
<223> OTHER INFORMATION: Mammalia; TDP-222

<400> SEQUENCE: 285

Ile Pro Lys Pro Phe Arg Ala Phe
1               5

<210> SEQ ID NO 286
<211> LENGTH: 8
<212> TYPE: PRT
<213> ORGANISM: Unknown
<220> FEATURE:
<223> OTHER INFORMATION: Mammalia; TDP-223

<400> SEQUENCE: 286

Pro Lys Pro Phe Arg Ala Phe Ala
1               5

<210> SEQ ID NO 287
<211> LENGTH: 8
<212> TYPE: PRT
<213> ORGANISM: Unknown
<220> FEATURE:
<223> OTHER INFORMATION: Mammalia; TDP-224

<400> SEQUENCE: 287

Lys Pro Phe Arg Ala Phe Ala Phe
1               5
```